(12) United States Patent
Dai et al.

(10) Patent No.: US 10,980,807 B2
(45) Date of Patent: Apr. 20, 2021

(54) INHIBITOR OF INDOLEAMINE-2,3-DIOXYGENASE (IDO)

(71) Applicant: InventisBio LLC, Florham Park, NJ (US)

(72) Inventors: Xing Dai, Short Hills, NJ (US); Yaolin Wang, Short Hills, NJ (US)

(73) Assignee: InventisBio LLC, Florham Park, NJ (US)

( * ) Notice: Subject to any disclaimer, the term of this patent is extended or adjusted under 35 U.S.C. 154(b) by 0 days.

(21) Appl. No.: 16/073,679

(22) PCT Filed: Feb. 8, 2017

(86) PCT No.: PCT/US2017/017063
§ 371 (c)(1),
(2) Date: Jul. 27, 2018

(87) PCT Pub. No.: WO2017/139414
PCT Pub. Date: Aug. 17, 2017

(65) Prior Publication Data
US 2020/0046697 A1     Feb. 13, 2020

Related U.S. Application Data

(60) Provisional application No. 62/362,875, filed on Jul. 15, 2016, provisional application No. 62/293,219, filed on Feb. 9, 2016.

(51) Int. Cl.
| | | |
|---|---|---|
| C07D 401/12 | (2006.01) | |
| C07D 401/14 | (2006.01) | |
| C07D 405/12 | (2006.01) | |
| C07D 405/14 | (2006.01) | |
| A61K 31/505 | (2006.01) | |
| A61K 31/196 | (2006.01) | |
| A61K 31/351 | (2006.01) | |
| A61K 31/382 | (2006.01) | |
| A61K 31/41 | (2006.01) | |
| A61K 31/415 | (2006.01) | |
| A61K 31/4155 | (2006.01) | |
| A61K 31/4184 | (2006.01) | |
| C07C 275/42 | (2006.01) | |
| C07D 233/88 | (2006.01) | |
| C07D 239/42 | (2006.01) | |
| C07D 257/04 | (2006.01) | |
| C07D 261/14 | (2006.01) | |
| C07D 309/08 | (2006.01) | |
| C07D 309/14 | (2006.01) | |
| C07D 335/02 | (2006.01) | |
| C07D 413/12 | (2006.01) | |

(52) U.S. Cl.
CPC .......... *A61K 31/505* (2013.01); *A61K 31/196* (2013.01); *A61K 31/351* (2013.01); *A61K 31/382* (2013.01); *A61K 31/41* (2013.01); *A61K 31/415* (2013.01); *A61K 31/4155* (2013.01); *A61K 31/4184* (2013.01); *C07C 275/42* (2013.01); *C07D 233/88* (2013.01); *C07D 239/42* (2013.01); *C07D 257/04* (2013.01); *C07D 261/14* (2013.01); *C07D 309/08* (2013.01); *C07D 309/14* (2013.01); *C07D 335/02* (2013.01); *C07D 413/12* (2013.01)

(58) Field of Classification Search
CPC .. C07D 401/12; C07D 401/14; C07D 405/12; C07D 405/14
See application file for complete search history.

(56) References Cited

U.S. PATENT DOCUMENTS

| | | |
|---|---|---|
| 3,669,956 A | 6/1972 | Borck et al. |
| 5,773,646 A | 6/1998 | Chandrakumar et al. |
| 5,852,192 A | 12/1998 | Himmelsbach et al. |
| 9,133,123 B2 | 9/2015 | Ashcraft et al. |
| 2008/0300261 A1 | 12/2008 | Blurton et al. |
| 2010/0197591 A1 | 8/2010 | Aspnes et al. |

(Continued)

FOREIGN PATENT DOCUMENTS

| | | |
|---|---|---|
| CN | 101784520 A | 7/2010 |
| CN | 105073768 A | 11/2015 |
| CN | 105209443 A | 12/2015 |

(Continued)

OTHER PUBLICATIONS

Coletti et al. Med. Chem. Commun., 2017, 8, 1378-1392 (Year: 2017).*

(Continued)

*Primary Examiner* — Emily A Bernhardt
(74) *Attorney, Agent, or Firm* — Nixon & Vanderhye P.C.

(57) ABSTRACT

The present disclosure provides compounds of Formula (I). The compounds described herein may be useful in treating a disease associated with IDO, for example, cancer or an infectious disease (e.g., viral or bacterial infectious diseases). Also, provided in the present disclosure are pharmaceutical compositions, kits, methods, and uses including or using a compound described herein.

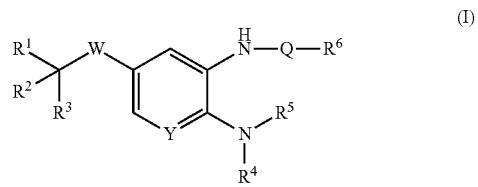

11 Claims, 4 Drawing Sheets

(56) References Cited

U.S. PATENT DOCUMENTS

2010/0228026 A1 9/2010 Yoshida et al.

FOREIGN PATENT DOCUMENTS

| EP | 0 008 226 A2 | 2/1980 |
|---|---|---|
| JP | 2002-510313 | 4/2002 |
| JP | 2004-203791 A | 7/2004 |
| JP | 2006-524248 A | 10/2006 |
| JP | 2018-506521 A | 3/2018 |
| WO | WO 1997/036862 A1 | 10/1997 |
| WO | WO 2004006858 A2 | 1/2004 |
| WO | WO 2007123269 A1 | 11/2007 |
| WO | WO2010089686 A | 8/2010 |
| WO | WO 2010/138901 A1 | 10/2010 |
| WO | WO 2010/127855 A1 | 11/2010 |
| WO | WO 2011/133920 A1 | 10/2011 |
| WO | WO 2011/143495 A1 | 11/2011 |
| WO | WO 2012176123 A1 | 12/2012 |
| WO | WO 2014/150646 A1 | 9/2014 |
| WO | WO 2014150677 A1 | 9/2014 |
| WO | WO 2015006520 A1 | 1/2015 |
| WO | WO 2015007516 A1 | 1/2015 |
| WO | WO 2015/121210 A1 | 8/2015 |
| WO | WO 2015/186056 A1 | 12/2015 |
| WO | WO-2016210414 A1 * | 12/2016 ............. A61K 31/18 |

OTHER PUBLICATIONS

Zhang et al. Frontiers in Pharmacology, vol. 9 p. 1-10. Available online at www.frontiersin.org (Year: 2018).*
International Search Report of PCT/US2017/017063 dated Apr. 10, 2017, WIPO.
STN Registry Search Results, RN 1347698-45-6 and RN 1347585-38-9, entered STN Dec. 2, 2011.

* cited by examiner

A

B

A.

B.

INHIBITOR OF INDOLEAMINE-2,3-DIOXYGENASE (IDO)

RELATED APPLICATIONS

This application is the U.S. national phase of International Application No. PCT/US2017/017063, filed Feb. 8, 2017, which claims priority under 35 U.S.C. § 119(e) to U.S. Provisional Patent Applications, U.S. Ser. No. 62/293,219, filed Feb. 9, 2016, and U.S. Ser. No. 62/362,875, filed Jul. 15, 2016, the entire contents of each of which is incorporated herein by reference.

BACKGROUND OF THE INVENTION

Indoleamine 2,3-dioxygenase (IDO), for example, Indoleamine 2,3-dioxygenase 1 (IDO1), is a family of heme-containing enzymes that catalyzes the degradation of the essential amino acid L-tryptophan to N-formylkynurenine. It plays an important role in the initial and rate limiting step in the breakdown of tryptophan.

It has been reported that IDO (e.g., IDO1), an enzyme induced by IFNγ, is one of the central regulators of immune responses in various physiological and pathological settings. IDO causes immunosuppression through breakdown of tryptophan in the tumor microenvironment. (Selvan et al., *Curr. Cancer Drug Targets*, 2015; Baren and Eynde Cancer Immunology Research, 2015). Overexpression of IDO was observed in various tumors (e.g., colorectal cancer, ovarian cancer, and breast cancer), which is thought to enable tumor cells escape from immunosurveillance. [Godin-Ethier et al., *Clinical Cancer Research*, 2011 Nov. 15; 17 (22): 6985-91]. It was also found that Treg cells regulates IDO mediated tryptophan catabolism in dendritic cells. (Fallarino, et. al. Nature Immunology 2003). In addition, IDO has been associated with other diseases such as viral infections and Alzheimer's. Accordingly, IDO is a promising target in cancer, e.g., cancer immune-therapy, as well as in other diseases such as infectious diseases and Alzheimer's.

SUMMARY OF THE INVENTION

The present disclosure provides compounds, such as compounds of Formula (I), which inhibit IDO such as IDO1 and hence, inhibit tryptophan catabolism and reduction of kynurenine in the tumor microenvironment and surrounding lymph nodes. The compounds described herein may be useful in treating proliferative diseases such as cancer (e.g., non-small cell lung cancer, small cell lung cancer, breast cancer, prostate cancer, ovarian cancer, bladder cancer, head and neck cancer, renal cell carcinoma, pancreatic cancer, brain cancer, cancers of the gastrointestinal tract, liver cancer, leukemia, lymphoma, melanoma, multiple myeloma, Ewing's sarcoma, osteosarcoma, and neuroblastoma) and infectious diseases such as viral or bacterial infectious diseases (e.g., hepatitis and HIV). Also provided are pharmaceutical compositions, kits, methods, and uses of any of the compounds described herein.

In one aspect, the present disclosure provides compounds of Formula (I):

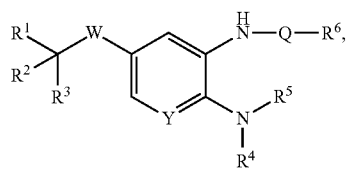

or pharmaceutically acceptable salts, wherein W is —O—, —S—, or a bond; Q is —C(═O)NH— or a bond; Y is —CR$^8$═ or —N═, as valency permits. In addition, R$^1$ is —C(═O)OH, —C(═O)OR$^{10}$, substituted or unsubstituted heterocyclyl, substituted or unsubstituted heteroaryl, —NHSO$_2$R$^9$, —C(═O)NHSO$_2$R$^9$, —C(═O)NHC(═O)OR$^{10}$, or —SO$_2$NHC(═O)R$^{10}$;

R$^2$ and R$^3$ are each independently hydrogen, halogen, substituted or unsubstituted C$_1$-C$_6$ alkyl, substituted or unsubstituted C$_1$-C$_6$ alkoxy, or R$^2$ and R$^3$ are joined to form a substituted or unsubstituted 3- to 8-membered carbocyclic ring, or substituted or unsubstituted 3- to 8-membered heterocyclic ring;

R$^4$ and R$^5$ are each independently hydrogen, substituted or unsubstituted C$_1$-C$_6$ alkyl, substituted or unsubstituted C$_2$-C$_6$ alkenyl, substituted or unsubstituted C$_5$-C$_8$ cycloalkenyl, substituted or unsubstituted C$_2$-C$_{10}$ alkynyl, substituted or unsubstituted aryl, substituted or unsubstituted C$_1$-C$_6$ alkoxy, substituted or unsubstituted C$_3$-C$_8$ cycloalkyl, substituted or unsubstituted 3- to 12-membered heterocyclyl (e.g., heterocycloalkyl), substituted or unsubstituted 5- to 6-membered monocyclic heteroaryl, substituted or unsubstituted 8- to 10-membered bicyclic heteroaryl, or arylsulfonyl; or R$^4$ and R$^5$ are joined together with the N they are attached to form optionally substituted, heterocyclyl, which may be monocyclic or bicyclic.

R$^6$ is substituted or unsubstituted C$_1$-C$_6$ alkyl, substituted or unsubstituted C$_3$-C$_8$ cycloalkyl, substituted or unsubstituted C$_2$-C$_6$ alkenyl, substituted or unsubstituted C$_2$-C$_6$ alkynyl, or substituted or unsubstituted C$_5$-C$_8$ cycloalkenyl, substituted or unsubstituted aryl, substituted or unsubstituted 4- to 7-membered monocyclic heterocyclyl (e.g., heterocycloalkyl), substituted or unsubstituted 7- to 10-membered bicyclic heterocyclyl, substituted or unsubstituted 5- to 6-membered monocyclic heteroaryl, substituted or unsubstituted 8- to 10-membered bicyclic heteroaryl, substituted or unsubstituted C$_1$-C$_6$ alkoxy, substituted or unsubstituted aryloxy, or —C(═O)R$^7$;

R$^7$ is hydrogen, substituted or unsubstituted C$_1$-C$_6$ alkyl, or substituted or unsubstituted aryl;

R$^8$ is independently hydrogen, halogen, —CN, —OH, substituted or unsubstituted C$_1$-C$_6$ alkyl, or substituted or unsubstituted C$_1$-C$_6$ alkoxy; and R$^9$ and R$^{10}$ are each independently hydrogen, or substituted or unsubstituted C$_1$-C$_6$ alkyl, substituted or unsubstituted C$_2$-C$_6$ alkenyl; or a pharmaceutically acceptable salt, wherein R$^1$, R$^2$, R$^3$, R$^4$, R$^5$, R$^6$, R$^7$, R$^8$, R$^9$, R$^{10}$, Y, and Q are as defined herein.

In certain embodiments, R$^1$ is —C(═O)OH, substituted or unsubstituted heterocyclyl, —NHSO$_2$R$^9$, —C(═O)NHSO$_2$R$^9$, —C(═O)NHC(═O)OR$^{10}$, or —SO$_2$NHC(═O)R$^{10}$.

In certain embodiments, R$^4$ and R$^5$ are each independently hydrogen, substituted or unsubstituted C$_1$-C$_6$ alkyl, substituted or unsubstituted C$_2$-C$_6$ alkenyl, substituted or unsubstituted C$_5$-C$_8$ cycloalkenyl, substituted or unsubstituted C$_2$-C$_{10}$ alkynyl, substituted or unsubstituted aryl, substituted or unsubstituted C$_1$-C$_6$ alkoxy, substituted or unsubstituted C$_3$-C$_8$ cycloalkyl, substituted or unsubstituted 3- to 12-membered heterocyclyl (e.g., heterocycloalkyl), substituted or unsubstituted 5- to 6-membered monocyclic heteroaryl, substituted or unsubstituted 8- to 10-membered bicyclic heteroaryl, substituted or unsubstituted aryl, or arylsulfonyl.

In certain embodiments, a compound of Formula (I) is of Formula (II):
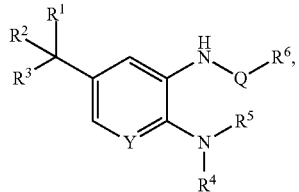
(II)
or a pharmaceutically acceptable salt, wherein $R^1$, $R^2$, $R^3$, $R^4$, $R^5$, $R^6$, Y, and Q are as described herein.
Exemplary compounds of Formula (II) include, but are not limited to:
1
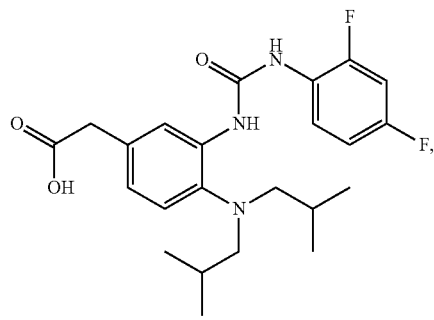
2
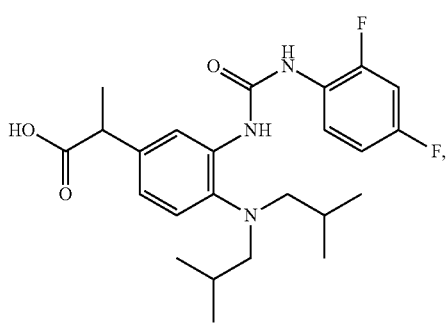
3
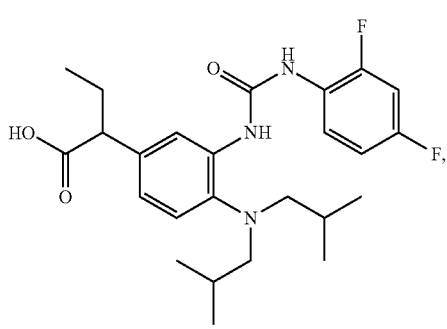
4
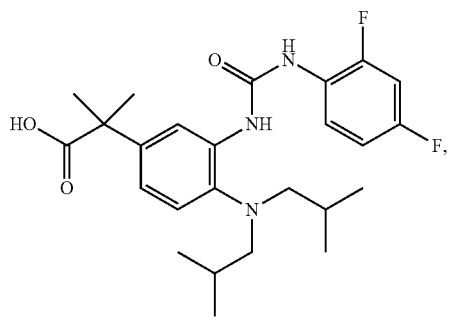
5
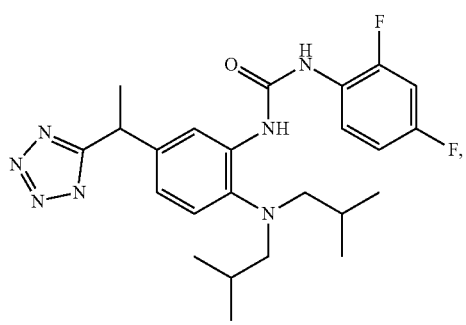
6
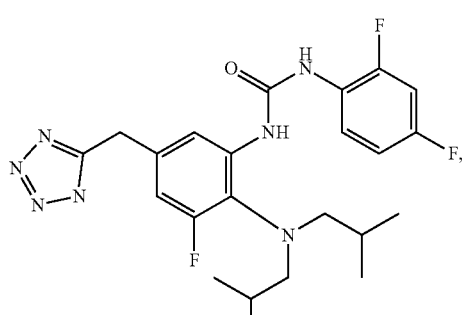
7
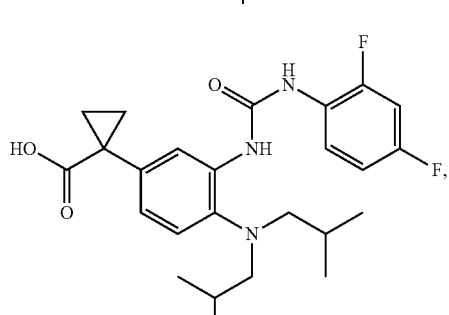
8
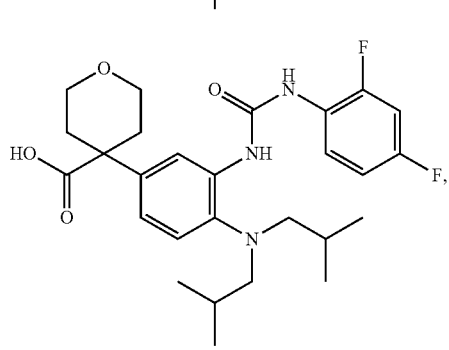

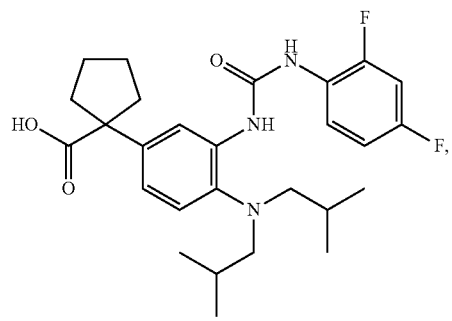
9
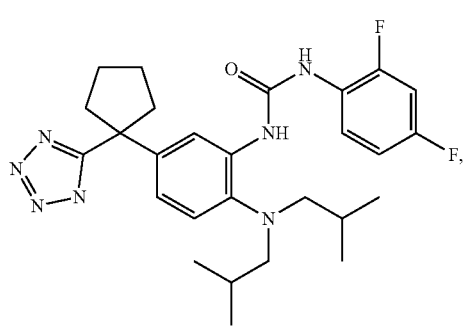
10
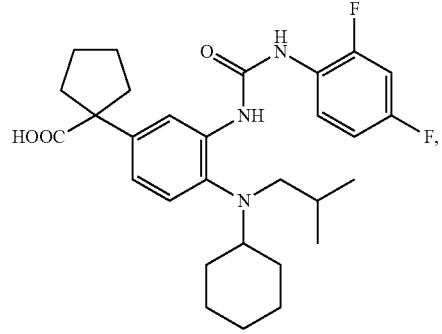
11
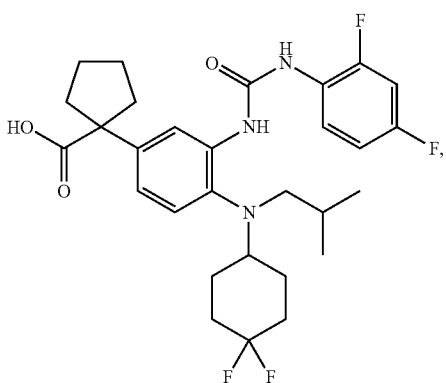
12
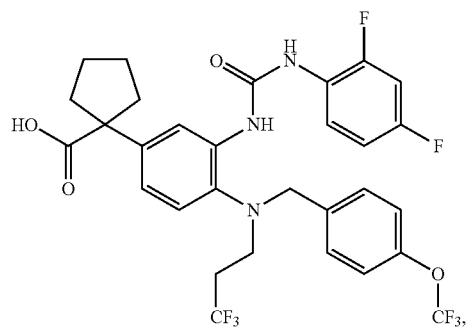
13
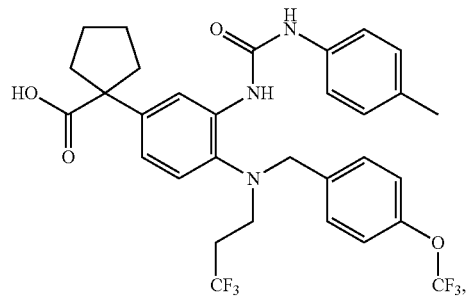
14
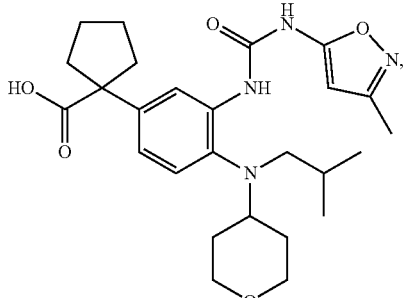
15
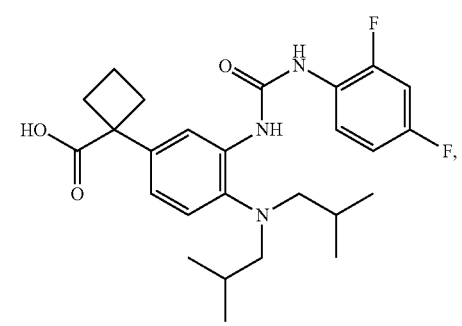
16
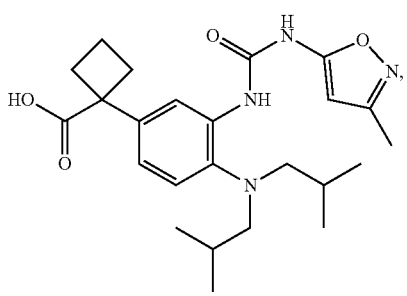
17

| 18 | 23 |
|---|---|
| 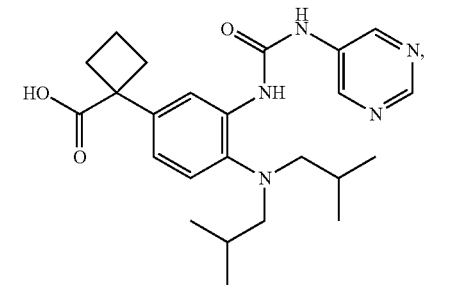 | 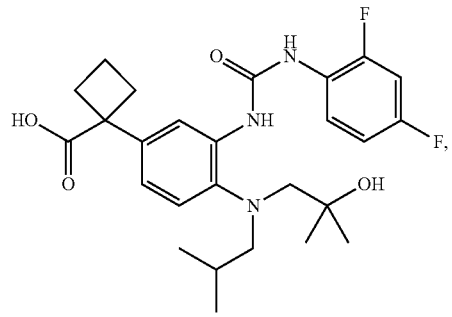 |
| 19 | 24 |
| 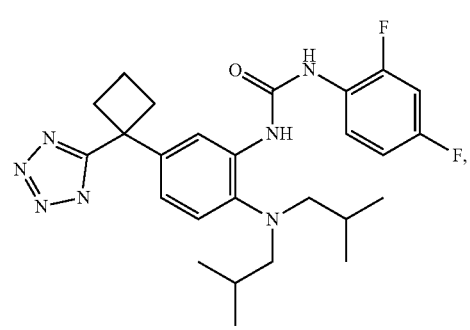 | 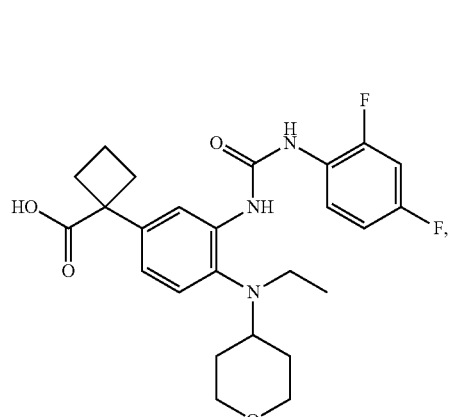 |
| 20 | 25 |
| 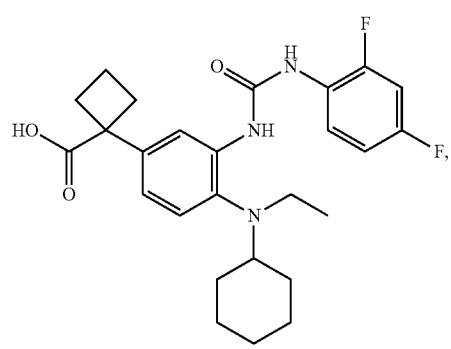 | 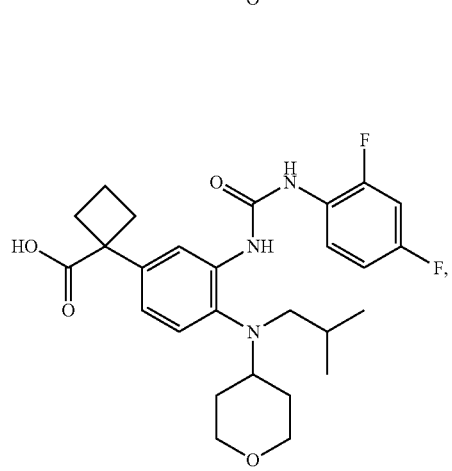 |
| 21 | |
| 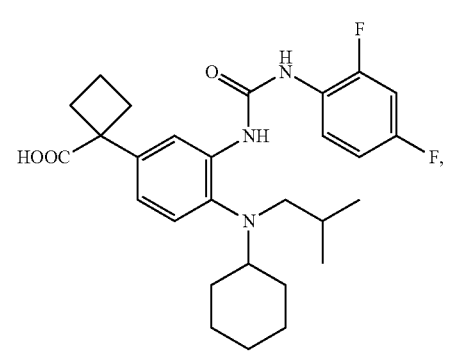 | |
| 22 | 26 |
| 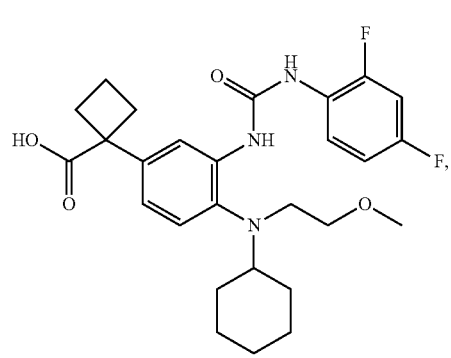 | 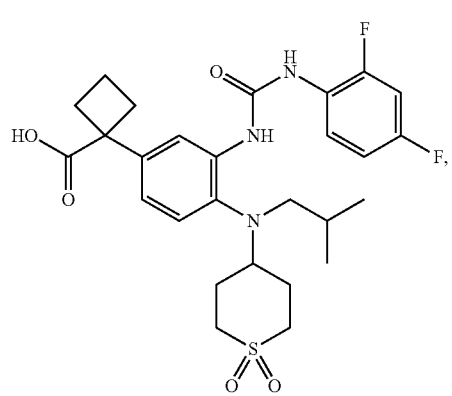 |

27
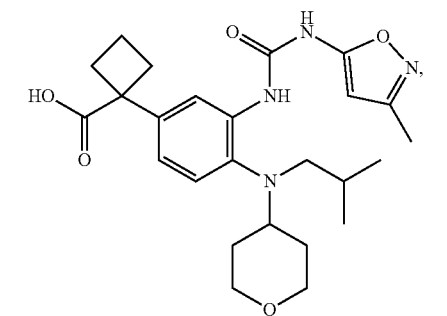
28
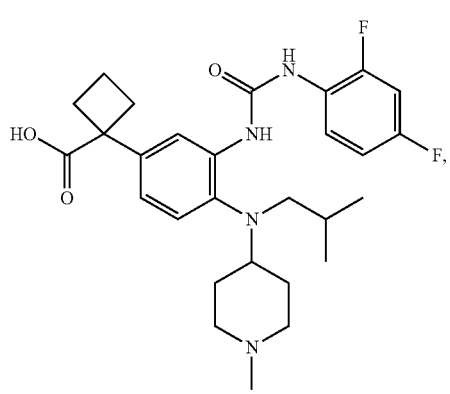
29
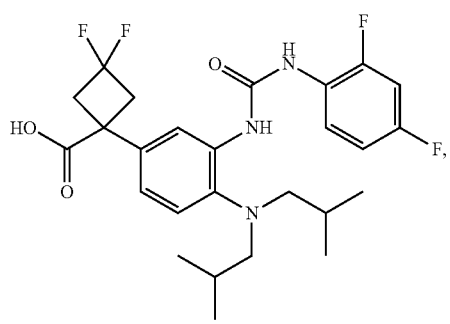
30
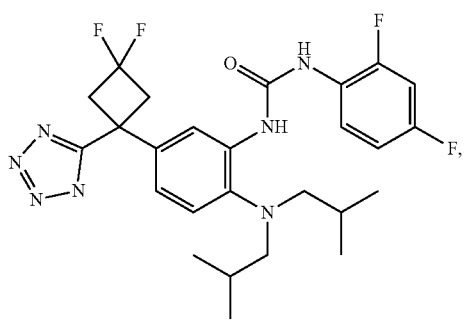
59
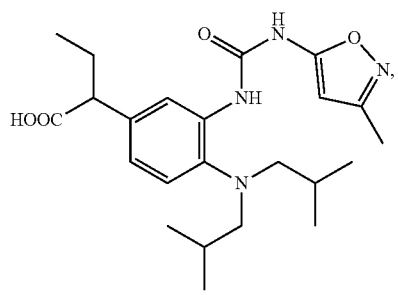
62
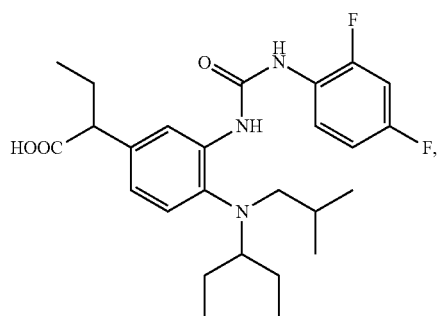
63
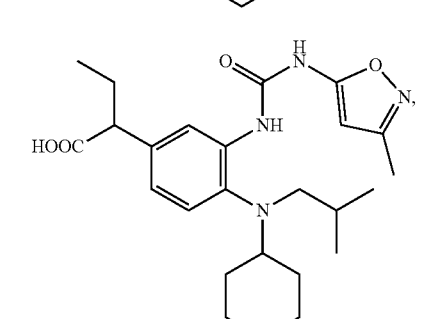
64
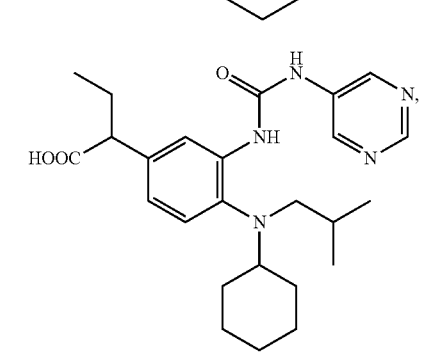
65
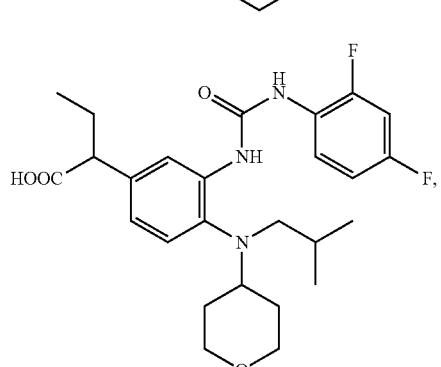
66
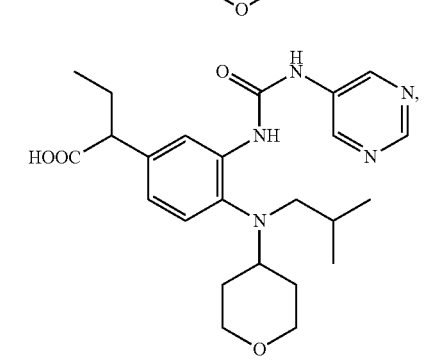

-continued
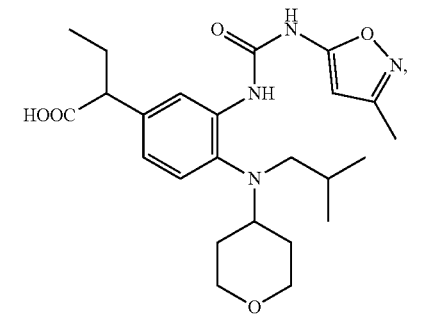
67
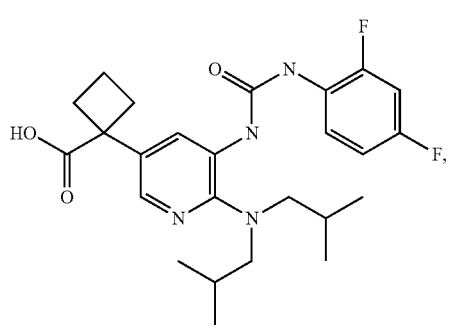
83
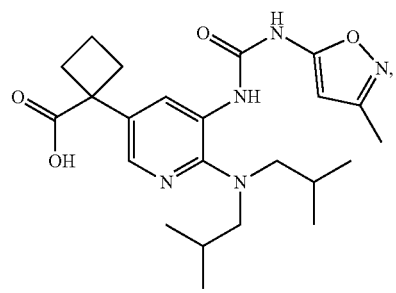
85
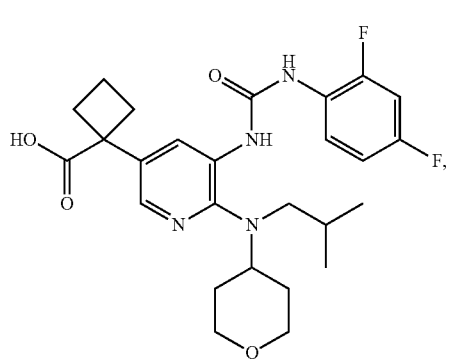
90
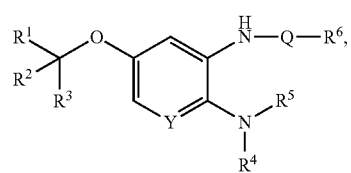
and pharmaceutically acceptable salts.
In certain embodiments, a compound of Formula (I) is of Formula (III):
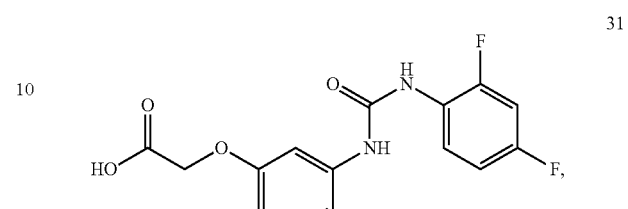
(III)
or a pharmaceutically acceptable salt, wherein $R^1$, $R^2$, $R^3$, $R^4$, $R^5$, $R^6$, Y, and Q are as defined herein.
Exemplary compounds of Formula (III) also include, but are not limited to:
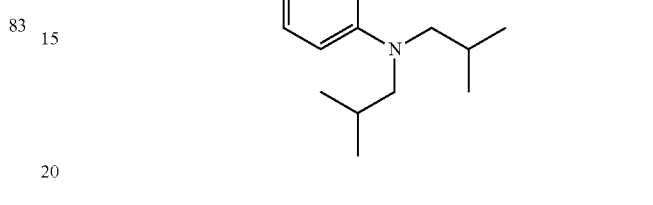
31
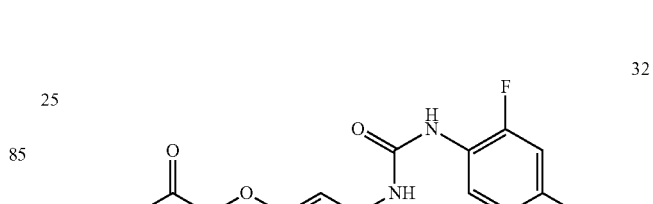
32
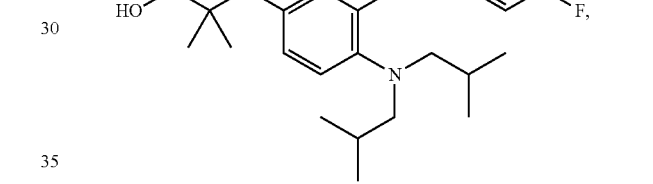
33
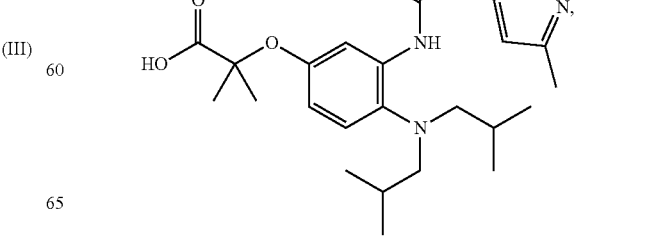
34

-continued
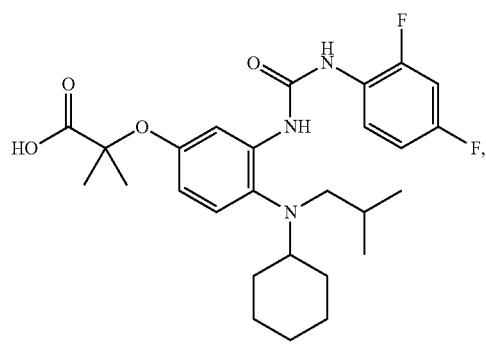
and pharmaceutically acceptable salts.
In certain embodiments, a compound of Formula (I) is of Formula (IV):
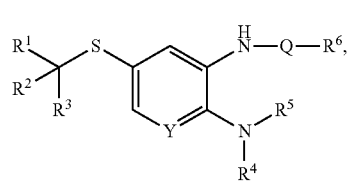
or a pharmaceutically acceptable salt, wherein $R^1$, $R^2$, $R^3$, $R^4$, $R^5$, $R^6$, Y, and Q are as defined herein.
Exemplary compounds of Formula (IV) include, but are not limited to:
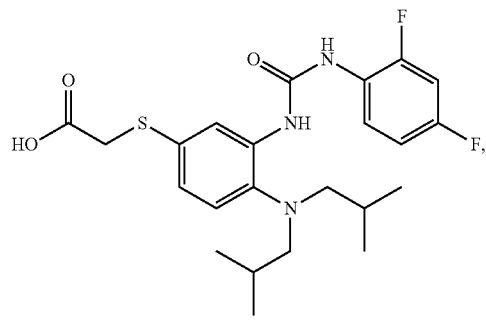
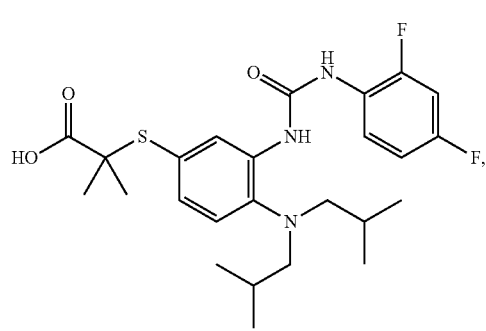
-continued
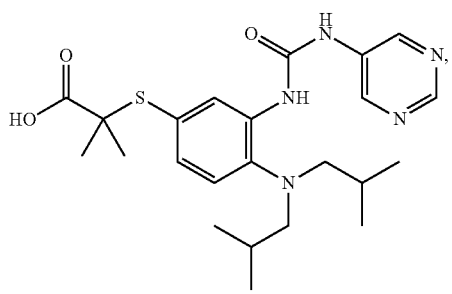
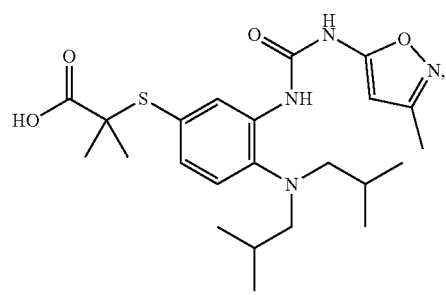
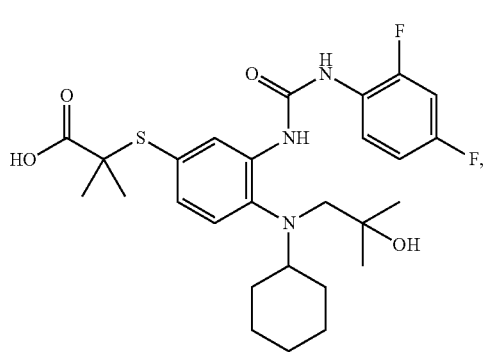
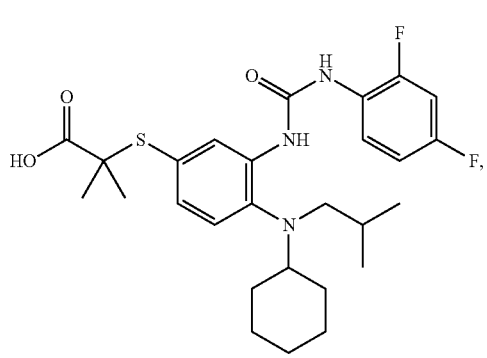
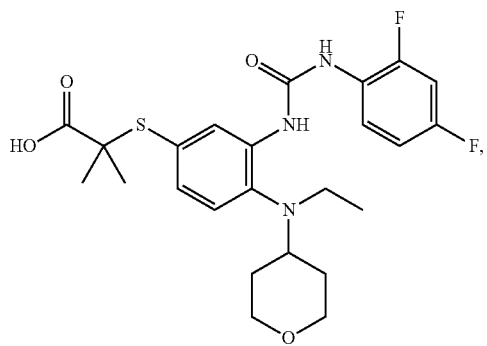

-continued
43
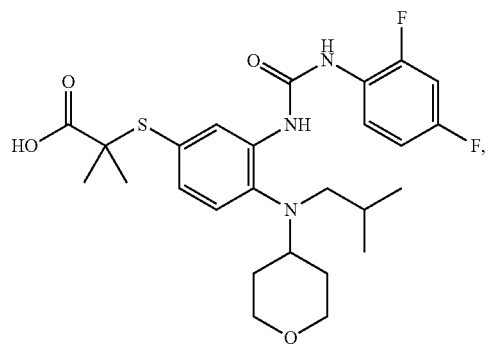
44
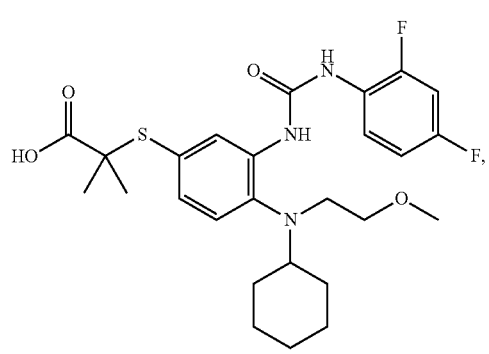
45
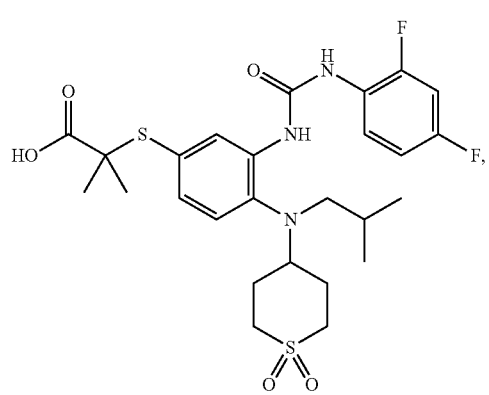
46
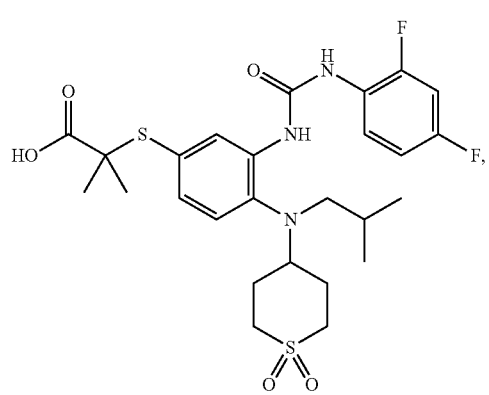
and pharmaceutically acceptable salts.
In certain embodiments, a compound of Formula (I) is of Formula (V):
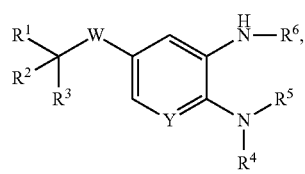
or a pharmaceutically acceptable salt, wherein $R^1$, $R^2$, $R^3$, $R^4$, $R^5$, $R^6$, W, and Y are as defined herein.
Exemplary compounds of Formula (V) include, but are not limited to:
47
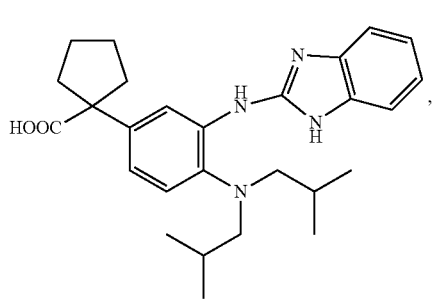
48
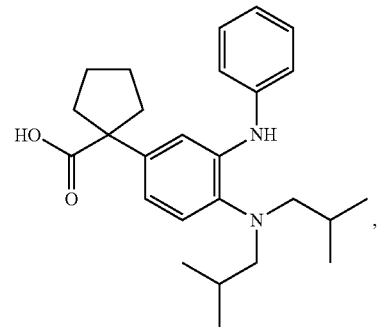
49
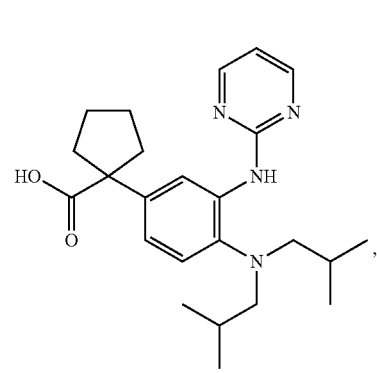

50 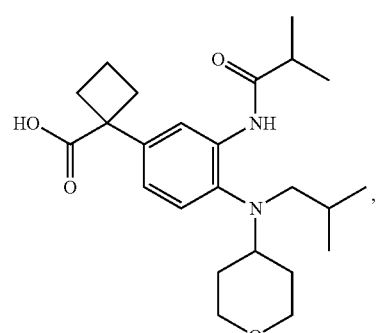
51 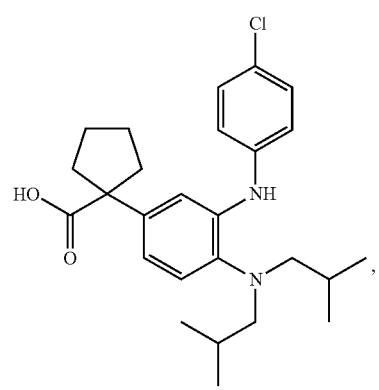
52 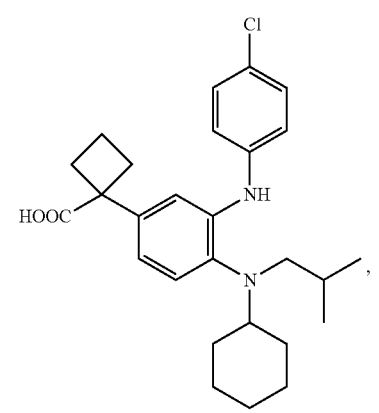
53 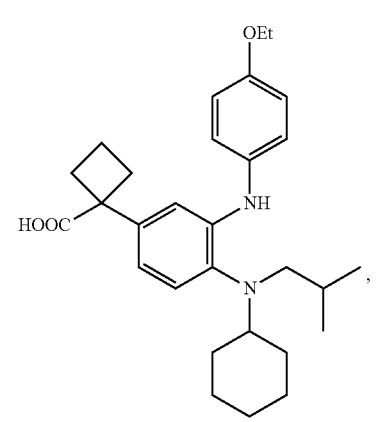
54 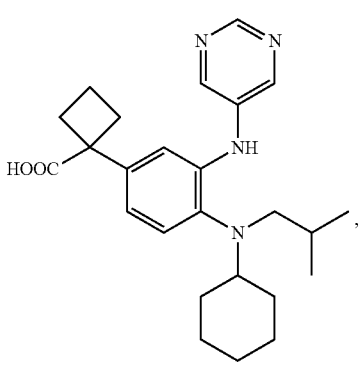
55 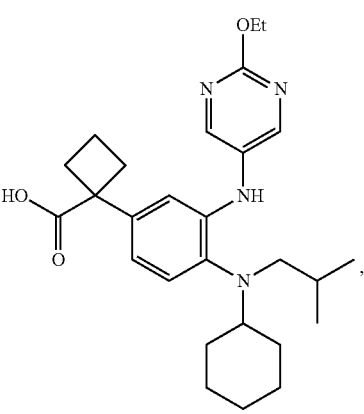
56 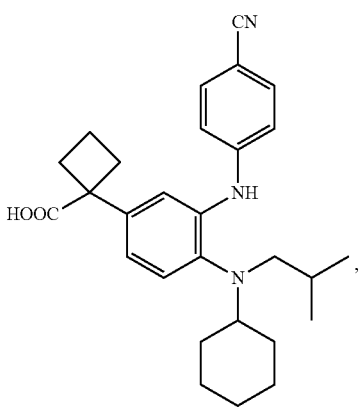
57 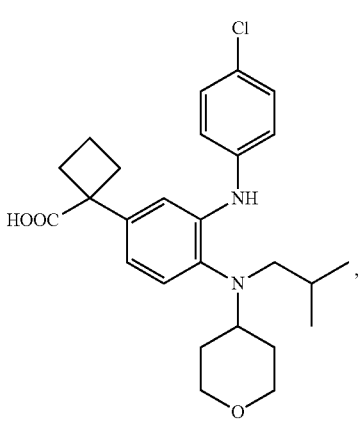

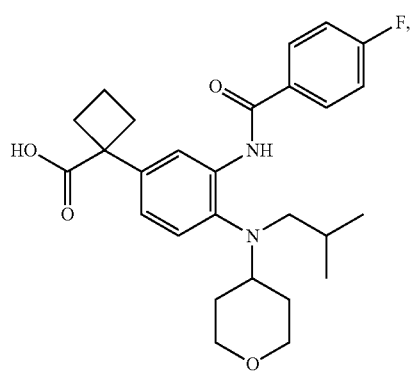
58
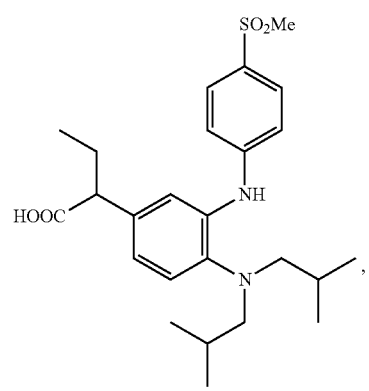
60
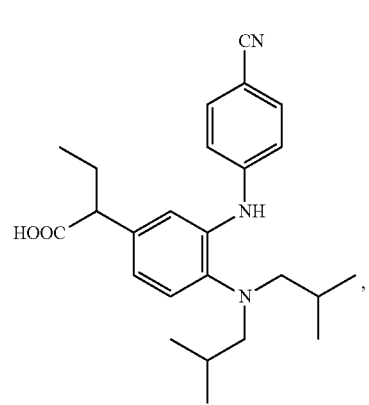
61
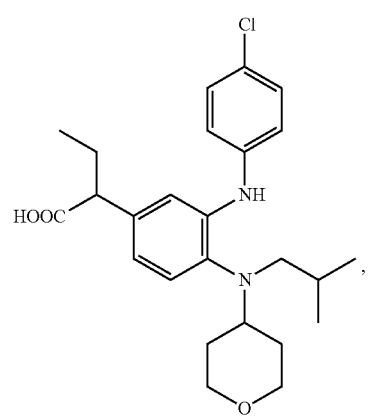
68
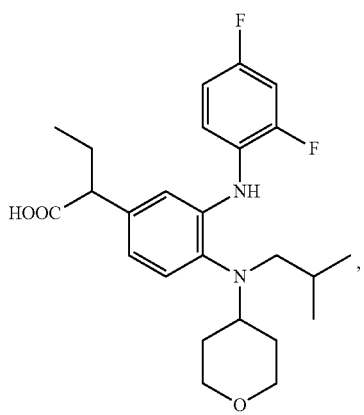
69
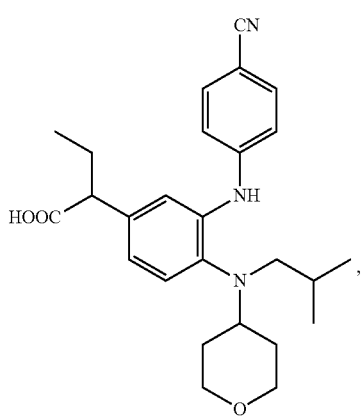
70
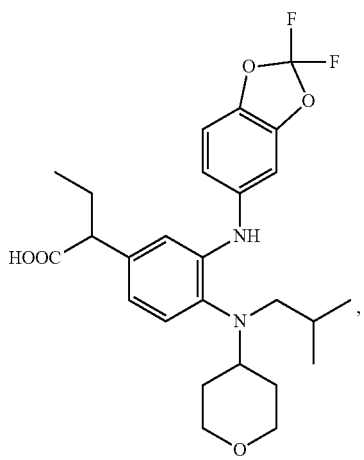
71

-continued
72
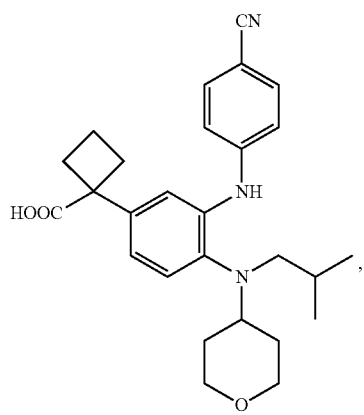
73
74
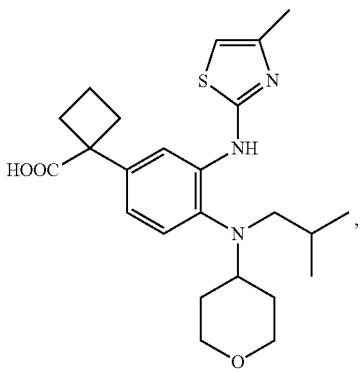
75
-continued
76
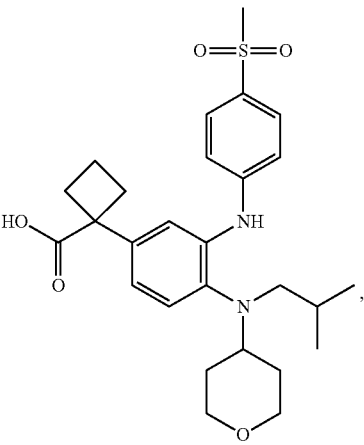
77
78
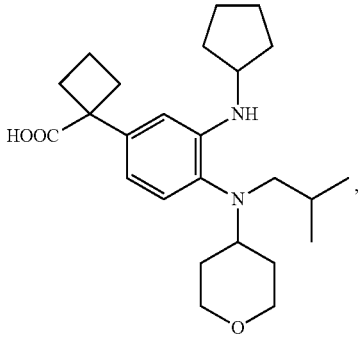
79
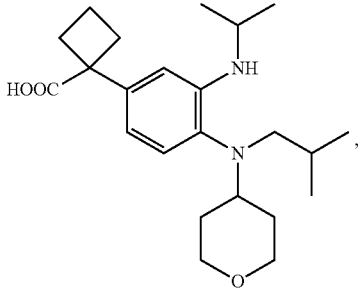

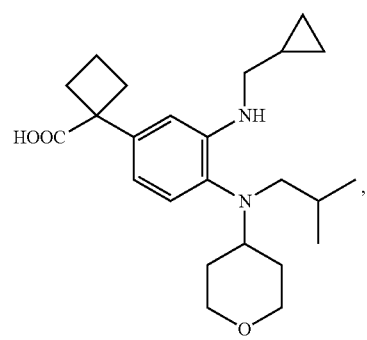
80
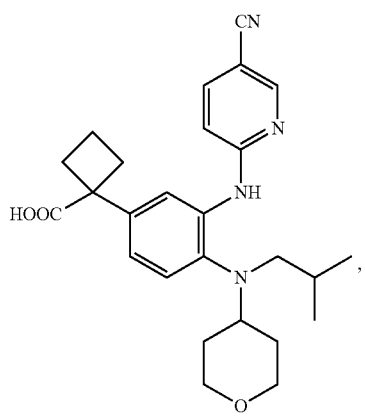
86
81
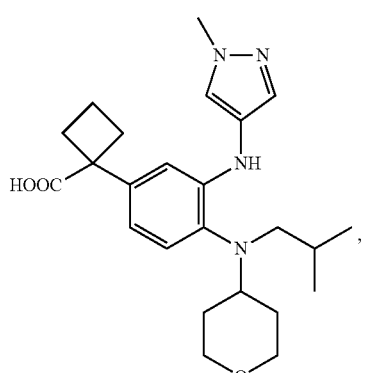
87
82
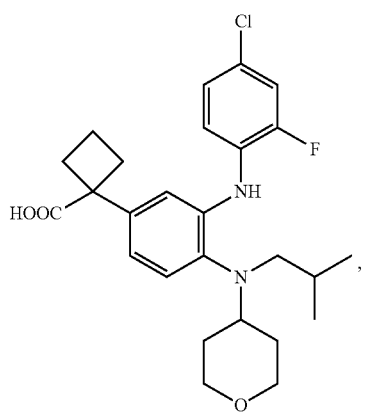
88
84
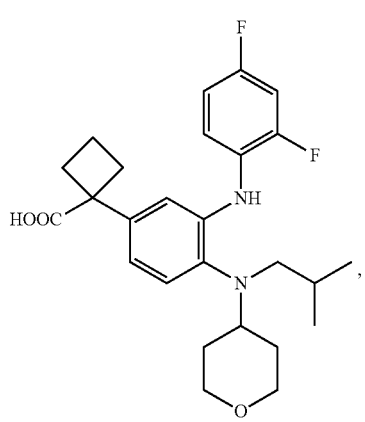
89

91
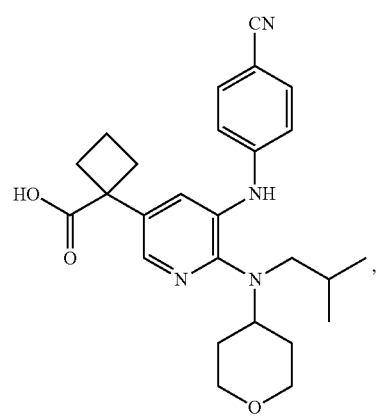
92
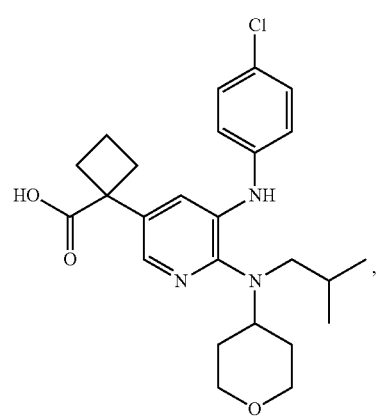
93
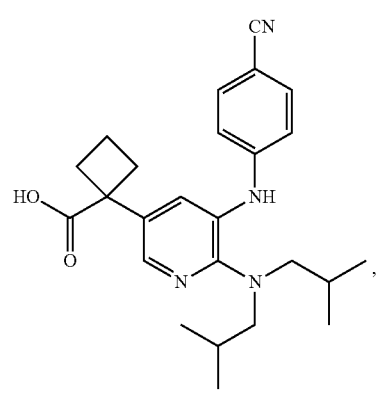
94
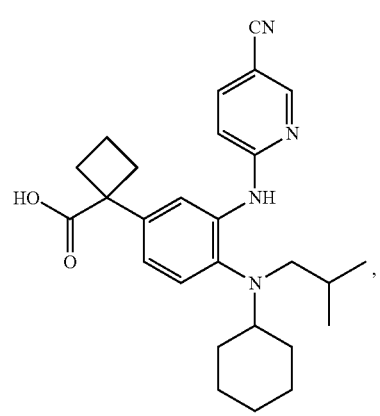
95
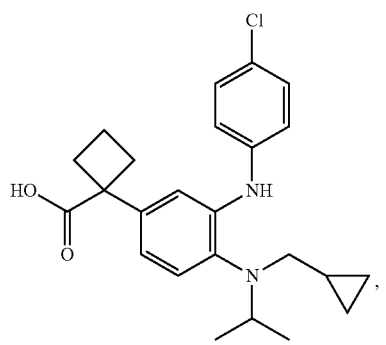
96
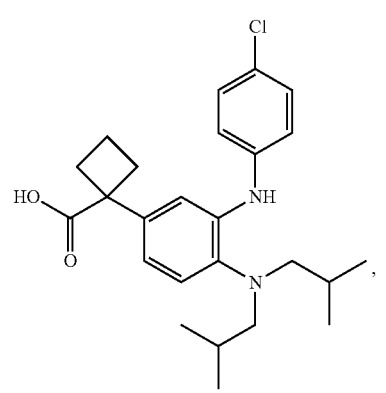
97
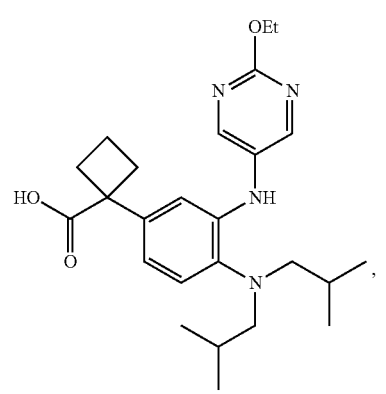
98
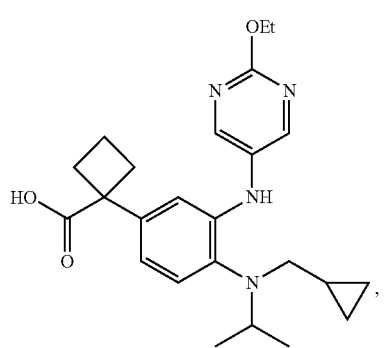

-continued
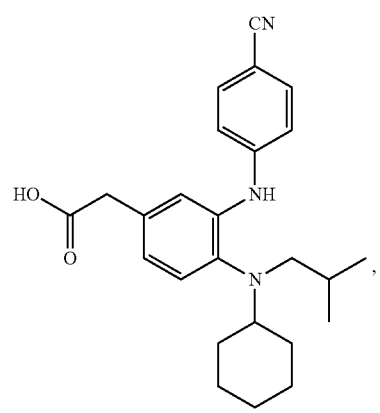
99
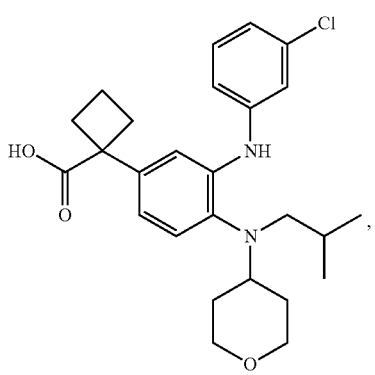
100
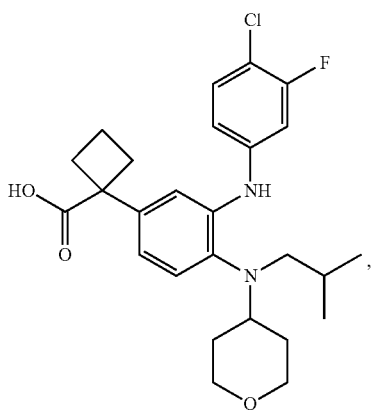
101
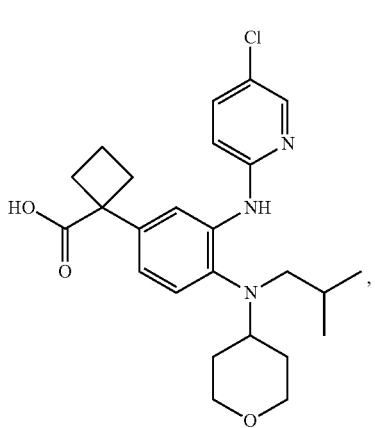
102
-continued
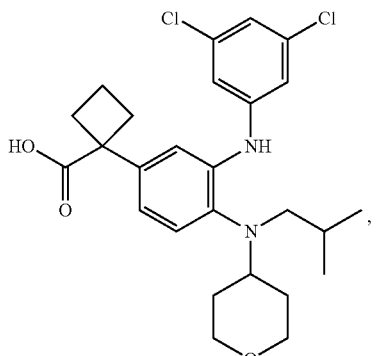
103
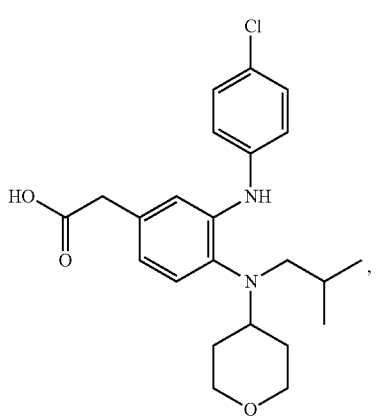
104
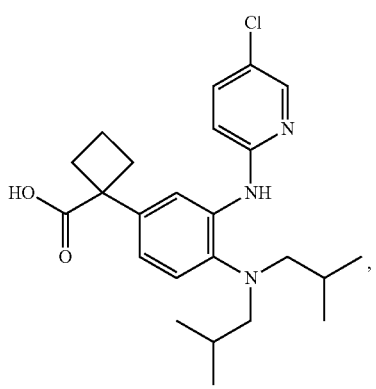
105
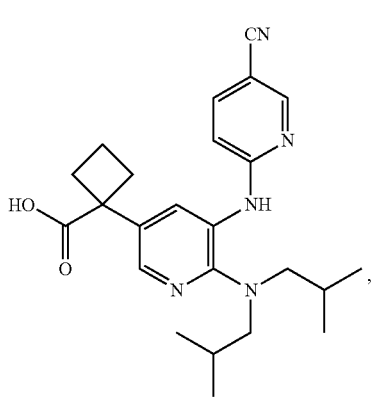
106

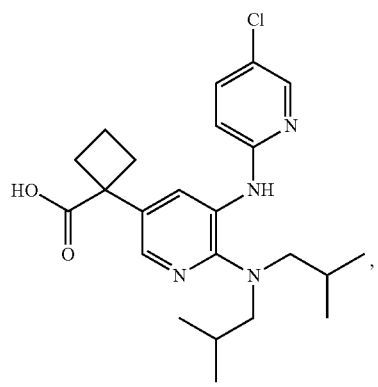
107
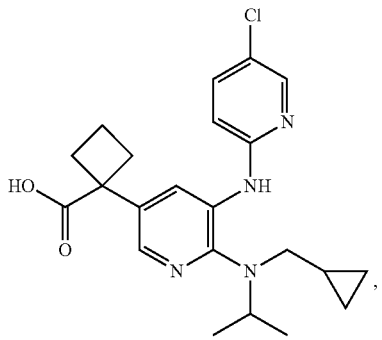
111
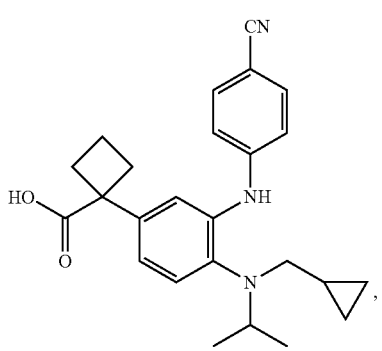
112
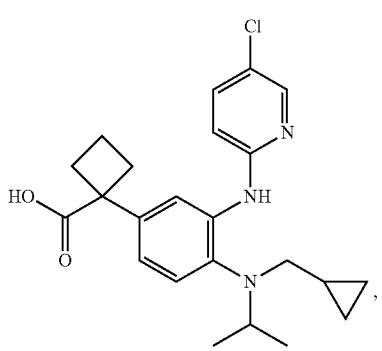
113
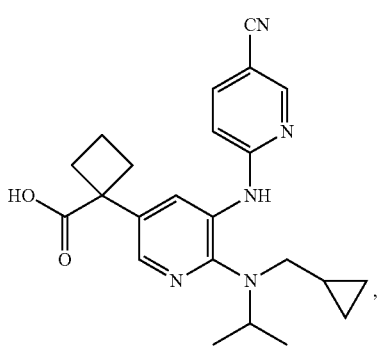
108
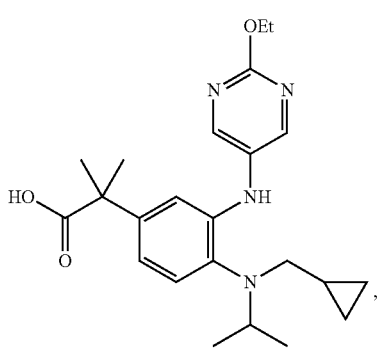
114

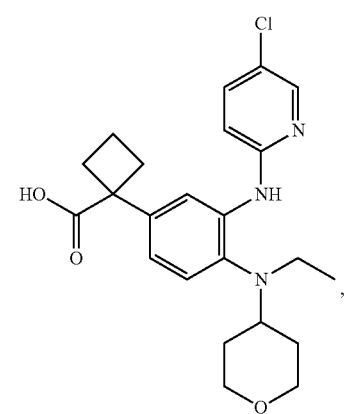
115
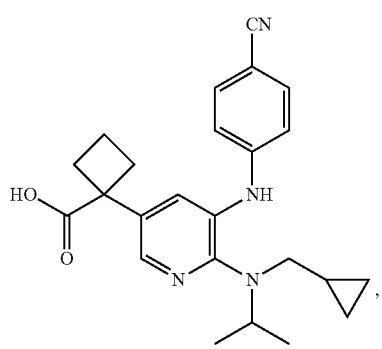
116
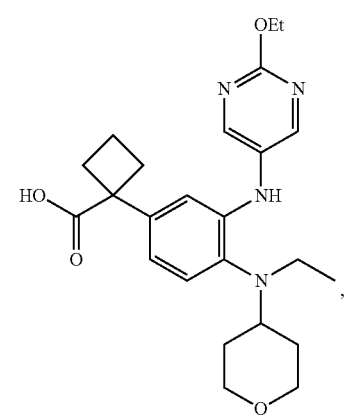
117
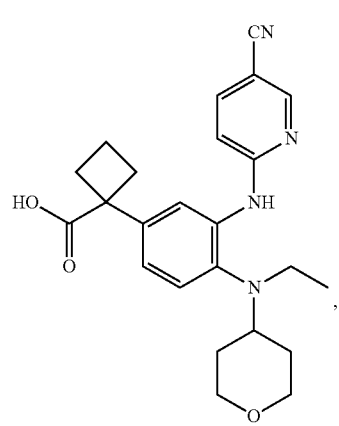
118
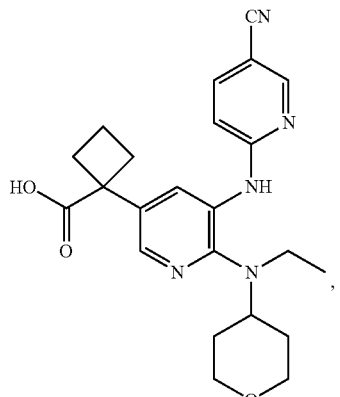
119
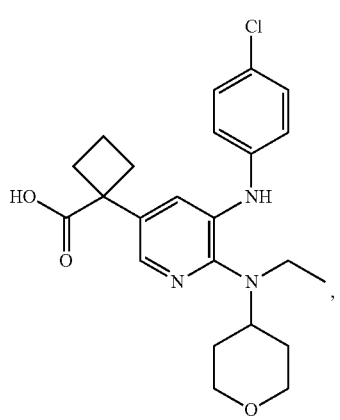
120
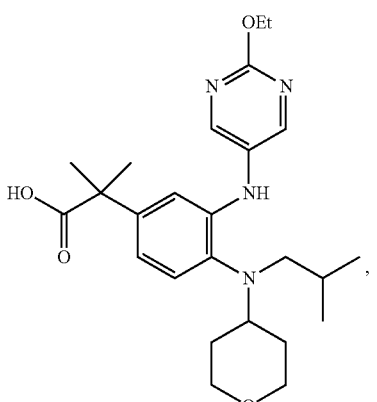
121
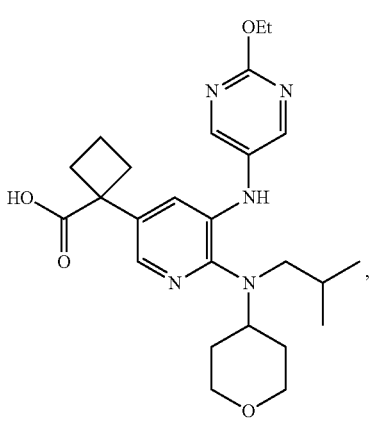
122

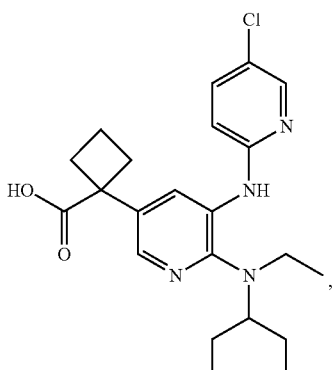

123

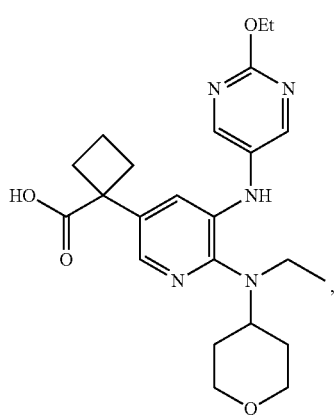

124

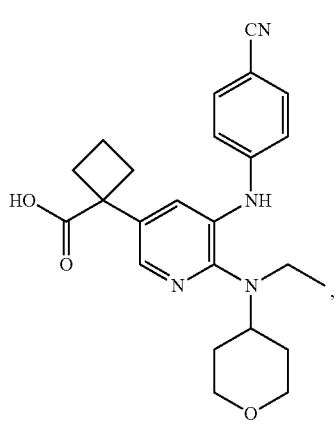

125

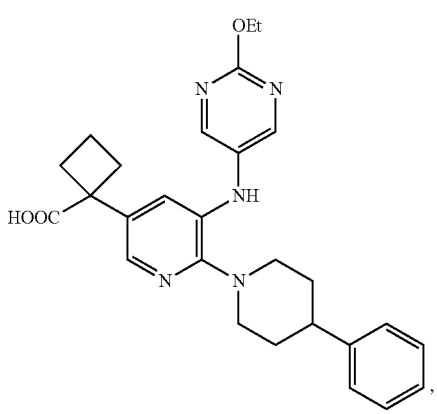

126

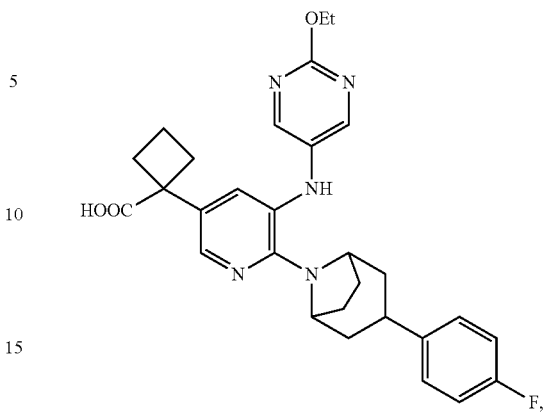

127

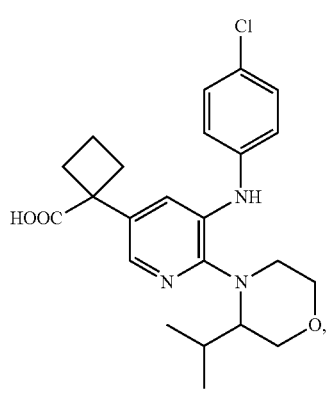

128 and pharmaceutically acceptable salts.

In another aspect, the present disclosure provides pharmaceutical compositions including one or more of the compounds described herein, and a pharmaceutically acceptable excipient. In certain embodiments, the pharmaceutical compositions described herein include an effective amount of a compound described herein for inhibiting IDO and tryptophan catabolism resulting in reduced kynurenine level. An effective amount described herein may be a therapeutically effective amount or prophylactically effective amount.

In yet another aspect, the present disclosure provides methods for treating a disease associated with IDO (e.g., a cancer or an infectious disease), the method comprising administering to a subject in need of the treatment an effective amount of any of the pharmaceutical compositions described herein.

In certain embodiments, a target cancer include, but not limited to, non-small cell lung cancer, small cell lung cancer, breast cancer, prostate cancer, ovarian cancer, bladder cancer, head and neck cancer, renal cell carcinoma, pancreatic cancer, brain cancer, cancers of the gastrointestinal tract, liver cancer, leukemia, lymphoma, melanoma, multiple myeloma, Ewing's sarcoma, osteosarcoma, neuroblastoma.

In certain embodiments, the subject being treated is a mammal (e.g., human or non-human mammal).

In certain embodiments, the present disclosure provides combined therapy of a cancer patient, using both an IDO inhibitory compound as described herein and another anti-cancer therapy, which includes, but is not limited to, an immunetherapy, a radiotherapy, surgery, a chemotherapy, and a cell therapy. In some examples, the other anti-cancer therapy involves the use of one or more anti-cancer agents.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition.

In yet another aspect, the present disclosure provides compounds and pharmaceutical compositions described herein for use in treating a proliferative disease such as cancer as described herein and/or for manufacturing a medicament for use in treating the target disease.

The details of one or more embodiments of the disclosure are set forth herein. Other features, objects, and advantages of the disclosure will be apparent from the Detailed Description, the Examples, and the Claims.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DEFINITIONS

Figure 1:
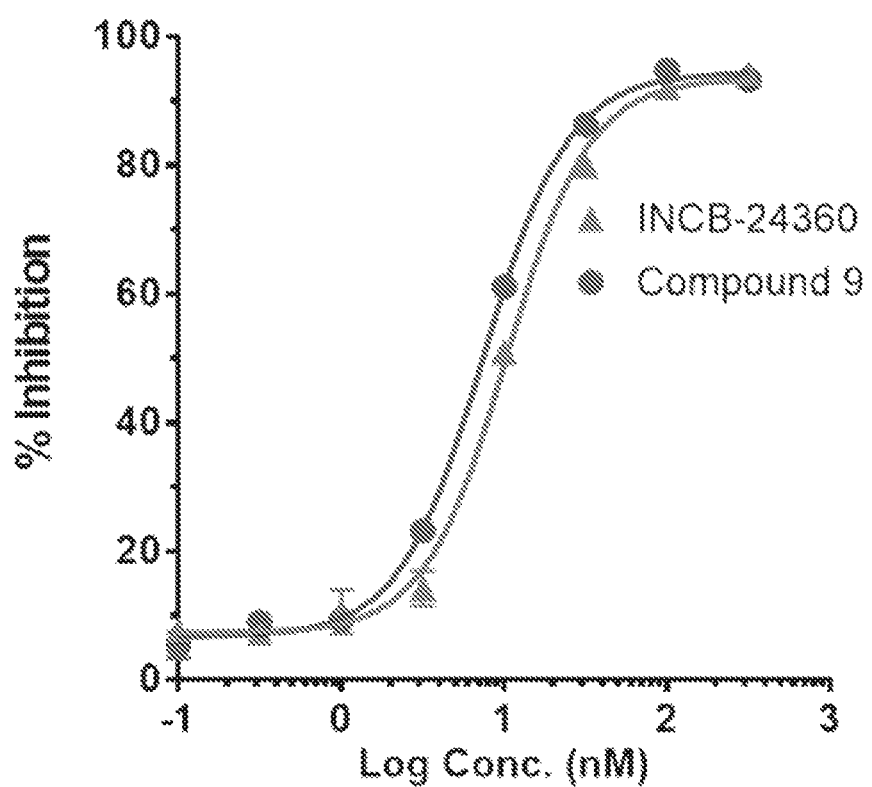
FIG. 1 is a chart showing the inhibition of kynurenine production in SKOV-3 cells by Compound 9 and INCB-24360.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

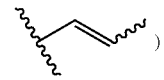

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0,1,2,3,4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0,1,2,3,4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ ($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —NH$_2$($C_{1-6}$ alkyl)$^+X^-$, —NH$_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated by reference herein.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl(CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

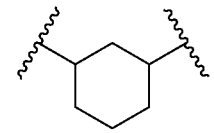 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of an unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

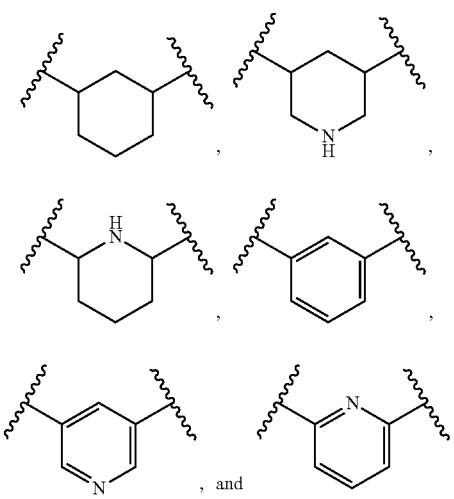

, and are all examples of a hydrocarbon chain. In contrast, in certain embodiments,

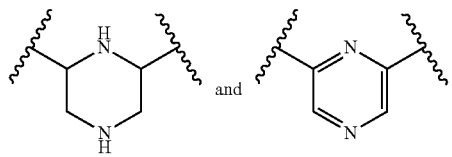 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

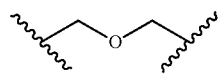 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of an IDO enzyme in a cell relative to vehicle.

When a compound, pharmaceutical composition, method, use, or kit is referred to as "selectively," "specifically," or "competitively" inhibiting the activity of an IDO enzyme, the compound, pharmaceutical composition, method, use, or kit inhibits the activity of the IDO enzyme to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the IDO enzyme.

The term "aberrant activity" refers to activity deviating from normal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)). A "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis,"
"metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

DETAILED DESCRIPTION

The present disclosure provides indoleamine 2,3-dioxygenase (IDO) inhibitors, for example, the compounds of Formula (I). The compounds described herein are useful in treating and/or preventing proliferative diseases (e.g., cancer) via the inhibition of IDO and inhibition of tryptophan catabolism resulting in reduction of the kynurenine level. Exemplary IDO inhibiting compounds described herein successfully demonstrated in vitro potency and in vivo efficacy. Moreover, these compounds showed better potency, and/or lower human hepatocyte clearance compared to other IDO inhibitors known in the art, e.g., INCB-24360 and others disclosed in WO2014150677 and WO2014150646. Also provided in the present disclosure are pharmaceutical compositions, kits, methods of using the IDO inhibitors described herein for treating proliferative diseases such as cancer.

IDO Inhibiting Compounds

One aspect of the present disclosure relates to the IDO inhibiting compounds as described herein, as well as their pharmaceutically acceptable salts, solvates, hydrates, polymorphs, co-crystals, tautomers, stereoisomers, isotopically labeled derivatives, or prodrugs. These compounds are useful in treating and/or preventing proliferative diseases in a subject.

In certain embodiments, a compound described herein is of Formula (I):

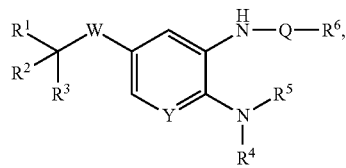

in which $R^1$–$R^6$, W, Y, and Q are as described herein, or pharmaceutically acceptable salt, solvate, hydrate, polymorph, co-crystal, tautomer, stereoisomer, isotopically labeled derivative, or prodrug thereof.

Formula (I) includes a linker W connecting substituents $R^1$, $R^2$, and $R^3$ with the aromatic ring containing Y. In some embodiments, W can be —O—. In some embodiments, W can be —S—. In some embodiments, W can be a bond.

Further, Formula (I) includes a linker Q connecting substituent $R^6$ with the —NH— linker attached to the aromatic ring containing Y. In some embodiments, Q can be —C(=O)NH—. In some embodiments, Q can be a bond. In some embodiments, -Q($R^6$) can be

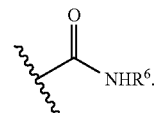

In Formula (I), Y is in an aromatic ring. In some embodiments, Y is —$CR^8$=, in which $R^8$ is as defined wherein. In some embodiments, $R^8$ can be hydrogen. In some embodiments, $R^8$ can be halogen (e.g., F, Cl, Br, or I). In some embodiments, $R^8$ can be —CN. In some embodiments, $R^8$ can be —OH. In some embodiments, $R^8$ can be substituted or unsubstituted $C_{1-6}$ alkyl (e.g., methyl, ethyl, propyl or butyl). In some embodiments, $R^8$ can be substituted or unsubstituted $C_{1-6}$ alkoxy (e.g., substituted or unsubstituted methoxy, or ethoxy). In one example, Y can be —CH=.

In some embodiments, $R^1$ in Formula (I) can be —C(=O)OH. In some embodiments, $R^1$ can be substituted or unsubstituted heterocyclyl (e.g., substituted or unsubstituted, 3- to 9-membered, monocyclic heterocyclyl comprising zero, one, or two double bonds in the heterocyclic ring system, wherein one, two, three, or four atoms in the heterocyclic ring system are independently nitrogen, oxygen, or sulfur). In some embodiments, $R^1$ can be substituted or unsubstituted heteroaryl (e.g., substituted or unsubstituted, 5- to 6-membered, monocyclic heteroaryl wherein one, two, three, or four atoms in the heteroaryl ring system are independently nitrogen, oxygen, or sulfur). In some embodiments, $R^1$ is substituted or unsubstituted 5-membered heteroaryl. In certain embodiments, $R^1$ is substituted or unsubstituted 6-membered heteroaryl. In some embodiments, $R^1$ can be of the formula:

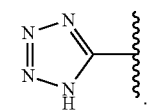

In some embodiments, $R^1$ can be —$NHSO_2R^9$ or —C(=O)$NHSO_2R^9$, in which $R^9$ is as defined herein. In some embodiments, $R^9$ can be hydrogen. In some embodiments, $R^9$ can be substituted or unsubstituted $C_{1-6}$ alkyl (e.g., methyl, ethyl, propyl or butyl). In some embodiments, $R^9$ can be substituted or unsubstituted $C_2$-$C_6$ alkenyl.

In some embodiments, $R^1$ can be —C(=O)NHC(=O)$OR^{10}$ or —$SO_2NHC(=O)R^{10}$, in which $R^{10}$ is as defined herein. In some embodiments, $R^{10}$ can be hydrogen. In some embodiments, $R^{10}$ can be substituted or unsubstituted $C_{1-6}$ alkyl (e.g., methyl, ethyl, propyl or butyl). In some embodiments, $R^{10}$ can be substituted or unsubstituted $C_2$-$C_6$ alkenyl.

In some embodiments, $R^1$ is —C(=O)$OR^{10}$, wherein $R^{10}$ is as defined herein. For example, $R^1$ can be optionally substituted —C(=O)O—$C_{1-6}$ alkyl.

In some embodiments, $R^2$ and/or $R^3$ in Formula (I) can be hydrogen. In some embodiments, $R^2$ and/or $R^3$ can be halogen (e.g., F, Cl, Br, or I). In some embodiments, $R^2$ and/or $R^3$ can be substituted or unsubstituted $C_{1-6}$ alkyl (e.g., substituted or unsubstituted, methyl, ethyl, propyl or butyl).

In some embodiments, $R^2$ and/or $R^3$ can be substituted or unsubstituted $C_{1-6}$ alkoxy (e.g., substituted or unsubstituted methoxy, or ethoxy).

In some embodiments, $R^2$ and $R^3$ can be joined to form a substituted or unsubstituted, monocyclic or bicyclic, 3- to 8-membered carbocyclic ring. In some embodiments, $R^2$ and $R^3$ can be joined to form a substituted or unsubstituted, monocyclic or bicyclic, 3- to 6-membered carbocyclic ring (e.g., substituted or unsubstituted, cyclopropyl, cyclobutyl, cyclopentyl, or cyclohexyl). In some embodiments, $R^2$ and $R^3$ can be joined to form a substituted or unsubstituted cyclopropyl ring. In some embodiments, $R^2$ and $R^3$ can be joined to form an unsubstituted cyclopropyl ring. In some embodiments, $R^2$ and $R^3$ can be joined to form a substituted or unsubstituted cyclobutyl ring. In some embodiments, $R^2$ and $R^3$ can be joined to form an unsubstituted cyclobutyl ring. In some embodiments, $R^2$ and $R^3$ can be joined to form a substituted cyclobutyl ring. In some embodiments, $R^2$ and $R^3$ can be joined to form a substituted cyclobutyl ring of the formula:

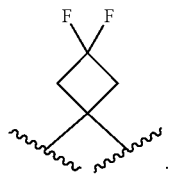 [SMILES: *C1(*)CC(F)(F)C1]

In some embodiments, $R^2$ and $R^3$ can be joined to form a substituted or unsubstituted cyclopentyl ring. In some embodiments, $R^2$ and $R^3$ can be joined to form an unsubstituted cyclopentyl ring. In some embodiments, $R^2$ and $R^3$ can be joined to form a substituted or unsubstituted, monocyclic or bicyclic, 3- to 8-membered heterocyclic ring. In some embodiments, $R^2$ and $R^3$ can be joined to form a substituted or unsubstituted, 3- to 9-membered heterocyclic ring (e.g., substituted or unsubstituted, 5- to 9-membered, monocyclic heterocyclic ring comprising zero, one, or two double bonds in the heterocyclic ring system, wherein one, two, or three atoms in the heterocyclic ring system are independently nitrogen, oxygen, or sulfur). In some embodiments, $R^2$ and $R^3$ can be joined to form a substituted or unsubstituted tetrahydropyranyl ring.

In some embodiments, $R^4$ and/or $R^5$ can be hydrogen. In some embodiments, $R^4$ and/or $R^5$ can be substituted or unsubstituted $C_{1-6}$ alkyl (e.g., substituted or unsubstituted, methyl, ethyl, propyl or butyl). In some embodiments, $R^4$ and/or $R^5$ can be substituted methyl. In some embodiments, $R^4$ and/or $R^5$ can be unsubstituted methyl. In some embodiments, $R^4$ and/or $R^5$ can be substituted ethyl. In some embodiments, $R^4$ and/or $R^5$ can be unsubstituted ethyl. In some embodiments, $R^4$ and/or $R^5$ can be propyl. In some embodiments, $R^4$ and/or $R^5$ can be unsubstituted isopropyl. In some embodiments, $R^4$ and/or $R^5$ can be isobutyl. In some embodiments, $R^4$ and/or $R^5$ can be of the formula:

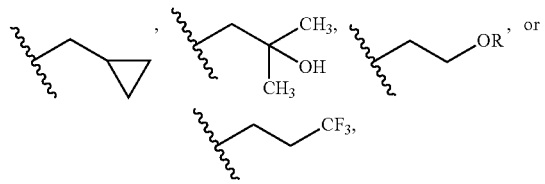

wherein R can be substituted or unsubstituted $C_{1-6}$ alkyl. In some embodiments, R can be substituted or unsubstituted, methyl, ethyl, propyl or butyl. In some embodiments, R can be —$CF_3$. In some embodiments, $R^4$ and/or $R^5$ can be substituted or unsubstituted $C_2$-$C_6$ alkenyl. In some embodiments, $R^4$ and/or $R^5$ can be substituted or unsubstituted $C_5$-$C_8$ cycloalkenyl. In some embodiments, $R^4$ and/or $R^5$ can be substituted or unsubstituted $C_2$-$C_{10}$ alkynyl (e.g., substituted or unsubstituted, propynyl or butynyl). In some embodiments, $R^4$ and/or $R^5$ can be substituted or unsubstituted aryl (e.g., phenyl, or benzyl). In some embodiments, $R^4$ can be of the formula:

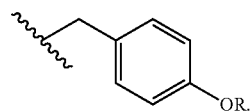

In some embodiments, $R^4$ and/or $R^5$ can be of the formula:

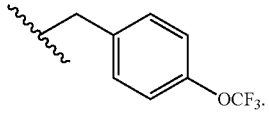

In some embodiments, $R^4$ and/or $R^5$ can be substituted or unsubstituted $C_1$-$C_6$ alkoxy (e.g., substituted or unsubstituted methoxy, or ethoxy). In some embodiments, $R^4$ and/or $R^5$ can be substituted or unsubstituted $C_3$-$C_8$ cycloalkyl (e.g., substituted or unsubstituted, cyclopropyl, cyclobutyl, cyclopentyl, or cyclohexyl). In some embodiments, $R^4$ and/or $R^5$ can be of the formula:

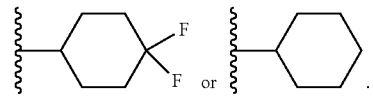

In some embodiments, $R^4$ and/or $R^5$ can be substituted or unsubstituted 3- to 12-membered heterocyclyl (e.g., substituted or unsubstituted, 3- to 12-membered, monocyclic or bicyclic heterocyclyl comprising zero, one, or two double bonds in the heterocyclic ring system, wherein one, two, or three atoms in the heterocyclic ring system are independently nitrogen, oxygen, or sulfur). In some embodiments, $R^4$ and/or $R^5$ can be of the formula:

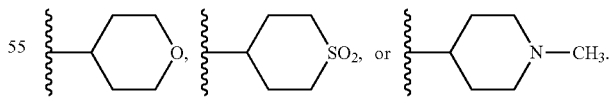

In some embodiments, $R^4$ and/or $R^5$ can be substituted or unsubstituted, 5- to 6-membered monocyclic heteroaryl, wherein one, two, three, or four atoms in the heteroaryl ring system are independently nitrogen, oxygen, or sulfur). In some embodiments, $R^4$ and/or $R^5$ can be substituted or unsubstituted 8- to 10-membered bicyclic heteroaryl, wherein one, two, three, or four atoms in the heteroaryl ring system are independently nitrogen, oxygen, or sulfur. In some embodiments, $R^4$ and/or $R^5$ can be substituted or unsubstituted aryl ($C_1$-$C_6$ alkyl). In some embodiments, $R^4$ and/or $R^5$ can be arylsulfonyl.

In some embodiments, $R^4$ and $R^5$ are independently one of the following:

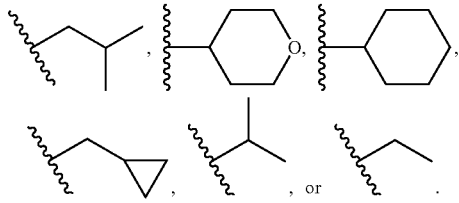

In some embodiments, $R^4$ and $R^5$ are independently one of the following:

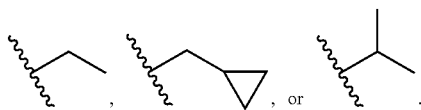

In some embodiments, $R^4$ and $R^5$ may be joined together with the N they are attached to form optionally substituted, monocyclic or bicyclic, heterocyclyl. In some embodiments, $R^4$ and $R^5$ may be joined together with the N they are attached to form optionally substituted 5- to 7-membered heterocyclyl. In some embodiments, $R^4$ and $R^5$ may be joined together with the N they are attached to form optionally substituted 6-membered heterocyclyl. In some embodiments, $R^4$ and $R^5$ may be joined together with the N they are attached to form optionally substituted 6-membered heterocyclyl containing one or two heteroatoms independently selected from the group consisting of N, S, and O. In certain embodiments, $R^4$ and $R^5$ may be joined together with the N they are attached to form an optionally substituted piperidine. In certain embodiments, $R^4$ and $R^5$ may be joined together with the N they are attached to form an optionally substituted morpholine. For example, in certain embodiments, $R^4$ and $R^5$ may be joined together with the N they are attached to form one of the following:

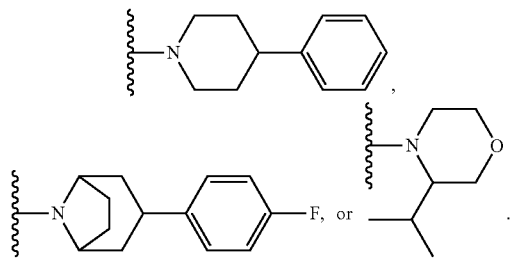

In some embodiments, $R^6$ in Formula (I) can be substituted or unsubstituted $C_{1-6}$ alkyl (e.g., substituted or unsubstituted, methyl, ethyl, propyl or butyl). In some embodiments, $R^6$ can be isopropyl. In some embodiments, $R^6$ can be substituted methyl. In some embodiments, $R^6$ can be

In some embodiments, $R^6$ can be substituted or unsubstituted $C_3$-$C_8$ cycloalkyl (e.g., substituted or unsubstituted, cyclopropyl, cyclobutyl, cyclopentyl, or cyclohexyl). In some embodiments, $R^6$ can be

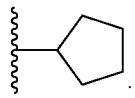

In some embodiments, $R^6$ can be substituted or unsubstituted benzoyl. In some embodiments, $R^6$ can be substituted or unsubstituted $C_2$-$C_6$ alkenyl. In some embodiments, $R^6$ can be substituted or unsubstituted $C_2$-$C_6$ alkynyl. In some embodiments, $R^6$ can be substituted or unsubstituted $C_5$-$C_8$ cycloalkenyl. In some embodiments, $R^6$ can be substituted or unsubstituted aryl (e.g., phenyl, or benzyl). In some embodiments, $R^6$ can be substituted or unsubstituted benzyl. In some embodiments, $R^6$ can be of the formula:

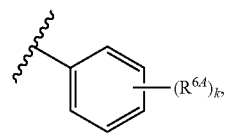

wherein $R^{6A}$ can be hydrogen, substituted or unsubstituted $C_1$-$C_6$ alkyl, halogen, —CN, —$OR^{6a}$, or substituted or unsubstituted sulfonyl group, wherein $R^{6a}$ can be hydrogen, or substituted or unsubstituted $C_1$-$C_6$ alkyl; and k can be 0, 1, or 2. In some embodiments, $R^{6a}$ can be substituted or unsubstituted, $C_1$-$C_6$ alkyl (e.g., methyl, ethyl, propyl or butyl). In some embodiments, $R^{6A}$ can be halogen (e.g., F, Cl, Br, or I). In some embodiments, $R^{6a}$ can be —CN. In some embodiments, k can be 0. In some embodiments, k can be 1. In some embodiments, k can be 2.

In some embodiments, $R^6$ can be of the formula:

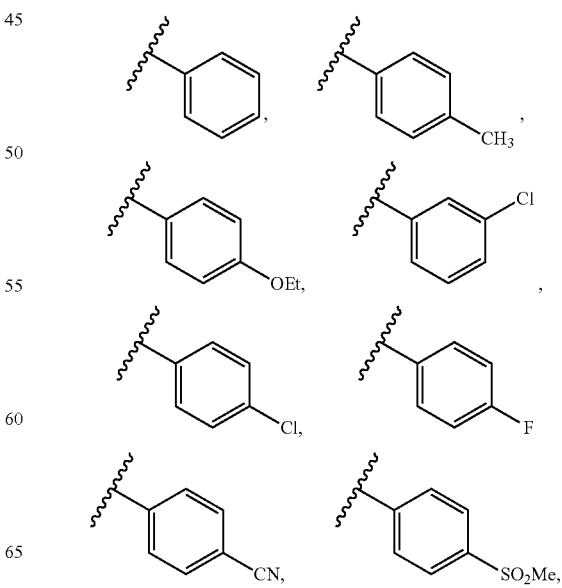

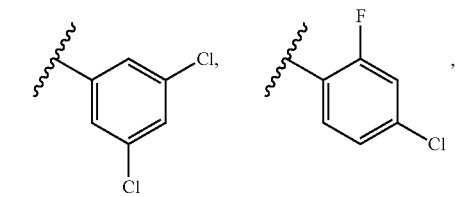

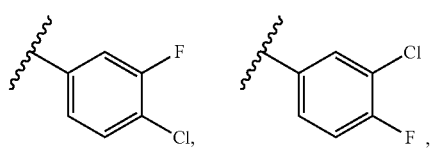

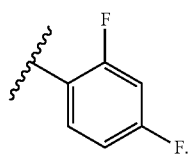

In some embodiments, R⁶ can be substituted or unsubstituted 4- to 7-membered (e.g., 4, 5, 6, or 7) monocyclic heterocyclyl, comprising zero, one, or two double bonds in the heterocyclic ring system, wherein one, two, or three atoms in the heterocyclic ring system are independently nitrogen, oxygen, or sulfur. In some embodiments, R⁶ can be

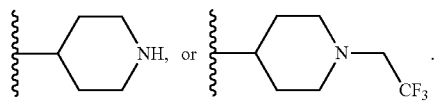

In some embodiments, R⁶ can be substituted or unsubstituted 7- to 10-membered bicyclic heterocyclyl, comprising zero, one, or two double bonds in the heterocyclic ring system, wherein one, two, or three atoms in the heterocyclic ring system are independently nitrogen, oxygen, or sulfur. In some embodiments, R⁶ can be substituted or unsubstituted 5- to 6-membered monocyclic heteroaryl, wherein one, two, three, or four atoms in the heteroaryl ring system are independently nitrogen, oxygen, or sulfur. In some embodiments, R⁶ can be of the formula:

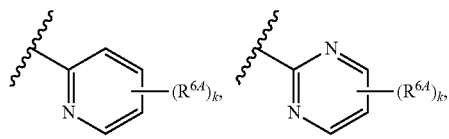

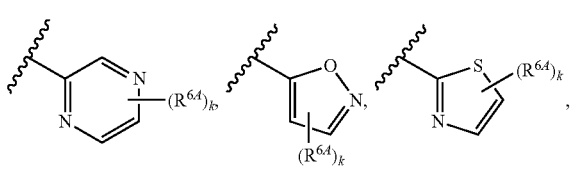

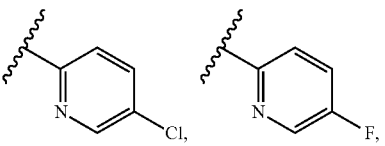

In some embodiments, R⁶ can be of the formula:

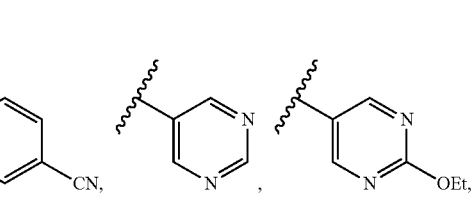

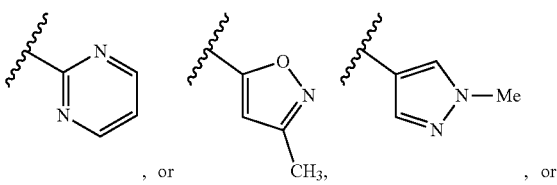

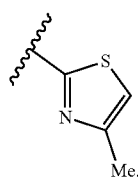

In some embodiments, R⁶ can be substituted or unsubstituted 8- to 10-membered bicyclic heteroaryl, wherein one, two, three, or four atoms in the heteroaryl ring system are independently nitrogen, oxygen, or sulfur. In some embodiments, R⁶ can be of the formula:

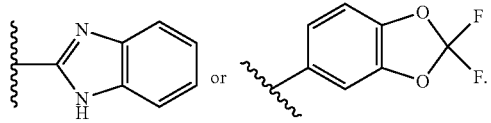 [SMILES: *c1nc2ccccc2[nH]1 ; *c1ccc2c(c1)OC(F)(F)O2]

In some embodiments, R⁶ can be substituted or unsubstituted $C_1$-$C_6$ alkoxy (e.g., substituted or unsubstituted methoxy, or ethoxy). In some embodiments, R⁶ can be substituted or unsubstituted aryloxy. In some embodiments, R⁶ can be —C(=O)R⁷, in which R⁷ is as defined herein. In some embodiments, R⁶ can be

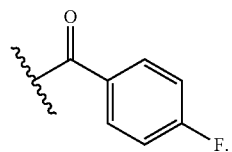 [SMILES: *C(=O)c1ccc(F)cc1]

In some embodiments, the compound of Formula (I) can be of one of the following formulae: Formula (II), Formula (III), Formula (IV), Formula (V), or a pharmaceutically acceptable salt, solvate, hydrate, polymorph, co-crystal, tautomer, stereoisomer, isotopically labeled derivative, or prodrug thereof.

In some embodiments, the compound of Formula (II) can be of the formula of compounds 1-30, 59, 62-67, 83, 85, 90, compounds described herein, or a pharmaceutically acceptable salt, solvate, hydrate, polymorph, co-crystal, tautomer, stereoisomer, isotopically labeled derivative, or prodrug thereof.

In some embodiments, the compound of Formula (III) can be of the formula of compounds 31-35, compounds described herein, or a pharmaceutically acceptable salt, solvate, hydrate, polymorph, co-crystal, tautomer, stereoisomer, isotopically labeled derivative, or prodrug thereof.

In some embodiments, the compound of Formula (IV) can be of the formula of compounds 36-46, or a pharmaceutically acceptable salt, solvate, hydrate, polymorph, co-crystal, tautomer, stereoisomer, isotopically labeled derivative, or prodrug thereof.

In some embodiments, the compound of Formula (V) can be of compounds 47-58, 60-61, 68-82, 84, 86-89, 91-125, and 126-128 described herein, or a pharmaceutically acceptable salt, solvate, hydrate, polymorph, co-crystal, tautomer, stereoisomer, isotopically labeled derivative, or prodrug thereof.

Exemplary IDO inhibitory compounds as described herein and their characterization are provided in Table 1 below:

TABLE 1

| Compound No. | Structure | [M + H]⁺ | ¹H-NMR |
|---|---|---|---|
| 51 | 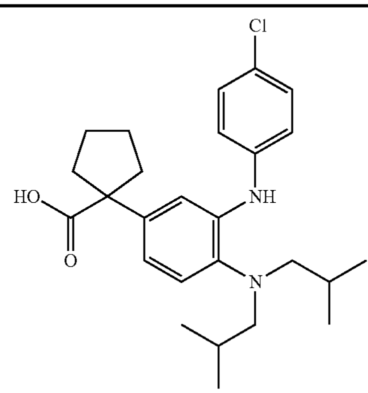 | 443.3 | H-NMR (400 MHz, CD₃OD, ppm): δ 7.45 (d, J = 2.0 Hz, 1H), 7.21-7.19 (m, 2H), 7.08-7.04 (m, 3H), 6.90 (dd, J = 2.0 Hz, 8.0 Hz, 1H), 2.57-2.55 (m, 6H), 1.79-1.62 (m, 8H), 0.86 (d, J = 6.4 Hz, 12H). |
| 52 | 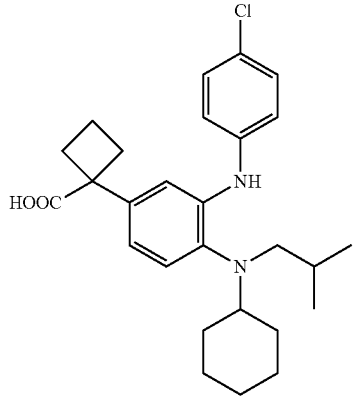 [SMILES: CC(C)CN(c1ccc(C2(C(=O)O)CCC2)cc1Nc1ccc(Cl)cc1)C1CCCCC1] | 455.2 | HNMR: (400 MHz, DMSO d6, ppm): δ 11.80 (brs, 1H), 6.78 (d, J = 8.8 Hz, 2H), 6.65 (d, J = 8.0 Hz, 1H), 6.60-659 (m, 2H), 6.57 (s, 1H), 6.55 (s, 1H), 6.32 (dd, J1 = 8.0 Hz, J2 = 2.0 Hz, 1H), 2.30 (d, J = 6.8 Hz, 2H), 2.21-2.14 (m, 2H), 2.08-2.05 (m, 1H), 1.92-1.87 (m, 2H), 1.47-1.38 (m, 1H), 1.35-1.30 (m, 1H), 1.26 (d, J = 11.6 Hz, 2H), 1.17-1.16 (m, 2H), 0.98 (s, 1H), 0.89-0.77 (m, 3H), 0.50-0.49 (m, 3H), 0.34 (d, J = 6.8 Hz, 6H). |

TABLE 1-continued

Characterization of the compounds of Formula (I)

| Compound No. | Structure | [M + H]+ | 1H-NMR |
|---|---|---|---|
| 53 | 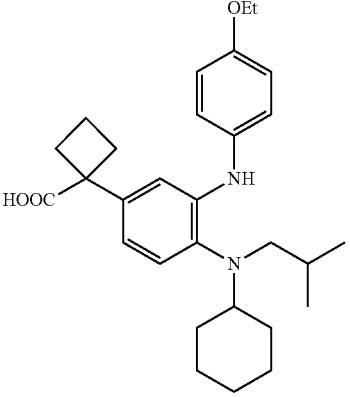 [SMILES: CCOc1ccc(Nc2cc(C3(C(=O)O)CCC3)ccc2N(CC(C)C)C2CCCCC2)cc1] | 465.3 | HNMR: (400 MHz, DMSO d6, ppm): δ 7.06 (d, J = 8.0 Hz, 1H), 6.98 (d, J = 8.8 Hz, 2H), 6.89 (d, J = 1.6 Hz, 1H), 6.84 (d, J = 8.8 Hz, 2H), 6.76 (s, 1H), 6.61 (dd, J1 = 8.0 Hz, J2 = 1.6 Hz, 1H), 3.95 (q, J = 7.2 Hz, 2H), 2.74 (d, J = 4.8 Hz, 2H), 2.61-2.54 (m, 2H), 2.51 (s, 1H), 2.31-2.26 (m, 2H), 1.84-1.80 (m, 1H), 1.79-1.77 (m, 3H), 1.66-1.63 (m, 2H), 1.47 (s, 1H), 1.35-1.28 (m, 2H), 1.27 (t, J = 7.2 Hz, 3H), 1.19 (s, 1H), 1.07-0.95 (m, 3H), 0.78 (d, J = 6.8 Hz, 6H). |
| 54 | 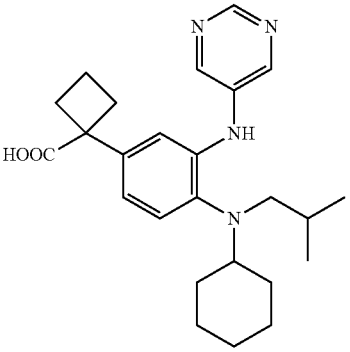 [SMILES: CC(C)CN(c1ccc(C2(C(=O)O)CCC2)cc1Nc1cncnc1)C1CCCCC1] | 423.1 | HNMR: (400 MHz, DMSO d6, ppm): δ 12.30 (s, 1H), 8.58 (s, 1H), 8.45 (s, 2H), 7.27 (s, 1H), 7.11 (d, J = 8.0 Hz, 1H), 7.06 (d, J = 2.0 Hz, 1H), 6.87 (dd, J1 = 8.0 Hz, J2 = 2.0 Hz, 1H), 2.74 (d, J = 6.4 Hz, 2H), 2.66-2.57 (m, 3H), 2.37-2.32 (m, 2H), 1.92-1.85 (m, 1H), 1.81-1.72 (m, 1H), 1.67-1.59 (m, 4H), 1.41-1.40 (m, 1H), 1.38-1.31 (m, 1H), 1.27-1.20 (m, 2H), 0.97-0.92 (m, 3H), 0.78 (d, J = 6.4 Hz, 6H). |
| 55 | 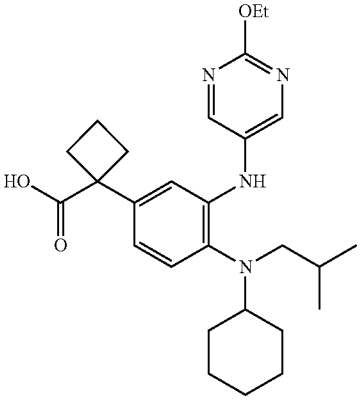 [SMILES: CCOc1ncc(Nc2cc(C3(C(=O)O)CCC3)ccc2N(CC(C)C)C2CCCCC2)cn1] | 467.2 | HNMR: (400 MHz, DMSO d6, ppm): δ 8.37 (s, 2H), 7.09 (d, J = 8.4 Hz, 1H), 6.89 (s, 1H), 6.79 (d, J = 2.0 Hz, 1H), 6.69 (dd, J1 = 8.0 Hz, J2 = 2.0 Hz, 1H), 4.26 (q, J = 7.2 Hz, 2H), 2.75-2.73 (m, 2H), 2.61-2.52 (m, 3H), 2.32-2.27 (m, 2H), 1.88-1.69 (m, 4H), 1.65-1.63 (m, 2H), 1.47-1.46 (m, 1H), 1.35-1.22 (m, 6H), 1.07-0.95 (m, 3H), 0.78 (d, J = 6.8 Hz, 6H). |

TABLE 1-continued

Characterization of the compounds of Formula (I)

| Compound No. | Structure | [M + H]⁺ | ¹H-NMR |
|---|---|---|---|
| 56 | 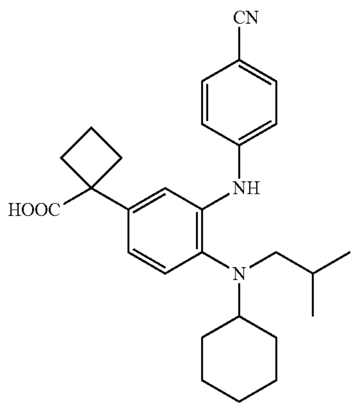 | 446.2 | HNMR: (400 MHz, DMSO d₆, ppm): δ 7.57 (s, 1H), 7.52 (d, J = 8.8 Hz, 2H), 7.10-7.07 (m, 2H), 6.96-6.92 (m, 3H), 2.72 (d, J = 6.4 Hz, 2H), 2.66-2.54 (m, 3H), 2.38-2.29 (m, 2H), 1.92-1.83 (m, 1H), 1.81-1.71 (m, 1H), 1.58 (t, J = 12 Hz, 4H), 1.39-1.32 (m, 2H), 1.27-1.21 (m, 2H), 0.93-0.91 (m, 1H), 0.87-0.82 (m, 2H), 0.77 (d, J = 6.4 Hz, 6H). |
| 57 | 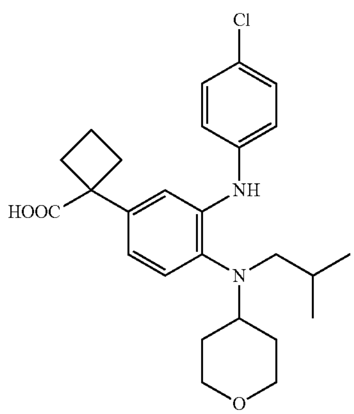 [SMILES: CC(C)CN(c1ccc(C2(C(=O)O)CCC2)cc1Nc1ccc(Cl)cc1)C1CCOCC1] | 457.1 | HNMR: (400 MHz, DMSO d₆, ppm): δ 12.26 (brs, 1H), 7.23 (d, J = 8.8 Hz, 2H), 7.16-7.13 (m, 2H), 7.06-7.04 (m, 3H), 6.77 (dd, J = 8.0 Hz, J = 2.0 Hz, 1H), 3.78-3.75 (m, 2H), 3.05 (t, J = 10.8 Hz, 2H), 2.81-2.73 (m, 3H), 2.65-2.59 (m, 2H), 2.37-2.30 (m, 2H), 1.87-1.82 (m, 1H), 1.77-1.74 (m, 1H), 1.61-1.58 (m, 2H), 1.52-1.43 (m, 2H), 1.34-1.31 (m, 1H), 0.78 (d, J = 6.8 Hz, 6H). |
| 58 | 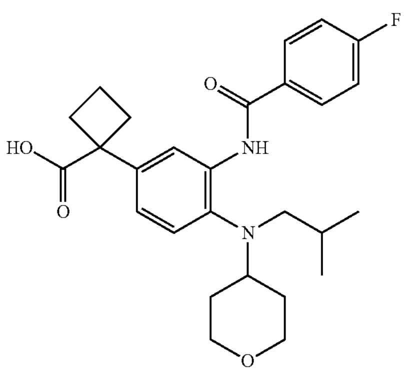 [SMILES: CC(C)CN(c1ccc(C2(C(=O)O)CCC2)cc1NC(=O)c1ccc(F)cc1)C1CCOCC1] | 469.1 | HNMR: (400 MHz, DMSO d₆, ppm): δ 12.33 (brs, 1H), 9.65 (s, 1H), 8.29 (d, J = 2.0 Hz, 1H), 7.89 (dd, J = 8.8 Hz, J = 5.2 Hz, 2H), 7.42 (t, J = 8.8 Hz, 2H), 7.32 (d, J = 8.4 Hz, 1H), 7.01 (dd, J = 8.4 Hz, J = 2.0 Hz, 1H), 3.78-3.75 (m, 2H), 3.17-3.12 (m 2H), 2.88-2.80 (m, 3H), 2.71-2.65 (m, 2H), 2.41-2.34 (m, 2H), 1.95-1.89 (m, 1H), 1.80-1.75 (m, 1H), 1.60-1.57 (m, 2H), 1.50-1.41 (m, 2H), 1.32-1.26 (m, 1H), 0.77 (d, J = 6.4 Hz, 6H). |
| 59A | 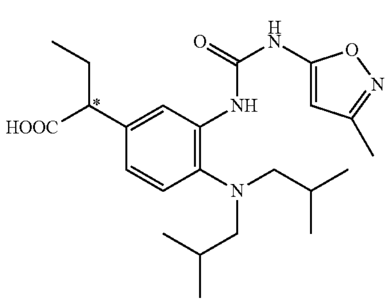 [SMILES: CCC(C(=O)O)c1ccc(N(CC(C)C)CC(C)C)c(NC(=O)Nc2cc(C)no2)c1] | 431.3 | Chiral HPLC [Column: IA, 100 mm, 4.6 mm, 0.6 mL/min, Mobile Phase: hexane (0.1% TFA)/IPA; Gradient: 5% IPA; Detector: 254 nm], Retention time = 10.98 mm, ¹H-NMR (300 MHz, CDCl₃, ppm) δ 8.54 (s, 1H), 8.14 (s, 1H), 7.45 (s, 1H), 7.15 (d, J = 8.1 Hz, 1H), 7.04 (d, J = 7.8 Hz, 1H), 6.09 (s, 1H), 3.51 (t, J = 8.1 Hz, 1H), 2.61 (d, J = 6 Hz, 4H), 2.19-2.10 (m, 2H), 1.89-1.80 (m, 2H), 1.73 (s, 2H), 0.96-0.91 (m, 15H). |

TABLE 1-continued

Characterization of the compounds of Formula (I)

| Compound No. | Structure | [M + H]+ | ¹H-NMR |
|---|---|---|---|
| 59B | 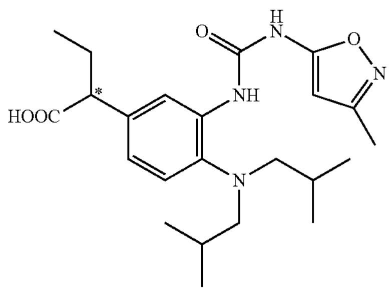 [SMILES: CCC(C(=O)O)c1ccc(N(CC(C)C)CC(C)C)c(NC(=O)Nc2cc(C)no2)c1] | 431.3 | Chiral HPLC [Column: IA, 100 mm, 4.6 mm, 0.6 mL/min, Mobile Phase: hexane (0.1% TFA)/IPA; Gradient: 5% IPA; Detector: 254 nm], Retention time = 13.14 min. ¹H-NMR (300 MHz, CDCl₃, ppm) δ 8.54 (s, 1H), 8.14 (s, 1H), 7.45 (s, 1H), 7.15 (d, J = 8.1 Hz, 1H), 7.04 (d, J = 7.8 Hz, 1H), 6.09 (s, 1H), 3.51 (t, J = 8.1 Hz, 1H), 2.61 (d, J = 6 Hz, 4H), 2.19-2.10 (m, 2H), 1.89-1.80 (m, 2H), 1.73 (s, 2H), 0.96-0.89 (m, 15 H) |
| 60A | 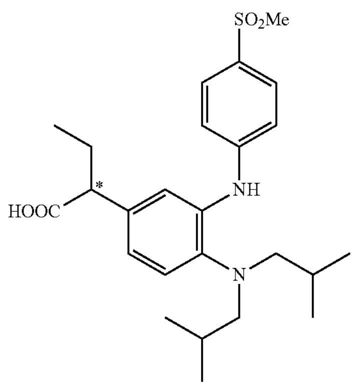 [SMILES: CCC(C(=O)O)c1ccc(N(CC(C)C)CC(C)C)c(Nc2ccc(S(C)(=O)=O)cc2)c1] | 461.2 | Chiral HPLC [Column: AD, 100 mm, 4.6 mm, 0.6 mL/min, Mobile Phase: hexane (0.1% TFA)/EtOH; Gradient: 20% EtOH; Detector: 254 nm], Retention time = 3.24 min. ¹H-NMR (300 MHz, CDCl₃, ppm) δ 7.79 (d, J = 8.7 Hz, 2H), 7.45-7.36 (m, 1H), 7.23-7.10 (m, 3H), 7.02-6.85 (m, 1H), 3.46 (t, J = 7.8 Hz, 1H), 3.06 (s, 3H), 2.86-2.37 (m, 3H), 2.21-2.00 (m, 1H), 1.93-1.51 (m, 3H), 1.0.3-0.51 (m, 16H). |
| 60B | 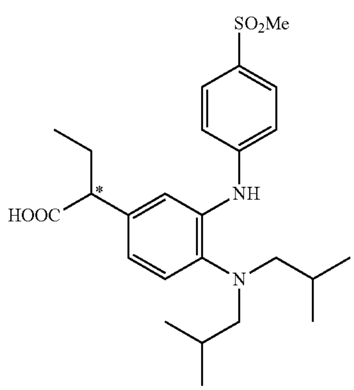 [SMILES: CCC(C(=O)O)c1ccc(N(CC(C)C)CC(C)C)c(Nc2ccc(S(C)(=O)=O)cc2)c1] | 461.2 | Chiral HPLC [Column: AD, 100 mm, 4.6 mm, 0.6 mL/min, Mobile Phase: hexane (0.1% TFA)/EtOH; Gradient: 20% EtOH; Detector: 254 nm], Retention time = 3.69 min. ¹H-NMR (300 MHz, CDCl₃, ppm) δ 7.79 (d, J = 8.7 Hz, 2H), 7.45-7.36 (m, 1H), 7.23-7.10 (m, 3H), 7.02-6.85 (m, 1H), 3.45 (t, J = 7.8 Hz, 1H), 3.06 (s, 3H), 2.86-2.40 (m, 3H), 2.21-2.00 (m, 1H), 1.93-1.56 (m, 3H), 1.03-0.57 (m, 16H). |
| 61 | 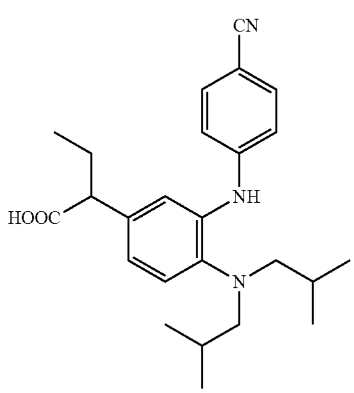 [SMILES: CCC(C(=O)O)c1ccc(N(CC(C)C)CC(C)C)c(Nc2ccc(C#N)cc2)c1] | 408.4 | 1HNMR (DMSO-d₆, 300 MHz, ppm) δ 7.78 (s, 1H), 7.54 (d, J = 8.7 Hz, 2H), 7.17-7.11 (m, 2H), 6.98-6.90 (m, 3H), 3.33 (t, J = 7.5 Hz, 1H), 2.65 (d, J = 7.2 Hz, 4H), 1.97-1.83 (m, 1H), 1.72-1.54 (m, 3H), 0.84-0.75 (m, 15H). |

TABLE 1-continued

Characterization of the compounds of Formula (I)

| Compound No. | Structure | [M + H]+ | 1H-NMR |
|---|---|---|---|
| 61A | 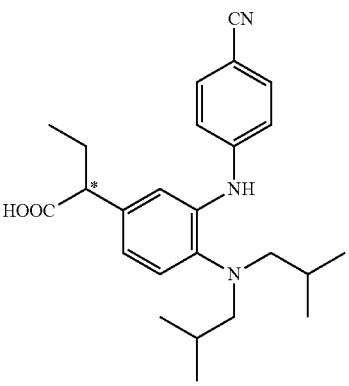 [SMILES: CCC(C(=O)O)c1ccc(N(CC(C)C)CC(C)C)c(Nc2ccc(C#N)cc2)c1] | 408.4 | Chiral HPLC [Column: IA-3, 100 mm, 4.6 mm, 0.6 mL/min, Mobile Phase: hexane (0.1% TFA)/IPA; Gradient: 20% IPA; Detector: 254 nm], Retention time = 3.30 min.<br>H-NMR (300 MHz, CDClC3, ppm), δ 7.53-7.42 (m, 3H), 7.38 (d, J = 1.5 Hz, 1H), 7.23-7.13 (m, 1H), 7.08 (d, J = 8.7 Hz, 2H), 6.93 (d, J = 7.8 Hz, 1H), 3.47 (t, J = 7.5 Hz, 1H), 2.68-2.45 (m, 3H), 2.16 -2.06 (m, 1H), 1.86-1.68 (m, 4H), 0.97 (t, J = 7.2 Hz, 3H), 0.89-0.86 (m, 12H). |
| 61B | 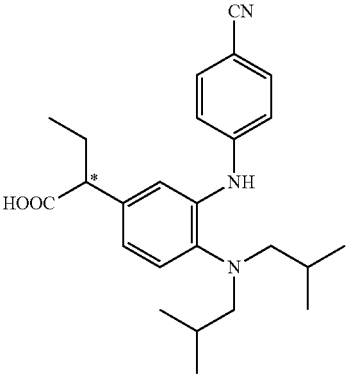 [SMILES: CCC(C(=O)O)c1ccc(N(CC(C)C)CC(C)C)c(Nc2ccc(C#N)cc2)c1] | 408.4 | Chiral HPLC [Column: IA-3, 100 mm, 4.6 mm, 0.6 mL/min, Mobile Phase: hexane (0.1% TFA)/IPA; Gradient: 20% IPA; Detector: 254 nm], Retention time = 2.81 min.<br>H-NMR (300 MHz, CDClC3, ppm): δ7.53-7.42 (m, 2H), 7.38 (d, J = 1.5 Hz, 1H), 7.18 (d, J = 8.4 Hz, 1H), 7.07 (d, J = 8.7 Hz, 2H), 6.93 (dd, J = 8.1, J = 1.5 Hz, 1H), 3.47 (t, J = 7.8 Hz, 1H), 2.68-2.45 (m, 3H), 2.16-2.06 (m, 1H), 1.86-1.68 (m, 4H), 0.97 (t, J = 7.2 Hz, 3H), 0.89-0.86 (m, 12H). |
| 62A | 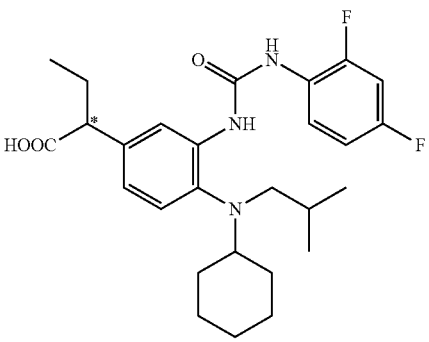 [SMILES: CCC(C(=O)O)c1ccc(N(CC(C)C)C2CCCCC2)c(NC(=O)Nc2ccc(F)cc2F)c1] | 488.3 | Chiral HPLC [Column: IA, 100 mm, 4.6 mm, 0.6 mL/min, Mobile Phase: hexane (0.1% TFA)/EtOH; Gradient: 30% EtOH; Detector: 254 nm], Retention time = 2.73 min.<br>1HNMR: (300 MHz, DMSO-d6, ppm): δ 12.18 (brs, 1H), 9.34 (s, 1H), 8.17 (s, 1H), 7.91-7.85 (m, 2H), 7.34-7.26 (m, 1H), 7.14-7.02 (m, 2H), 6.87 (d, J = 6.3 Hz, 1H), 3.31-3.27 (m, 1H), 2.87-2.75 (m, 2H), 2.54-2.43 (m, 1H), 1.97-1.86 (m, 3H), 1.70-1.57 (m, 3 H), 1.53-1.50 (m, J = 9, 1H), 1.34-0.97 (m, 6 H), 0.86-0.80 (m, 9H). |
| 62B | 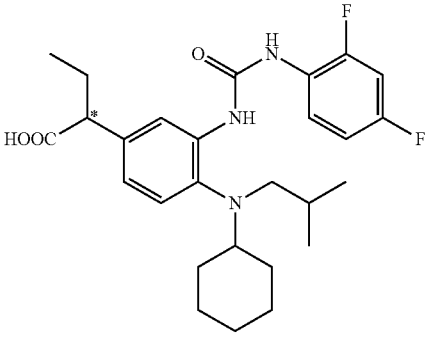 [SMILES: CCC(C(=O)O)c1ccc(N(CC(C)C)C2CCCCC2)c(NC(=O)Nc2ccc(F)cc2F)c1] | 488.3 | Chiral HPLC [Column: IA, 100 mm, 4.6 mm, 0.6 mL/min, Mobile Phase: hexane (0.1% TFA)/EtOH; Gradient: 30% EtOH; Detector: 254 nm], Retention time = 3.17 min.<br>1HNMR: (300 MHz, DMSO-d6, ppm): δ 9.36 (s, 1H), 8.17 (s, 1H), 7.94-7.85 (m, 2 H), 7.34-7.27 (m, 1H), 7.14-7.05 (m, 2H), 6.88 (d, J = 6.3 Hz, 1H), 3.33-3.28 (m, 1H), 2.77-2.76 (m, 2H), 2.54-2.50 (m, 1H), 1.95-1.86 (m, 3H), 1.70-1.49 (m, 4H), 1.34-1.03 (m, 6H), 0.86-0.80 (m, 9H). |

TABLE 1-continued

Characterization of the compounds of Formula (I)

| Compound No. | Structure | [M + H]+ | ¹H-NMR |
|---|---|---|---|
| 63A | 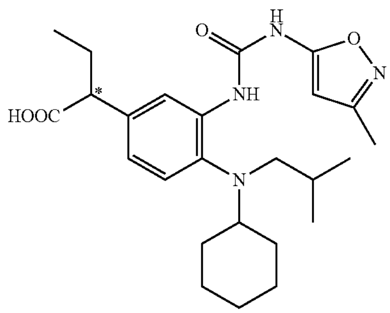 [SMILES: CCC(C(=O)O)c1ccc(N(CC(C)C)C2CCCCC2)c(NC(=O)Nc2cc(C)no2)c1] | 457.3 | Chiral HPLC [Column: AD, 100 mm, 4.6 mm, 0.6 mL/min, Mobile Phase: hexane (0.1% TFA)/EtOH; Gradient: 10% EtOH; Detector: 254 nm], Retention time = 2.98 min.<br>¹HNMR: (300 MHz, DMSO-d₆, ppm): δ 11.25 (brs, 1H), 8.34 (s, 1H), 8.02 (d, J = 1.8 Hz, 1H), 7.18 (d, J = 8.1 Hz, 1H), 6.91 (d, J = 8.4 Hz, 1H), 5.99 (s, 1H), 3.35-3.30 (m, 1H), 2.78-2.73 (m, 2H), 2.17 (s, 3H), 1.98-1.89 (m, 3H), 1.71-1.58 (m, 3H), 1.53-1.50 (m, 1H), 1.31-0.98 (m, 6H), 0.91-0.80 (m, 9H). |
| 63B | 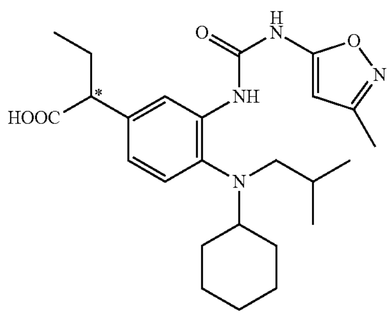 [SMILES: CCC(C(=O)O)c1ccc(N(CC(C)C)C2CCCCC2)c(NC(=O)Nc2cc(C)no2)c1] | 457.3 | Chiral HPLC [Column: AD, 100 mm, 4.6 mm, 0.6 mL/min, Mobile Phase: hexane (0.1%TFA)/EtOH; Gradient: 10% EtOH; Detector: 254 nm], Retention time = 3.39 min.<br>¹HNMR: (300 MHz, DMSO-d₆, ppm): δ 11.26 (s, 1H), 8.34 (s, 1H), 8.02 (d, J = 1.5 Hz, 1H), 7.17 (d, J = 8.1 Hz, 1H), 6.91 (d, J = 8.4 Hz, 1H), 5.99 (s, 1H), 3.35-3.30 (m, 1H), 2.78-2.73 (m, 2H), 2.17 (s, 3H), 1.98-1.89 (m, 3H), 1.71-1.58 (m, 3H), 1.54-1.50 (m, 1H), 1.32-1.00 (m, 6H), 0.86-0.80 (m, 9H). |
| 64A | 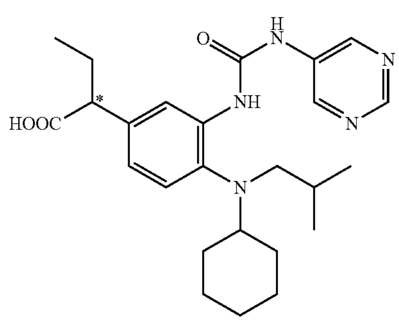 [SMILES: CCC(C(=O)O)c1ccc(N(CC(C)C)C2CCCCC2)c(NC(=O)Nc2cncnc2)c1] | 454.3 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 2.16 min.<br>¹HNMR: (300 MHz, DMSO-d₆, ppm): δ 9.96 (s, 1H), 8.93 (s, 2H), 8.82 (s, 1H), 8.27 (s, 1H), 8.04 (s, 1H), 7.19 (d, J = 8.4 Hz, 1H), 6.91-6.89 (m 1H), 3.36-3.31 (m, 1H), 2.81-2.73 (s, 2H), 2.60-2.51 (m, 1H), 1.99-1.92 (m, 3H), 1.71-1.50 (m, 4H), 1.34-1.01 (m, 6H), 0.86-0.67 (m, 9H). |
| 64B | 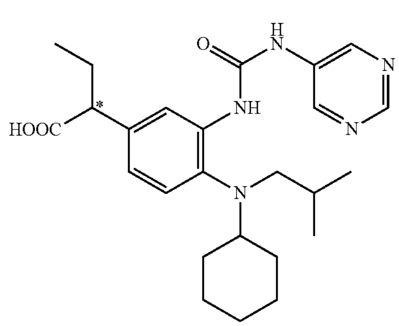 [SMILES: CCC(C(=O)O)c1ccc(N(CC(C)C)C2CCCCC2)c(NC(=O)Nc2cncnc2)c1] | 454.3 | Chiral HPLC [Column: AD, 100 mm, 4.6 mm, 0.6 mL/min, Mobile Phase: hexane (0.1% TFA)/IPA; Gradient: 30% IPA; Detector: 254 nm], Retention time = 2.68 min.<br>¹HNMR: (300 MHz, DMSO-d₆, ppm): δ 12.26 (brs, 1H), 9.95 (s, 1H), 8.93 (s, 2H), 8.82 (s, 1H), 8.27 (s, 1H), 8.03 (d, J = 1.8 Hz, 1H), 7.19 (d, J = 8.4 Hz, 1H), 6.92-6.89 (dd, J = 1.8, 8.4 Hz, 2H), 2.96-2.73 (m, 2H), 2.57-2.51 (m, 1H), 2.01-1.92 (m, 3H), 1.71-1.50 (m, 4H), 1.34-0.92 (m, 6H), 0.87-0.68 (m, 9H). |

TABLE 1-continued

Characterization of the compounds of Formula (I)

| Compound No. | Structure | [M + H]⁺ | ¹H-NMR |
|---|---|---|---|
| 65 | 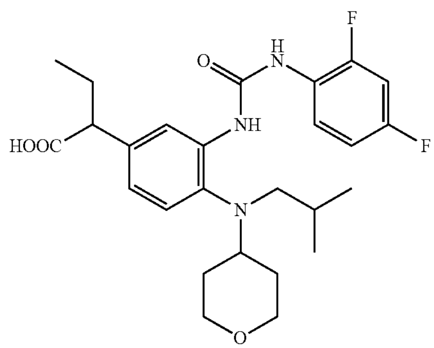 [SMILES: CCC(C(=O)O)c1ccc(N(CC(C)C)C2CCOCC2)c(NC(=O)Nc2ccc(F)cc2F)c1] | 490.4 | ¹HNMR (300 MHz, CD₃OD, ppm) δ 8.06 (m, 1H), 7.89-7.81 (m, 1H), 7.24-6.98 (m, 4H), 3.97-3.93 (m, 2H), 3.54-3.38 (m, 3H), 2.88-2.84 (m, 3H), 2.13-2.04 (m, 1H), 1.85-1.65 (m, 5H), 1.47-1.39 (m, 1H), 0.97-0.89 (m, 9H). |
| 65A | 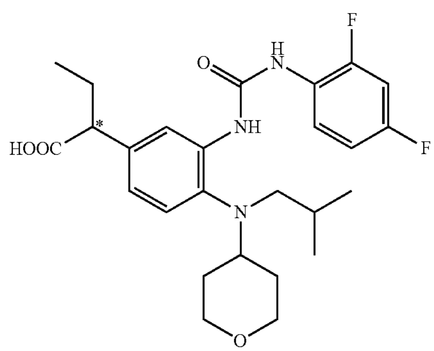 [SMILES: CCC(C(=O)O)c1ccc(N(CC(C)C)C2CCOCC2)c(NC(=O)Nc2ccc(F)cc2F)c1] | 490.4 | Chiral HPLC [Column: AD-3, 100 mm, 4.6 mm, 0.6 mL/min, Mobile Phase: hexane (0.1% TFA)/IPA; Gradient: 10% IPA; Detector: 254 nm], Retention time = 11.59 min.<br>H-NMR (300 MHz, CD₃OD, ppm): δ 8.02 (s, 1H), 7.86-7.78 (m, 1H), 7.22-7.10 (m, 1H), 7.06-6.96 (m, 3H), 3.92 (d, J = 8.7 Hz, 2H), 3.68-3.31 (m, 2H), 2.99-2.69 (m, 3H), 2.30-1.95 (m, 1H), 1.93-1.50 (m, 5H), 1.50-1.20 (m, 2H), 1.15-0.70 (m, 9H)). |
| 65B | 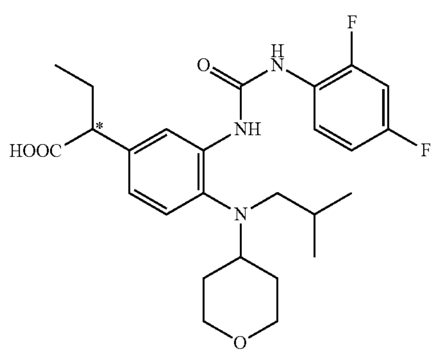 [SMILES: CCC(C(=O)O)c1ccc(N(CC(C)C)C2CCOCC2)c(NC(=O)Nc2ccc(F)cc2F)c1] | 490.4 | Chiral HPLC [Column: AD-3, 100 mm, 4.6 mm, 0.6 mL/min, Mobile Phase: hexane (0.1% TFA)/IPA; Gradient: 10% IPA; Detector: 254 nm], Retention time = 13.85 min.<br>H-NMR (300 MHz, CD₃OD, ppm): δ 8.02 (s, 1H), 7.86-7.78 (m, 1H), 7.21-7.11 (m, 1H), 7.04-6.93 (m, 3H), 3.93 (d, J = 9.0 Hz, 2H), 3.58-3.31 (m, 2H), 3.00-2.70 (m, 3H), 2.28-1.95 (m, 1H), 1.93-1.50 (m, 5H), 1.50-1.40 (m, 1H), 1.40-1.20 (m, 1H), 1.10-0.75 (m, 9H). |
| 66A | 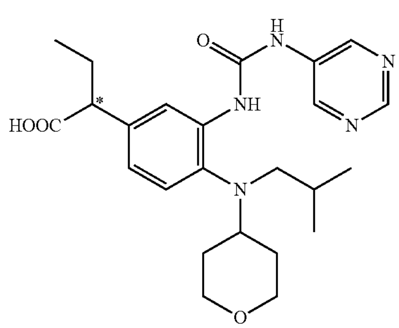 [SMILES: CCC(C(=O)O)c1ccc(N(CC(C)C)C2CCOCC2)c(NC(=O)Nc2cncnc2)c1] | 456.2 | Chiral HPLC [Column: IC, 100 mm, 4.6 mm, 0.6 mL/min, Mobile Phase: hexane (0.1% TFA)/IPA; Gradient: 10% IPA; Detector: 254 nm], Retention time = 23.48 min.<br>¹H-NMR (300 MHz, CD₃OD, ppm): δ 8.99 (s, 2H), 8.79 (s, 1H), 8.16 (d, J = 1.5 Hz, 1H), 7.26 (d, J = 8.4 Hz, 1H), 7.05 (dd, J = 8.4 Hz, 1.8 Hz, 1H), 3.95-3.90 (m, 2H), 3.53-3.37 (m, 3H), 3.07-2.85 (m, 3H), 2.01-2.03 (m, 1H), 1.83-1.71 (m, 3H), 1.67-1.54 (m, 2H), 1.46-1.36 (m, 1H), 0.96-0.86 (m, 9H). |

TABLE 1-continued

Characterization of the compounds of Formula (I)

| Compound No. | Structure | [M + H]⁺ | ¹H-NMR |
|---|---|---|---|
| 66B | 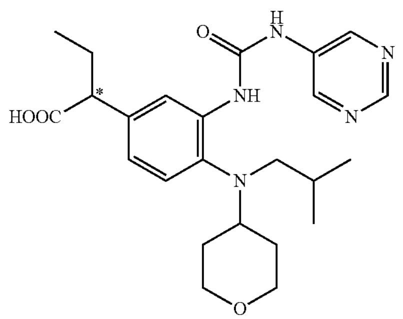 [SMILES: CCC(C(=O)O)c1ccc(N(CC(C)C)C2CCOCC2)c(NC(=O)Nc2cncnc2)c1] | 456.2 | Chiral HPLC [Column: IC, 100 mm, 4.6 mm, 0.6 mL/min, Mobile Phase: hexane (0.1% TFA)/IPA; Gradient: 10% IPA; Detector 254 nm], Retention time = 18.91 min. ¹HNMR (300 MHz, CD₃OD, ppm): δ 8.99 (s, 2H), 8.79 (s, 1H), 8.16 (d, J = 1.5 Hz, 1H), 7.26 (d, J = 8.4 Hz, 1H), 7.05 (dd, J = 8.4 Hz, 1.8 Hz, 1H), 3.95-3.90 (m, 2H), 3.53-3.37 (m, 3H), 3.07-2.85 (m, 3H), 2.01-2.03 (m, 1H), 1.83-1.71 (m, 3H), 1.67-1.54 (m, 2H), 1.46-1.36 (m, 1H), 0.96-0.86 (m, 9H). |
| 67 | 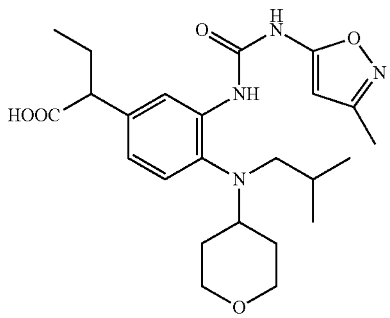 [SMILES: CCC(C(=O)O)c1ccc(N(CC(C)C)C2CCOCC2)c(NC(=O)Nc2cc(C)no2)c1] | 459.3 | ¹HNMR (300 MHz, CD₃OD, ppm): δ 8.17 (s, 1H), 7.27 (d, J = 9.0 Hz, 1H), 7.05 (d, J = 9.0 Hz, 1H), 6.08 (s, 1H), 3.94 (d, J = 12.0 Hz, 1H), 3.47-3.38 (m, 3H), 2.86 (m, 3H), 2.26 (s, 3H), 2.15-2.05 (m, 1H), 1.85-1.76 (m, 3H), 1.68-1.56 (m, 2H), 1.43-1.38 (m, 1H), 0.95 (t, J = 7.2 Hz, 3H), 0.88 (d, J = 6.6 Hz, 6H). |
| 68A | 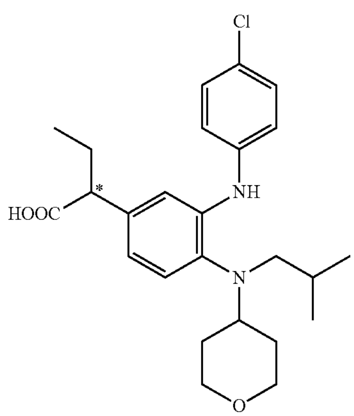 [SMILES: CCC(C(=O)O)c1ccc(N(CC(C)C)C2CCOCC2)c(Nc2ccc(Cl)cc2)c1] | 445.2 | Chiral HPLC [Column: AD, 100 mm, 4.6 mm, 0.6 mL/min, Mobile Phase: hexane (0.1% TFA)/IPA; Gradient: 5% IPA; Detector: 254 nm], Retention time = 6.12 min. ¹HNMR: (300 MHz, DMSO-d₆, ppm): δ 7.33-7.07 (m, 7H), 6.81-6.79 (m, 1H), 3.81-3.79 (m, 2H), 3.35-3.30 (m, 1H), 3.14-3.10 (m, 2H), 2.96-2.74 (m, 3H), 1.95-1.86 (m, 1H), 1.66-1.32 (m, 5H), 0.86-0.80 (m, 9H). |
| 68B | 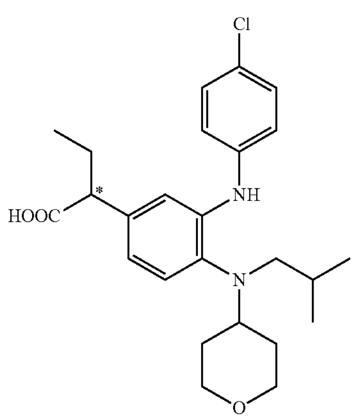 [SMILES: CCC(C(=O)O)c1ccc(N(CC(C)C)C2CCOCC2)c(Nc2ccc(Cl)cc2)c1] | 445.2 | Chiral HPLC [Column: AD, 100 mm, 4.6 mm, 0.6 mL/min, Mobile Phase: hexane (0.1% TFA)/IPA; Gradient: 5% IPA; Detector: 254 nm], Retention time = 6.40 min. ¹HNMR: (300 MHz, DMSO-d₆, ppm): δ 7.33-7.07 (m, 7H), 6.82-6.79 (m, 1H), 3.81-3.78 (m, 2H), 3.35-3.30 (m, 1H), 3.14-3.06 (m, 2H), 2.96-2.73 (m, 3H), 1.95-1.86 (m, 1H), 1.66-1.23 (m, 5H), 0.86-0.80 (m, 9H). |

TABLE 1-continued

Characterization of the compounds of Formula (I)

| Compound No. | Structure | [M + H]⁺ | ¹H-NMR |
|---|---|---|---|
| 69 | 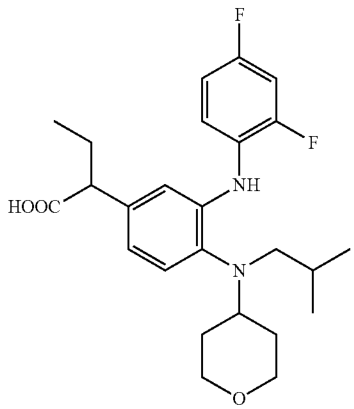 [SMILES: CCC(C(=O)O)c1ccc(N(CC(C)C)C2CCOCC2)c(Nc2ccc(F)cc2F)c1] | 447.2 | ¹HNMR: (300 MHz, DMSO-d₆, ppm): δ 7.43-7.29 (m, 2H), 7.20-7.17 (m, 2H), 7.07-7.02 (m, 2H), 6.76 (d, J = 7.8 Hz, 1H), 3.83-3.76 (m, 2H), 3.45-3.12 (m, 4H), 2.93-2.79 (m, 3H), 1.94-1.82 (m, 1H), 1.67-1.32 (m, 5H), 0.89-0.73 (m, 9H). |
| 70A | 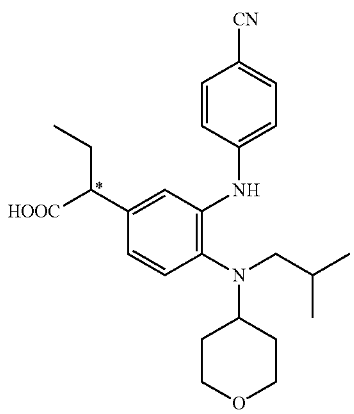 [SMILES: CCC(C(=O)O)c1ccc(N(CC(C)C)C2CCOCC2)c(Nc2ccc(C#N)cc2)c1] | 436.2 | Chiral HPLC [Column: IA, 100 mm, 4.6 mm, 0.6 mL/min, Mobile Phase: hexane (0.1% TFA)/EtOH; Gradient: 10% EtOH; Detector: 254 nm], Retention time = 5.61 min. ¹HNMR: (300 MHz, DMSO-d₆, ppm): δ 7.76 (s, 1H), 7.57 (d, J = 8.4 Hz, 2H), 7.30-7.13 (m, 2H), 7.08-6.90 (m, 3H), 3.78-3.76 (m, 2H), 3.40-3.35 (m, 1H), 3.04-2.91 (m, 2H), 2.77-2.69 (m, 2H), 1.97-1.86 (m, 1H), 1.69-1.31 (m, 7H), 0.84-0.79 (m, 9H). |
| 70B | 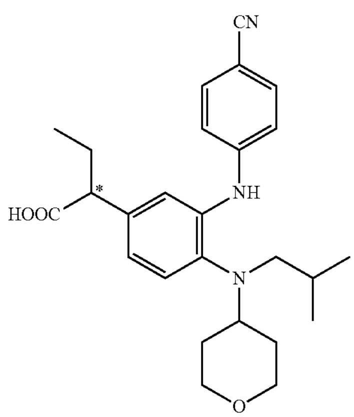 [SMILES: CCC(C(=O)O)c1ccc(N(CC(C)C)C2CCOCC2)c(Nc2ccc(C#N)cc2)c1] | 436.2 | Chiral HPLC [Column: IA, 100 mm, 4.6 mm, 0.6 mL/min, Mobile Phase: hexane (0.1% TFA)/EtOH; Gradient: 10% EtOH; Detector: 254 nm], Retention time = 6.10 min. ¹HNMR: (300 MHz, DMSO-d₆, ppm): δ 7.76 (s, 1H), 7.57 (d, J = 8.4 Hz, 2H), 7.30-7.12 (m, 2H), 7.04-6.90 (m, 3H), 3.78 (m, 2H), 3.40-3.35 (m, 1H), 3.04-2.91 (m, 2H), 2.77-2.69 (m, 2H), 1.97-1.86 (m, 1H), 1.69-1.31 (m, 7H), 0.84-0.79 (m, 9H). |

TABLE 1-continued

Characterization of the compounds of Formula (I)

| Compound No. | Structure | [M + H]⁺ | ¹H-NMR |
|---|---|---|---|
| 71 | 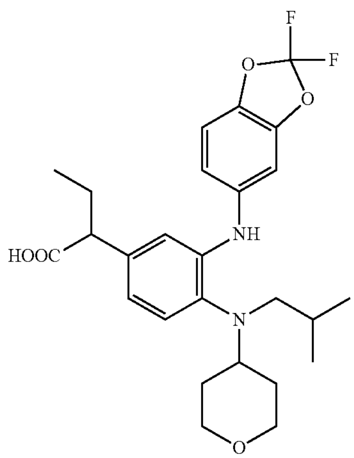 [SMILES: CCC(C(=O)O)c1ccc(N(CC(C)C)C2CCOCC2)c(Nc2ccc3c(c2)OC(F)(F)O3)c1] | 491.2 | ¹HNMR (300 MHz, CD$_3$OD, ppm): δ 7.22-7.19 (m, 2H), 7.10 (d, J = 8.7 Hz, 1H), 7.03 (d, J = 2.4 Hz, 1H), 6.90-6.83 (m, 2H), 3.92 (dd, J = 3.9 Hz, J = 11.1 Hz, 2H), 3.40-3.25 (m, 3H), 2.95-2.86 (m, 3H), 2.11-1.95 (m, 1H), 1.81-1.41 (m, 6H), 0.95-0.88 (m, 9H). |
| 71A | 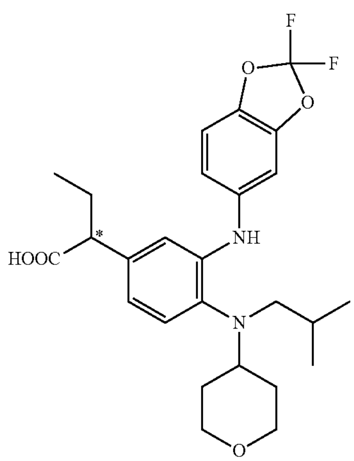 [SMILES: CCC(C(=O)O)c1ccc(N(CC(C)C)C2CCOCC2)c(Nc2ccc3c(c2)OC(F)(F)O3)c1] | 491.2 | Chiral HPLC [Column: YMC-SB, 150 mm, 4.6 mm, 1 mL/min, Mobile Phase: hexane (0.1% TFA)/EtOH; Gradient: 5% EtOH; Detector: 254 nm], Retention time = 6.29 min.<br>¹HNMR (300 MHz, CD$_3$OD, ppm): δ 7.17-7.15 (m, 2H), 7.05 (d, J = 8.7 Hz, 1H), 6.99 (d, J = 2.1 Hz, 1H), 6.86-6.78 (m, 2H), 3.90-3.85 (m, 2H), 3.36-3.21 (m, 3H), 2.90-2.86 (m, 1H), 2.83 (d, J = 3.9 Hz, 2H), 2.08-1.99 (m, 1H), 1.75-1.55 (m, 5H), 1.48-1.40 (m, 1H), 0.92-0.85 (m, 9H). |
| 71B | 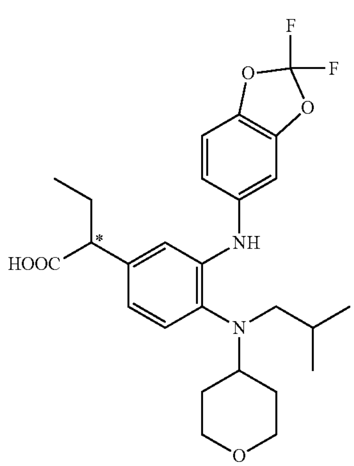 [SMILES: CCC(C(=O)O)c1ccc(N(CC(C)C)C2CCOCC2)c(Nc2ccc3c(c2)OC(F)(F)O3)c1] | 491.2 | Chiral HPLC [Column: YMC-SB, 150 mm, 4.6 mm, 1 mL/min, Mobile Phase: hexane (0.1% TFA)/EtOH; Gradient: 5% EtOH; Detector: 254 nm], Retention time = 6.78 min.<br>H-NMR (300 MHz, CD$_3$OD, ppm): δ 7.19-7.16 (m, 2H), 7.07 (d, J = 8.7 Hz, 1H), 7.00 (d, J = 2.1 Hz, 1H), 6.87-6.80 (m, 2H), 3.90-3.85 (m, 2H), 3.36-3.21 (m, 3H), 2.90-2.86 (m, 1H), 2.83 (d, J = 3.9 Hz, 2H), 2.08-1.99 (m, 1H), 1.75-1.55 (m, 5H), 1.47-1.40 (m, 1H), 0.93-0.86 (m, 9H). |

TABLE 1-continued

Characterization of the compounds of Formula (I)

| Compound No. | Structure | [M + H]+ | ¹H-NMR |
|---|---|---|---|
| 72 | 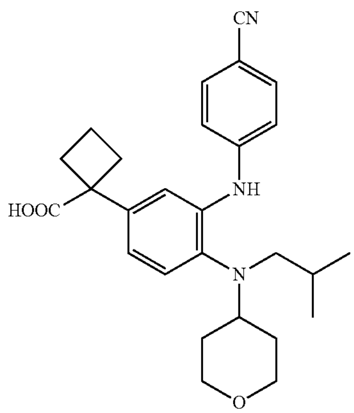 [SMILES: CC(C)CN(c1ccc(C2(C(=O)O)CCC2)cc1Nc1ccc(C#N)cc1)C1CCOCC1] | 448.2 | ¹HNMR: (400 MHz, DMSO-d6, ppm): δ 7.72 (s, 1H), 7.53 (d, J = 8.8 Hz, 2H), 7.15 (d, J = 8.4 Hz, 1H), 7.10 (d, J = 2.0 Hz, 1H), 6.98 (d, J = 8.8 Hz, 2H), 6.94 (dd, J1 = 8.4 Hz, J2 = 2.0 Hz, 1H), 3.74 (d, J = 11.2 Hz, 2H), 2.98-2.92 (m, 2H), 2.88-2.85 (m, 1H), 2.72 (d, J = 6.8 Hz, 2H), 2.66-2.60 (m, 2H), 2.37-2.32 (m, 2H), 1.90-1.83 (m, 1H), 1.81-1.72 (m, 1H), 1.49 (s, 4H), 1.37-1.30 (m, 1H), 0.75 (d, J = 6.4 Hz, 6H). |
| 73 | 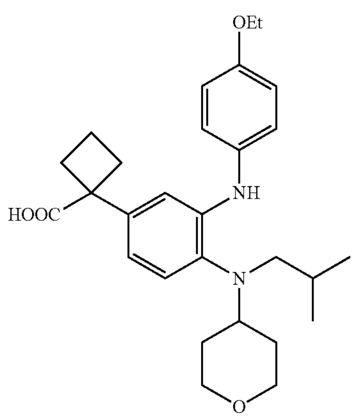 [SMILES: CCOc1ccc(Nc2cc(C3(C(=O)O)CCC3)ccc2N(CC(C)C)C2CCOCC2)cc1] | 467.2 | ¹HNMR: (400 MHz, DMSO-d6, ppm): δ 12.17 (brs, 1H), 7.10 (d, J = 8.0 Hz, 1H), 7.01 (d, J = 8.8 Hz, 2H), 6.89-6.88 (m, 2H), 6.84 (d, J = 8.8 Hz, 2H), 6.62 (dd, J1 = 8.0 Hz, J2 = 2.0 Hz, 1H), 3.95 (q, J = 6.8 Hz, 2H), 3.80-3.77 (m, 2H), 3.16-3.10 (m 2H), 2.81-2.74 (m, 3H), 2.62-2.57 (m, 2H), 2.32-2.25 (m, 2H), 1.84-1.80 (m, 1H), 1.75-1.73 (m, 1H), 1.71-1.63 (m, 2H), 1.54-1.46 (m, 2H), 1.36-1.34 (m, 1H), 1.30-1.26 (m, 3H), 0.80 (d, J = 6.8 Hz, 6H). |
| 74 | 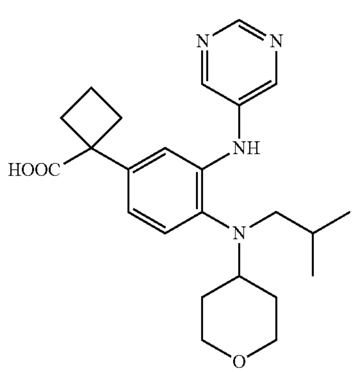 [SMILES: CC(C)CN(c1ccc(C2(C(=O)O)CCC2)cc1Nc1cncnc1)C1CCOCC1] | 425.3 | ¹HNMR: (400 MHz, DMSO-d6, ppm): δ 12.31 (s, 1H), 8.61 (s, 1H), 8.50 (s, 2H), 7.41 (s, 1H), 7.17 (d, J = 8.0 Hz, 1H), 7.07 (d, J = 1.2 Hz, 1H), 6.87-6.85 (m, 1H), 3.78-3.75 (m, 2H), 3.09-3.04 (m, 2H), 2.91-2.86 (m, 1H), 2.74 (d, J = 6.8 Hz, 2H), 2.66-2.59 (m, 2H), 2.38-2.31 (m, 2H), 1.94-1.83 (m, 1H), 1.80-1.73 (m, 1H), 1.59-1.53 (m, 2H), 1.55-1.44 (m, 2H), 1.35-1.30 (m, 1H), 0.78 (d, J = 6.8 Hz, 6H). |

TABLE 1-continued

Characterization of the compounds of Formula (I)

| Compound No. | Structure | [M + H]⁺ | ¹H-NMR |
|---|---|---|---|
| 75 | 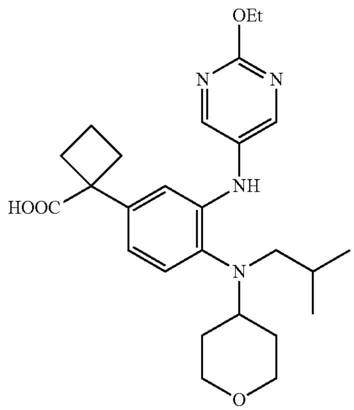 [SMILES: CCOc1ncc(Nc2cc(C3(C(=O)O)CCC3)ccc2N(CC(C)C)C2CCOCC2)cn1] | 469.3 | ¹HNMR: (400 MHz, DMSO-d6, ppm): δ 12.22 (s, 1H), 8.38 (s, 2H), 7.13 (d, J = 8.0 Hz, 1H), 7.03 (s, 1H), 6.77 (s, 1H), 6.69 (d, J = 8.0 Hz, 1H), 4.27 (q, J = 7.2 Hz, 2H), 3.79 (d, J = 8.0 Hz, 2H), 3.14 (t, J = 11.6 Hz, 2H), 2.84 (t, J = 11.2 Hz, 1H), 2.75 (d, J = 6.0 Hz, 2H), 2.61-2.55 (m, 2H), 2.33-2.26 (m, 2H), 1.85-1.80 (m, 1H), 1.77-1.65 (m, 3H), 1.54-1.46 (m, 2H), 1.36-1.33 (m, 1H), 1.29 (t, J = 7.2 Hz, 3H), 0.79 (d, J = 6.4 Hz, 6H). |
| 76 | 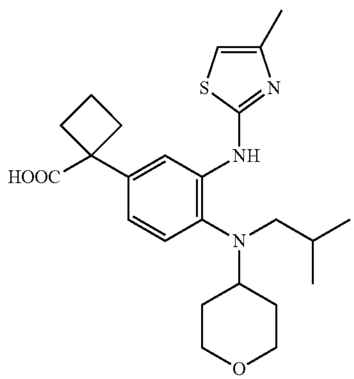 [SMILES: Cc1csc(Nc2cc(C3(C(=O)O)CCC3)ccc2N(CC(C)C)C2CCOCC2)n1] | 444.2 | ¹HNMR: (400 MHz, DMSO-d6, ppm): δ 12.28 (brs, 1H), 8.76 (s, 1H), 7.94 (d, J = 2.0 Hz, 1H), 7.22 (d, J = 8.4 Hz, 1H), 6.84 (dd, J1 = 8.4 Hz, J2 = 2.0 Hz, 1H), 6.48 (s, 1H), 3.80-3.77 (m, 2H), 3.14 (t, J = 11.2 Hz, 2H), 2.85-2.70 (m, 3H), 2.67-2.64 (m, 2H), 2.41-2.34 (m, 2H), 2.18 (s, 3H), 1.95-1.74 (m, 2H), 1.69-1.60 (m, 2H), 1.48-1.38 (m, 2H), 1.32-1.25 (m, 1H), 0.79 (d, J = 6.4 Hz, 6H). |
| 77 | 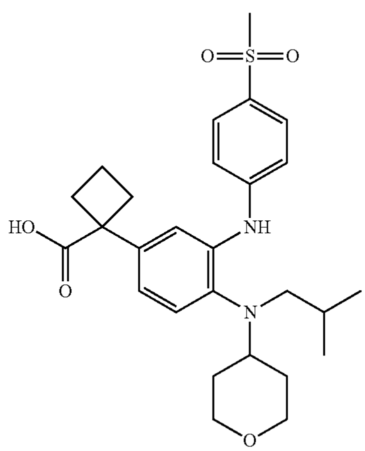 [SMILES: CC(C)CN(c1ccc(C2(C(=O)O)CCC2)cc1Nc1ccc(S(C)(=O)=O)cc1)C1CCOCC1] | 501.3 | ¹HNMR: (400 MHz, DMSO-d6, ppm): δ 12.31 (brs, 1H), 7.67-7.63 (m, 3H), 7.17-7.14 (m, 2H), 7.07 (d, J = 8.8 Hz, 2H), 6.92 (dd, J1 = 8.4 Hz, J2 = 1.6 Hz, 1H), 3.74 (d, J = 10.8 Hz, 2H), 3.07 (s, 3H), 2.98 (t, J = 10.0 Hz, 2H), 2.89-2.84 (m, 1H), 2.74 (d, J = 6.8 Hz, 2H), 2.67-2.60 (m, 2H), 2.38-2.33 (m, 2H), 1.89-1.85 (m, 1H), 1.82-1.74 (m, 1H), 1.52-1.49 (m, 4H), 1.39-1.30 (m, 1H), 0.77 (d, J = 6.4 Hz, 6H). |
| 79 | 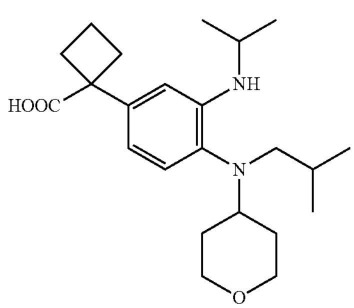 [SMILES: CC(C)CN(c1ccc(C2(C(=O)O)CCC2)cc1NC(C)C)C1CCOCC1] | 389.3 | ¹HNMR: (400 MHz, DMSO-d6, ppm): δ 7.02 (d, J = 7.6 Hz, 1H), 6.57-6.55 (m, 2H), 3.91 (dd, J1 = 11.2 Hz, J2 = 3.2 Hz, 2H), 3.61-3.58 (m, 1H), 3.32-3.26 (m, 1H), 3.26-3.21 (m, 1H), 2.96 (d, J = 9.2 Hz, 1H), 2.78-2.71 (m, 3H), 2.58-2.42 (m, 3H), 1.96-1.37 (m, 7H), 1.21 (dd, J1 = 36.0 Hz, J2 = 6.4 Hz, 6H), 0.83 (dd, J1 = 32.8 Hz, J2 = 6.4 Hz, 6H). |

TABLE 1-continued

Characterization of the compounds of Formula (I)

| Compound No. | Structure | [M + H]⁺ | ¹H-NMR |
|---|---|---|---|
| 80 | 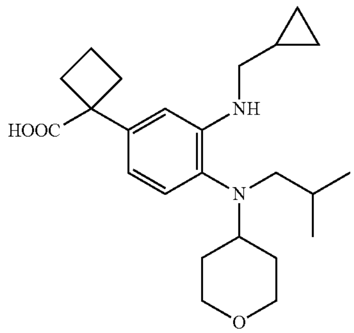 [SMILES: CC(C)CN(c1ccc(C2(C(=O)O)CCC2)cc1NCC1CC1)C1CCOCC1] | 401.2 | ¹HNMR: (400 MHz, DMSO-d6, ppm): δ 7.02 (d, J = 8.0 Hz, 1H), 6.59-6.57 (m, 2H), 3.92 (d, J = 11.2 Hz, 2H), 3.36-3.23 (m, 2H), 3.08-2.98 (m, 2H), 2.84-2.71 (m, 4H), 2.59-2.53 (m, 1H), 2.49-2.42 (m, 2H), 1.97-1.94 (m, 1H), 1.85-1.60 (m, 5H), 1.42-1.38 (m, 1H), 1.10-1.08 (m, 1H), 0.83(dd, J1 = 29.6 Hz, J2 = 6.4 Hz, 6H), 0.51 (dd, J1 = 8.0 Hz, J2 = 1.2 Hz, 2H), 0.23-0.20 (m, 2H). |
| 81 | 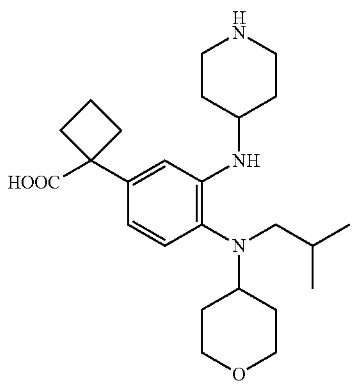 [SMILES: CC(C)CN(c1ccc(C2(C(=O)O)CCC2)cc1NC1CCNCC1)C1CCOCC1] | 430.3 | ¹HNMR (300 MHz, CD₃OD, ppm): δ 7.10 (d, J = 8.0 Hz, 1H), 6.66-6.62 (m, 2H), 3.92-3.90 (m, 2H), 3.69-3.64 (m, 1H), 3.45-3.39 (m, 2H), 3.38-3.30 (m, 2H), 3.21-3.12 (m, 2H), 3.05-2.99 (m, 1H), 2.89-2.87 (m, 1H), 2.76-2.66 (m, 3H), 2.51-2.43 (m, 2H), 2.35-2.25 (m, 2H), 2.01-1.40 (m, 9H), 0.88 (d, J = 6.4 Hz, 3H), 0.80 (d, J = 6.4 Hz, 3H). |
| 82 | 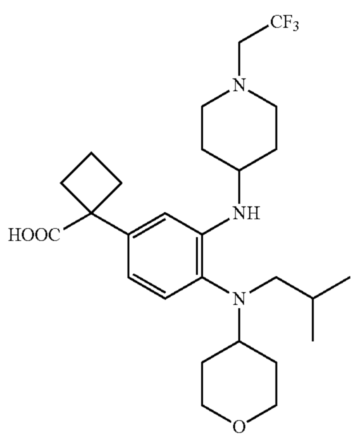 [SMILES: CC(C)CN(c1ccc(C2(C(=O)O)CCC2)cc1NC1CCN(CC(F)(F)F)CC1)C1CCOCC1] | 512.3 | ¹HNMR: (400 MHz, DMSO-d6, ppm): δ 12.15 (brs, 1H), 6.98 (d, J = 8.0 Hz, 1H), 6.44-6.41 (m, 2H), 4.84 (d, J = 8.4 Hz, 1H), 3.84-3.78 (m, 2H), 3.29-3.21 (m, 2H), 3.18-3.11 (m, 4H), 2.90-2.82 (m, 3H), 2.66-2.61 (m, 3H), 2.55-2.49 (m, 2H), 2.36-2.29 (m, 2H), 1.87-1.59 (m, 6H), 1.52-1.38 (m, 3H), 1.27-1.20 (m, 2H), 0.80 (d, J = 6.4 Hz, 3H), 0.74 (d, J = 6.4 Hz, 3H). |
| 84 | 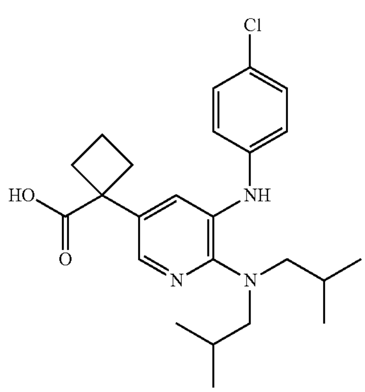 [SMILES: CC(C)CN(CC(C)C)c1ncc(C2(C(=O)O)CCC2)cc1Nc1ccc(Cl)cc1] | 430.2 | ¹HNMR: (400 MHz, DMSO-d6, ppm): δ 12.36 (brs, 1H), 7.84 (d, J = 2.0 Hz, 1H), 7.40 (s, 1H), 7.18 (d, J = 2.0 Hz, 1H), 7.14 (d, J = 8.8 Hz, 2H), 6.67 (d, J = 8.8 Hz, 2H), 3.02 (d, J = 7.2 Hz, 4H), 2.63-2.56 (m 2H), 2.35-2.28 (m, 2H), 1.89-1.81 (m, 1H), 1.80-1.64 (m, 3H), 0.70 (d, J = 6.8 Hz, 12H). |

TABLE 1-continued

Characterization of the compounds of Formula (I)

| Compound No. | Structure | [M + H]+ | ¹H-NMR |
|---|---|---|---|
| 85 | 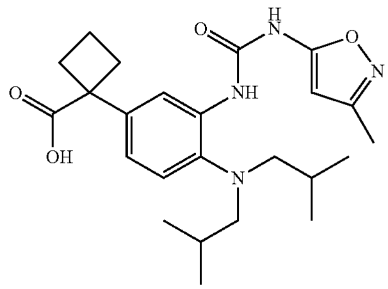 [SMILES: Cc1cc(NC(=O)Nc2cc(C3(C(=O)O)CCC3)ccc2N(CC(C)C)CC(C)C)on1] | 444.3 | ¹HNMR: (400 MHz, DMSO-d6, ppm): δ 8.28 (d, J = 2.0 Hz, 1H), 8.01 (d, J = 2.0 Hz, 1H), 6.03 (s, 1H), 2.91 (d, J = 7.2 Hz, 4H), 2.82-2.75 (m, 2H), 2.43-2.36 (m, 2H), 2.21 (s, 3H), 1.98-1.95 (m, 1H), 1.84-1.81 (m, 1H), 1.74-1.68 (m, 2H), 0.83 (d, J = 6.4 Hz, 12H). |
| 86 | 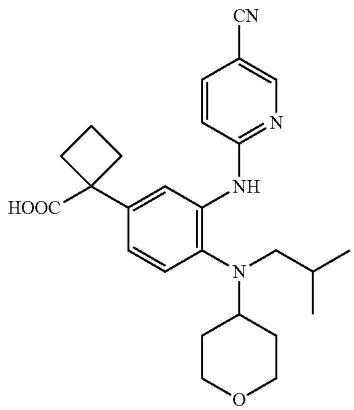 [SMILES: CC(C)CN(c1ccc(C2(C(=O)O)CCC2)cc1Nc1ccc(C#N)cn1)C1CCOCC1] | 449.3 | ¹HNMR: (400 MHz, DMSO-d6, ppm): δ 12.30 (brs, 1H), 8.66 (s, 1H), 8.53 (d, J = 2.0 Hz, 1H), 7.97 (d, J = 1.6 Hz, 1H), 7.87 (dd, J1 = 8.4 Hz, J2 = 2.0 Hz, 1H), 7.21 (d, J = 8.4 Hz, 1H), 6.99-6.93 (m, 2H), 3.79-3.75 (m, 2H), 3.09-3.04 (m 2H), 2.89-2.84 (m, 1H), 2.76 (d, J = 6.4 Hz, 2H), 2.69-2.63 (m, 2H), 2.41-2.33 (m, 2H), 1.94-1.85 (m, 1H), 1.80-1.73 (m, 1H), 1.60-1.57 (m, 2H), 1.53-1.43 (m, 2H), 1.35-1.26 (m, 1H), 0.77 (d, J = 6.8 Hz, 6H). |
| 87 | 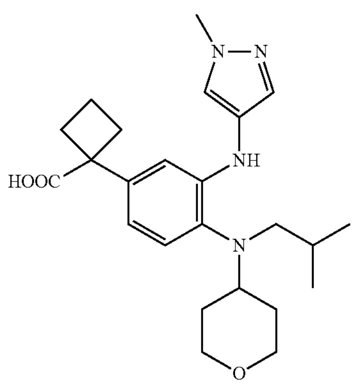 [SMILES: CC(C)CN(c1ccc(C2(C(=O)O)CCC2)cc1Nc1cnn(C)c1)C1CCOCC1] | 427.3 | ¹HNMR (400 MHz, CD₃OD, ppm): δ 7.51 (s, 1H), 7.34 (s, 1H), 7.09 (d, J = 8.0 Hz, 1H), 6.79 (d, J = 2.0 Hz, 1H), 6.67 (dd, J1 = 8.0 Hz, J2 = 2.0 Hz, 1H), 3.90 (d, J = 11.2 Hz, 2H), 3.84 (s, 3H), 3.34-3.31 (m, 2H), 2.86-2.67 (m, 5H), 2.43-2.36 (m, 2H), 1.92-1.83 (m, 1H), 1.82-1.42 (m, 6H), 0.85 (s, 6H). |
| 88 | 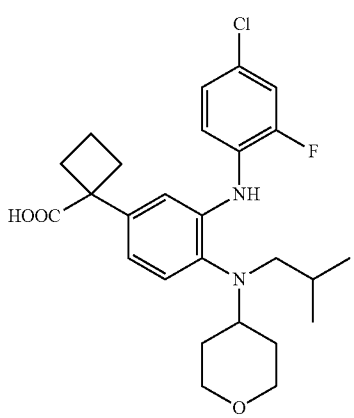 [SMILES: CC(C)CN(c1ccc(C2(C(=O)O)CCC2)cc1Nc1ccc(Cl)cc1F)C1CCOCC1] | 475.3 | ¹HNMR: (400 MHz, DMSO-d6, ppm): δ 7.44 (d, J = 10.8 Hz, 1H), 7.33-7.29 (m, 2H), 7.22-7.17 (m, 2H), 7.03 (d, J = 1.6 Hz, 1H), 6.79 (dd, J1 = 8.0 Hz, J2 = 1.6 Hz, 1H), 3.77 (d, J = 8.0 Hz, 2H), 3.11 (t, J = 11.6 Hz, 2H), 2.81-2.76 (m, 3H), 2.66-2.60 (m, 2H), 2.38-2.33 (m, 2H), 1.89-1.84 (m, 1H), 1.80-1.74 (m, 1H), 1.59-1.56 (m, 2H), 1.50-1.41 (m, 2H), 1.33-1.26 (m, 1H), 0.78 (d, J = 6.4 Hz, 6H). |

TABLE 1-continued

Characterization of the compounds of Formula (I)

| Compound No. | Structure | [M + H]+ | ¹H-NMR |
|---|---|---|---|
| 89 | 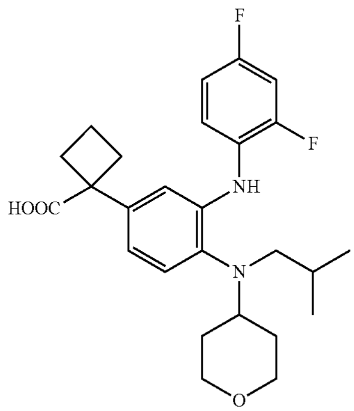 [SMILES: CC(C)CN(c1ccc(C2(C(=O)O)CCC2)cc1Nc1ccc(F)cc1F)C1CCOCC1] | 459.3 | ¹HNMR (400 MHz, CD₃OD, ppm): δ 7.40-7.34 (m, 1H), 7.18 (d, J = 8.4 Hz, 1H), 7.07 (d, J = 2.0 Hz, 1H), 7.03-6.97 (m, 1H), 6.90-6.85 (m, 1H), 6.82 (dd, J1 = 8.0 Hz, J2 = 1.6 Hz, 1H), 3.88 (dd, J1 = 11.2 Hz, J2 = 3.6 Hz, 2H), 3.25-3.22 (m, 2H), 2.88-2.83 (m, 3H), 2.77-2.70 (m, 2H), 2.46-2.39 (m, 2H), 2.02-1.91 (m, 1H), 1.88-1.78 (m, 1H), 1.73-1.70 (m, 2H), 1.66-1.56 (m, 2H), 1.47-1.37 (m, 1H), 0.85 (d, J = 6.4 Hz, 6H). |
| 90 | 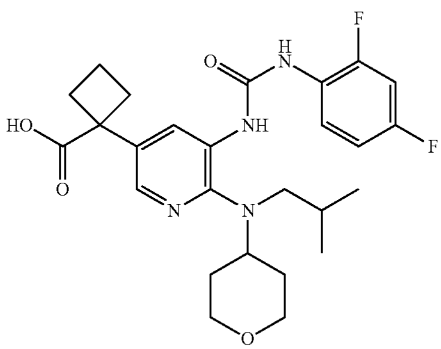 [SMILES: CC(C)CN(c1ncc(C2(C(=O)O)CCC2)cc1NC(=O)Nc1ccc(F)cc1F)C1CCOCC1] | 503.3 | H-NMR: (400 MHz, DMSO-d₆, ppm): δ 9.48 (s, 1H), 8.19-8.14 (m, 2H), 7.95-7.90 (m, 2H), 7.28-7.24 (m, 1H), 7.01-6.97 (m, 1H), 3.79 (d, J = 8.8 Hz, 2H), 3.15-3.10 (m, 2H), 2.97-2.86 (m, 3H), 2.67-2.65 (m, 2H), 2.21-2.19(m, 2H), 1.88-1.82 (m, 1H), 1.65-1.51 (m, 5H), 1.27-1.24 (m, 1H), 0.76 (d, J = 7.2 Hz, 6H). |
| 91 | 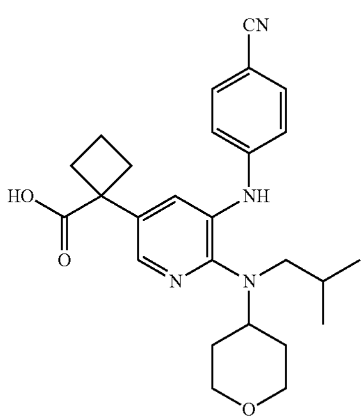 [SMILES: CC(C)CN(c1ncc(C2(C(=O)O)CCC2)cc1Nc1ccc(C#N)cc1)C1CCOCC1] | 449.3 | H-NMR: (400 MHz, DMSO-d₆, ppm): δ 8.00-7.97 (m, 2H), 7.49 (d, J = 8.4 Hz, 2H), 7.37 (s, 1H), 6.78 (d, J = 8.4 Hz, 2H), 3.74 (d, J = 8.4 Hz, 2H), 3.10-2.90 (m, 5H), 2.67-2.60 (m, 2H), 2.29-2.23 (m, 2H), 1.86-1.72 (m, 2H), 1.56-1.34 (m, 5H), 0.74 (d, J = 6.4 Hz, 6H). |

TABLE 1-continued

Characterization of the compounds of Formula (I)

| Compound No. | Structure | [M + H]⁺ | ¹H-NMR |
|---|---|---|---|
| 92 | 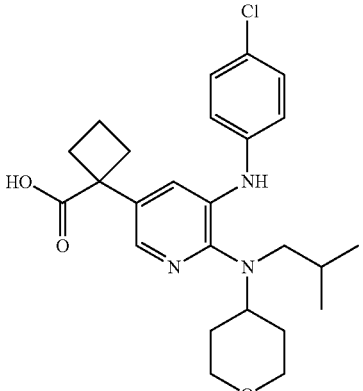 | 458.3 | H-NMR (400 MHz, DMSO-d₆, ppm): δ 7.84 (d, J = 2.0 Hz, 1H), 7.30 (d, J = 2.0 Hz, 1H), 7.19-7.17 (m, 3H), 6.88 (d, J = 8.8 Hz, 2H), 3.77-3.73 (m, 2H), 3.10-2.90 (m, 5H), 2.64-2.58 (m, 2H), 2.33-2.26 (m, 2H), 1.89-1.72 (m, 2H), 1.61-1.51 (m, 2H), 1.44-1.37 (m, 3H), 0.76 (d, J = 7.6 Hz, 6H). |
| 93 | 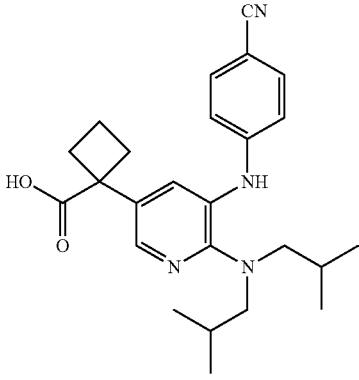 [SMILES: CC(C)CN(CC(C)C)c1ncc(C2(C(=O)O)CCC2)cc1Nc1ccc(C#N)cc1] | 421.3 | H-NMR (400 MHz, DMSO-d₆, ppm): δ 8.26 (s, 1H), 7.96 (d, J = 2.0 Hz, 1H), 7.48 (d, J = 8.8 Hz, 2H), 7.21 (d, J = 2.4 Hz, 1H), 6.61 (d, J = 8.8 Hz, 2H), 3.09 (d, J = 6.8 Hz, 4H), 2.65-2.58 (m, 2H), 2.37-2.30 (m, 2H), 1.95-1.65 (m, 4H), 0.68 (d, J = 6.8 Hz, 12H). |
| 94 | 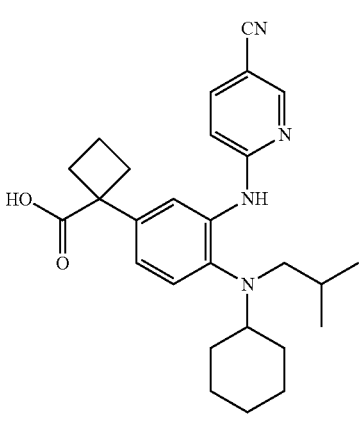 [SMILES: CC(C)CN(c1ccc(C2(C(=O)O)CCC2)cc1Nc1ccc(C#N)cn1)C1CCCCC1] | 447.3 | H-NMR (400 MHz, DMSO-d₆, ppm): δ 8.51 (s, 2H), 7.86 (dd, J1 = 8.8 Hz, J2 = 2.0 Hz, 1H), 7.83 (s, 1H), 7.15 (d, J = 8.4 Hz, 1H), 6.94-6.90 (m, 2H), 2.75 (d, J = 6.8 Hz, 2H), 2.68-2.62 (m, 2H), 2.55-2.52 (m, 1H), 2.38-2.33 (m, 2H), 1.92-1.84 (m, 1H), 1.78-1.73 (m, 1H), 1.69 (d, J = 11.6 Hz, 2H), 1.60-1.59 (m, 2H), 1.42-1.40 (m, 1H), 1.33-1.20 (m, 3H), 0.93-0.90 (m, 3H), 0.77 (d, J = 6.4 Hz, 6H). |
| 95 | 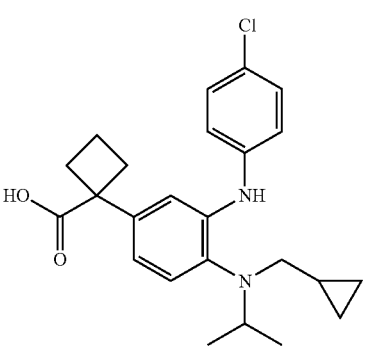 [SMILES: CC(C)N(CC1CC1)c1ccc(C2(C(=O)O)CCC2)cc1Nc1ccc(Cl)cc1] | 413.3 | H-NMR (400 MHz, DMSO-d₆, ppm): δ 7.39 (s, 1H), 7.22-7.19 (m, 2H), 7.15 (d, J = 8.0 Hz, 1H), 7.06-7.05 (m, 2H), 7.03 (s, 1H), 6.76 (dd, J₁ = 8.4Hz, J₂ = 2.0 Hz, 1H), 3.13-3.07 (m, 1H), 2.74 (d, J = 6.4 Hz, 2H), 2.65-2.59 (m, 2H), 2.37-2.29 (m, 2H), 1.91-1.82 (m, 1H), 1.80-1.70 (m, 1H), 0.91 (d, J = 6.8 Hz, 6H), 0.69-0.59 (m, 1H), 0.26-0.22 (m, 2H), 0.02-0.01 (m, 2H). |

TABLE 1-continued

Characterization of the compounds of Formula (I)

| Compound No. | Structure | [M + H]⁺ | ¹H-NMR |
|---|---|---|---|
| 96 | 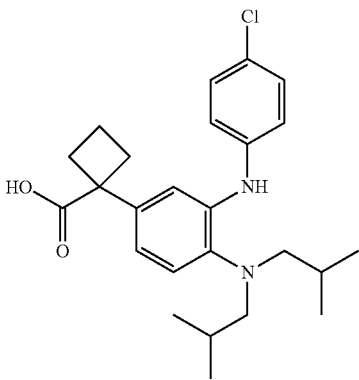 [SMILES: CC(C)CN(CC(C)C)c1ccc(C2(C(=O)O)CCC2)cc1Nc1ccc(Cl)cc1] | 429.3 | H-NMR (400 MHz, CD₃OD, ppm): δ 7.23-7.16 (m, 4H), 7.06-7.04 (m, 2H), 6.83 (dd, J1 = 8.0 Hz, J2 = 2.0 Hz, 1H), 2.79-2.73 (m, 2H), 2.61 (d, J = 7.2 Hz, 4H), 2.49-2.42 (m, 2H), 1.99-1.95 (m, 1H), 1.87-1.84 (m, 1H), 1.74-1.68 (m, 2H), 0.89 (d, J = 6.4 Hz, 12H). |
| 97 | 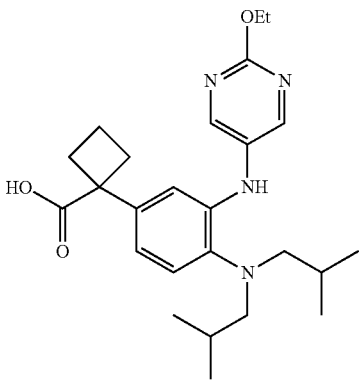 [SMILES: CCOc1ncc(Nc2cc(C3(C(=O)O)CCC3)ccc2N(CC(C)C)CC(C)C)cn1] | 441.3 | H-NMR (400 MHz, DMSO-d₆, ppm): δ 8.33 (s, 2H), 7.13 (d, J = 8.0 Hz, 1H), 6.94 (s, 1H), 6.80 (d, J = 2.0 Hz, 1H), 6.73 (dd, J1 = 8.0 Hz, J2 = 2.0 Hz, 1H), 4.25 (q, J = 7.2 Hz, 2H), 2.60-2.47 (m, 6H), 2.33-2.25 (m, 2H), 1.86-1.58 (m, 4H), 1.28 (t, J = 7.2 Hz, 3H), 0.80 (d, J = 6.4 Hz, 12H). |
| 98 | 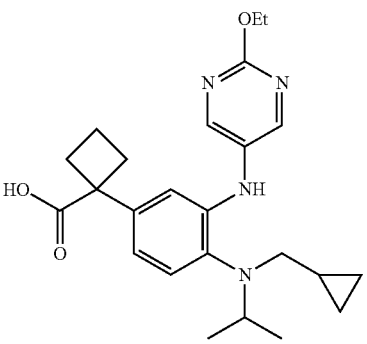 [SMILES: CCOc1ncc(Nc2cc(C3(C(=O)O)CCC3)ccc2N(CC2CC2)C(C)C)cn1] | 425.3 | H-NMR (400 MHz, DMSO-d₆, ppm): δ 8.38 (s, 2H), 7.20 (d, J = 8.0 Hz, 1H), 6.94 (d, J = 2.0 Hz, 1H), 6.83 (dd, J1 = 8.0 Hz, J2 = 2.0 Hz, 1H), 4.37 (q, J = 7.2 Hz, 2H), 3.25-3.19 (m, 1H), 2.82 (d, J = 6.8 Hz, 2H), 2.77-2.70 (m, 2H), 2.46-2.38 (m, 2H), 2.00-1.93 (m, 1H), 1.86-1.79 (m, 1H), 1.38 (t, J = 7.2 Hz, 3H), 1.02 (d, J = 6.4 Hz, 6H), 0.74-0.68 (m, 1H), 0.31-0.26 (m, 2H), 0.02-0.00 (m, 2H). |
| 99 | 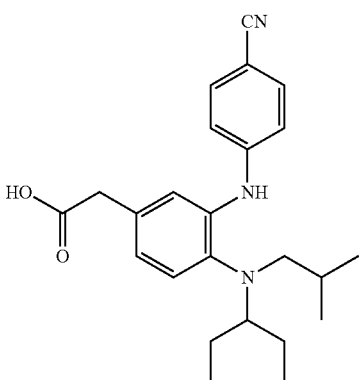 | 406.3 | H-NMR (400 MHz, DMSO-d₆, ppm): δ 7.57-7.52 (m, 3H), 7.15 (s, 1H), 7.08-7.00 (m, 3H), 6.89 (d, J = 7.6 Hz, 1H), 3.48 (s, 2H), 2.74-2.72 (m, 2H), 2.60-2.50 (m, 1H), 1.64-1.56 (m, 4H), 1.40-1.34 (m, 2H), 1.26-1.23 (m, 2H), 0.90-0.80 (m, 3H), 0.77 (d, J = 6.8 Hz, 6H). |

TABLE 1-continued

Characterization of the compounds of Formula (I)

| Compound No. | Structure | [M + H]⁺ | ¹H-NMR |
|---|---|---|---|
| 100 | 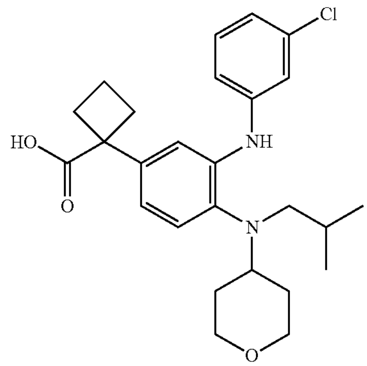 [SMILES: CC(C)CN(c1ccc(C2(C(=O)O)CCC2)cc1Nc1cccc(Cl)c1)C1CCOCC1] | 457.3 | H-NMR (400 MHz, DMSO-d₆, ppm): δ 7.23 (s, 1H), 7.18 (t, J = 8.0 Hz, 1H), 7.14 (d, J = 8.4 Hz, 1H), 7.08 (d, J = 1.6 Hz, 1H), 7.05 (s, 1H), 6.97 (d, J = 8.0 Hz, 1H), 6.82-6.79 (m, 2H), 3.76 (dd, J1 = 11.2 Hz, J2 = 3.2 Hz, 2H), 3.03 (t, J = 11.2 Hz, 2H), 2.85-2.79 (m, 1H), 2.73 (d, J = 6.4 Hz, 2H), 2.66-2.59 (m, 2H), 2.37-2.29 (m, 2H), 1.89-1.83 (m, 1H), 1.80-1.72 (m, 1H), 1.59-1.57 (m, 2H), 1.52-1.42 (m, 2H), 1.36-1.29 (m, 1H), 0.77 (d, J = 6.8 Hz, 6H). |
| 101 | 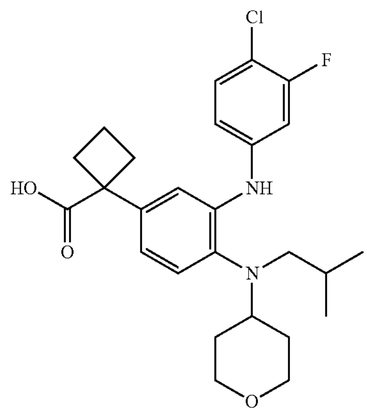 [SMILES: CC(C)CN(c1ccc(C2(C(=O)O)CCC2)cc1Nc1ccc(Cl)c(F)c1)C1CCOCC1] | 475.3 | H-NMR (400 MHz, DMSO-d₆, ppm): δ 7.33-7.29 (m, 2H), 7.14 (d, J = 8.4 Hz, 1H), 7.07 (d, J = 2.0 Hz, 1H), 6.96 (dd, J1 = 12.4 Hz, J2 = 2.4 Hz, 1H), 6.86-6.84 (m, 2H), 3.76 (dd, J1 = 10.8 Hz, J2 = 2.8 Hz, 2H), 3.02 (t, J = 6.4 Hz, 2H), 2.86-2.80 (m, 1H), 2.73 (d, J = 6.4 Hz, 2H), 2.66-2.59 (m, 2H), 2.37-2.30 (m, 2H), 1.92-1.83 (m, 1H), 1.81-1.71 (m, 1H), 1.57-1.42 (m, 4H), 1.35-1.29 (m, 1H), 0.76 (d, J = 6.4 Hz, 6H). |
| 102 | 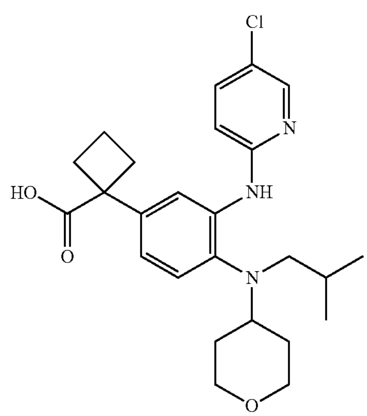 [SMILES: CC(C)CN(c1ccc(C2(C(=O)O)CCC2)cc1Nc1ccc(Cl)cn1)C1CCOCC1] | 458.3 | H-NMR (400 MHz, DMSO-d₆, ppm): δ 8.18 (s, 1H), 8.15 (d, J = 2.8 Hz, 1H), 8.10 (d, J = 2.0 Hz, 1H), 7.64 (dd, J1 = 8.8 Hz, J2 = 2.8 Hz, 1H), 7.18 (d, J = 8.4 Hz, 1H), 6.97 (d, J = 8.8 Hz, 1H), 6.82 (dd, J1 = 8.0 Hz, J2 = 2.0 Hz, 1H), 3.79-3.76 (m, 2H), 3.10 (t, J = 10.8 Hz, 2H), 2.83-2.80 (m, 1H), 2.76 (d, J = 6.8 Hz, 2H), 2.69-2.63 (m, 2H), 2.40-2.34 (m, 2H), 1.92-1.86 (m, 1H), 1.84-1.71 (m, 1H), 1.64-1.62 (m, 2H), 1.52-1.42 (m, 2H), 1.35-1.25 (m, 1H), 0.79 (d, J = 6.4 Hz, 6H). |
| 103 | 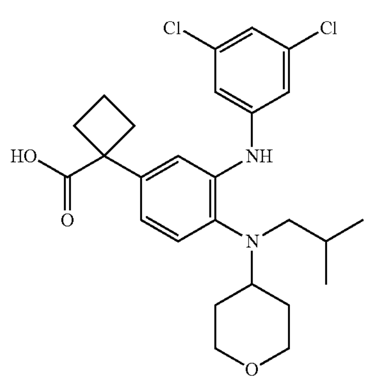 [SMILES: CC(C)CN(c1ccc(C2(C(=O)O)CCC2)cc1Nc1cc(Cl)cc(Cl)c1)C1CCOCC1] | 491.2 | H-NMR (400 MHz, DMSO-d₆, ppm): δ 12.31 (brs, 1H), 7.47 (s, 1H), 7.15 (d, J = 8.0 Hz, 1H), 7.06 (d, J = 1.6 Hz, 1H), 6.94 (d, J = 1.2 Hz, 2H), 6.90 (dd, J = 8.0 Hz, J = 1.6 Hz, 1H), 6.84 (s, 1H), 3.77 (d, J = 10.8 Hz, 2H), 3.05-2.99 (m, 2H), 2.92-2.85 (m, 1H), 2.72 (d, J = 6.4 Hz, 2H), 2.67-2.61 (m, 2H), 2.37-2.30 (m, 2H), 1.91-1.84 (m, 1H), 1.80-1.74 (m, 1H), 1.56-1.47 (m, 4H), 1.36-1.29 (m, 1H), 0.76 (d, J = 6.8 Hz, 6H). |

TABLE 1-continued

Characterization of the compounds of Formula (I)

| Compound No. | Structure | [M + H]⁺ | ¹H-NMR |
|---|---|---|---|
| 104 | 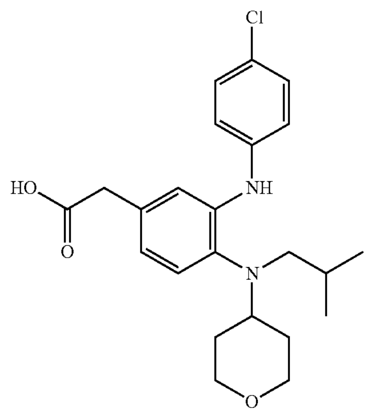 [SMILES: CC(C)CN(c1ccc(CC(=O)O)cc1Nc1ccc(Cl)cc1)C1CCOCC1] | 417.2 | H-NMR (400 MHz, DMSO-d₆, ppm): δ 12.26 (brs, 1H), 7.24-7.20 (m, 3H), 7.13-7.08 (m, 4H), 6.73 (d, J = 7.6 Hz, 1H), 3.76 (d, J = 10.8 Hz, 2H), 3.45 (s, 2H), 3.06 (t, J = 11.2 Hz, 2H), 2.81-2.74 (m, 3H), 1.62-1.59 (m, 2H), 1.51-1.43 (m, 2H), 1.36-1.31 (m, 1H), 0.78 (d, J = 6.0 Hz, 6H). |
| 105 | 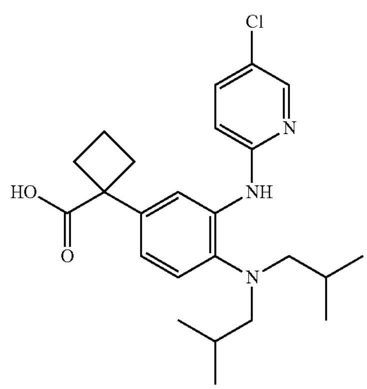 | 430.3 | H-NMR (400 MHz, DMSO-d₆, ppm): δ 12.22 (brs, 1H), 8.23 (s, 1H), 8.17 (d, J = 2.8 Hz, 1H), 8.05 (d, J = 2.0 Hz, 1H), 7.65 (dd, J1 = 8.8 Hz, J2 = 2.8 Hz, 1H), 7.20 (d, J = 8.0 Hz, 1H), 6.83 (dd, J1 = 8.0 Hz, J2 = 2.0 Hz, 1H), 6.79 (d, J = 8.8 Hz, 1H), 2.69-2.63 (m, 2H), 2.56 (d, J = 6.8 Hz, 4H), 2.40-2.32 (m, 2H), 1.88-1.86 (m, 1H), 1.77-1.76 (m, 1H), 1.65-1.58 (m, 2H), 0.83 (d, J = 6.8 Hz, 12H). |
| 106 | 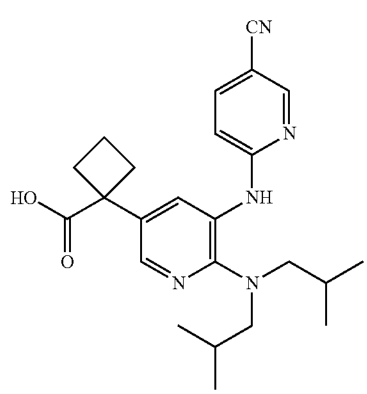 [SMILES: CC(C)CN(CC(C)C)c1ncc(C2(C(=O)O)CCC2)cc1Nc1ccc(C#N)cn1] | 422.3 | H-NMR (400 MHz, DMSO-d₆, ppm): δ 9.05 (s, 1H), 8.41 (d, J = 2.0 Hz, 1H), 7.94 (d, J = 2.0 Hz, 1H), 7.84 (dd, J = 2.0 Hz, 8.8 Hz, 1H), 7.55 (d, J = 2.0 Hz, 1H), 6.63 (d, J = 8.8 Hz, 1H), 3.09 (d, J = 6.8 Hz, 4H), 2.66-2.60 (m, 2H), 2.38-2.31 (m, 2H), 1.93-1.68 (m, 4H), 0.70 (d, J = 6.4 Hz, 12H). |

TABLE 1-continued

Characterization of the compounds of Formula (I)

| Compound No. | Structure | [M + H]⁺ | ¹H-NMR |
|---|---|---|---|
| 107 | 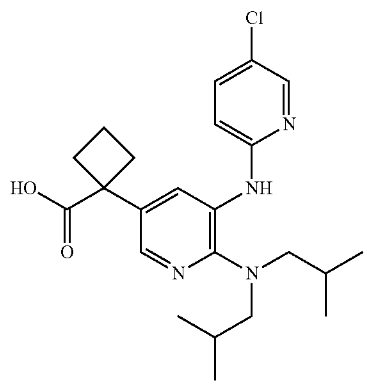 [SMILES: CC(C)CN(CC(C)C)c1ncc(C2(C(=O)O)CCC2)cc1Nc1ccc(Cl)cn1] | 431.3 | H-NMR (400 MHz, DMSO-d₆, ppm): δ 8.29 (s, 1H), 8.05 (d, J = 2.8 Hz, 1H), 7.85 (d, J = 2.4 Hz, 1H), 7.79 (d, J = 2.4 Hz, 1H), 7.60 (dd, J = 2.8 Hz, 8.8 Hz, 1H), 6.70 (d, J = 8.8 Hz, 1H), 3.02 (d, J = 6.8 Hz, 4H), 2.67-2.60 (m, 2H), 2.39-2.32 (m, 2H), 1.91-1.67 (m, 4H), 0.74 (d, J = 6.4 Hz, 12H). |
| 108 | 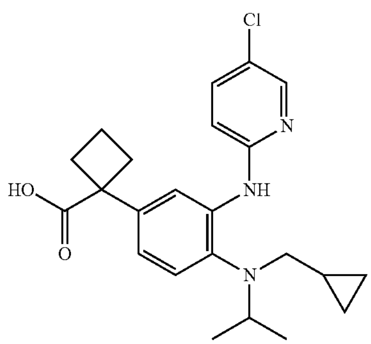 [SMILES: CC(C)N(CC1CC1)c1ccc(C2(C(=O)O)CCC2)cc1Nc1ccc(Cl)cn1] | 405.3 | H-NMR (400 MHz, DMSO-d₆, ppm): δ 8.90 (s, 1H), 8.52 (d, J = 2.4 Hz, 1H), 7.96 (d, J = 1.6 Hz, 1H), 7.85 (dd, J1 = 2.4 Hz, J2 = 8.4 Hz, 1H), 7.22 (d, J = 8.4 Hz, 1H), 6.97 (d, J = 8.4 Hz, 1H), 6.94-6.92 (dd, J1 = 2.0 Hz, J2 = 8.0 Hz, 1H), 3.16-3.10 (m, 1H), 2.75 (d, J = 6.8 Hz, 2H), 2.69-2.63 (m, 2H), 2.40-2.33 (m, 2H), 1.93-1.84 (m, 1H), 1.82-1.72 (m, 1H), 0.91 (d, J = 6.4 Hz, 6H), 0.63-0.59 (m, 1H), 0.26-0.21 (m, 2H), 0.03-0.00 (m, 2H). |
| 109 | 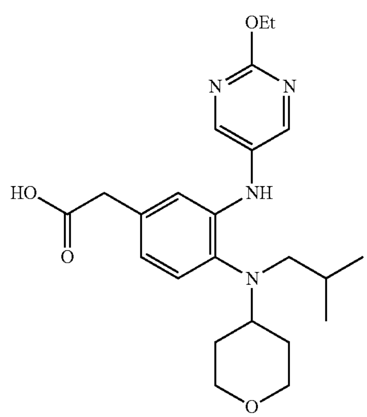 [SMILES: CCOc1ncc(Nc2cc(CC(=O)O)ccc2N(CC(C)C)C2CCOCC2)cn1] | 429.3 | H-NMR (400 MHz, DMSO-d₆, ppm): δ 8.41 (s, 2H), 7.12-7.05 (m, 2H), 6.84 (s, 1H), 6.66 (d, J = 7.2 Hz, 1H), 4.28 (q, J = 7.2 Hz, 2H), 3.81-3.78 (m, 2H), 3.41 (s, 2H), 3.14 (t, J = 11.6 Hz, 2H), 2.83-2.76 (m, 3H), 1.72-1.67 (m, 2H), 1.55-1.45 (m, 2H), 1.36-1.28 (m, 4H), 0.79 (d, J = 6.8 Hz, 6H). |
| 110 | 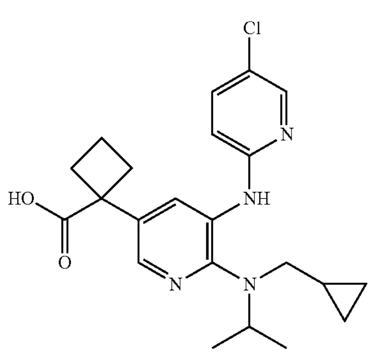 [SMILES: CC(C)N(CC1CC1)c1ncc(C2(C(=O)O)CCC2)cc1Nc1ccc(Cl)cn1] | 406.3 | H-NMR (400 MHz, DMSO-d₆, ppm): δ 9.01 (s, 1H), 8.48 (d, J = 1.6 Hz, 1H), 7.98 (d, J = 2.0 Hz, 1H), 7.87-7.85 (m, 2H), 6.79 (d, J = 9.2 Hz, 1H), 3.64-3.60 (m, 1H), 2.98 (d, J = 6.4 Hz, 2H), 2.70-2.63 (m, 2H), 2.47-2.35 (m, 2H), 1.93-1.79 (m, 2H), 0.91 (d, J = 6.4 Hz, 6H), 0.81-0.76 (m, 1H), 0.29-0.25 (m, 2H), 0.02-0.00 (m, 2H). |

TABLE 1-continued

Characterization of the compounds of Formula (I)

| Compound No. | Structure | [M + H]⁺ | ¹H-NMR |
|---|---|---|---|
| 111 | 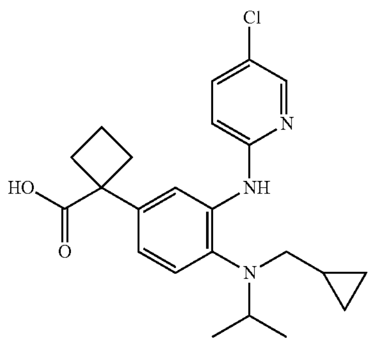 [SMILES: CC(C)N(CC1CC1)c1ccc(C2(C(=O)O)CCC2)cc1Nc1ccc(Cl)cn1] | 415.2 | H-NMR (400 MHz, DMSO-d$_6$, ppm): δ 8.48 (s, 1H), 8.11 (dd, J = 2.0 Hz, 5.6 Hz, 2H), 7.91 (d, J = 2.0 Hz, 1H), 7.64 (dd, J = 2.4 Hz, 8.8 Hz, 1H), 6.93 (d, J = 8.8 Hz, 1H), 3.58-3.55 (m, 1H), 2.99 (d, J = 6.4 Hz, 2H), 2.70-2.64 (m, 2H), 2.47-2.36 (m, 2H), 1.96-1.77 (m, 2H), 0.96 (d, J = 6.8 Hz, 6H), 0.76-0.71 (m, 1H), 0.27-0.22 (m, 2H), 0.03-0.00 (m, 2H). |
| 112 | 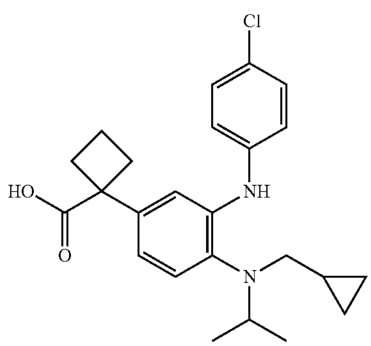 | 404.3 | H-NMR (400 MHz, DMSO-d$_6$, ppm): δ 8.01 (s, 1H), 7.51 (d, J = 7.6 Hz, 2H), 7.17 (d, J = 8.4 Hz, 1H), 7.09 (s, 1H), 6.99 (d, J = 8.4 Hz, 2H), 6.93 (d, J = 8.4 Hz, 1H), 3.21-3.14 (m, 1H), 2.74 (d, J = 6.0 Hz, 2H), 2.66-2.60 (m, 2H), 2.37-2.32 (m, 2H), 1.90-1.83 (m, 1H), 1.81-1.75 (m, 1H), 0.85 (d, J = 6.4 Hz, 6H), 0.74-0.67 (m, 1H), 0.28-0.26 (m, 2H), 0.01-0.00 (m, 2H). |
| 113 | 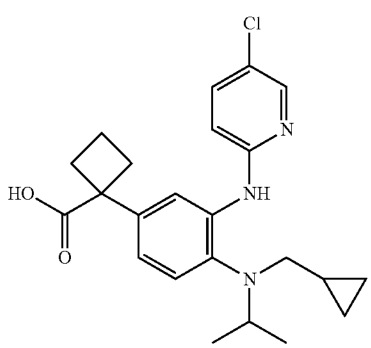 [SMILES: CC(C)N(CC1CC1)c1ccc(C2(C(=O)O)CCC2)cc1Nc1ccc(Cl)cn1] | 414.2 | H-NMR (400 MHz, DMSO-d$_6$, ppm): δ 8.41 (s, 1H), 8.14 (d, J = 2.4 Hz, 1H), 8.07 (d, J = 2.0 Hz, 1H), 7.61 (dd, J1 = 2.4 Hz, J2 = 8.8 Hz, 1H), 7.19 (d, J = 8.0 Hz, 1H), 6.97 (d, J = 8.8 Hz, 1H), 6.83-6.81 (dd, J1 = 2.0 Hz, J2 = 8.0 Hz, 1H), 3.12-3.05 (m, 1H), 2.75 (d, J = 6.8 Hz, 2H), 2.69-2.62 (m, 2H), 2.39-2.35 (m, 2H), 1.92-1.84 (m, 1H), 1.81-1.71 (m, 1H), 0.94 (d, J = 6.4 Hz, 6H), 0.62-0.58 (m, 1H), 0.23-0.21 (m, 2H), 0.02-0.00 (m, 2H). |
| 114 | 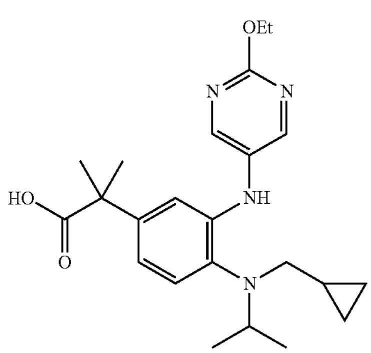 [SMILES: CCOc1ncc(Nc2cc(C(C)(C)C(=O)O)ccc2N(CC2CC2)C(C)C)cn1] | 413.3 | H-NMR (400 MHz, DMSO-d$_6$, ppm): δ 8.32 (s, 2H), 7.34 (s, 1H), 7.13 (d, J = 8.4 Hz, 1H), 6.93 (d, J = 2.0 Hz, 1H), 6.81 (dd, J1 = 2.0 Hz, J2 = 8.4 Hz, 1H), 4.25 (q, J = 7.2 Hz, 2H), 3.20-3.14 (m, 1H), 2.74 (d, J = 6.8 Hz, 2H), 1.38 (s, 6H), 1.28 (t, J = 7.2 Hz, 3H), 0.90 (d, J = 6.4 Hz, 6H), 0.69-0.64 (m, 1H), 0.27-0.23 (m, 2H), 0.02-0.01 (m, 2H). |

TABLE 1-continued

Characterization of the compounds of Formula (I)

| Compound No. | Structure | [M + H]+ | 1H-NMR |
|---|---|---|---|
| 115 | 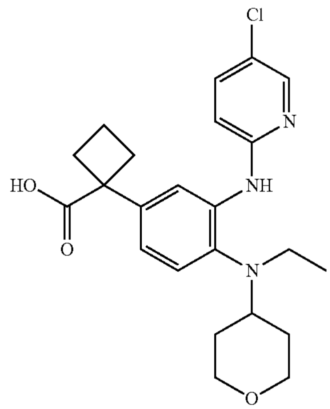 | 430.2 | H-NMR (400 MHz, DMSO-$d_6$, ppm): δ 12.22 (s, 1H), 8.36 (s, 1H), 8.16-8.13 (m, 2H), 7.62 (dd, J = 8.8 Hz, J = 2.8 Hz, 1H), 7.15 (d, J = 8.0 Hz, 1H), 7.05 (d, J = 8.8 Hz, 1H), 6.83-6.81 (m, 1H), 3.78-3.75 (m, 2H), 3.15 (t, J = 11.2 Hz, 2H), 3.00-2.91 (m, 3H), 2.69-2.63(m, 2H), 2.41-2.34 (m, 2H), 1.91-1.73 (m, 2H), 1.64-1.62 (m, 2H), 1.45-1.35 (m, 2H), 0.81-0.77 (m, 3H). |
| 116 | 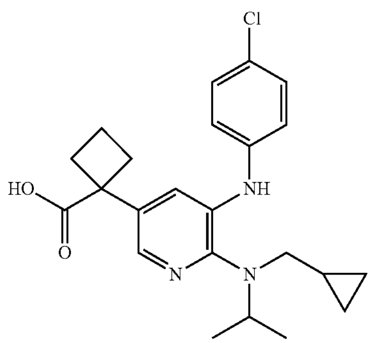 [SMILES: CC(C)N(CC1CC1)c1ncc(C2(C(=O)O)CCC2)cc1Nc1ccc(Cl)cc1] | 405.2 | H-NMR (400 MHz, DMSO-$d_6$, ppm): δ 8.45 (s, 1H), 7.96 (s, 1H), 7.51 (d, J = 8.8 Hz, 2H), 7.40 (s, 1H), 6.76 (d, J = 8.8 Hz, 2H), 3.87-3.80 (m, 1H), 2.98 (d, J = 6.0 Hz, 2H), 2.68-2.61 (m, 2H), 2.42-2.34 (m, 2H), 1.95-1.76 (m, 2H), 0.94-0.85 (m, 1H), 0.81 (d, J = 6.4 Hz, 6H), 0.35-0.33 (m, 2H), 0.05-0.03 (m, 2H). |
| 117 | 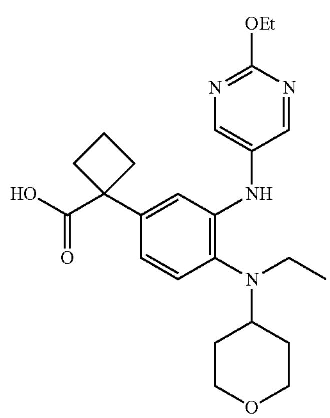 [SMILES: CCOc1ncc(Nc2cc(C3(C(=O)O)CCC3)ccc2N(CC)C2CCOCC2)cn1] | 441.3 | H-NMR (400 MHz, DMSO-$d_6$, ppm): δ 12.2 (brs, 1H), 8.38 (s, 2H), 7.32 (s, 1H), 7.10 (d, J = 8.0 Hz, 1H), 6.80 (s, 1H), 6.70 (d, J = 8.0 Hz, 1H), 4.29-4.24 (m, 2H), 3.78 (d, J = 11.2 Hz, 2H), 3.20-3.15 (m, 2H), 3.02-2.93 (m, 3H), 2.62-2.56 (m, 2H), 2.34-2.27 (m, 2H), 1.87-1.62 (m, 4H), 1.46-1.37 (m, 2H), 1.30-1.27 (m, 3H), 0.83-0.80 (m, 3H). |

TABLE 1-continued
Characterization of the compounds of Formula (I)
| Compound No. | Structure | [M + H]⁺ | ¹H-NMR |
|---|---|---|---|
| 118 | 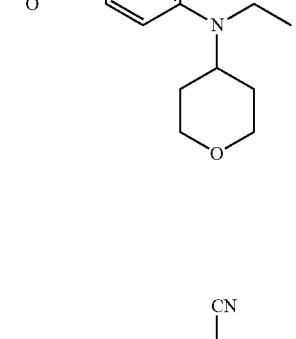 | 421.2 | H-NMR (400 MHz, DMSO-d$_6$, ppm): δ 8.89 (d, J = 6.4 Hz, 1H), 8.52 (d, J = 2.0 Hz, 1H), 7.99-7.98 (m, 1H), 7.87 (dd, J = 8.8 Hz, J = 2.0 Hz, 1H), 7.24 (s, 1H), 7.04 (d, J = 8.8 Hz, 1H), 6.98 (s, 1H), 3.77 (d, J = 9.6 Hz, 2H), 3.15-3.04 (m, 5H), 2.70-2.63 (m, 2H), 2.41-2.33 (m, 2H), 1.92-1.73 (m, 2H), 1.61-1.59 (m, 2H), 1.47-1.38 (m, 2H), 0.83-0.79 (m, 3H). |
| 119 | 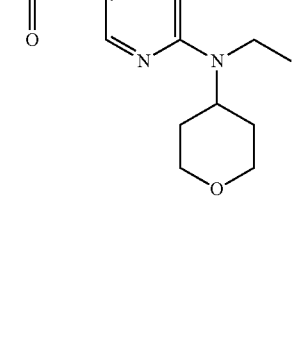 | 422.2 | H-NMR (400 MHz, DMSO-d$_6$, ppm): δ 9.01 (d, J = 9.6 Hz, 1H), 8.48 (d, J = 2.0 Hz, 1H), 7.98-7.97 (m, 2H), 7.87 (dd, J = 8.8 Hz, J = 1.6 Hz, 1H), 6.88 (d, J = 8.8 Hz, 1H), 3.78-3.76 (m, 3H), 3.17-3.05 (m, 4H), 2.70-2.64 (m, 2H), 2.42-2.35 (m, 2H), 1.95-1.78 (m, 2H), 1.61-1.54 (m, 2H), 1.49-1.46 (m, 2H), 0.86-0.83 (m, 3H). |
| 120 | 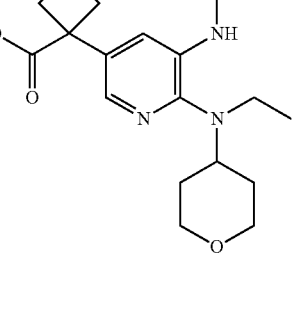 | 430.2 | H-NMR (400 MHz, DMSO-d$_6$, ppm): δ 7.85 (d, J = 2.4 Hz, 1H), 7.51 (s, 1H), 7.27 (d, J = 2.0 Hz, 1H), 7.18 (d, J = 8.8 Hz, 2H), 6.87 (d, J = 8.8 Hz, 2H), 3.78-3.75 (m, 2H), 3.52-3.45 (m, 1H), 3.15-3.07 (m, 4H), 2.66-2.59 (m, 2H), 2.39-2.32 (m, 2H), 1.94-1.85 (m, 1H), 1.83-1.73 (m, 1H), 1.58-1.48 (m, 2H), 1.45-1.42 (m, 2H), 0.83 (t, J = 7.2 Hz, 3H). |

TABLE 1-continued

Characterization of the compounds of Formula (I)

| Compound No. | Structure | [M + H]+ | ¹H-NMR |
|---|---|---|---|
| 121 | 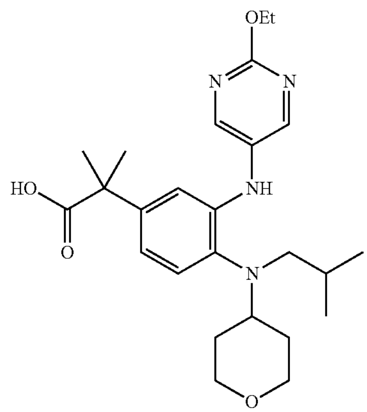 [SMILES: CCOc1ncc(Nc2cc(C(C)(C)C(=O)O)ccc2N(CC(C)C)C2CCOCC2)cn1] | 457.3 | H-NMR (400 MHz, DMSO-d$_6$, ppm): δ 8.36 (s, 2H), 7.12 (d, J = 8.4 Hz, 1H), 7.02 (s, 1H), 6.87 (d, J = 1.6 Hz, 1H), 6.77 (d, J = 7.6 Hz, 1H), 4.26 (q, J1 = 7.2 Hz, 2H), 3.79-3.76 (dd, J1 = 3.2 Hz, J2 = 10.8 Hz, 2H), 3.12 (t, J = 11.2 Hz, 2H), 2.86-2.83 (m, 1H), 2.75-2.73 (m, 2H), 1.66-1.63 (m, 2H), 1.53-1.43 (m, 2H), 1.35 (s, 6H), 1.32-1.30 (m, 1H), 1.28 (t, J = 7.2 Hz, 3H), 0.78 (d, J = 6.8 Hz, 6H). |
| 122 | 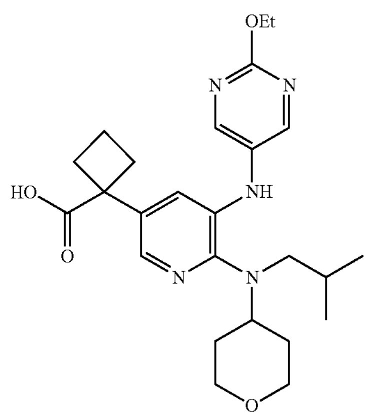 [SMILES: CCOc1ncc(Nc2cc(C3(C(=O)O)CCC3)cnc2N(CC(C)C)C2CCOCC2)cn1] | 470.3 | H-NMR (400 MHz, DMSO-d$_6$, ppm): δ 8.31 (s, 2H), 7.76 (d, J = 2.0 Hz, 1H), 7.16-7.13 (m, 2H), 4.27 (q, J = 7.2 Hz, 2H), 3.80 (d, J = 10.4 Hz, 2H), 3.37-3.31 (m, 1H), 3.17-3.12 (m, 2H), 2.96 (d, J = 6.8 Hz, 2H), 2.62-2.57 (m, 2H), 2.38-2.31 (m, 2H), 1.87-1.80 (m, 1H), 1.80-1.70 (m, 1H), 1.62-1.53 (m, 4H), 1.40-1.30 (m, 1H), 1.30 (t, J = 7.2 Hz, 3H), 0.79 (d, J = 6.4 Hz, 6H). |
| 123 | 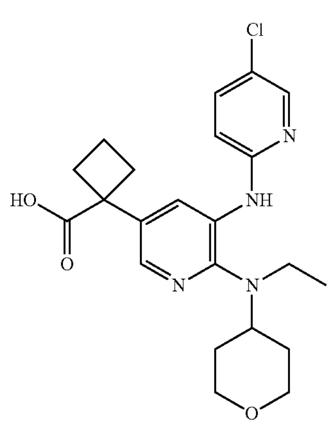 [SMILES: CCN(c1ncc(C2(C(=O)O)CCC2)cc1Nc1ccc(Cl)cn1)C1CCOCC1] | 431.2 | H-NMR (400 MHz, DMSO-d$_6$, ppm): δ 8.38 (s, 1H), 8.21 (d, J = 2.4 Hz, 1H), 8.11 (d, J = 2.4 Hz, 1H), 7.89 (d, J = 2.4 Hz, 1H), 7.64 (dd, J = 2.4 Hz, 8.8 Hz, 1H), 6.99 (d, J = 8.8 Hz, 1H), 3.79-3.76 (m, 2H), 3.38-3.35 (m, 1H), 3.17-3.09 (m, 4H), 2.70-2.64 (m, 2H), 2.46-2.36 (m, 2H), 1.94-1.78 (m, 2H), 1.57-1.52 (m, 4H), 0.82 (t, J = 6.8 Hz, 3H). |

TABLE 1-continued

Characterization of the compounds of Formula (I)

| Compound No. | Structure | [M + H]⁺ | ¹H-NMR |
|---|---|---|---|
| 124 | 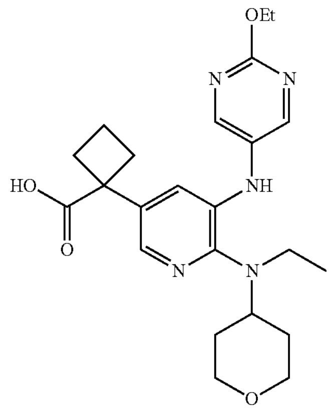 [SMILES: CCOc1ncc(Nc2cc(C3(C(=O)O)CCC3)cnc2N(CC)C2CCOCC2)cn1] | 442.3 | H-NMR (400 MHz, DMSO-d₆, ppm): δ 8.26 (s, 2H), 7.79 (d, J = 2.0 Hz, 1H), 7.42 (s, 1H), 7.09 (d, J = 2.0 Hz, 1H), 4.26 (q, J = 7.2 Hz, 2H), 3.79-3.76 (m, 2H), 3.42-3.37 (m, 1H), 3.20-3.14 (m, 2H), 3.11 (q, J = 6.8 Hz, 2H), 2.64-2.58 (m, 2H), 2.39-2.31 (m, 2H), 1.89-1.76 (m, 2H), 1.53-1.48 (m, 4H), 1.27 (t, J = 7.2 Hz, 3H), 0.86 (t, J = 6.8 Hz, 3H). |
| 125 | 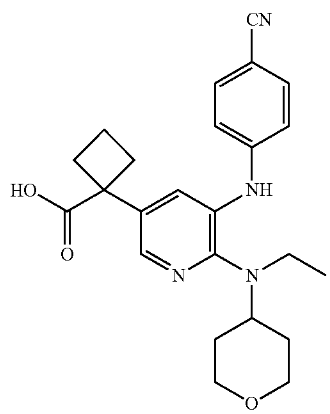 [SMILES: CCN(c1ncc(C2(C(=O)O)CCC2)cc1Nc1ccc(C#N)cc1)C1CCOCC1] | 421.2 | H-NMR (400 MHz, DMSO-d₆, ppm): δ 8.29 (s, 1H), 7.98 (d, J = 2.4 Hz, 1H), 7.50 (d, J = 8.8 Hz, 2H), 7.33 (d, J = 2.4 Hz, 1H), 6.75 (d, J = 8.8 Hz, 2H), 3.77-3.74 (m, 2H), 3.63-3.58 (m, 1H), 3.16 (q, J = 6.8 Hz, 2H), 3.08-3.02 (m, 2H), 2.67-2.60 (m, 2H), 2.40-2.33 (m, 2H), 1.93-1.77 (m, 2H), 1.62-1.52 (m, 2H), 1.36-1.34 (m, 2H), 0.86 (t, J = 6.8 Hz, 3H). |
| 126 | 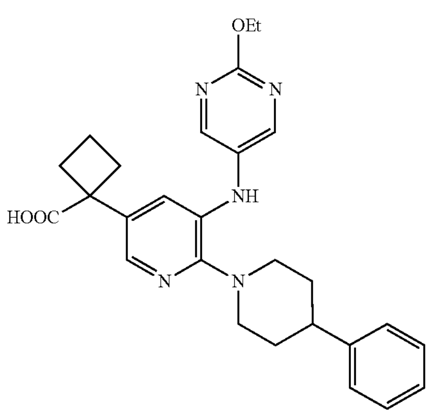 [SMILES: CCOc1ncc(Nc2cc(C3(C(=O)O)CCC3)cnc2N2CCC(c3ccccc3)CC2)cn1] | 474.1 | H-NMR (400 MHz, DMSO-d₆, ppm): δ 8.16 (s, 2H), 7.92 (s, 1H), 7.78 (d, J = 2.4 Hz, 1H), 7.26-7.22 (m, 3H), 7.17-7.15 (m, 1H), 7.13-7.08 (m, 2H), 4.28 (q, J = 7.2 Hz, 2H), 3.59 (d, J = 12.4 Hz, 2H), 2.73 (t, J = 11.7 Hz, 2H), 2.64 (tt, J = 15.3, 6.1 Hz, 2H), 2.54 (dd, J = 25.6, 13.4 Hz, 1H), 2.42-2.32 (m, 2H), 1.94 (ddd, J = 23.8, 13.4, 7.4 Hz, 1H), 1.85-1.73 (m, 1H), 1.64 (d, J = 10.8 Hz, 2H), 1.38-1.22 (m, 5H). |

TABLE 1-continued

Characterization of the compounds of Formula (I)

| Compound No. | Structure | [M + H]+ | 1H-NMR |
|---|---|---|---|
| 127 | 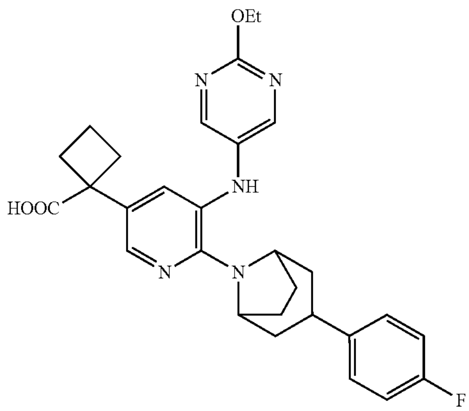 [SMILES: CCOc1ncc(Nc2cc(C3(C(=O)O)CCC3)cnc2N2C3CCC2CC(c2ccc(F)cc2)C3)cn1] | 518.1 | H-NMR (400 MHz, DMSO-d6, ppm): δ 12.38 (brs, 1H), 8.03 (d, J = 8.8 Hz, 2H), 7.80 (d, J = 2.0 Hz, 1H), 7.61(s, 1H), 7.16-7.11 (m, 3H), 7.04-6.99 (m, 2H), 4.41 (s, 2H), 4.24 (q, J = 7.2 Hz, 2H), 2.65-2.59 (m, 2H), 2.38-2.31 (m, 2H), 2.15-2.08 (m, 2H), 1.89-1.85 (m, 1H), 1.82-1.75 (m, 1H), 1.73-1.69 (m, 2H), 1.51-1.47 (m, 2H), 1.39-1.33 (m, 2H), 1.28-1.24 (t, J = 7.2 Hz, 3H), 1.20 (s, 1H). |
| 128 | 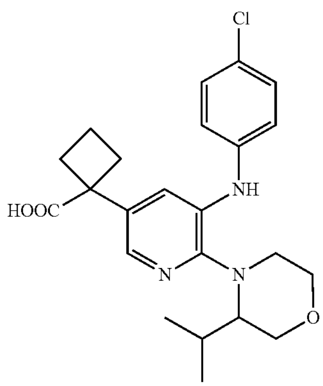 [SMILES: CC(C)C1COCCN1c1ncc(C2(C(=O)O)CCC2)cc1Nc1ccc(Cl)cc1] | 430.1 | H-NMR (400 MHz, DMSO-d6, ppm): δ 12.40 (brs, 1H), 7.85 (d, J = 2.0 Hz, 1H), 7.59 (s, 1H), 7.22-7.17 (m, 3H), 6.80-6.78 (m, 2H), 3.70 (dd, J = 7.3, 4.1 Hz, 1H), 3.56 (dd, J = 11.1, 4.4 Hz, 1H), 3.58-3.30 (m, 2H), 3.27-3.21 (m, 2H), 3.11-3.09 (m, 1H), 2.62 (ddd, J = 11.8, 8.8, 5.5 Hz, 2H), 2.47-2.30 (m, 2H), 2.07-2.05 (m, 1H), 1.89-1.71 (m, 2H), 0.72 (d, J = 6.8 Hz, 3H), 0.59 (d, J = 6.8 Hz, 3H). |

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of Formula (I) provided herein can be prepared from readily available starting materials using the following general methods and procedures. Exemplary schematic illustrations for synthesizing the compounds of the invention described herein are provided below. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

The compounds of the invention may be prepared according to the general Scheme A. Compounds A1, where G=halogen are commercially available or can be assembled via standard transformations known to those of ordinary proficiency in the art of organic/medicinal chemistry. Compounds A2 can be prepared from A1 by base or palladium promoted displacement of the halogen by amines $HNR^4R^5$ in a solvent such as THF, DMF, NMP or the like. Reduction of the nitro group can be done under reductive conditions such as but not limited to palladium on charcoal under an atmosphere of hydrogen and in a solvent such as methanol or ethyl acetate to afford intermediates A3. Treatment of anilines A3 with an isocyanate A4, in a solvent such as THF at a temperature between ambient and the boiling point of the solvent, to afford intermediate A5. Nitriles A5 could be hydrolyzed under either acidic or alkaline conditions to make I-a. On the other hand, nitriles A5 could be converted into tetrazoles I-b by heating with an azide such as $NaN_3$, $TMSN_3$ or tributyltinazide in a solvent such as toluene at or near the boiling point.

Scheme A. Preparation of Compounds of Formula (I)

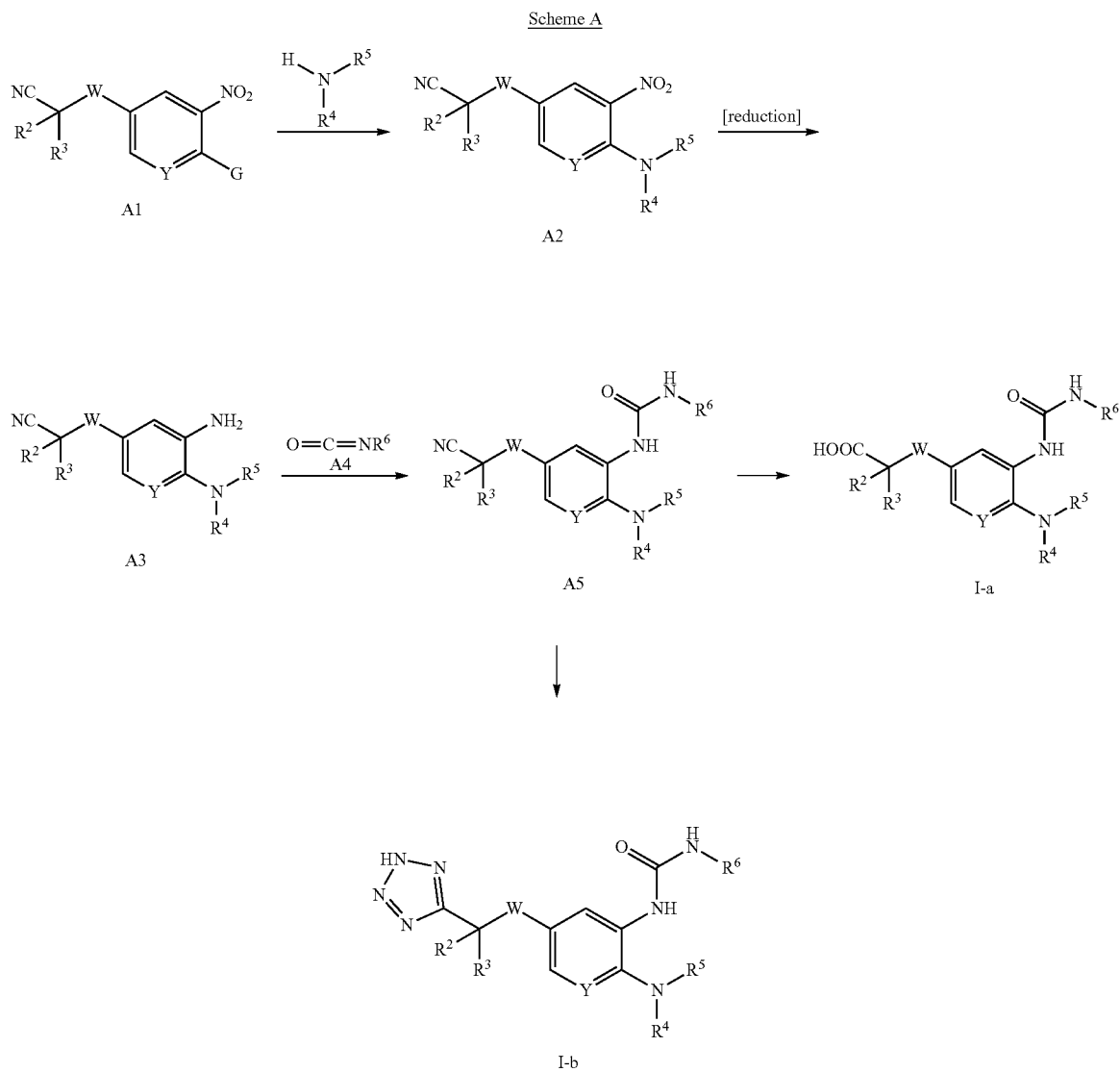

Scheme B. Preparation of Acid Derivatives I-a.

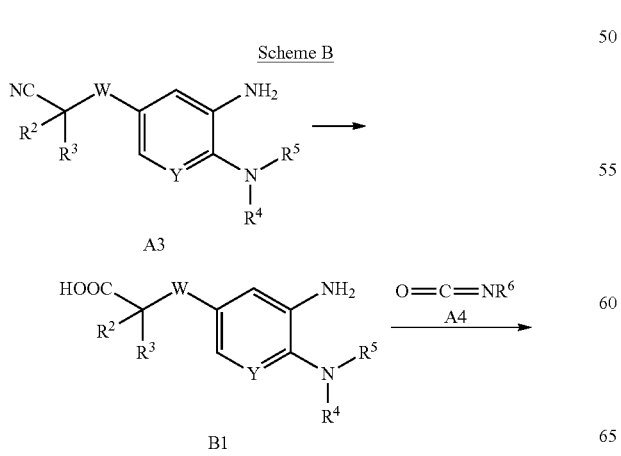

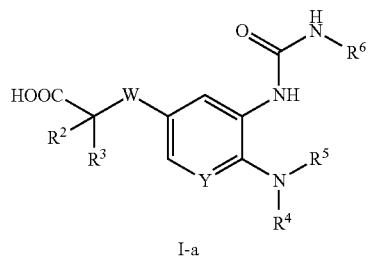

Scheme B illustrates an alternative way to convert intermediates A3 to acid derivatives I-a. Nitriles A3 could be hydrolyzed under either acidic or alkaline conditions to make B1. Treatment of anilines B1 with an isocyanate A4, in a solvent such as THF at a temperature between ambient and the boiling point of the solvent, to afford I-a.

Scheme C. Preparation of Compounds of Formula (I)

Scheme D. Preparation of Compounds of Formula (I)

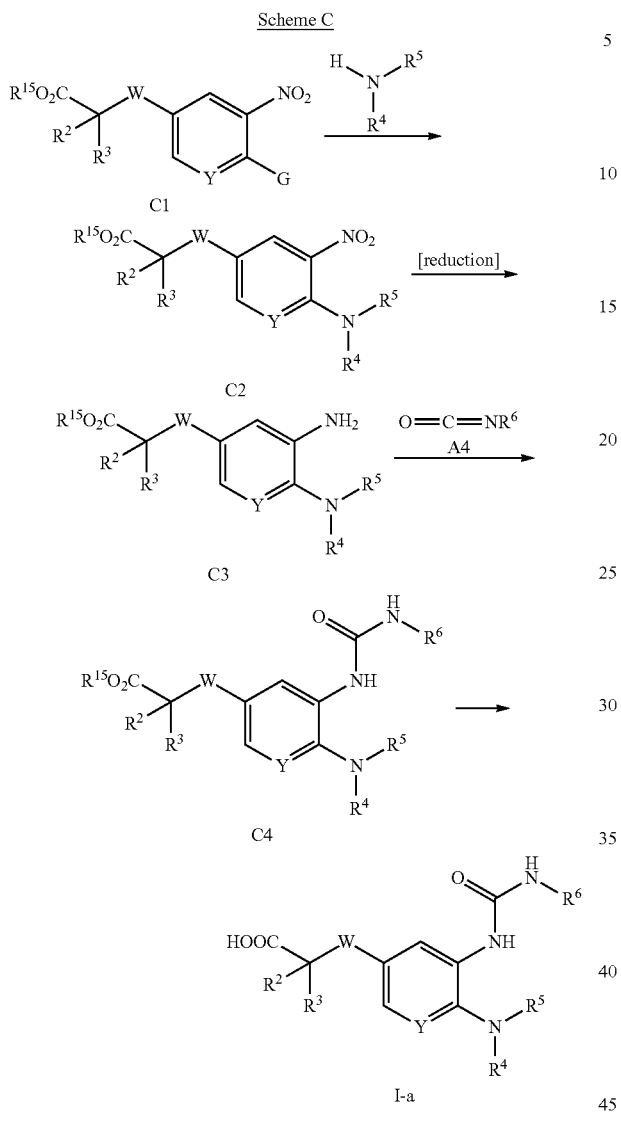

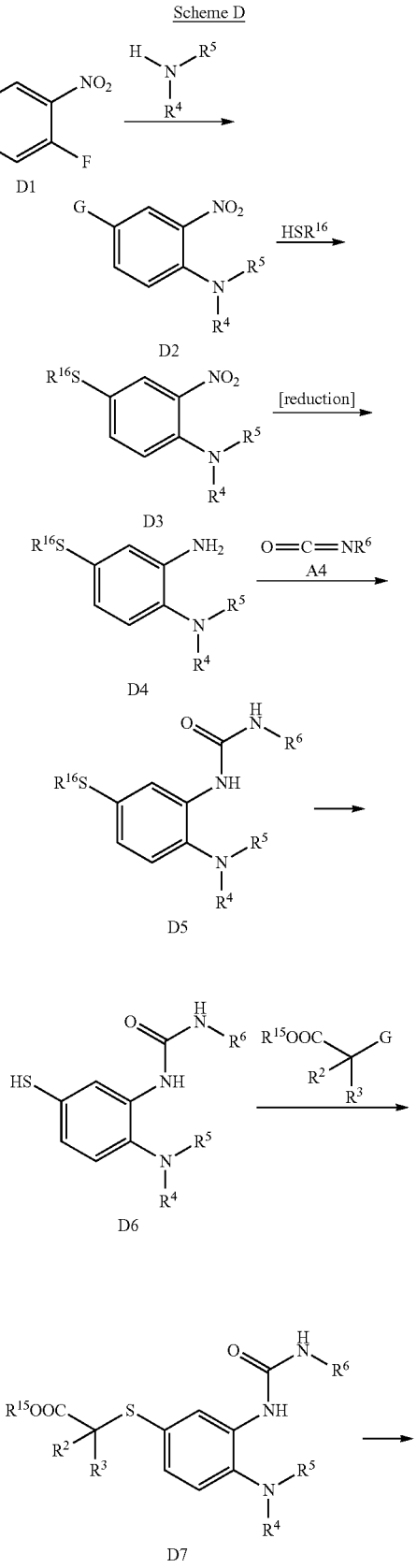

The compounds of the invention may also be prepared according to the general Scheme C. Compounds C1, where G=halogen are commercially available or can be assembled via standard transformations known to those of ordinary proficiency in the art of organic/medicinal chemistry. Compounds C2 can be prepared from C1 by base or palladium promoted displacement of the halogen by amines $HNR^4R^5$ in a solvent such as THF, DMF, NMP or the like. Reduction of the nitro group can be done under reductive conditions such as but not limited to palladium on charcoal under an atmosphere of hydrogen and in a solvent such as methanol or ethyl acetate to afford intermediates C3. Treatment of anilines C3 with an isocyanate A4, in a solvent such as THF at a temperature between ambient and the boiling point of the solvent, to afford intermediate C4. The saponification of C4 to I-a could be generally accomplished by the use of an alkali metal hydroxide in aqueous or mixed aqueous/organic solvents.

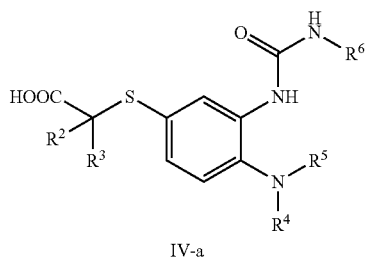

IV-a

The compounds of the invention may also be prepared according to the general Scheme D. Compounds D1, where G=halogen are commercially available or can be assembled via standard transformations known to those of ordinary proficiency in the art of organic/medicinal chemistry. Compounds D2 can be prepared from D1 by base or palladium promoted displacement of the halogen by amines $HNR^4R^5$ in a solvent such as THF, DMF, NMP or the like. Palladium promoted cross-coupling could generate thiol ether D3. Reduction of the nitro group can be done under reductive conditions such as but not limited to palladium on charcoal under an atmosphere of hydrogen and in a solvent such as methanol or ethyl acetate to afford intermediates D4. Treatment of anilines D4 with an isocyanate A4, in a solvent such as THF at a temperature between ambient and the boiling point of the solvent, to afford intermediate D5. De-protection of thiol ether D5 could provide thiol D6, which may be converted to ester derivatives D7 under displacement conditions. The saponification of D7 to IV-a could be generally accomplished by the use of an alkali metal hydroxide in aqueous or mixed aqueous/organic solvents.

Scheme E. Preparation of Compounds of Formula (I)

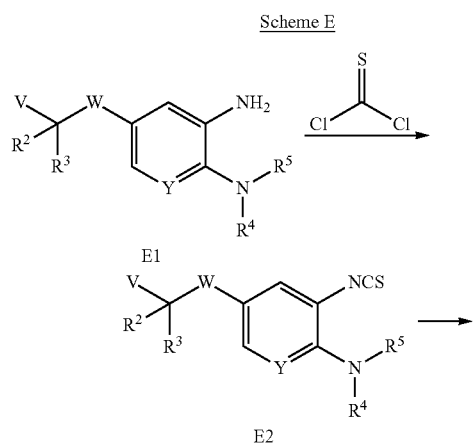

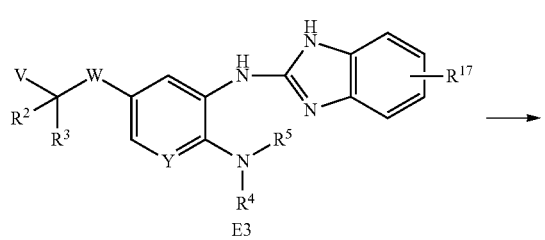

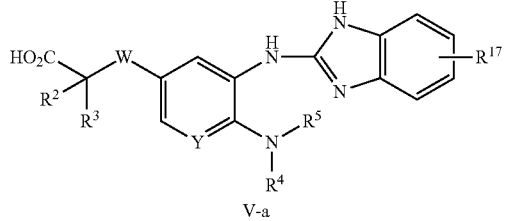

V-a

Referring to Scheme E, compounds E1 where V is CN or ester can be prepared using the transformation described above. Anilines E1 may be converted to isothiocyanates by treating with reagents such as thionyl chloride. Treated the isothiocyanates with o-dimines, following by heating the reaction in the presence of base, could form benzimidazoles E3. The saponification of E3 to V-a could be generally accomplished by the use of an alkali metal hydroxide in aqueous or mixed aqueous/organic solvents.

Scheme F. Preparation of Compounds of Formula (I)

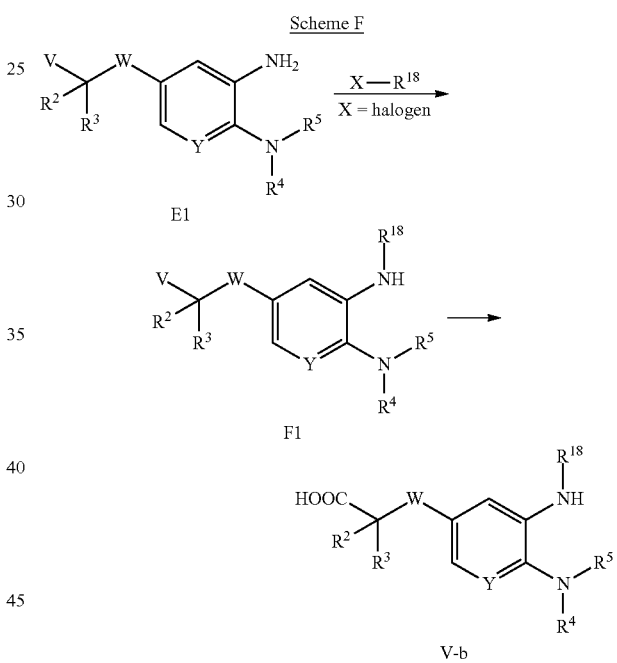

V-b

In Scheme F, compounds F1 can be prepared from amine E1 by base or palladium promoted displacement of the halogen of X—$R^{18}$. The saponification of F1 to V-b could be generally accomplished by the use of an alkali metal hydroxide in aqueous or mixed aqueous/organic solvents.

Scheme G. Preparation of Compounds of Formula (I)

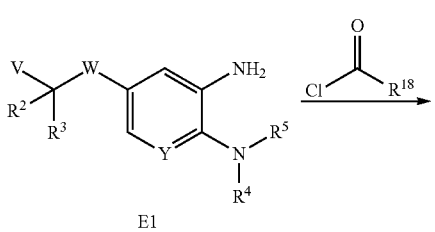

-continued

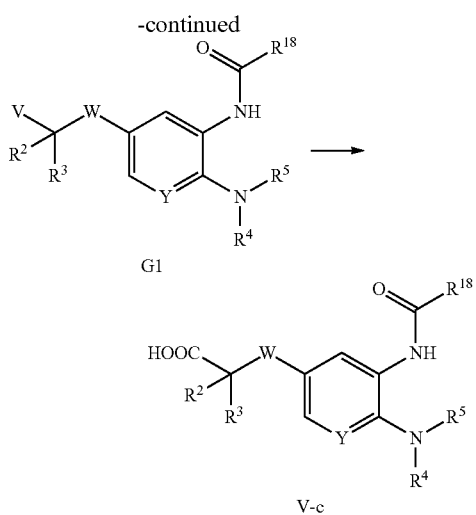

G1

V-c

In Scheme G, compounds F1 can be prepared from amine E1 by amide formation such as treating with acyl chloride in the presence of base. The saponification of G1 to V-c could be generally accomplished by the use of an alkali metal hydroxide in aqueous or mixed aqueous/organic solvents.

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating and/or preventing proliferative diseases (e.g., cancer) and infectious diseases (e.g., viral or bacterial infectious diseases). In some examples, the pharmaceutical compositions described herein may further comprise a second therapeutic agent, such as those described herein, e.g., an anti-cancer agent or an antiviral agent.

In certain embodiments, the cell contacted with an effective amount of a compound or pharmaceutical composition described herein is in vitro. In certain embodiments, the contacted cell is ex vivo. In certain embodiments, the cell described herein is in vivo. In certain embodiments, the cell described herein is a malignant cell (e.g., malignant blood cell).

In certain embodiments, the compound described herein is provided in an effective amount in the pharmaceutical composition. In certain embodiments, the effective amount is a therapeutically effective amount (e.g., amount effective for treating a proliferative disease in a subject in need thereof). In certain embodiments, the proliferative disease is cancer. In certain embodiments, the proliferative disease is cancer, e.g., non-small cell lung cancer, small cell lung cancer, breast cancer, renal cell carcinoma, bladder cancer, head and neck cancer, ovarian cancer, brain cancer, cancers of the gastrointestinal tract, liver cancer, pancreatic cancer, melanoma, leukemia, lymphoma, etc. In certain embodiments, the effective amount is a prophylactically effective amount (e.g., amount effective for preventing a proliferative disease in a subject in need thereof and/or for keeping a subject in need thereof in remission of a proliferative disease).

Pharmaceutical compositions described herein can be prepared by any method known in the pharmaceutical industry. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a proliferative disease (e.g., non-small cell lung cancer small cell lung cancer, breast cancer, renal cell carcinoma, bladder cancer, head and neck cancer, ovarian cancer, brain cancer, cancers of the gastrointestinal tract, liver cancer, pancreatic cancer, melanoma, leukemia, lymphoma, etc.) in a subject in need thereof, and/or preventing a proliferative disease in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, and/or preventing a proliferative disease in a subject in need thereof. A kit described herein may include one or more additional pharmaceutical agents described herein as a separate composition.

Methods of Treatment

As shown in the Examples below, exemplary IDO inhibiting compounds described herein successfully demonstrated in vitro potency and in vivo efficacy. The compounds described herein are useful in treating and/or preventing proliferative diseases (e.g., cancer) via the inhibition of IDO and inhibition of tryptophan catabolism resulting in reduction of the kynurenine level. Moreover, these compounds showed lower human hepatic clearance compared to other IDO inhibitors known in the art, including INCB-24360 and others disclosed in WO2014150677 and WO2014150646. Accordingly, the present disclosure provides methods for treating diseases associated with IDO with one or more of the IDO inhibiting compounds described herein. Diseases associated with IDO include, but are not limited to, cancer, infectious diseases, and Alzheimer's disease. In certain embodiments, the infectious disease is a viral infection.

Accordingly, the present disclosure provides methods of treating a proliferative disease in a subject in need thereof, the methods comprising administering to the subject an effective amount (e.g., therapeutically effective amount) of a compound, or pharmaceutical composition thereof, described herein.

Another aspect of the present disclosure relates to methods of preventing proliferative disease in a subject in need thereof, the methods comprising administering to the subject an effective amount (e.g., prophylactically effective amount) of a compound, or pharmaceutical composition thereof, described herein.

The compounds and pharmaceutical compositions described herein are useful in treating and/or preventing proliferative diseases. In certain embodiments, the proliferative disease is cancer (e.g., cancer (non-small cell lung cancer, small cell lung cancer), breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, or osteosarcoma). In certain embodiments, the proliferative disease is an inflammatory disease. In certain embodiments, the proliferative disease is an immune-related disease.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes treating the subject in need of the treatment a second anti-cancer therapy, such as chemotherapy, immunotherapy (e.g., anti-PD-1 or anti-PD-L1 antibody), cell therapy (e.g., CAR-T cell therapy), surgery, and/or transplantation (e.g., bone marrow transplantation). In some examples, the second anti-cancer therapy involves the use of one or more anti-cancer agents, e.g., those known in the art, including anti-cancer drugs in clinical use or in clinical trials.

The compounds and compositions provided herein can be administered by any route, including enteral (e.g., oral), parenteral, and/or intravenous. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is half a day, one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein. In certain embodiments, a dose described herein includes independently between 100 mg and 300 mg, inclusive, of a compound described herein. In certain embodiments, a dose described herein includes independently between 300 mg and 1000 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, and/or in preventing a proliferative disease in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent). In certain embodiments, the additional pharmaceutical agent is an anti-cancer agent, anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, cell therapy (e.g., CAR-T cell therapy), immunotherapy (e.g., anti-PD-1 or anti-PD-L1 antibody, or a cancer vaccine), and chemotherapy. Treatment with the IDO inhibiting compound may be performed prior to, concurrently with, or after the other therapy.

When any of the IDO inhibiting compounds described herein is used for treating a viral infection, it may be co-used with a second anti-viral agent, which may be different from any of the IDO inhibiting compounds described herein. In some examples, the anti-viral agent is an anti-viral vaccine. The second anti-viral agent may be administered prior to, concurrently, or after the administration of the IDO inhibiting compound.

Other combined therapies involving IDO inhibitors, as known in the art, are also within the scope of the present disclosure. See, for example, WO2015006520, the relevant disclosures of which are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1

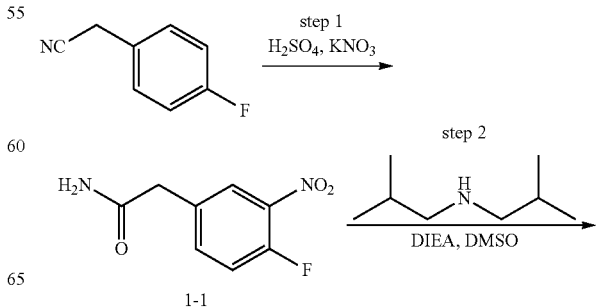

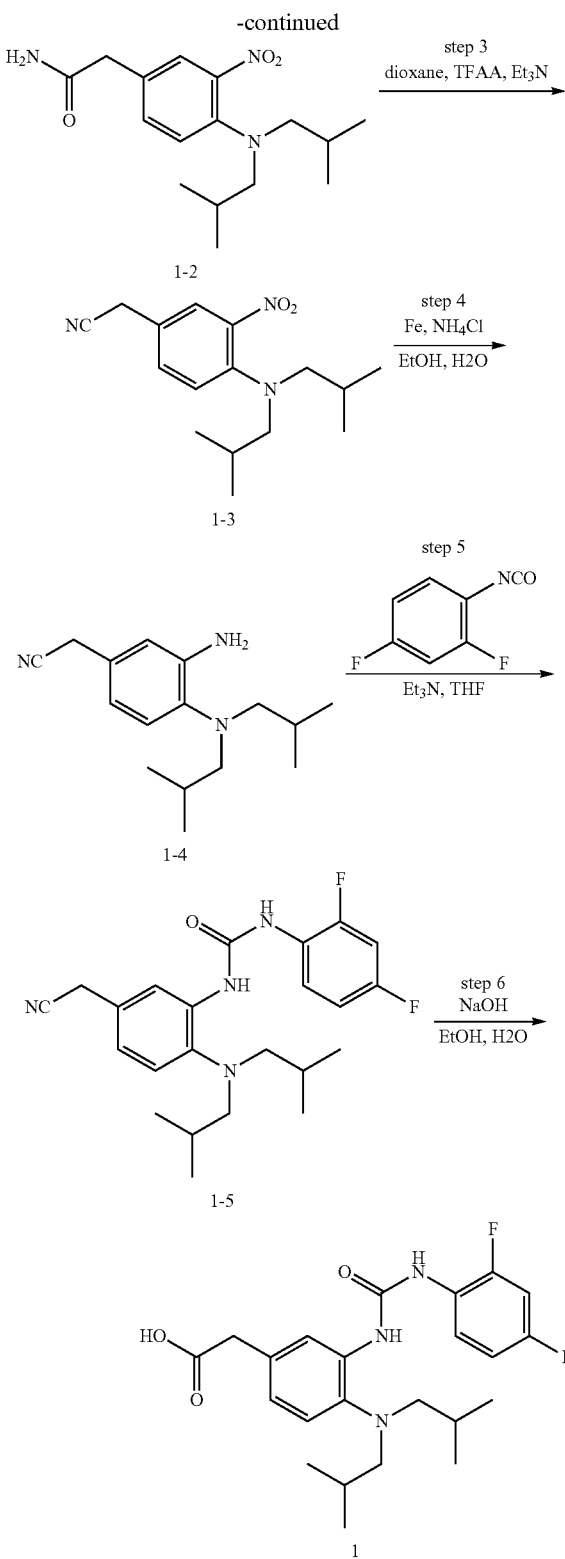

of water/ice. The resulting solution was extracted with 3×100 mL of ethyl acetate. The combined organic layer was washed with 3×100 mL of brine, dried over anhydrous sodium sulfate and concentrated under vacuum to give 2-(4-fluoro-3-nitrophenyl)acetamide (6 g, 82% yield).

Step 2. Synthesis of 1-2

Into a 250-mL 3-necked round-bottom flask, was placed a solution of 2-(4-fluoro-3-nitrophenyl)acetamide (6 g, 30.28 mmol) in DMSO (60 mL), bis(2-methylpropyl)amine (5.86 g, 45.34 mmol), and DIEA (7.81 g, 60.66 mmol). The resulting solution was heated to 100° C. and stirred at the same temperature for overnight. The reaction mixture was cooled to room temperature, and then quenched by addition of 50 mL of water. The resulting solution was extracted with 3×100 mL of ethyl acetate. The combined organic layer was washed with 3×100 mL of brine, dried over anhydrous sodium sulfate and concentrated under vacuum. The residue was applied onto a silica gel column with ethyl acetate/petroleum ether (1:10~1:3) to afford 2-[4-[bis(2-methylpropyl)amino]-3-nitrophenyl]acetamide (7 g, 75% yield).

Step 3. Synthesis of 1-3

Into a 250-mL 3-necked round-bottom flask, was placed a solution of 2-[4-[bis(2-methylpropyl)amino]-3-nitrophenyl]acetamide (7 g, 22.77 mmol) in dioxane (70 mL), TFAA (7 mL), and triethylamine (3 mL). The resulting solution was heated to 100° C. and stirred at the same temperature overnight. The reaction mixture was cooled to room temperature. The reaction was then quenched by addition of 50 mL of water. The resulting solution was extracted with 3×100 mL of ethyl acetate. The combined organic layer was washed with 3×100 mL of brine, dried over anhydrous sodium sulfate and concentrated under vacuum. The residue was applied onto a silica gel column with ethyl acetate/petroleum ether (1:20~1:3) to afford 2-[4-[bis(2-methylpropyl)amino]-3-nitrophenyl]acetonitrile (6.1 g, 93% yield).

Step 4. Synthesis of 1-4

Into a 100-mL round-bottom flask, was placed a solution of 2-[4-[bis(2-methylpropyl)amino]-3-nitrophenyl]acetonitrile (3 g, 10.37 mmol) in ethanol/$H_2O$ (30/10 mL), Fe (3.49 g), and $NH_4Cl$ (380 mg, 7.10 mmol). The resulting solution was stirred for 2 h at 80° C. The reaction mixture was cooled to room temperature. The resulting mixture was concentrated under vacuum. The resulting solution was extracted with 3×50 mL of ethyl acetate. The combined organic layers was washed with 3×50 mL of brine, dried over anhydrous sodium sulfate and concentrated under vacuum. The residue was applied onto a silica gel column with ethyl acetate/petroleum ether (1:10-1:1) to afford 2-[3-amino-4-[bis(2-methylpropyl)amino]phenyl]acetonitrile (1.1 g, 41% yield).

Step 5. Synthesis of 1-5

Into a 100-mL 3-necked round-bottom flask, was placed a solution of 2-[3-amino-4-[bis(2-methylpropyl)amino]phenyl]acetonitrile (1.1 g, 4.24 mmol) in tetrahydrofuran (50 mL), 2,4-difluoro-1-isocyanatobenzene (790 mg, 5.09 mmol), and triethylamine (860 mg, 8.50 mmol). The resulting solution was stirred for 3 h at room temperature. The resulting mixture was concentrated under vacuum. The residue was applied onto a silica gel column with ethyl acetate/petroleum ether (1:10~1:3) to afford 3-[2-[bis(2-methylpropyl)amino]-5-(cyanomethyl)phenyl]-1-(2,4-difluorophenyl)urea (700 mg, 40% yield).

Step 6. Synthesis of 1

Into a 8-mL sealed tube, was placed a solution of 1-[2-[bis(2-methylpropyl)amino]-5-(cyanomethyl)phenyl]-3-(2,4-difluorophenyl)urea (300 mg, 0.72 mmol) in ethanol/$H_2O$ (5/1 mL), and sodium hydroxide (15% aq.) (1 mL). The resulting solution was stirred at 60° C. for overnight. The Step 1. Synthesis of 1-1

Into a 100-mL 3-necked round-bottom flask, was placed a solution of 2-(4-fluorophenyl)acetonitrile (5 g, 37.00 mmol) in sulfuric acid (50 mL). This was followed by addition of potassium nitrate (5.6 g), in portions at 0° C. in 10 min. The resulting solution was stirred overnight at room temperature. The reaction mixture was poured into 150 mL reaction mixture was cooled to room temperature and concentrated under vacuum. The pH value of the solution was adjusted to 6 with hydrogen chloride (1 N). The resulting mixture was concentrated under vacuum. The crude product was purified by Prep-HPLC with the following conditions: Column, Waters X-bridge RP18, 19*150 mm, 5 um; mobile phase, ACN/water (0.05% $NH_3H_2O$) from 20% to 38% within 5.6 min, flow rate: 20 mL/min; Detector, 254 nm. This resulted in 72.2 mg (23% yield) of 2-[4-[bis(2-methylpropyl)amino]-3-[[(2,4-difluorophenyl)carbamoyl]amino]phenyl]acetic acid as off-white solid. LCMS (ES, m/z): 434 [M+H]$^+$. HNMR (300 MHz, DMSO-$d_6$, ppm): δ 9.27 (s, 1H), 8.06 (s, 1H), 7.96-7.88 (m, 1H), 7.78 (d, J=1.8 Hz, 1H), 7.33-7.25 (m, 1H), 7.12 (d, J=8.1 Hz, 1H), 7.07-7.00 (m, 1H), 6.86 (dd, J=8.4, 2.1 Hz, 1H), 3.38 (s, 2H), 2.66 (d, J=6.9 Hz, 4H), 1.69-1.61 (m, 2H), 0.84 (d, J=6.6 Hz, 12H).

Example 2

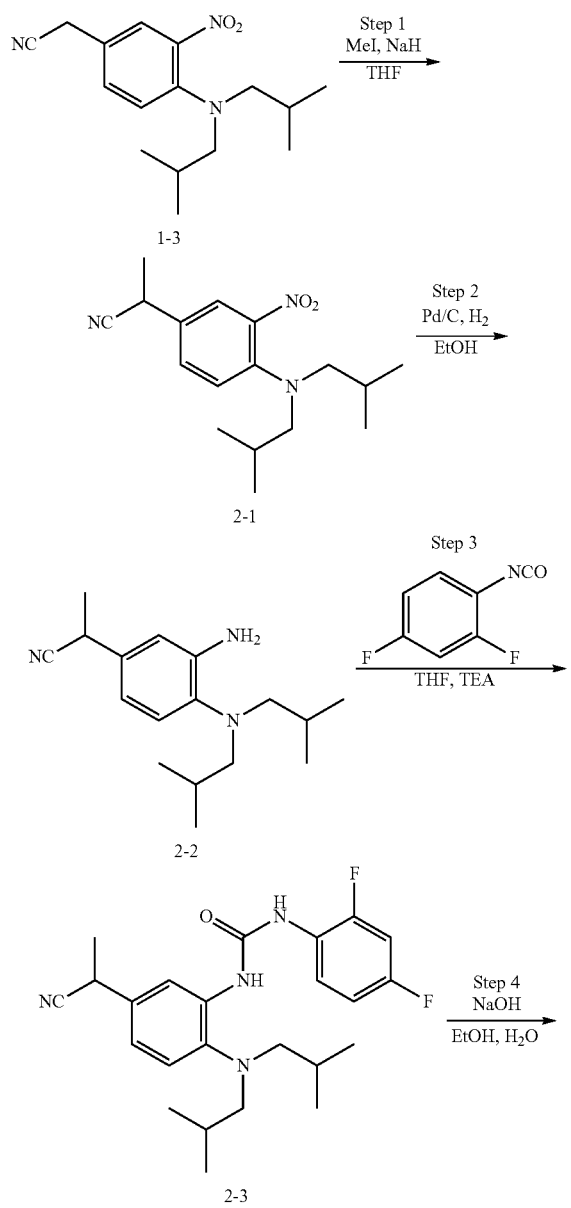

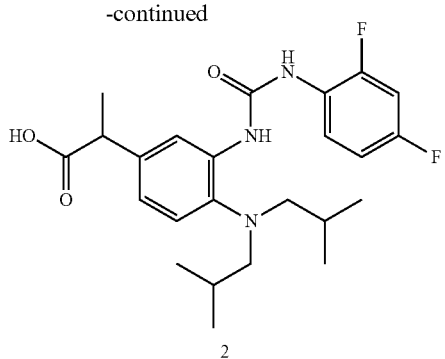

Step 1. Synthesis of 2-1

To a solution of 2-[4-[bis(2-methylpropyl)amino]-3-nitrophenyl]acetonitrile (2 g, 6.91 mmol) in tetrahydrofuran (20 mL) at 0° C., was added sodium hydride (250 mg, 6.25 mmol) portionwise. After stirring at room temperature for 1 h, the reaction was cooled to 0° C., and iodomethane (1.18 g, 8.31 mmol) was added dropwise. The reaction mixture was then stirred at room temperature for another 2 h before quenched by the addition of saturated ammonium chloride solution (20 mL). The mixture was extracted with ethyl acetate (50 mL×3), and washed with brine (50 mL×3). The organic phase was dried over anhydrous sodium sulfate and concentrated under vacuum. The residue was purified by Flash-Prep-HPLC [Column: C18; Mobile phase A: Water (0.05% ammonium hydrogen carbonate), mobile phase B: acetonitrile; Gradient: 35% acetonitrile to 78% acetonitrile in 30 min] to afford the desired product (660 mg, 31% yield).

Step 2. Synthesis of 2-2

To a solution of 2-[4-[bis(2-methylpropyl)amino]-3-nitrophenyl]propanenitrile (600 mg, 1.98 mmol) in ethanol (20 mL), was added palladium on carbon (300 mg). The reaction was stirred for 2 h under $H_2$ balloon at room temperature. The solids were filtered out, and the filtrate was concentrated under vacuum to afford the desired product (530 mg, 72% yield).

Step 3. Synthesis of 2-3

To a solution of 2-[3-amino-4-[bis(2-methylpropyl)amino]phenyl]propanenitrile (546 mg, 2.00 mmol) in tetrahydrofuran (20 mL), were added triethylamine (610 mg, 6.03 mmol) and 2,4-difluoro-1-isocyanatobenzene (456 mg, 2.94 mmol). After stirring at room temperature for 3 h, the reaction was concentrated under vacuum and the residue was purified by Flash-Prep-HPLC [Column: C18; Mobile phase A: Water (0.05% ammonium hydrogen carbonate), mobile phase B: acetonitrile; Gradient: 45% acetonitrile to 85% acetonitrile in 30 min] to afford the desired product (450 mg, 40% yield).

Step 4. Synthesis of 2

To a solution of 3-[2-[bis(2-methylpropyl)amino]-5-(1-cyanoethyl)phenyl]-1-(2,4-difluorophenyl)urea (60 mg, 0.14 mmol) in ethanol (4 mL) and water (1 mL), was added sodium hydroxide (400 mg, 10.00 mmol). After stirring at 60° C. for 16 h, the reaction mixture was cooled to room temperature and concentrated under vacuum. The residue was dissolved in water (10 mL), and hydrogen chloride (4 N) was employed to adjust the pH to 4. The mixture was then extracted with ethyl acetate (20 mL×3). The organic phase was washed with brine (20 mL×3), dried over anhydrous sodium sulfate and concentrated under vacuum. The residue was purified by Prep-HPLC [Column: Waters X-bridge C18, 19×150 mm; Mobile phase A: water (0.05% trifluoroacetic acid), Mobile phase B: acetonitrile; Gradient: 25% acetonitrile to 60% acetonitrile; 8 min; Detector: 254 nm] to afford the desired product (15.8 mg, 25% yield). LCMS (ES, m/z): 448.3 [M+H]+; 1HNMR: (300 MHz, DMSO-d6, ppm): δ 9.29 (s, 1H), 8.06 (s, 1H), 7.93-7.91 (m, 1H), 7.84 (d, J=1.8 Hz, 1H), 7.35-7.25 (m, 1H), 7.17-7.11 (m, 1H), 7.06-6.97 (m, 1H), 6.91-6.88 (m, 1H), 3.58-3.51(m, 1H), 2.66 (d, J=6.9 Hz, 4H), 1.69-1.61 (m, 2H), 1.32 (d, J=7.2 Hz, 3H), 0.84 (d, J=6.6 Hz, 12H).

Example 3

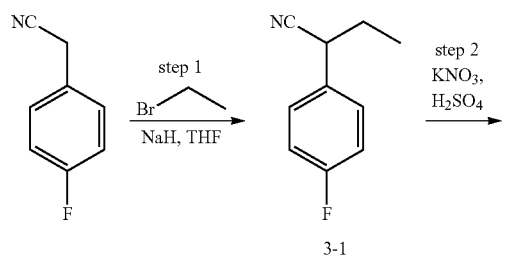

3-1

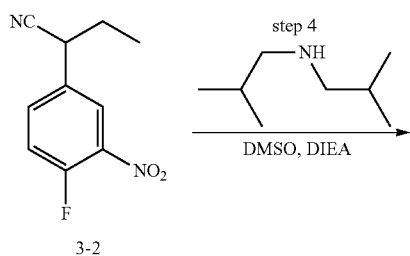

3-2

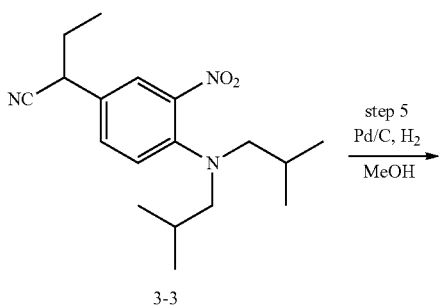

3-3

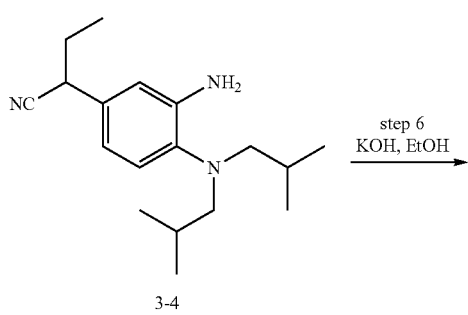

3-4

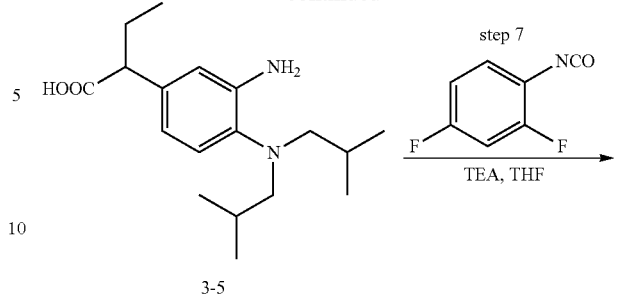

3-5

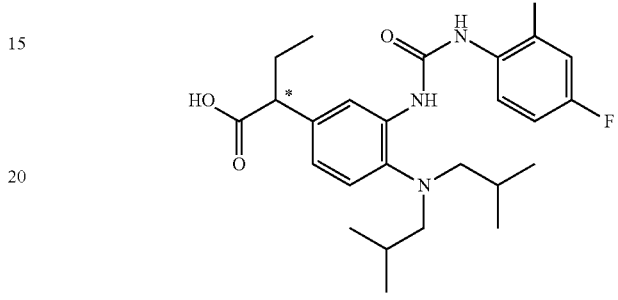

3A

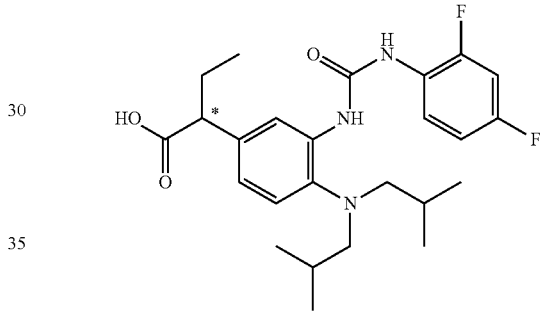

3B

Step 1. Synthesis of 3-1

To a solution of 2-(4-fluorophenyl)acetonitrile (11 g, 81.40 mmol) in tetrahydrofuran (250 mL) at 0° C., was added sodium hydride (3.91 g, 97.75 mmol). The reaction was then warmed to room temperature and stirred for 30 min. The reaction mixture was cooled to 0° C. again and bromoethane (9.76 g, 89.57 mmol) was added. The reaction was then stirred at room temperature for overnight. Water (100 mL) was added and the mixture was extracted with ethyl acetate (100 mL×2). The organic layer was dried over anhydrous sodium sulfate and concentrated under vacuum. The residue was purified by silica gel column with ethyl acetate/petroleum ether (1/10) as eluent to afford 2-(4-fluorophenyl)butanenitrile (9 g, 83% yield).

Step 2. Synthesis of 3-2

To a solution of 2-(4-fluorophenyl)butanenitrile (9 g, 55.21 mmol) in sulfuric acid (200 mL) at 0° C., was added potassium nitrate (8.28 g, 82.82 mmol). The reaction was then stirred at 25° C. for 1 h. The reaction was quenched by addition of water/ice (600 mL) and the mixture was extracted with ethyl acetate (100 mL×3). The organic layer was washed with saturated aqueous sodium bicarbonate (30 mL×2), dried over anhydrous sodium sulfate, and concentrated under vacuum. The residue was purified by silica gel column chromatography with ethyl acetate/petroleum ether (1/4) as eluent to afford 2-(4-fluoro-3-nitrophenyl)butanenitrile (5 g, 44% yield).

Step 3. Synthesis of 3-3

To a solution of 2-(4-fluoro-3-nitrophenyl)butanenitrile (5 g, 24 mmol) and diisopropylethylamine (6.2 g, 48 mmol) in dimethylsulfoxide (100 mL), was added bis(2-methylpropyl)amine (3.7 g, 28.8 mmol). The reaction was then warmed to 100° C. and stirred for 1 h. After cooling down to room temperature, ethyl acetate (200 mL) was added and the mixture was washed with water (100 mL×2). The organic layer was dried over anhydrous sodium sulfate and concentrated under vacuum. The residue was purified by silica gel column with ethyl acetate/petroleum ether (1/10) to afford 2-[4-[bis(2-methylpropyl)amino]-3-nitrophenyl]butanenitrile (4 g, 53% yield).

Step 4. Synthesis of 3-4

A mixture of 2-[4-[bis(2-methylpropyl)amino]-3-nitrophenyl]butanenitrile (4 g, 12.60 mmol) and palladium on carbon (0.4 g) in methanol (20 mL) was stirred under hydrogen atmosphere (1 atm) at 25° C. for overnight. The reaction was filtered through Celite and the filtrate was concentrated under vacuum. The residue was purified by silica gel column with ethyl acetate/petroleum ether (1/10) to afford 2-[3-amino-4-[bis(2-methylpropyl)amino]phenyl]butanenitrile (3 g, 83% yield).

Step 5. Synthesis of 3-5

A mixture of 2-[3-amino-4-[bis(2-methylpropyl)amino]phenyl]butanenitrile (1.16 g, 4.04 mmol) and potassium hydroxide (1.13 g, 20.14 mmol) in ethanol (10 mL) and water (2 mL) was stirred in a sealed tube at 100° C. for 3 days. The pH value of the solution was adjusted to 7 with hydrogen chloride (2 N). Water (50 mL) was added and the mixture was extracted with ethyl acetate (50 mL×3). The organic phase was dried over anhydrous sodium sulfate and concentrated under vacuum to afford 4-[3-amino-4-[bis(2-methylpropyl)amino]phenyl] oxane-4-carboxylic acid (1.16 g, 94% yield).

Step 6. Synthesis of 3-6

A mixture of 2-[3-amino-4-[bis(2-methylpropyl)amino]phenyl]butanoic acid (1.16 g, 3.79 mmol), 2,4-difluoro-1-isocyanatobenzene (707 mg, 4.56 mmol), and triethylamine (768 mg, 7.59 mmol) in tetrahydrofuran (10 mL) was stirred at 25° C. for overnight. The mixture was concentrated and the residue was purified by prep-HPLC to afford the desired product as racemic form. (Column: XBridge RP, 5 um, 19*150 mm; Mobile Phase A: NH$_4$HCO$_3$ 10 mmol/L in water; Mobile Phase B: ACN; Flow rate: 30 mL/min; Gradient: 45% B to 85% B in 8 min; Detector: 254 nm).

Step 7. Chiral Separation

The racemic product from step 6 was separated by chiral prep-HPLC with the following conditions to afford examples 3A and 3B. (Column: IA, 20 mmd*250 mmd; Mobile Phase: hexane with 3% alcohol; Flow rate: 15 mL/min; Detector: 254 nm.).

Example 3A: Retention time: 30.07 min. LRMS: (ES, m/z): 462.4 [M+H]$^+$. $^1$HNMR: (300 MHz, DMSO-d$_6$): δ 12.22 (s, 1H), 9.30 (s, 1H), 8.07 (s, 1H), 7.97-7.89 (m, 1H), 7.84 (s, 1H), 7.33-7.25 (m, 1H), 7.14 (d, J=8.4, 1H), 7.06-6.99 (m, 1H), 6.88 (d, J=6.9 Hz, 1H), 3.30 (t, J=7.8, 1H), 2.65 (d, J=6.3, 4H), 1.97-1.85 (m, 1H), 1.70-1.55 (m, 3H), 0.83-0.78 (m, 15H).

Example 3B: Retention time: 38.62 min. LRMS (ES, m/z): 462.4 [M+H]$^+$. $^1$HNMR: (300 MHz, DMSO-d$_6$): δ 12.20 (s, 1H), 9.30 (s, 1H), 8.07 (s, 1H), 7.97-7.89 (m, 1H), 7.83 (s, 1H), 7.35-7.27 (m, 1H), 7.15 (d, J=8.4, 1H), 7.07-7.01 (m, 1H), 6.90-6.87 (m, 1H), 3.33-3.27 (m, 1H), 2.66 (d, J=6.6, 4H), 1.97-1.87 (m, 1H), 1.69-1.57 (m, 3H), 0.85-0.80 (m, 15H).

Example 4

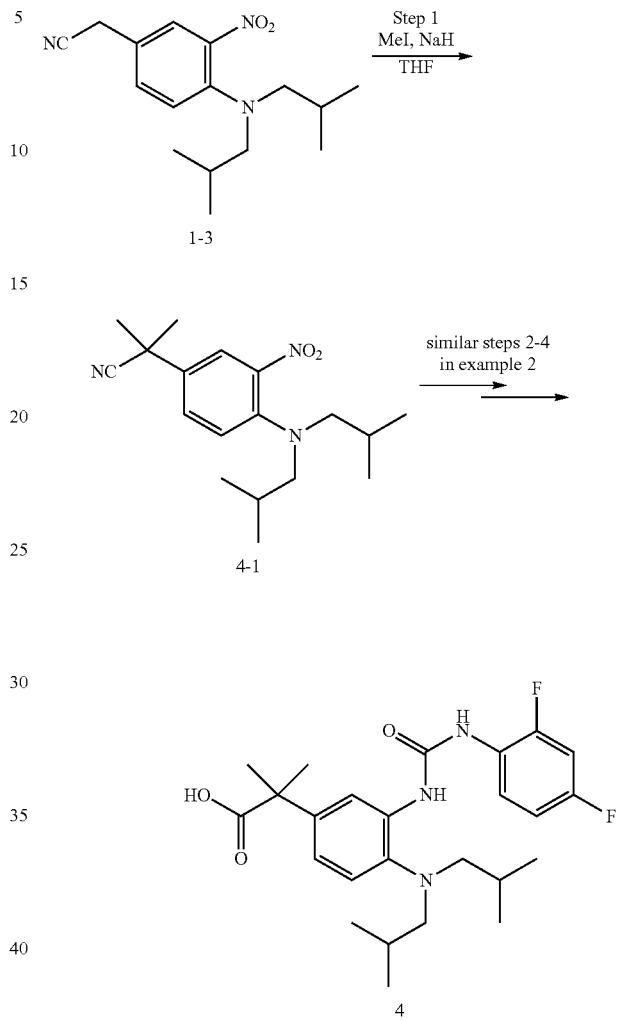

Step 1. Synthesis of 4-1

To a solution of 2-[4-[bis(2-methylpropyl)amino]-3-nitrophenyl]acetonitrile (0.7 g, 3.46 mmol) in tetrahydrofuran (7 mL) at 0° C., was added sodium hydride (250 mg, 10.37 mmol) portionwise. The mixture was then stirred at 0° C. for 1 h, and iodomethane (0.858 g, 6.05 mmol) was added. After stirring at room temperature for another 16 h, the reaction was quenched by addition of saturated ammonium chloride solution. The mixture was extracted with ethyl acetate (50 mL×2), and washed with brine (50 mL×2). The combined organic phase was dried over anhydrous sodium sulfate and concentrated under vacuum. The residue was purified by silica gel column with ethyl acetate/petroleum ether (1/15) as the eluent to afford the desired product (300 mg, 39% yield).

Followed the similar steps in example 2 to synthesize 4

Example 4: LRMS (ES, m/z): 462.40[M+H]$^+$; $^1$H-NMR: (300 MHz, DMSO-d$_6$, ppm): δ 12.05 (brs, 1H), 9.27 (s, 1H), 8.06 (s, 1H), 7.96-7.88 (m, 2H), 7.33.7.26 (m, 1H), 7.15-7.12 (m, 1H), 7.07-6.94 (m, 2H), 2.65 (d, J=6.9 Hz, 4H), 1.69-1.60 (m, 2H), 1.42 (s, 6H), 0.84 (d, J=6.6 Hz, 12H)

Example 5

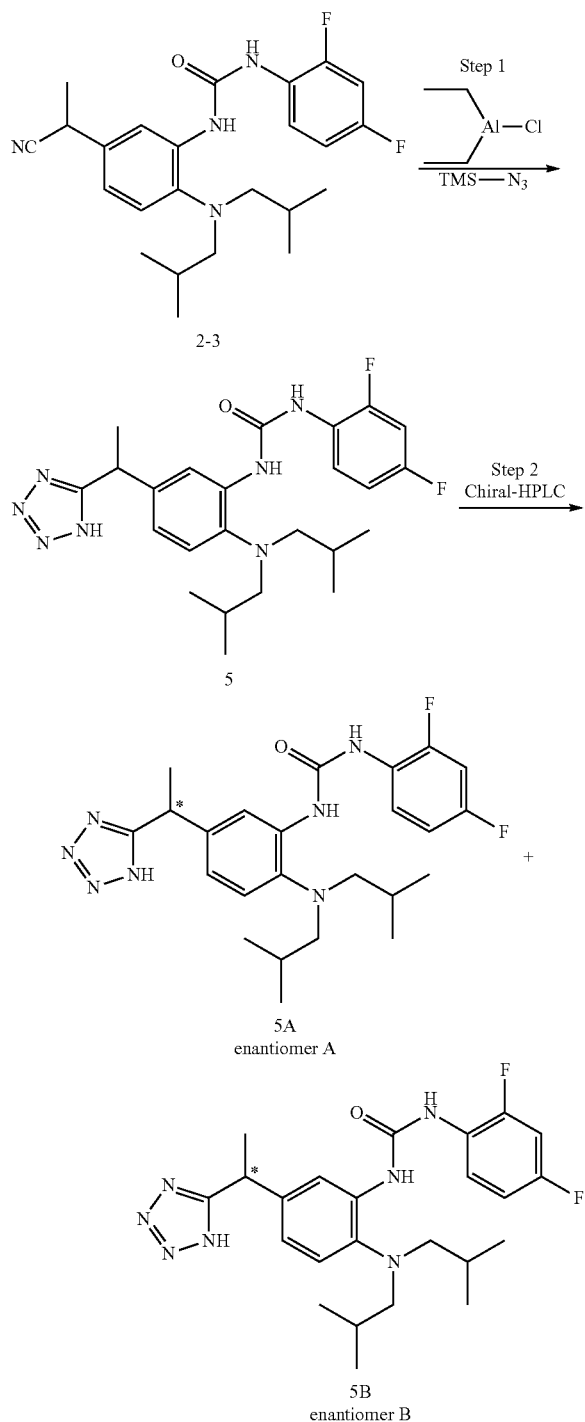

Step 1. Synthesis of 5

To a solution of azidotrimethylsilane (185 mg, 1.61 mmol) in toluene (15 mL), was added a solution of chlorodiethylalumane (194 mg, 1.61 mmol) in toluene (1.8 mL). After stirring at room temperature for 6 h, a solution of 3-[2-[bis(2-methylpropyl)amino]-5-(1-cyanoethyl)phenyl]-1-(2,4-difluorophenyl)urea (230 mg, 0.54 mmol) in toluene (20 mL) was added. The resulting mixture was stirred at 110° C. for another 16 h. The reaction was cooled to room temperature and concentrated under vacuum. The residue was dissolved in ethyl acetate (50 mL), and the mixture was washed with brine (30 mL×3). The organic phase was dried over anhydrous sodium sulfate and concentrated under vacuum. The residue was purified by Prep-HPLC with the following conditions [Column: Waters X-bridge C18, 19×150 nm; Mobile phase A: water (0.05% ammonia), Mobile phase B: acetonitrile; Gradient: 25% acetonitrile to 52% acetonitrile; 6.8 min, 25 mL/min; Detector, 254 nm]. The collected fraction was combined and concentrated under vacuum to afford the desired racemic product (60 mg, 24% yield) as a white solid.

Step 2. Chiral Separation

The racemate (60 mg) was resolved by Chiral-Prep-HPLC with the following conditions [Column: AD-H; Mobile phase A: 5% hexane, Mobile phase B: ethanol; Gradient: 5% ethanol; 25 mL/min; Detector, 254 nm]. The collected fraction was combined and concentrated under vacuum to afford the desired product 5A (15.3 mg, 26% yield, RT=4.33 min) and 5B (13.3 mg, 22% yield, RT=5.45 min) as a white solid.

Compound 5A: LCMS (ES, m/z): 472.5 [M+H]$^+$. $^1$HNMR (300 MHz, DMSO-$d_6$): δ 9.30 (s, 1H), 8.06 (s, 1H), 7.95-7.86 (m, 1H), 7.80 (d, J=1.8 Hz, 1H), 7.33-7.28 (m, 1H), 7.16-7.14(m, 1H), 7.07-7.01(m, 1H), 6.85 (dd, J=8.4, 1.8 Hz, 1H), 4.45-4.42 (m, 1H), 2.65 (d, J=6.6 Hz, 4H), 1.70-1.59 (m, 5H), 0.83 (d, J=6.6 Hz, 12H).

Compound 5B: LCMS (ES, m/z): 472.5 [M+H]$^+$. $^1$HNMR (300 MHz, DMSO-$d_6$): δ 9.29 (s, 1H), 8.05 (s, 1H), 7.95-7.87 (m, 1H), 7.80 (d, J=2.1 Hz, 1H), 7.33-7.26 (m, 1H), 7.15-7.12(m, 1H), 7.07-7.01(m, 1H), 6.85 (dd, J=8.4, 1.8 Hz, 1H), 4.44-4.38 (m, 1H), 2.64 (d, J=6.6 Hz, 4H), 1.67-1.56(m, 5H), 0.83 (d, J=6.6 Hz, 12H).

Example 6

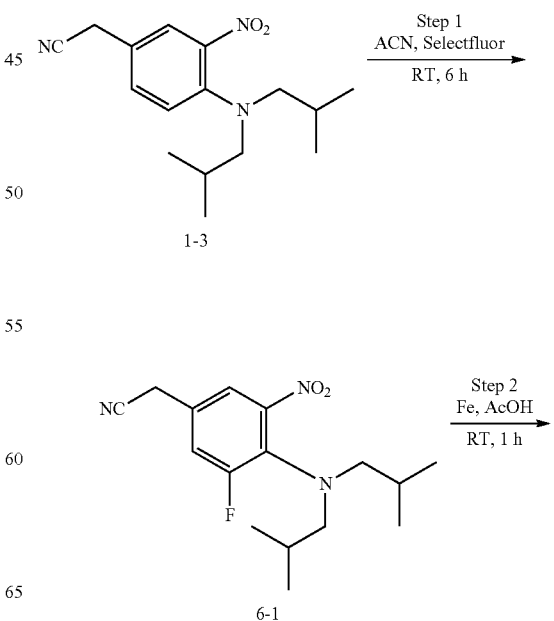

-continued

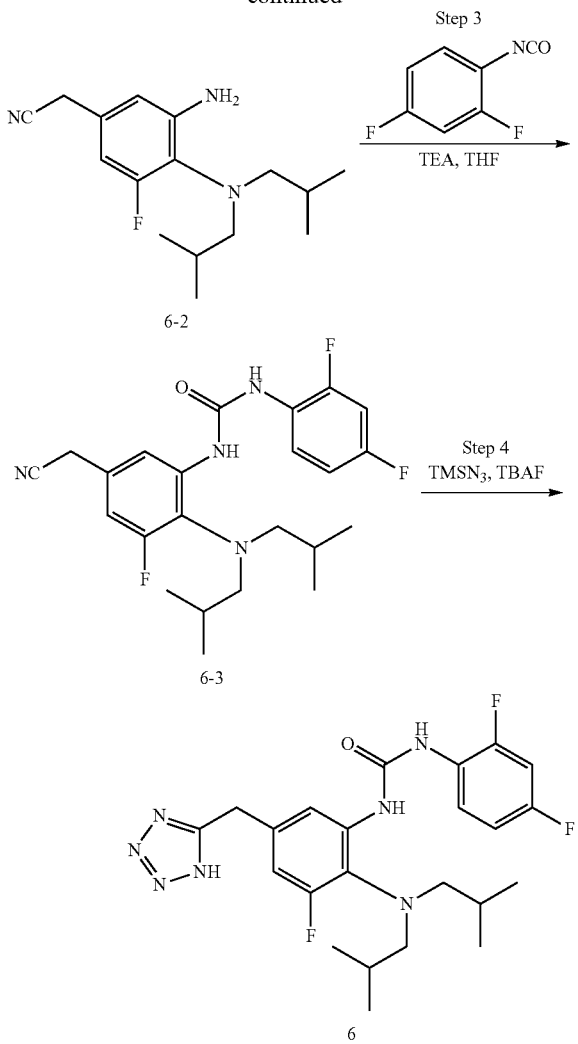

Step 1. Synthesis of 6-1

To a solution of 2-[4-[bis(2-methylpropyl)amino]-3-nitrophenyl]acetonitrile (2.0 g, 6.91 mmol) in acetonitrile (30 mL) was added selectfluor (4.9 g, 13.84 mmol) portionwise. The resulted mixture was stirred at room temperature for 6 h. The reaction was then concentrated under vacuum. The residue was purified by silica gel column with ethyl acetate/petroleum ether (1/10) as eluent to afford the desired product (0.55 g, 26%).

Step 2. Synthesis of 6-2

To a solution of 2-[4-[bis(2-methylpropyl)amino]-3-fluoro-5-nitrophenyl]acetonitrile (550 mg, 1.79 mmol) in acetic acid (5 mL) was added iron (1.0 g, 17.86 mmol). The reaction was stirred at room temperature for 1 h. The mixture was filtered through Celite and the filtrate was concentrated under vacuum. The residue was dissolved in ethyl acetate (50 mL), washed with saturated aqueous sodium bicarbonate (20 mL) and water (20 mL). The organic phase was concentrated under vacuum, and the residue was purified by silica gel column with ethyl acetate/petroleum ether (1/10) as eluent to afford the desired product (0.4 g, 81%).

Step 3. Synthesis of 6-3

To a solution of 2-[3-amino-4-[bis(2-methylpropyl)amino]-5-fluorophenyl]acetonitrile (190 mg, 0.68 mmol) in tetrahydrofuran (3 mL) was added 2,4-difluoro-1-isocyanatobenzene (160 mg, 1.03 mmol) and triethylamine (0.21 g, 2.04 mmol). The mixture was then stirred at room temperature for 3 h. The reaction was diluted with ethyl acetate (20 mL), and then washed with water (10 mL×2). The organic phase was concentrated under vacuum. The residue was purified by silica gel column with ethyl acetate/petroleum ether (1/2) as eluent to afford the desired product (0.14 g, 47%).

Step 4. Synthesis of 6

A solution of 3-[2-[bis(2-methylpropyl)amino]-5-(cyanomethyl)-3-fluorophenyl]-1-(2,4-difluorophenyl)urea (140 mg, 0.32 mmol), trimethylsilyl azide (300 mg, 2.60 mmol) and tetrabutylammonium fluoride (500 mg, 1.91 mmol) in toluene (3 mL) was stirred at 90° C. for 1 h. The mixture was cooled to room temperature and diluted with ethyl acetate (20 mL). The mixture was washed with water (10 mL×2). The organic phase was concentrated under vacuum. The residue (420 mg) was purified by Prep-HPLC with the following conditions: [Column, X Bridge Shield RP18 OBD Column, 5 um, 19*150 mm; mobile phase, water (0.05% TFA) and ACN/MeOH (15% up to 60.0% in 8 min); Detector, UV 254 nm] to afford the desired product (36.2 mg, 24%) as an off white solid. LCMS (ES, m/z): 476.4 [M+H]$^+$; $^1$HNMR: (300 MHz, DMSO-d$_6$, ppm): δ 9.43 (s, 1H), 8.34 (s, 1H), 7.93-7.84 (m, 1H), 7.79 (s, 1H), 7.73-7.68 (m, 1H), 7.34-7.26 (m, 1H), 7.07-7.05 (m, 1H), 6.67 (dd, J=11.4 Hz, 1.5 Hz, 1H), 4.11 (s, 2H), 3.51-3.42 (m, 2H), 2.79 (m, 4H), 0.83 (d, J=4.5 Hz, 12H).

Example 7

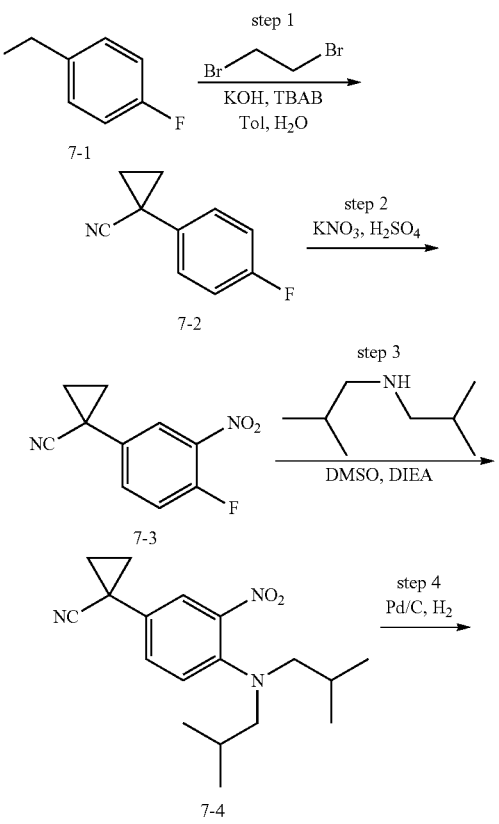

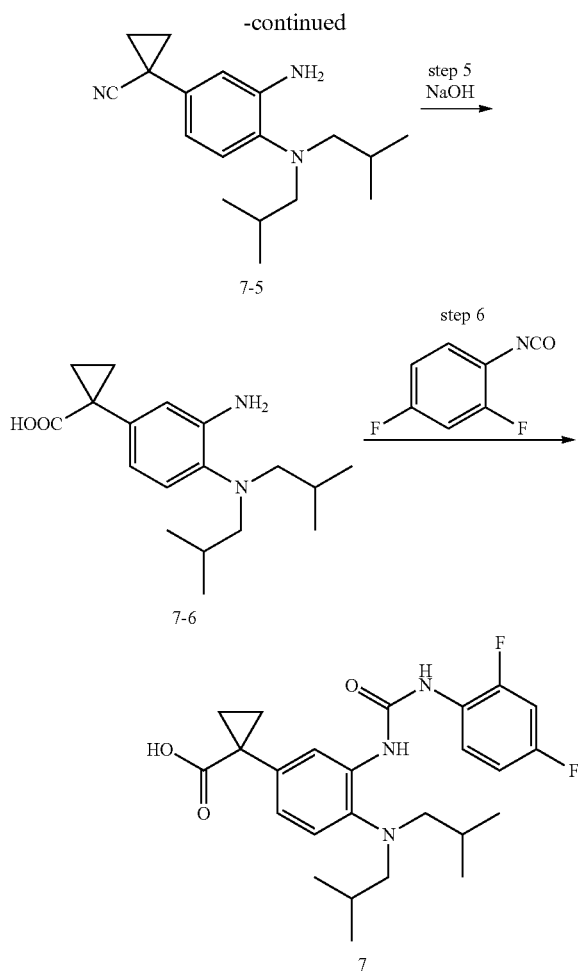

Step 1. Synthesis of 7-2

To a solution of 2-(4-fluorophenyl)acetonitrile (8 g, 59.20 mmol) in toluene (160 mL) at 0° C., were added 1,2-dibromoethane (11.28 g, 60.04 mmol), potassium hydroxide (27 g, 481.20 mmol, 8.00 equiv), tetrabutyl ammonium bromide (200 mg, 0.62 mmol) and water (8 mL). The reaction mixture was heated to 100° C. and stirred for 1.5 h. The reaction was cooled down, quenched with water (100 mL), and extracted with ethyl acetate (100 mL×3). The combined organic layer was dried over anhydrous sodium sulfate and concentrated under vacuum. The residue was purified by silica gel column with ethyl acetate/petroleum ether (1/10) as eluent to afford 1-(4-fluorophenyl) cyclopropane-1-carbonitrile (5 g, 52%).

Step 2. Synthesis of 7-3

To a solution of 1-(4-fluorophenyl)cyclopropane-1-carbonitrile (5 g, 31.02 mmol) in sulfuric acid (100 mL) at 0° C., was added potassium nitrate (4.7 g, 46.49 mmol). The mixture was then warmed up to room temperature and stirred for 40 min. The reaction was quenched with water/ice (300 mL) and the mixture was extracted with ethyl acetate (100 mL×3). The organic layer was washed with saturated aqueous sodium bicarbonate (30 mL×3), dried over anhydrous sodium sulfate and concentrated under vacuum. The residue was purified by silica gel column chromatography with ethyl acetate/petroleum ether (1/4) as eluent to afford 1-(4-fluoro-3-nitrophenyl) cyclopropane-1-carbonitrile (1.6 g, 25%).

Step 3. Synthesis of 7-4

To a solution of 1-(4-fluoro-3-nitrophenyl) cyclopropane-1-carbonitrile (1.6 g, 7.76 mmol) and N,N-diisopropylethylamine (2 g, 15.48 mmol) in dimethylsufoxide (50 mL), was added bis(2-methylpropyl)amine (1.2 g, 9.28 mmol). The mixture was stirred at 100° C. for 2.5 h. The reaction was cooled down, quenched with water (150 mL), and extracted with ethyl acetate (100 mL×3). The organic layer was dried over anhydrous sodium sulfate and concentrated under vacuum. The residue was purified by silica gel column with ethyl acetate/petroleum ether (1/8) to afford 1-[4-[bis(2-methylpropyl) amino]-3-nitrophenyl] cyclopropane-1-carbonitrile (1.94 g, 79%).

Step 4. Synthesis of 7-5

A mixture of 1-[4-[bis(2-methylpropyl)amino]-3-nitrophenyl] cyclopropane-1-carbonitrile (1.9 g, 6.02 mmol) and palladium on carbon (0.19 g) in methanol (20 mL) was stirred under hydrogen atmosphere (1 atm) at room temperature for 2 h. The mixture was filtered through Celite and the filtrate was concentrated under vacuum. The residue was purified by silica gel column with ethyl acetate/petroleum ether (1/8) to afford 1-[3-amino-4-[bis(2-methylpropyl) amino]phenyl]cyclopropane-1-carbonitrile (1.0 g, 58%).

Step 5. Synthesis of 7-6

A mixture of 1-[3-amino-4-[bis(2-methylpropyl)amino]phenyl]cyclopropane-1-carbonitrile (500 mg, 1.75 mmol) and potassium hydroxide (5 mL, 3 M in $H_2O$) in ethanol (10 mL) was stirred in a sealed tube at 100° C. for overnight. After cooled to the room temperature, the pH value of the solution was adjusted to 7 with aqueous hydrogen chloride (2 N) and the mixture was then extracted with ethyl acetate (30 mL×3). The organic phase was dried over anhydrous sodium sulfate and concentrated under vacuum to afford 1-[3-amino-4-[bis(2-methylpropyl)amino]phenyl]cyclopropane-1-carboxylic acid (530 mg, 99%).

Step 6. Synthesis of 7

To a solution of 1-[3-amino-4-[bis(2-methylpropyl) amino]phenyl]cyclopropane-1-carboxylic acid (530 mg, 1.74 mmol) and 2,4-difluoro-1-isocyanatobenzene (324 mg, 2.09 mmol) in tetrahydrofuran (353 mg, 4.89 mmol), was added triethylamine (5 mL). The reaction mixture was stirred at 25° C. for 3 h. The resulting mixture was concentrated under vacuum and then purified by prep-HPLC (Column: XBridge Shield RP18 OBD Column, 5 um, 19×150 mm; Mobile Phase A: Water with 0.05% $NH_4HCO_3$, Mobile Phase B: ACN; Flow rate: 25 mL/min; Gradient: 25% B to 85% B in 8 min; detector: UV 254 nm) to afford 1-[4-[bis (2-methylpropyl)amino]-3-[[(2,4-difluorophenyl)carbamoyl]amino]phenyl]cyclopropane-1-carboxylic acid (146.8 mg, 18% yield). LRMS: (ES, m/z): $[M+H]^1$=460.3. $^1HNMR$ (300 MHz, DMSO-$d_6$): δ 12.25 (s, br, 1H), 9.29 (s, 1H), 8.04 (s, 1H), 7.96-7.85 (m, 1H), 7.84 (s, 1H), 7.34-7.26 (m, 1H), 7.10 (d, J=8.1 Hz, 1H), 7.09-6.93 (m, 1H), 6.91 (d, J=2.1 Hz, 1H), 2.65 (d, J=6.9 Hz, 4H), 1.70-1.59 (m, 2H), 1.42-1.39 (m, 2H), 1.09-1.05 (m, 2H), 0.86 (d, J=6.6 Hz, 12H).

Example 8

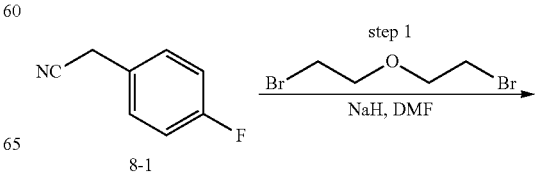

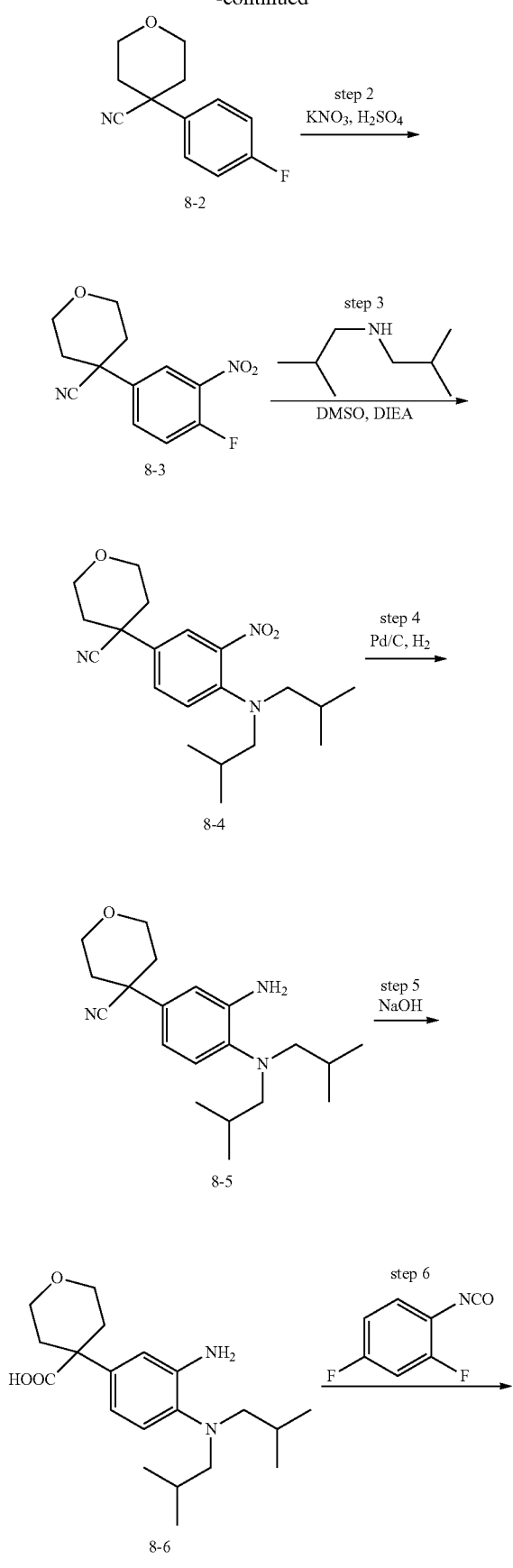
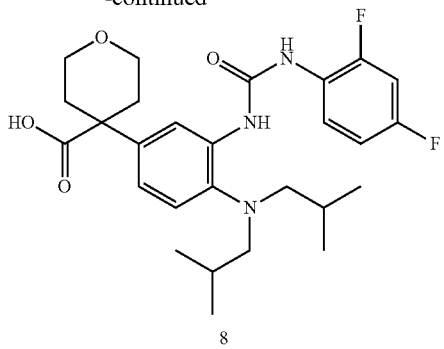

Step 1. Synthesis of 8-2

To a solution of 2-(4-fluorophenyl)acetonitrile (5 g, 37 mmol) in N,N-dimethylformamide (20 mL) at 0° C., was added sodium hydride (3.7 g, 154 mmol). The reaction was then warmed to room temperature and stirred for 30 min. The reaction mixture was cooled to 0° C. again and 1-bromo-2-(2-bromoethoxy)ethane (8.59 g, 37 mmol) was added. The reaction was then stirred at room temperature overnight. Water (100 mL) was added and the mixture was extracted with ethyl acetate (50 mL×3). The organic layer was dried over anhydrous sodium sulfate and concentrated under vacuum. The residue was purified by silica gel column with ethyl acetate/petroleum ether (1/9) as eluent to afford 4-(4-fluorophenyl)oxane-4-carbonitrile (3.69 g, 49%).

Step 2. Synthesis of 8-3

To a solution of 4-(4-fluorophenyl)oxane-4-carbonitrile (3.69 g, 17.98 mmol) in sulfuric acid (30 mL) at 0° C., was added potassium nitrate (2.73 g, 27.00 mmol). The reaction mixture was then stirred at 25° C. for 1 h. The reaction was quenched by addition of water/ice (250 mL) and the mixture was extracted with ethyl acetate (50 mL×3). The organic layer was washed with saturated aqueous sodium bicarbonate (20 mL×2), dried over anhydrous sodium sulfate and concentrated under vacuum. The residue was purified by silica gel column chromatography with ethyl acetate/petroleum ether (1/9) as eluent to afford 4-(4-fluoro-3-nitrophenyl)oxane-4-carbonitrile (2.38 g, 53%).

Step 3. Synthesis of 8-4

To a solution of 4-(4-fluoro-3-nitrophenyl)oxane-4-carbonitrile (2.30 g, 9.19 mmol) and diisopropylethylamine (2.37 g, 18.37 mmol) in dimethylsulfoxide (10 mL), was added bis(2-methylpropyl)amine (1.42 g, 11.02 mmol). The reaction mixture was then warmed to 100° C. and stirred for 4.5 h. The reaction was quenched by addition of water (100 mL) and the mixture was extracted with ethyl acetate (100 mL×3). The organic layer was dried over anhydrous sodium sulfate and concentrated under vacuum. The residue was purified by silica gel column with ethyl acetate/petroleum ether (1/5) to afford 4-[4-[bis(2-methylpropyl) amino]-3-nitrophenyl] oxane-4-carbonitrile (2.7 g, 82%).

Step 4. Synthesis of 8-5

A mixture of 4-[4-[bis(2-methylpropyl)amino]-3-nitrophenyl]oxane-4-carbonitrile (2.7 g, 7.51 mmol) and palladium on carbon (0.3 g) in methanol (50 mL) was stirred under hydrogen atmosphere (1 atm) at 25° C. for 4.5 h. Then the reaction mixture was filtered through celite and the filtrate was concentrated under vacuum. The residue was purified by silica gel column with ethyl acetate/petroleum ether (1/4) to afford 4-[3-amino-4-[bis(2-methylpropyl) amino]phenyl]oxane-4-carbonitrile (1.62 g, 65%).

Step 5. Synthesis of 8-6

A mixture of 4-[3-amino-4-[bis(2-methylpropyl)amino]phenyl]oxane-4-carbonitrile (500 mg, 1.52 mmol) and potassium hydroxide (3 M in H$_2$O, 5 mL) in ethanol (10 mL) was stirred in a sealed tube at 100° C. for 2 days. Water (50 mL) was added and the mixture was extracted with ethyl acetate (50 mL×3). The organic phase was dried over anhydrous sodium sulfate and concentrated under vacuum to afford 4-[3-amino-4-[bis(2-methylpropyl)amino]phenyl]oxane-4-carboxylic acid (520 mg, 98%).

Step 6. Synthesis of 8

A mixture of 4-[3-amino-4-[bis(2-methylpropyl)amino]phenyl]oxane-4-carboxylic acid (520 mg, 1.49 mmol), 2,4-difluoro-1-isocyanatobenzene (279 mg, 1.80 mmol) and triethylamine (303 mg, 2.99 mmol) in tetrahydrofuran (5 mL) was stirred at 25° C. for 3 h. Water (20 mL) was added and the mixture was extracted with ethyl acetate (50 mL×3). The organic layer was concentrated and the residue was purified by prep-HPLC (Column: XBridge Shield RP18 OBD Column, 5 um, 19×150 mm; Mobile Phase A: Water with 0.05% NH$_4$HCO$_3$, Mobile Phase B: ACN; Flow rate: 25 mL/min; Gradient: 25% B to 85% B in 8 min; detector: UV 254 nm) to afford 4-[4-[bis(2-methylpropyl)amino]-3-[[(2,4-difluorophenyl)carbamoyl]amino]phenyl]oxane-4-carboxylic acid (88.56 mg, 12%) as a white solid. LRMS (ES, m/z): [M+H]$^+$=504.5. $^1$HNMR (300 MHz, DMSO-d$_6$) δ 9.30 (s, 1H), 8.04 (s, 1H), 7.97-7.89 (m, 2H), 7.34-7.26 (m, 1H), 7.15 (d, J=8.4 Hz, 1H), 7.07-6.98 (m, 2H), 3.80 (d, J=11.7, 2H), 3.54-3.41 (m, 2H), 2.66 (d, J=6.9 Hz, 4H), 2.34 (d, J=13.2 Hz, 2H), 1.75-1.60, (m, 4H), 0.84 (d, J=6.6 Hz, 12H).

Example 9

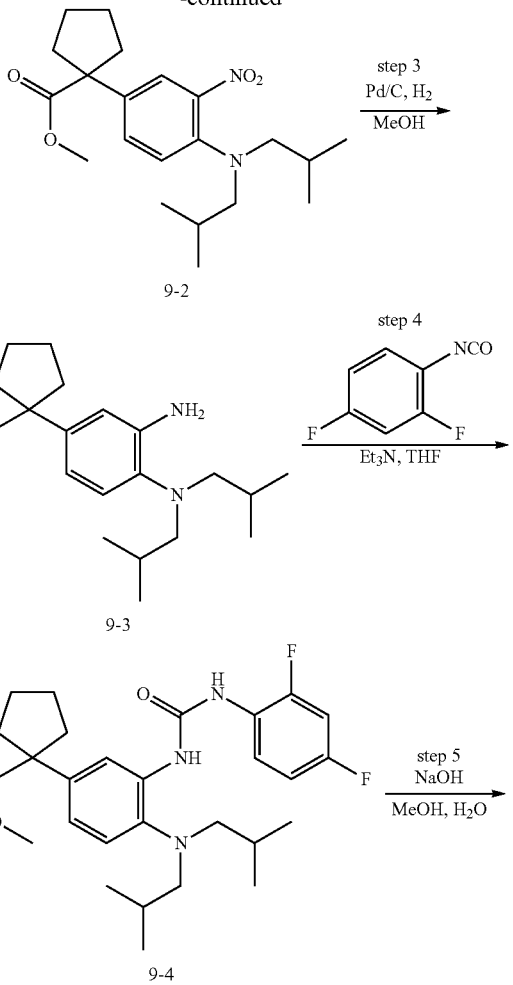

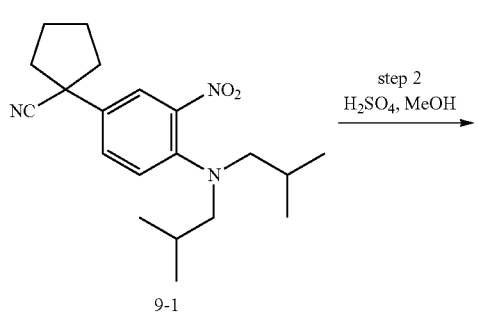

Step 1. Synthesis of 9-1

Into a 250-mL 3-necked round-bottom flask, was placed a solution of 2-[4-[bis(2-methylpropyl)amino]-3-nitrophenyl]acetonitrile (5 g, 17.28 mmol) in DMSO (100 mL), followed by addition of sodium hydride (2.77 g, 69.25 mmol) in portions at 10° C. The resulting mixture was stirred at room temperature for 1 h. 1,4-Dibromobutane (7.47 g, 34.60 mmol) was added dropwise in 5 min with stirring at 10° C. The resulting solution was stirred at room temperature for overnight. The reaction was then quenched by addition of 50 mL of water, and extracted with 3×100 mL of ethyl acetate. The combined organic layer was washed with 3×100 mL of brine. The mixture was dried over anhydrous sodium sulfate and concentrated under vacuum.

The residue was applied onto a silica gel column with ethyl acetate/petroleum ether (1:10~1:3) to afford 1-[4-[bis(2-methylpropyl)amino]-3-nitrophenyl]cyclopentane-1-carbonitrile (2.5 g, 42% yield).

Step 2. Synthesis of 9-2

Into a 50-mL round-bottom flask, was placed methanol (10 mL), 1-[4-[bis(2-methylpropyl)amino]-3-nitrophenyl]cyclopentane-1-carbonitrile (1 g, 2.91 mmol), and sulfuric acid (5 mL). The resulting solution was heated to reflux for 48 h. The reaction was cooled to room temperature. The pH value of the solution was adjusted to 8 with sodium carbonate (10% aqueous solution). The resulting mixture was extracted with 3×50 mL of ethyl acetate. The combined organic phase was washed with 3×50 mL of brine, dried over anhydrous sodium sulfate, and concentrated under vacuum. The residue was applied onto a silica gel column with ethyl acetate/petroleum ether (1:20~1:5) to afford methyl 1-[4-[bis(2-methylpropyl)amino]-3-nitrophenyl]cyclopentane-1-carboxylate (450 mg, 41% yield).

Step 3. Synthesis of 9-3

To a solution of methyl 1-[4-[bis(2-methylpropyl)amino]-3-nitrophenyl]cyclopentane-1-carboxylate (450 mg, 1.20 mmol) in methanol (5 mL), was added palladium on carbon (500 mg). The flask was evacuated and flushed three times with nitrogen, followed by flushing with hydrogen. The mixture was stirred at room temperature under an atmosphere of hydrogen (balloon) for 3 h. The solid was filtered out. The resulting mixture was concentrated under vacuum. The residue was applied onto a silica gel column with ethyl acetate/petroleum ether (1:10-1:1) to afford methyl 1-(3-amino-4-(diisobutylamino)phenyl)cyclopentanecarboxylate (350 mg, 85% yield).

Step 4. Synthesis of 9-4

Into a 25-mL round-bottom flask, was placed tetrahydrofuran (5 mL), methyl 1-[3-amino-4-[bis(2-methylpropyl)amino]phenyl]cyclopentane-1-carboxylate (350 mg, 1.01 mmol), triethylamine (202 mg, 2.00 mmol), and 2,4-difluoro-1-isocyanatobenzene (188 mg, 1.21 mmol). The resulting solution was stirred at room temperature for 4 h. The reaction was concentrated under vacuum. The residue was applied onto a silica gel column with ethyl acetate/petroleum ether (1:10-1:3) to afford methyl 1-[4-[bis(2-methylpropyl)amino]-3-[[(2,4-difluorophenyl)carbamoyl]amino]phenyl]cyclopentane-1-carboxylate (250 mg, 49% yield).

Step 5. Synthesis of 9

Into a 25-mL round-bottom flask, was placed a solution of methyl 1-[4-[bis(2-methylpropyl)amino]-3-[[(2,4-difluorophenyl)carbamoyl]amino]phenyl]cyclopentane-1-carboxylate (250 mg, 0.50 mmol) in methanol (5 mL), and sodium hydroxide (1 mL, 15% aq.). The resulting solution was stirred at room temperature for 4 h. The resulting mixture was concentrated under vacuum. The pH value of the solution was adjusted to 6 with hydrogen chloride (1 N). The resulting solution was extracted with 3×10 mL of ethyl acetate. The combined organic layers was washed with 3×10 mL of brine, and concentrated under vacuum. The crude product was purified by Flash-Prep-HPLC with the following conditions: Column: SunFire C18 5 um 19*150 mm; mobile phase; CH$_3$CN/water (0.05% NH$_3$H$_2$O; Gradient: 51% to 65% in 7 min; Flow rate: 20 mL/min; Detector, UV 254 nm. This resulted in 79.5 mg (33% yield) of 1-[4-[bis(2-methylpropyl)amino]-3-[[(2,4-difluorophenyl)carbamoyl]amino]phenyl]cyclopentane-1-carboxylic acid as an off-white solid. LCMS: (ES, m/z): 488.3 [M+H]$^+$. HNMR: (300 MHz, DMSO-d$_6$, ppm): δ 12.10 (s, 1H), 9.25 (s, 1H), 8.03 (s, 1H), 7.95-7.87 (m, 2H), 7.31 (t, J=2.7 Hz, 1H), 7.12 (d, J=8.4 Hz, 1H), 7.07-7.00 (m, 1H), 6.94 (dd, J=8.4, 2.4 Hz, 1H), 2.65 (d, J=6.9 Hz, 4H), 2.49-2.45 (m, 2H), 1.76-1.58 (m, 8H), 0.84 (d, J=6.6 Hz, 12H).

Example 10

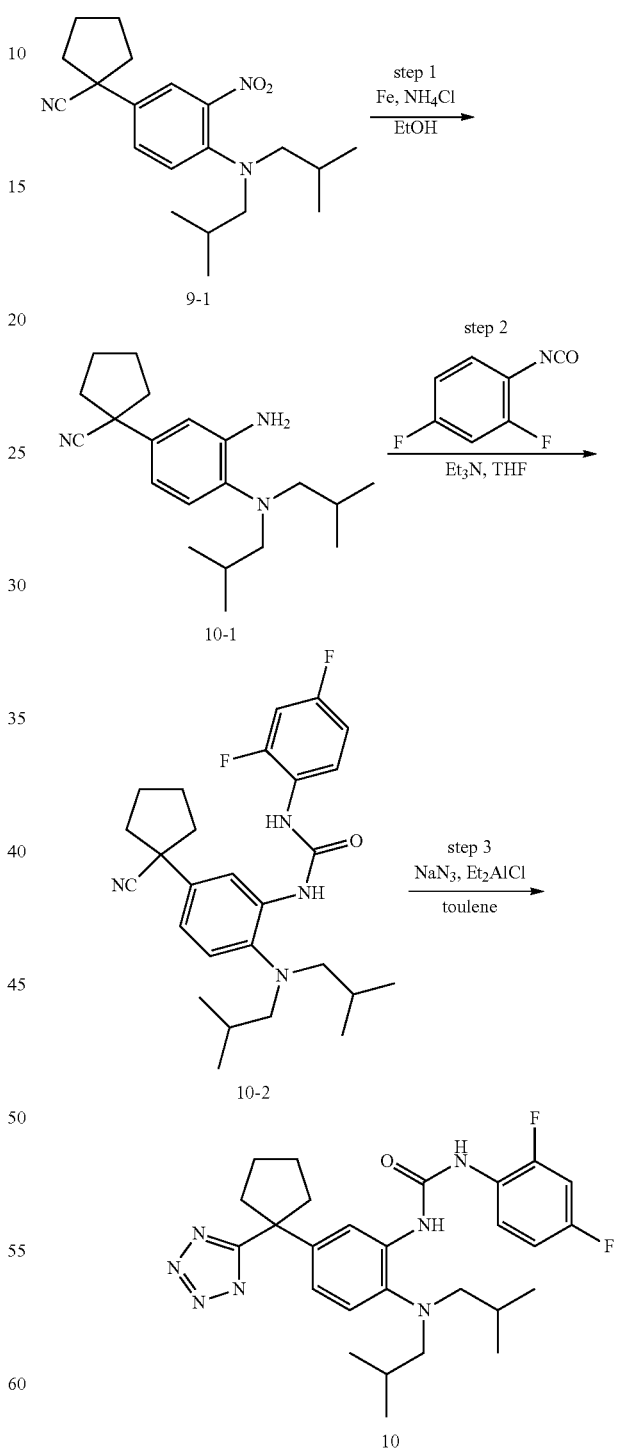

Step 1. Synthesis of 10-1

Into a 100-mL round-bottom flask, was placed a solution of 1-[4-[bis(2-methylpropyl)amino]-3-nitrophenyl]cyclopentane-1-carbonitrile (1.5 g, 4.37 mmol) in ethanol (30 mL), Fe (1.47 g, 26.25 mmol), and NH₄Cl (162 mg, 3.03 mmol). The resulting solution was stirred at 80° C. for 3 h. The reaction mixture was cooled to room temperature. The solid was filtered out and the filtrate was concentrated under vacuum. The residue was dissolved in 150 mL of ethyl acetate, washed with water (50 mL) and brine (3×50 mL), dried over anhydrous sodium sulfate, and concentrated under vacuum. The residue was applied onto a silica gel column with ethyl acetate/petroleum ether (1:10-1:1) to afford 1-[3-amino-4-[bis(2-methylpropyl)amino]phenyl]cyclopentane-1-carbonitrile (600 mg, 44% yield).

Step 2. Synthesis of 10-2

Into a 50-mL 3-necked round-bottom flask, was placed tetrahydrofuran (10 mL), triethylamine (387 mg, 3.82 mmol), and 1-[3-amino-4-[bis(2-methylpropyl)amino]phenyl]cyclopentane-1-carbonitrile (600 mg, 1.91 mmol). This was followed by addition of 2,4-difluoro-1-isocyanatobenzene (356 mg, 2.30 mmol) dropwise with stirring at 0° C. The resulting solution was stirred at room temperature for 3 h. The reaction was concentrated under vacuum. The residue was applied onto a silica gel column with ethyl acetate/petroleum ether (1:20~1:3) to afford 3-[2-[bis(2-methylpropyl)amino]-5-(1-cyanocyclopentyl)phenyl]-1-(2,4-difluorophenyl)urea (500 mg, 56% yield).

Step 3. Synthesis of 10

Into a 50-mL 2-necked round-bottom flask purged and maintained with an inert atmosphere of nitrogen, was placed azidosodium (62 mg, 0.95 mmol), and toluene (3 mL). This was followed by addition of diethylaluminum chloride (0.9M) (1.07 mL) dropwise with stirring at 0° C. The resulting solution was stirred at room temperature for 7 h. To this was added a solution of 1-[2-[bis(2-methylpropyl)amino]-5-(1-cyanocyclopentyl)phenyl]-3-(2,4-difluorophenyl)urea (300 mg, 0.64 mmol) in toluene (1 mL). The resulting solution was heated and stirred at 120° C. overnight. The reaction was cooled to room temperature and quenched by addition of 10 mL of water. The resulting solution was extracted with 3×50 mL of ethyl acetate. The combined organic layers was washed with 3×50 mL of brine, dried over anhydrous sodium sulfate, and concentrated under vacuum. The crude product was purified by Prep-HPLC with the following conditions: Column, waters sunfire C18 19*150 mm 5 um; mobile phase, CH₃CN/Water (0.05% TFA), 65%-74% (7 min); Detector, 254 nm. This resulted in 60 mg (15% yield) of 3-[2-[bis(2-methylpropyl)amino]-5-[1-(1H-1,2,3,4-tetrazol-5-yl)cyclopentyl]phenyl]-1-(2,4-difluorophenyl)urea as a trifluoroacetic acid salt. LCMS. (ES, m/z): 512 [M+H—CF₃COOH]⁺. HNMR (300 MHz, DMSO-d₆, ppm) δ 9.29 (s, 1H), 8.02 (s, 1H), 7.94-7.86 (m, 2H), 7.30 (t, J=6.0 Hz, 1H), 7.27 (d, J=6.3 Hz, 1H), 7.11-7.02 (m, 1H), 6.85 (dd, J=8.4, 2.1 Hz, 1H), 2.73-2.63 (m, 6H), 2.18-2.13 (m, 2H), 1.76-1.66 (m, 2H), 1.66-1.60 (m, 2H), 1.58-1.49 (m, 2H), 0.82 (d, J=6.6 Hz, 12H).

Example 11

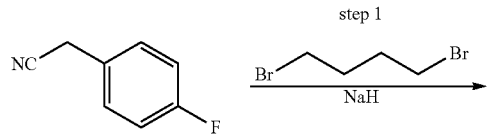

step 1

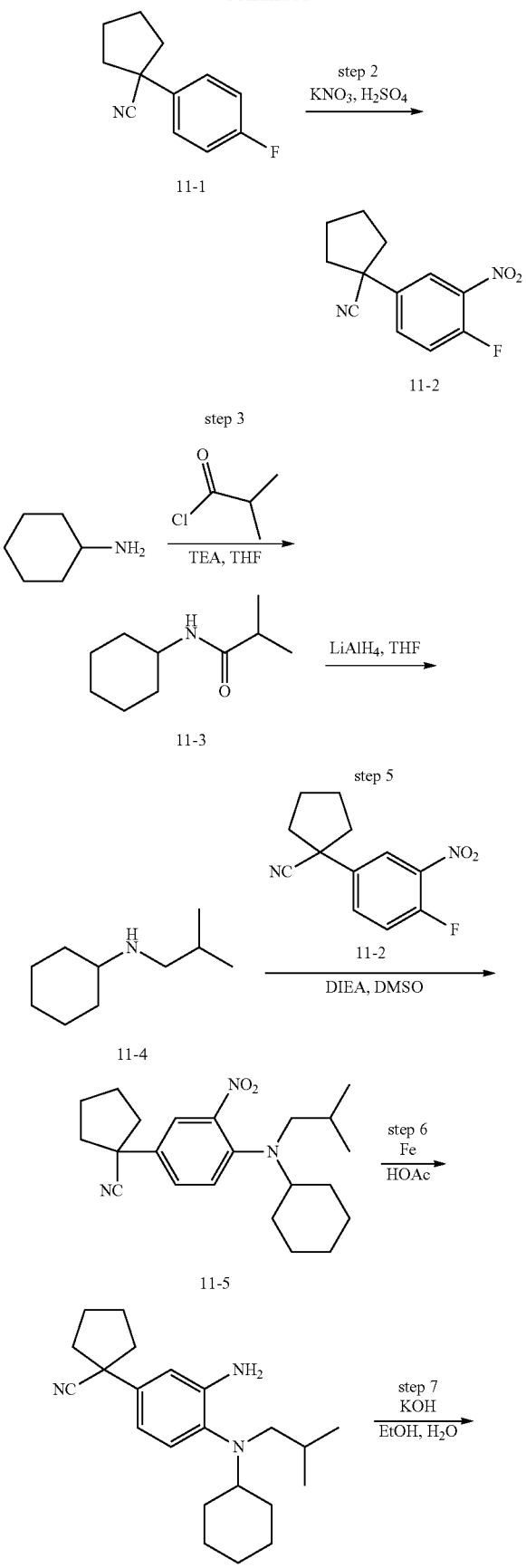

-continued

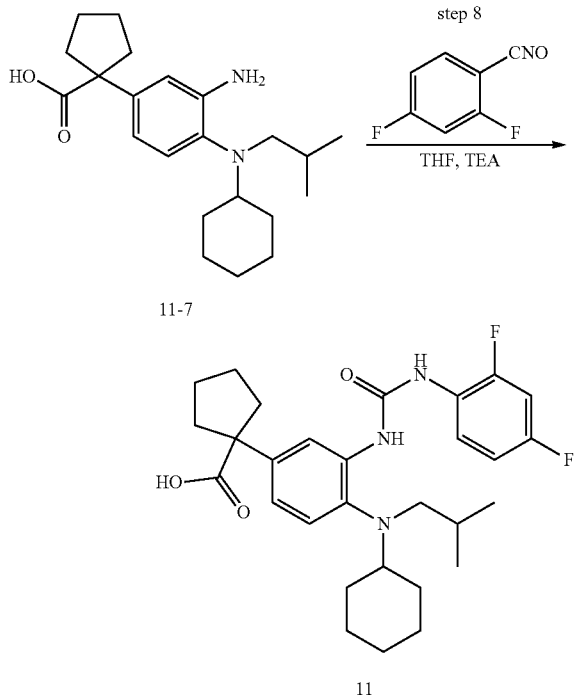

Step 1. Synthesis of 11-1

To a solution of 2-(4-fluorophenyl)acetonitrile (20.0 g, 148 mmol) in tetrahydrofuran (200 mL) at 0° C., was added sodium hydride (17.8 g, 440 mmol) in portions. The mixture was then stirred at 0° C. for 30 min. A solution of 1,4-dibromobutane (38.4 g, 178 mmol) in tetrahydrofuran (100 mL) was added dropwise, and the reaction mixture was stirred at room temperature for another 4 h. The reaction was then cooled to 0° C., and quenched by addition of water (10 mL). The resulted mixture was diluted with ethyl acetate (1 L), and was washed with water (600 mL) and brine (600 mL). The combined organic phase was dried over anhydrous sodium sulfate, and concentrated under vacuum. The residue was purified by silica gel column with ethyl acetate/petroleum ether (1/8) as the eluent to afford the desired product (22.1 g, 71% yield).

Step 2. Synthesis of 11-2

To a solution of 1-(4-fluorophenyl)cyclopentanecarbonitrile (22.1 g, 117 mmol) in concentrated sulfuric acid (200 mL) at 0° C., was added potassium nitrate (17.7 g, 175 mmol) portionwise. The resulting mixture was then stirred at 0° C. for 10 min. The reaction was poured into ice water (1 L) carefully. The mixture was extracted with ethyl acetate (600 mL×2), dried over anhydrous sodium sulfate, and concentrated under vacuum. The residue was purified by silica gel column with ethyl acetate/petroleum ether (1/6) as the eluent to afford the desired product (15.2 g, 55% yield).

Step 3. Synthesis of 11-3

To a solution of cyclohexanamine (5 g, 50.42 mmol) and triethylamine (8 mL) in tetrahydrofuran (45 mL) at 0° C., was added 2-methylpropanoyl chloride (5 g, 46.93 mmol) dropwise. The mixture was then stirred at room temperature for 3 days. The reaction was quenched by addition of saturated ammonium chloride (150 mL), and extracted with dichloromethane (150 mL). The combined organic phase was washed with brine (200 mL×2), dried over anhydrous sodium sulfate, and concentrated under vacuum to afford the desired product (7.5 g, 88% yield).

Step 4. Synthesis of 11-4

To a solution of N-cyclohexyl-2-methylpropanamide (7 g, 41.36 mmol) in tetrahydrofuran (140 mL) at 0° C., was added lithium aluminium tetrahydride (6.5 g, 171.28 mmol) in several portions. The mixture was then stirred at 70° C. for overnight. The mixture was cooled to 0° C. and quenched by the addition of saturated ammonium chloride (250 mL). The solid was filtered out and filter cake was washed with ethyl acetate (200 mL×2). The combined organic phase was separated and washed with brine (300 mL×2), dried over anhydrous sodium sulfate, and concentrated under vacuum to afford the desired product (4 g, 62% yield).

Step 5. Synthesis of 11-5

To a solution of 1-(4-fluoro-3-nitrophenyl)cyclopentane-1-carbonitrile (1 g, 4.27 mmol) in dimethyl sufoxide (20 mL), was added N-(2-methylpropyl)cyclohexanamine (1 g, 6.44 mmol) and N,N-diisopropylethylamine (1.65 g, 12.77 mmol) sequentially. The mixture was then stirred at 100° C. for 16 h. The reaction was cooled to room temperature and diluted with water (100 mL). The mixture was extracted with ethyl acetate (100 mL×3), and washed with brine (100 mL×5). The organic phase was dried over anhydrous sodium sulfate, and concentrated under vacuum. The residue was purified by silica gel column with ethyl acetate/petroleum ether (1/99) to afford the desired product (1 g, 63% yield).

Step 6. Synthesis of 11-6

To a solution of 1-[4-[cyclohexyl(2-methylpropyl)amino]-3-nitrophenyl]cyclopentane-1-carbonitrile (1 g, 2.71 mmol) in acetic acid (10 mL) was added iron (1.5 g, 26.86 mmol). The mixture was then stirred at room temperature for 1 h. Ethyl acetate (150 mL) was added and the solid was filtered off. The filtrate was diluted with water (100 mL), and the pH value was adjusted to 9 by addition of saturated aqueous sodium bicarbonate. The organic phase was separated and washed with brine (100 mL×2), dried over anhydrous sodium sulfate, and concentrated under vacuum. The residue was purified by silica gel column with ethyl acetate/petroleum ether (1/25-1/20) to afford the desired product (597 mg, 65% yield).

Step 7. Synthesis of 11-7

To a solution of 1-[3-amino-4-[cyclohexyl(2-methylpropyl)amino]phenyl]cyclopentane-1-carbonitrile (200 mg, 0.589 mmol) in ethanol (10 mL) and water (2 mL), was added potassium hydroxide (3 g, 53.47 mmol). The mixture was then stirred at 100° C. for 3 days. The mixture was cooled to room temperature and concentrated under vacuum. The residue was dissolved in water (50 mL) and the pH value was adjusted to 6 with hydrogen chloride (1 N). The mixture was extracted with dichloromethane (50 mL×2), and washed with brine (30 mL×2). The organic phase was dried over anhydrous sodium sulfate and concentrated under vacuum. The residue was purified by Flash-Prep-HPLC with the following conditions: [Column, C18 silica gel; mobile phase (A: MeCN, B: H$_2$O (0.1% TFA), MeCN=50%; Detector, UV 254 nm) to afford the desired product (85 mg, 40% yield).

Step 8. Synthesis of 11

To a solution of 1-[3-amino-4-[cyclohexyl(2-methylpropyl)amino]phenyl]cyclopentane-1-carboxylic acid (85 mg, 0.24 mmol) in tetrahydrofuran (50 mL), was added 2,4-difluoro-1-isocyanatobenzene (51 mg, 0.33 mmol) and triethylamine (111 mg, 1.10 mmol) sequentially. The reaction was then stirred at room temperature for 2 h. The mixture was concentrated under vacuum. The residue was re-dissolved in water (50 mL), and the pH value was adjusted to 6 with HCl (1 N). The mixture was extracted with dichloromethane (50 mL×2), and washed with brine (30 mL×2).

The organic phase was dried over anhydrous sodium sulfate, and concentrated under vacuum. The residue was purified by Flash-Prep-HPLC with the following conditions: [Column, C18 silica gel; mobile phase (A: MeCN, B: H$_2$O), MeCN=96%; Detector, UV 254 nm] to afford the desired product (26.6 mg, 22% yield) as a white solid. LCMS (ES, m/z): 514.50 [M+1]$^+$; $^1$HNMR (300 MHz, DMSO-D$_6$, ppm): δ 12.23 (s, 1H), 9.37 (t, J=4.6 Hz, 1H), 8.14 (s, 1H), 7.99 (d, J=2.2 Hz, 1H), 7.90 (td, J=9.2, 6.2 Hz, 1H), 7.32 (td, J=8.8, 4.5 Hz, 1H), 7.22-6.99 (m, 2H), 6.99-6.85 (m, 1H), 2.76 (d, J=7.3 Hz, 2H), 1.90-1.80 (m, 2H), 1.77-1.47 (m, 9H), 1.40-1.00 (m, 9H), 0.82 (d, J=6.5 Hz, 6H).

Example 12

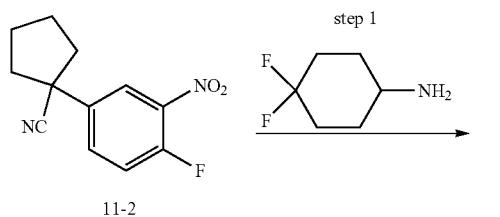

11-2

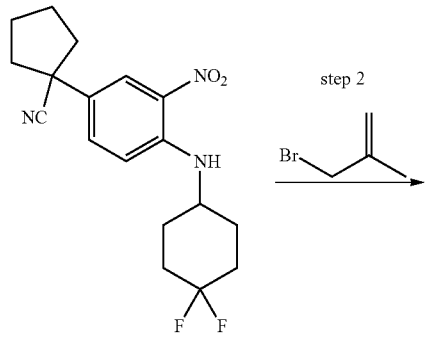

12-1

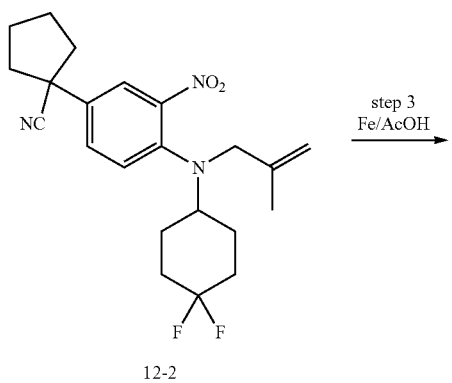

12-2

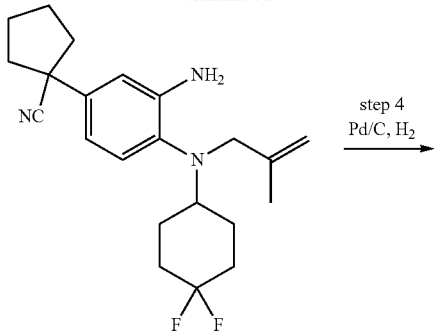

12-3

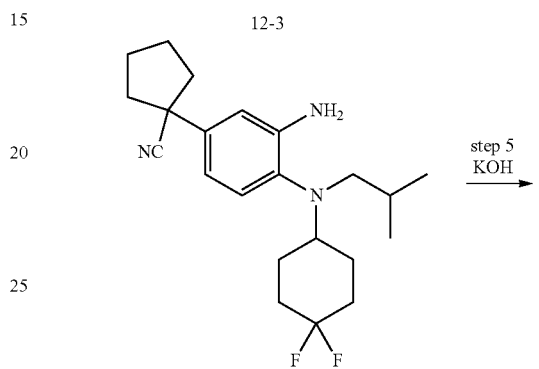

12-4

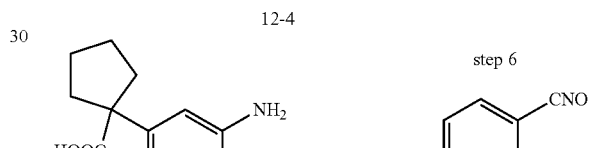

12-5

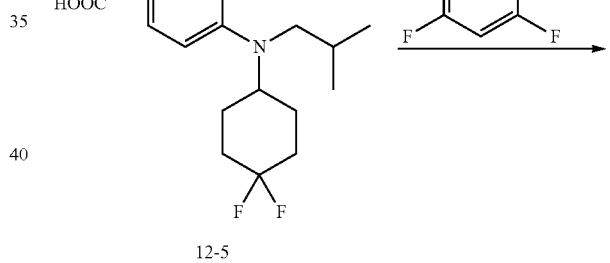

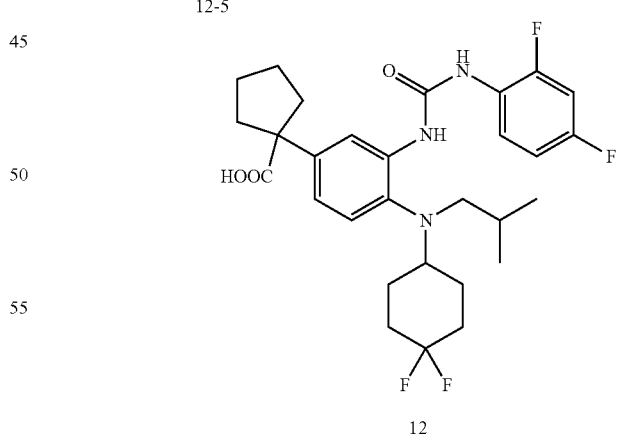

12

Step 1. Synthesis of 12-1

A solution of 1-(4-fluoro-3-nitrophenyl)cyclopentane-1-carbonitrile (1.5 g, 6.40 mmol), 4,4-difluorocyclohexan-1-amine (950 mg, 7.03 mmol) and N,N-diisopropylethylamine (1.65 g) in dimethylsufoxide (20 mL) was stirred at 100° C. for overnight. The mixture was cooled to room temperature, diluted with ethyl acetate (80 mL), and washed with water (60 mL) and brine (60 mL). The organic phase was dried over anhydrous sodium sulfate and concentrated under vacuum. The residue was purified by silica gel column with ethyl acetate/petroleum ether (1/10) as the eluent to afford the desired product (2.1 g, 94% yield).

Step 2. Synthesis of 12-2

To a solution of 1-[4-[(4,4-difluorocyclohexyl)amino]-3-nitrophenyl]cyclopentane-1-carbonitrile (2.1 g, 6.01 mmol) in tetrahydrofuran (25 mL) was added sodium hydride (720 mg, 18.00 mmol) in portions at 0° C. The mixture was then stirred at 0° C. for 30 min followed by addition of a solution of 3-bromo-2-methylprop-1-ene (1.22 g, 9.04 mmol) in tetrahydrofuran (5 mL). The reaction was then stirred at room temperature for overnight. The mixture was quenched by addition of saturated ammonium chloride solution (5 mL) at 0° C., and then diluted with 80 mL of ethyl acetate. The organic phase was washed with water (60 mL) and brine (60 mL), dried over anhydrous sodium sulfate, and concentrated under vacuum. The residue was purified by silica gel column with ethyl acetate/petroleum ether (1/15) as the eluent to afford the desired product (1.0 g, 41% yield).

Step 3. Synthesis of 12-3

To a solution of 1-[4-[(4,4-difluorocyclohexyl)(2-methylprop-2-en-1-yl)amino]-3-nitrophenyl]cyclopentane-1-carbonitrile (1.0 g, 2.48 mmol) in acetic acid (10 mL) was added iron (690 mg, 12.32 mmol). The mixture was then stirred at room temperature for 30 min. Ethyl acetate (60 mL) was added and the solid was filtered off. The reaction mixture was washed with saturated aqueous sodium bicarbonate (30 mL×3), water (30 mL) and brine (30 mL). The organic phase was dried over anhydrous sodium sulfate and concentrated under vacuum. The residue was purified by silica gel column with ethyl acetate/petroleum ether (1/8) as the eluent to afford the desired product (0.8 g, 86% yield).

Step 4. Synthesis of 12-4

To a solution of 1-[3-amino-4-[(4,4-difluorocyclohexyl)(2-methylprop-2-en-1-yl)amino]phenyl]cyclopentane-1-carbonitrile (280 mg, 0.75 mmol) in ethyl acetate (3 mL) was added palladium on carbon (28 mg) and triethylamine (0.3 mL). The reaction was then stirred under hydrogen balloon at room temperature for 30 min. The mixture was filtered through Celite and the filtrate was concentrated under vacuum. The residue was purified by silica gel column with ethyl acetate/petroleum ether (1/8) to afford the desired product (0.16 g, 57% yield).

Step 5. Synthesis of 12-5

To a solution of 1-[3-amino-4-[(4,4-difluorocyclohexyl)(2-methylpropyl)amino]phenyl]cyclopentane-1-carbonitrile (160 mg, 0.43 mmol) in ethanol (4 mL) and water (1 mL) was added potassium hydroxide (1.12 g, 19.96 mmol). The mixture was then stirred at 100° C. for 2 days. The mixture was cooled to room temperature and diluted with water (10 mL), extracted with ethyl acetate (10 mL×2), and washed with brine (10 mL). The organic phase was dried over anhydrous sodium sulfate and concentrated under vacuum to afford the desired product (90 mg, 54% yield).

Step 6. Synthesis of 12

A solution of 1-[3-amino-4-[(4,4-difluorocyclohexyl)(2-methylpropyl)amino]phenyl]cyclopentane-1-carboxylic acid (90 mg, 0.23 mmol), 2,4-difluoro-1-isocyanatobenzene (53 mg, 0.34 mmol) and triethylamine (69 mg, 0.69 mmol) in tetrahydrofuran (3 mL) was stirred at room temperature for 0.5 h. Ethyl acetate (20 mL) was then added and the organic phase was washed with water (10 mL) and brine(10 mL). The organic phase was dried over anhydrous sodium sulfate and concentrated under vacuum. The residue was purified by Prep-HPLC with the following conditions: [Column: X Bridge Shield RP18 OBD Column, 5 um,19*150 mm; mobile phase, Waters (10 MMOL/L NH$_4$HCO$_3$) and ACN (35.0% ACN up to 70.0% in 8 min); Detector, 254 nm] to afford the desired product (52.1 mg, 42% yield) as an off-white solid. LCMS (ES, m/z): 550.50 [M+H]$^+$; $^1$HNMR (300 MHz, DMSO-d$_6$, ppm): δ 9.40 (s, 1H), 8.24 (s, 1H), 8.09 (d, J=2.1 Hz, 1H), 7.96-7.88 (m, 1H), 7.35-7.27 (m, 1H), 7.15-6.94 (m, 3H), 2.89-2.76 (m, 3H), 2.08-1.24 (m, 17H), 0.82 (d, J=6.6 Hz, 6H).

Example 13

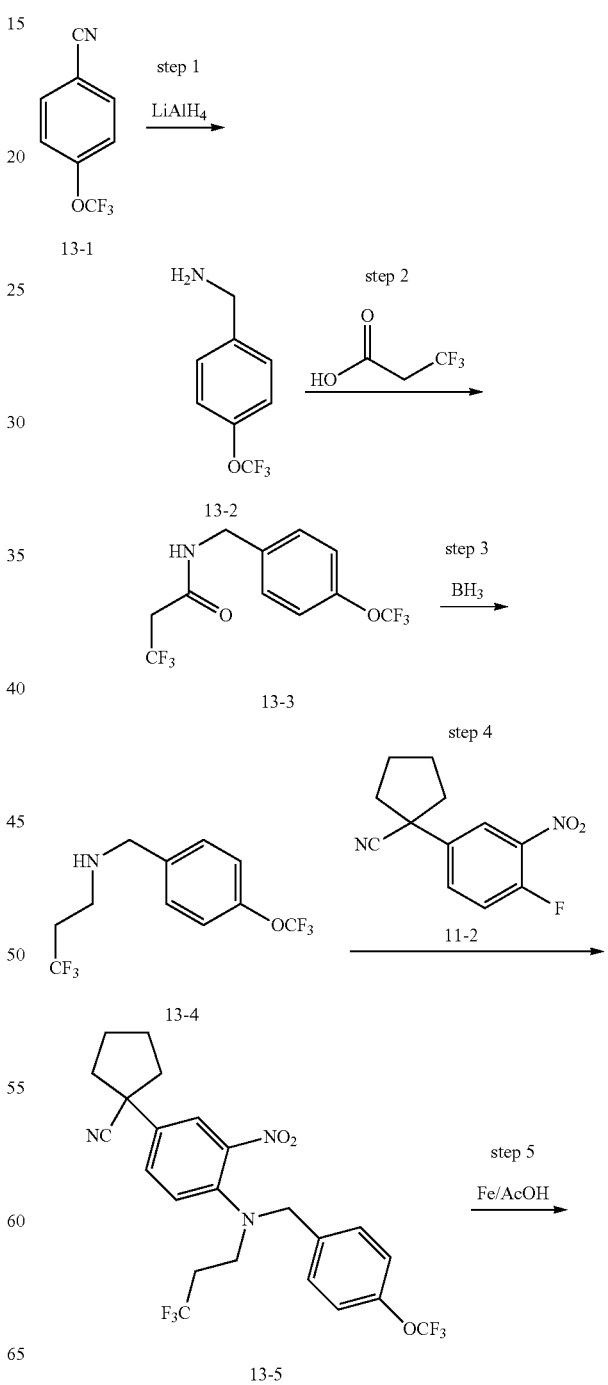

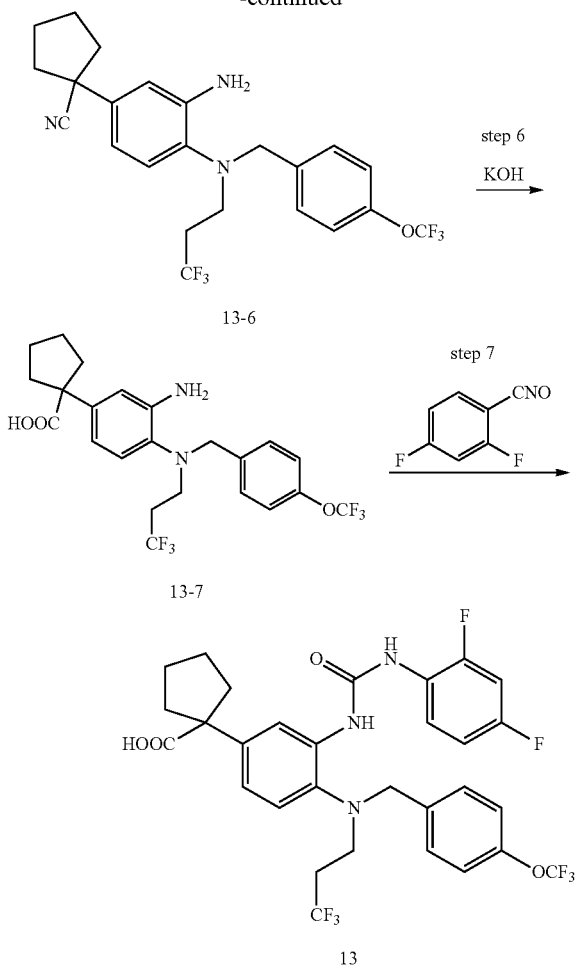

Step 1. Synthesis of 13-2

To a solution of lithium aluminium tetrahydride (3.0 g, 88.44 mmol) in tetrahydrofuran (30 mL) at 0° C., was added a solution of 4-(trifluoromethoxy)benzonitrile (5.0 g, 26.72 mmol) in tetrahydrofuran (30 mL) dropwise. The reaction was then stirred at room temperature for 3 h. The mixture was diluted with tetrahydrofuran (50 mL) at 0° C., then quenched by the addition of water (3 mL), 15% sodium hydroxide (3 mL) and water (3 mL). The mixture was stirred at room temperature for 15 min. The mixture was filtered through Celite and the filtrate was dried over anhydrous magnesium sulfate and concentrated under vacuum to afford the desired product (3.1 g, 61% yield).

Step 2. Synthesis of 13-3

To a solution of 3,3,3-trifluoropropanoic acid (2.28 g, 17.81 mmol) and N,N-diisopropylethylamine (4.2 g) in N,N-dimethylformamide (25 mL), was added HATU (9.25 g) in portions at 0° C. The mixture was then stirred for 5 min at 0° C., followed by addition of a solution of [4-(trifluoromethoxy)phenyl]methanamine (3.1 g, 16.22 mmol) in N,N-dimethylformamide (25 mL). The reaction was allowed to warm to room temperature and stirred for another 3 h. Water (300 mL) was added, and the mixture was extracted with ethyl acetate (200 mL×3). The combined organic phase was dried over anhydrous sodium sulfate and concentrated under vacuum. The residue was purified by silica gel column with ethyl acetate/petroleum ether (1/2) as the eluent to afford the desired product (2.4 g, 49% yield).

Step 3. Synthesis of 13-4

A solution of 3,3,3-trifluoro-N-[[4-(trifluoromethoxy)phenyl]methyl]propanamide (2.3 g, 7.64 mmol) in borane-tetrahydrofuran complex (10 mL, 1 M) was stirred at 60° C. for 1 h. The reaction was quenched by addition of methanol (10 mL) and concentrated HCl (3 mL), and stirred at 60° C. for another 1 h. The mixture was concentrated under vacuum, and then diluted with water (20 mL) and extracted with ethyl acetate (20 mL×3). The combined organic phase was dried over anhydrous sodium sulfate and concentrated under vacuum. The residue was purified by silica gel column with ethyl acetate/petroleum ether (1/3) as the eluent to afford the desired product (1.0 g, 46% yield).

Step 4. Synthesis of 13-5

A solution of [4-(trifluoromethoxy)phenyl]methyl](3,3,3-trifluoropropyl)amine (720 mg, 2.51 mmol), 1-(4-fluoro-3-nitrophenyl)cyclopentane-1-carbonitrile (590 mg, 2.52 mmol) and N,N-diisopropylethylamine (0.65 g) in dimethyl sufoxide (10 mL) was stirred at 130° C. for overnight. The mixture was cooled to room temperature, diluted with ethyl acetate (60 mL), and washed with water (30 mL×2) and brine (30 mL). The organic phase was dried over anhydrous sodium sulfate and concentrated under vacuum. The residue was purified by silica gel column with ethyl acetate/petroleum ether (1/10) as the eluent to afford the desired product (0.47 g, 37% yield).

Step 5. Synthesis of 13-6

To a solution of 1-[3-nitro-4-([[4-(trifluoromethoxy)phenyl]methyl](3,3,3-trifluoropropyl)amino)phenyl]cyclopentane-1-carbonitrile (470 mg, 0.94 mmol) in acetic acid (5 mL) was added iron (0.26 g). The mixture was then stirred at room temperature for 0.5 h. Ethyl acetate (30 mL) was added, and the mixture was filtered through Celite. The filtrate was concentrated under vacuum. The residue was purified by silica gel column with ethyl acetate/petroleum ether (1/10) to afford the desired product (0.33 g, 75% yield).

Step 6. Synthesis of 13-7

To a solution of 1-[3-amino-4-([[4-(trifluoromethoxy)phenyl]methyl](3,3,3-trifluoropropyl)amino)phenyl]cyclopentane-1-carbonitrile (330 mg, 0.70 mmol) in water (1 mL) and ethanol (4 mL), was added KOH (1.12 g, 19.96 mmol). The mixture was then stirred at 100° C. for overnight. The reaction was cooled to room temperature, diluted with water (10 mL), extracted with ethyl acetate (20 mL×2), and washed with brine (10 mL). The organic phase was dried over anhydrous sodium sulfate and concentrated under vacuum to afford the desired product (160 mg, 47% yield).

Step 7. Synthesis of 13

To a solution of 2,4-difluoro-1-isocyanatobenzene (38 mg, 0.25 mmol) in tetrahydrofuran (3 mL), was added 1-[3-amino-4-([[4-(trifluoromethoxy)phenyl]methyl](3,3,3-trifluoropropyl)amino)phenyl]cyclopentane-1-carboxylic acid (80 mg, 0.16 mmol) and triethylamine (48 mg). The mixture was stirred at room temperature for 0.5 h, followed by addition of ethyl acetate (20 mL). The resulting mixture was washed with of water (10 mL) and brine (10 mL). The organic phase was dried over anhydrous sodium sulfate and concentrated under vacuum. The residue was purified by Prep-HPLC with the following conditions: [Column: X Bridge Prep C18 OBD Column, 30*50 mm, 5 um, 13 nm; mobile phase, Waters (0.1% FA) and ACN (60.0% ACN up to 90.0% in 8 min, hold 90.0% in 2 min); Detector, UV 254 nm] to afford the desired product (47.4 mg, 45% yield) as an off-white solid. LCMS $C_{30}H_{27}F_8N_3O_4$ (ES, m/z): 646.4 $[M+H]^+$; $^1$HNMR (300 MHz, DMSO-$d_6$): δ 12.23 (brs, 1H), 9.34 (s, 1H), 8.55 (s, 1H), 8.11-8.01 (m, 2H), 7.44 (d, J=8.7

Hz, 2H), 7.37-7.27 (m, 3H), 7.24-7.15 (m, 1H), 7.08-7.02 (m, 1H), 6.92-6.88 (m, 1H), 4.18 (s, 2H), 3.21-3.09 (m, 2H), 2.73-2.50 (m, 4H), 1.74-1.61 (m, 6H).

Example 14

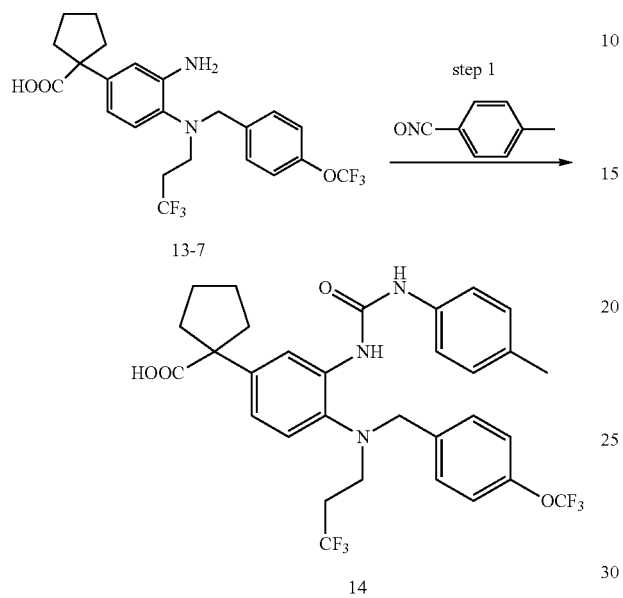

Step 1. Synthesis of 14

A solution of 1-[3-amino-4-([[4-(trifluoromethoxy)phenyl]methyl](3,3,3-trifluoropropyl)amino)phenyl]cyclopentane-1-carboxylic acid (80 mg, 0.16 mmol), 1-isocyanato-4-methylbenzene (32 mg, 0.24 mmol) and triethylamine (48 mg) in tetrahydrofuran (3 mL) was stirred at room temperature for 0.5 h. Ethyl acetate (20 mL) was added and the resulting mixture was washed with water (10 mL) and brine (10 mL). The organic phase was dried over anhydrous sodium sulfate and concentrated under vacuum. The residue was purified by Prep-HPLC with the following conditions: [Column: X Bridge Prep C18 OBD Column, 19*150 mm 5 um; mobile phase, Waters (0.1% FA) and ACN (50.0% ACN up to 80.0% in 8 min, hold 80.0% in 2 min); Detector, UV 254 nm] to afford the desired product (31.5 mg, 32% yield) as an off-white solid. LCMS (ES, m/z): 624.30 [M+H]$^+$; $^1$HNMR (300 MHz, DMSO-d$_6$): δ 9.39 (s, 1H), 8.23 (s, 1H), 8.18 (d, J=2.1 Hz, 1H), 7.46-7.36 (m, 4H), 7.26 (d, J=8.1 Hz, 2H), 7.18-7.12 (m, 3H), 6.90-6.87 (m, 1H), 4.17 (s, 2H), 3.13-3.08 (m, 2H), 2.50-2.45 (m, 4H), 2.26 (s, 3H), 1.75-1.62 (m, 6H).

Example 15

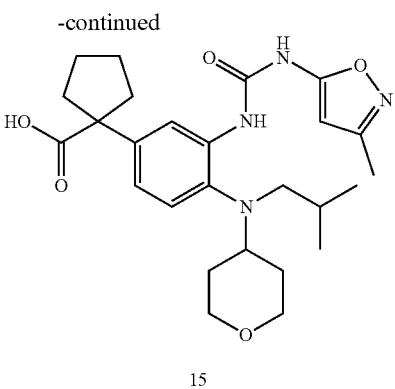

15

Step 1. Synthesis of 15-1

To a solution of 2-methylpropan-1-amine (480 mg, 6.56 mmol) in dichloromethane (10 mL), was added oxan-4-one (723 mg, 7.22 mmol) and acetic acid (0.05 mL). The resulting mixture was stirred at room temperature for 0.5 h before sodium cyanoborohydride (1.66 g, 26.42 mmol) was added. After stirring at room temperature for another 3 h, the mixture was quenched by the addition of a solution of ammonium chloride (50 mL), and extracted with dichloromethane (50 mL×2). The organic phase was washed with brine (50 mL×2), dried over anhydrous sodium sulfate, and concentrated under vacuum to afford the desired product (0.80 g, 78% yield).

Step 2. Synthesis of 15-2

To a solution of 1-(4-fluoro-3-nitrophenyl)cyclopentane-1-carbonitrile (1.0 g, 4.274 mmol) in dimethyl sulfoxide (30 mL) at room temperature, were added N,N-diisopropylethylamine (1.1 g, 8.548 mmol) and N-(2-methylpropyl)oxan-4-amine (1.0 g, 6.411 mmol). The resulting solution was stirred overnight at 130° C. The reaction was quenched by addition of water (30 mL) and the mixture was extracted with ethyl acetate (30 mL×3). The combined organic layer was washed with brine (40×3), dried over anhydrous sodium sulfate, and concentrated under vacuum. The residue was applied onto a silica gel column with ethyl acetate/petroleum ether (1:25) as eluent to afford the desired product (0.30 g, 19% yield).

Step 3. Synthesis of 15-3

To a solution of 1-[4-[(2-methylpropyl)(oxan-4-yl) amino]-3-nitrophenyl]cyclopentane-1-carbonitrile (0.3 g, 0.808 mmol) in methanol (10 mL) was added palladium on carbon under $N_2$. The suspension was degassed under vacuum and purged with $H_2$ several times. The resulting mixture was stirred under $H_2$ balloon at 25° C. overnight. The solids were filtered off and the filter cake was washed with methanol (10 mL×3). The filtrate was concentrated under vacuum and applied onto a silica gel column with ethyl acetate/petroleum ether (2:7) as eluent to afford the desired product (0.18 g, 65% yield).

Step 4. Synthesis of 15-4

To a solution of 1-[3-amino-4-[(2-methylpropyl)(oxan-4-yl)amino]phenyl]cyclopentane-1-carboxylic acid (0.18 g, 0.528 mmol) in ethanol (10 mL) were added potassium hydroxide (0.29 g, 5.28 mmol) and water (6 mL). The resulting solution was stirred at 130° C. for 3 days. The reaction mixture was cooled to room temperature with a water/ice bath. The pH value of the solution was adjusted to 5 with hydrochloric acid (1 N) and the mixture was extracted with ethyl acetate (20 mL×3). The combined organic layer was washed with brine (30 mL×3), dried over anhydrous sodium sulfate, and concentrated under vacuum to afford the desired product (0.16 g, 84% yield).

Step 5. Synthesis of 15

To a solution of 3-methyl-1,2-oxazol-5-amine (0.12 g, 1.22 mmol) in dichloromethane (12 mL), were added N,N-diisopropylethylamine (0.21 g, 1.663 mmol) and triphosgene (0.12 mg, 0.41 mmol) under $N_2$. The resulting solution was stirred for 20 minutes at room temperature, followed by the addition of 1-[3-amino-4-[(2-methylpropyl)(oxan-4-yl) amino]phenyl]cyclopentane-1-carboxylic acid (0.11 g, 0.31 mmol, 1.00 equiv) and then triethylamine (0.19 g, 1.83 mmol, 6.00 equiv). The reaction was stirred at room temperature for another 2 hours. The reaction was quenched by addition of methanol (8 mL) and water (20 mL), and the mixture was extracted with dichloromethane (20 mL×3). The combined organic layer was washed with brine (30 mL×3), dried over anhydrous sodium sulfate, and concentrated under vacuum. The crude product was purified by prep-HPLC [Column, Xbridge, RP18, 19*150 mm; mobile phase, A: formic acid (aq) (0.1%), B: acetonitrile (35%-75% in 8 min); rate, 25 mL/min; Detector, 254 nm] to afford the product (72.3 mg, 49% yield) as a white solid. LCMS: (ES, m/z): [M+H]+ 485.4. $^1$HNMR (300 MHz, $CD_3OD$, ppm) δ 8.25 (d, J=2.1 Hz, 1H), 7.22 (d, J=8.4 Hz, 1H), 7.09 (dd, J=2.1 Hz, J=8.4 Hz, 1H), 6.06 (s, 1H), 3.94-3.89 (m, 2H), 3.31 (s, 2H), 2.92-2.83 (m, 3H), 2.65-2.61 (m, 2H), 2.24 (s, 3H), 1.93-1.87 (m, 2H), 1.78 (s, 6H), 1.76-1.57 (m, 2H), 1.48-1.32 (m, 1H), 0.85 (d, J=6 Hz, 6H).

Example 16

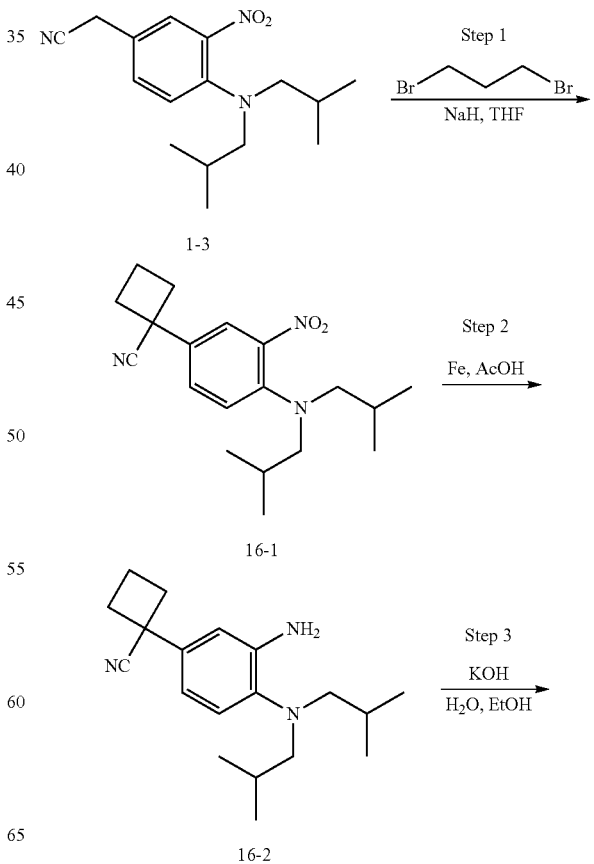

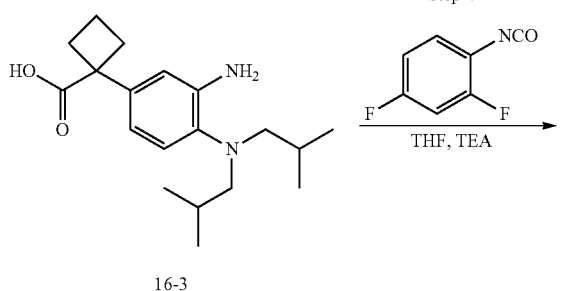

Step 1. Synthesis of 16-1

To a solution of 2-[4-[bis(2-methylpropyl)amino]-3-nitrophenyl]acetonitrile (1.0 g, 3.46 mmol) in tetrahydrofuran (10 mL) at 0° C., was added sodium hydride (410 mg, 10.25 mmol) portionwise. At the same temperature, the mixture was stirred for 30 min, followed by addition of a solution of 1,3-dibromopropane (840 mg, 4.16 mmol) in THF (2 mL). The resulting mixture was stirred at room temperature for another 3 h. The reaction was then quenched by addition of water (2 mL). The mixture was diluted with ethyl acetate (60 mL), and washed with water (30 mL) and brine (30 mL). The organic phase was dried over anhydrous sodium sulfate and concentrated under vacuum. The residue was purified by silica gel column with ethyl acetate/petroleum ether (1/10) as the eluent to afford the desired product (0.4 g, 35% yield).

Step 2. Synthesis of 16-2

To a solution of 1-[4-[bis(2-methylpropyl)amino]-3-nitrophenyl]cyclobutane-1-carbonitrile (400 mg, 1.21 mmol) in acetic acid (10 mL) was added iron (680 mg, 12.14 mmol). The resulting mixture was stirred at room temperature for 1 h. The reaction was filtered through Celite and the filtrate was diluted with ethyl acetate (50 mL), and washed with saturated aqueous sodium carbonate (20 mL) and water (20 mL). The organic phase was dried over anhydrous sodium sulfate and concentrated under vacuum. The residue was purified by silica gel column with ethyl acetate/petroleum ether (1/10) as the eluent to afford the desired product (0.198 g, 54% yield).

Step 3. Synthesis of 16-3

To a solution of 1-[3-amino-4-[bis(2-methylpropyl)amino]phenyl]cyclobutane-1-carbonitrile (198 mg, 0.66 mmol) in ethanol (4 mL) and water (2 mL) at room temperature, was added potassium hydroxide (110 mg, 1.96 mmol). The reaction was then stirred at 100° C. for overnight. The mixture was cooled to room temperature, diluted with water (20 mL), and extracted with ethyl acetate (20 mL×3). The organic phase was dried over anhydrous sodium sulfate and concentrated under vacuum. The residue was purified by silica gel column with dichloromethane/methanol (10/1) as the eluent to afford the desired product (110 mg, 52% yield).

Step 4. Synthesis of 16

To a solution of 1-[3-amino-4-[bis(2-methylpropyl)amino]phenyl]cyclobutane-1-carboxylic acid (82 mg, 0.26 mmol) in tetrahydrofuran (3 mL), was added triethylamine (53 mg, 0.52 mmol) and 2,4-difluoro-1-isocyanatobenzene (60 mg, 0.39 mmol). The reaction was then stirred at room temperature for 1 h. The mixture was diluted with ethyl acetate (20 mL), and washed with water (10 mL×2). The organic phase was concentrated under vacuum. The residue was purified by Prep-HPLC with the following conditions: [Column, X Bridge Shield RP18 OBD Column, 5 um,19*150 mm; mobile phase, water (10 mmol/L $NH_4HCO_3$) and ACN (15.0% ACN up to 65.0% in 8 min); Detector, UV 254; 220 nm] to afford the desired product (44.7 mg, 37% yield). LCMS (ES, m/z): 474.50 $[M+H]^+$; $^1$HNMR: (300 MHz, DMSO-D$_6$, ppm): δ 9.23 (s, 1H), 8.01-7.88 (m, 2H), 7.77 (s, 1H), 7.31-7.25 (m, 1H), 7.08-7.00 (m, 2H), 6.86 (d, J=6.9 Hz, 1H), 2.90-2.61 (m, 6H), 2.30-2.20 (m, 2H), 1.82-1.62 (m, 4H), 0.83 (d, J=6.6 Hz, 12H).

Example 17

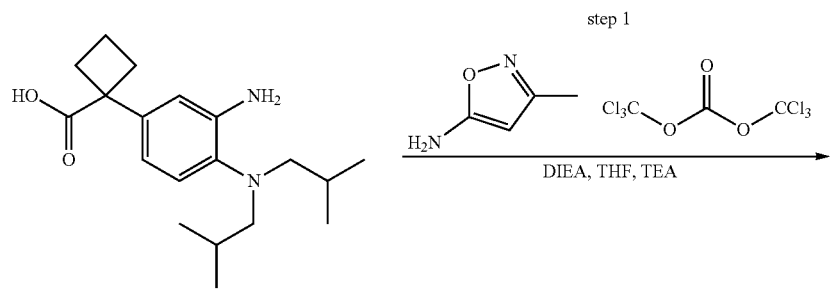

step 1

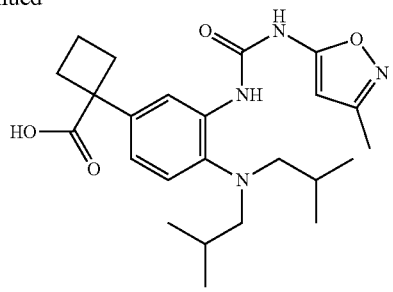

17

Step 1. Synthesis of 17

To a solution of 3-methyl-1,2-oxazol-5-amine (98.1 mg, 1.00 mmol) and N,N-diisopropylethylamine (175 mg, 1.35 mmol) in tetrahydrofuran (3 mL) at room temperature, was added a solution of ditrichloromethyl carbonate (101 mg, 0.34 mmol) in THF (3 mL). The reaction was stirred for 15 min. Triethylamine (152 mg, 1.50 mmol) and 1-[3-amino-4-[bis(2-methylpropyl)amino]phenyl]cyclobutane-1-carboxylic acid (80 mg, 0.25 mmol) was added, and the resulting mixture was stirred at room temperature for another 2 h. The reaction was concentrated under vacuum. The residue was dissolved in methanol (4 mL) and purified by Prep-HPLC with the following conditions: [Column: X bridge, C18, 19*50 mm; Mobile Phase, H$_2$O (0.05% NH4HCO3)/MeCN, 35%-55% in 8 min; Rate: 25 mL/min; Detector, 254 nm] to afford the desired product (27.5 mg, 6% yield) as a white solid. LCMS (ES, m/z): 443.5 [M+H]$^+$; $^1$HNMR: (300 MHz, DMSO-d$_6$, ppm): δ 8.26 (s, 1H), 7.88 (d, J=2.1 Hz, 1H), 7.17 (d, J=8.3 Hz, 1H), 6.91 (dd, J=8.2, 2.2 Hz, 1H), 5.99 (s, 1H), 2.75-2.60 (m, 6H), 2.40-2.25 (m, 2H), 2.16 (s, 3H), 1.91-1.80 (m, 1H), 1.77-1.70 (m, 1H), 1.68-1.55 (m, 2H), 0.82 (d, J=6.5 Hz, 12H).

Example 18

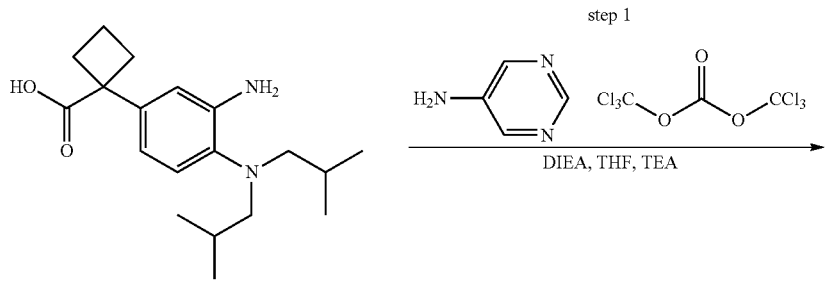

16-3

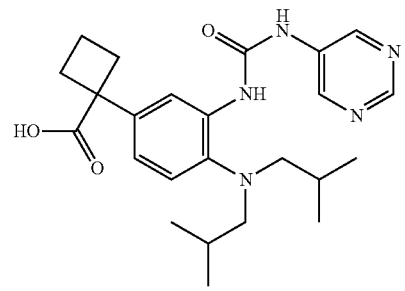

18

Step 1. Synthesis of 18

To a solution of pyrimidin-5-amine (95.1 mg, 1.00 mmol) and N,N-diisopropylethylamine (175 mg, 1.35 mmol) in tetrahydrofuran (3 mL) at room temperature, was added a solution of ditrichloromethyl carbonate (101 mg, 0.34 mmol) in THF (3 mL) dropwise. After stirring for 15 min, triethylamine (152 mg, 1.50 mmol) and 1-[3-amino-4-[bis(2-methylpropyl)amino]phenyl]cyclobutane-1-carboxylic acid (80 mg, 0.25 mmol) was added. The resulting mixture was stirred at room temperature for another 2 h. The reaction was then concentrated under vacuum. The residue was purified by Prep-HPLC with the following conditions: [Column: X bridge, C18, 19*50 mm; Mobile Phase, $H_2O$ (0.05% $NH_4HCO_3$)/MeCN, 35%-55% in 8 min; Rate: 25 mL/min; Detector, 254 nm] to afford the desired product (72.7 mg, 17% yield) of as a white solid. LCMS (ES, m/z): 440.5 $[M+H]^+$. $^1$HNMR (300 MHz, DMSO-$d_6$, ppm): δ 10.01 (s, 1H), 8.93 (s, 2H), 8.81 (s, 1H), 8.20 (s, 1H), 7.90 (d, J=2.1 Hz, 1H), 7.19 (d, J=8.3 Hz, 1H), 6.92 (dd, J=8.3, 2.2 Hz, 1H), 2.68 (d, J=6.9 Hz, 6H), 2.42-2.26 (m, 2H), 1.94-1.50 (m, 4H), 0.86 (d, J=6.5 Hz, 12H).

Example 19

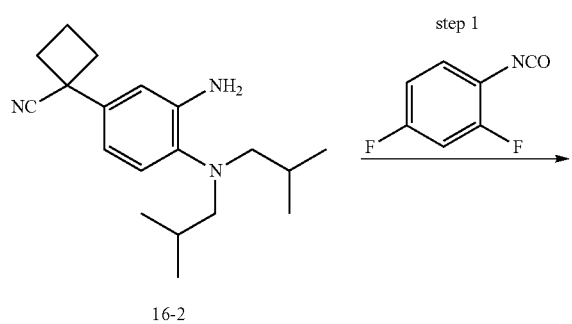

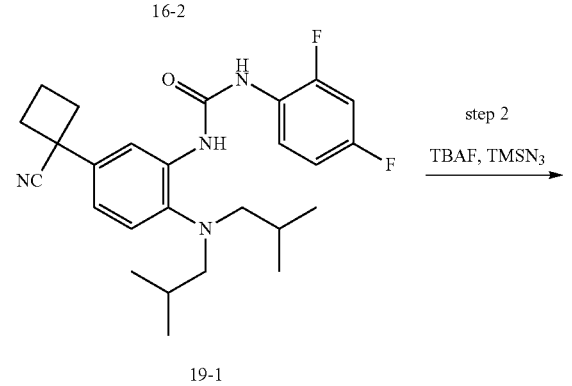

Step 1. Synthesis of 19-1

To a solution of 1-[3-amino-4-[bis(2-methylpropyl)amino]phenyl]cyclobutane-1-carbonitrile (270 mg, 0.90 mmol) in tetrahydrofuran (5 mL), was added 2,4-difluoro-1-isocyanatobenzene (210 mg, 1.35 mmol) and triethylamine (182 mg, 1.80 mmol). The mixture was then stirred at room temperature for 2 h. The reaction was diluted with ethyl acetate (20 mL), and washed with water (10 mL) and brine (10 mL). The organic phase was dried over anhydrous sodium sulfate and concentrated under vacuum. The residue was by silica gel column with ethyl acetate/petroleum ether (1/1) as the eluent to afford the desired product (230 mg, 56% yield).

Step 2. Synthesis of 19

A solution of 3-[2-[bis(2-methylpropyl)amino]-5-(1-cyanocyclobutyl)phenyl]-1-(2,4-difluorophenyl)urea (120 mg, 0.26 mmol), trimethylsilyl azide (152 mg, 1.32 mmol), and tetrabutylammonium fluoride (345 mg, 1.32 mmol) was stirred at 90° C. for 1 h. The mixture was cooled to room temperature, diluted with ethyl acetate (10 mL), and washed with water (10 mL×2). The organic phase was concentrated under vacuum. The residue was purified by silica gel column with ethyl acetate/petroleum ether (5/1) as the eluent to afford the desired product (43.4 mg, 33% yield) as a white solid. LCMS (ES, m/z): 498.5$[M+H]^+$. $^1$HNMR: (300 MHz, DMSO-$d_6$, ppm): δ 9.28 (s, 1H), 8.03 (s, 1H), 7.82-7.81 (m, 1H), 7.80 (s, 1H), 7.29 (m, 2H), 7.14-7.12 (m, 1H), 6.87 (m, 1H), 2.81-2.79 (m, 2H), 2.65-2.62 (m, 6H), 1.89 (m, 2H), 1.63-1.61 (m, 2H), 0.83 (d, J=6.6 Hz, 12H).

Example 20

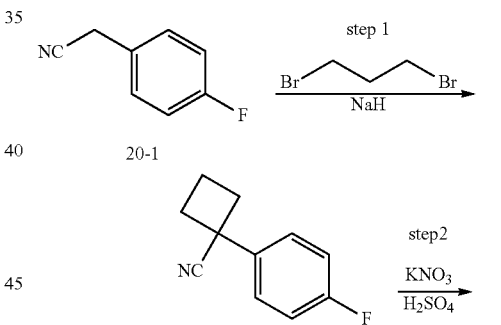

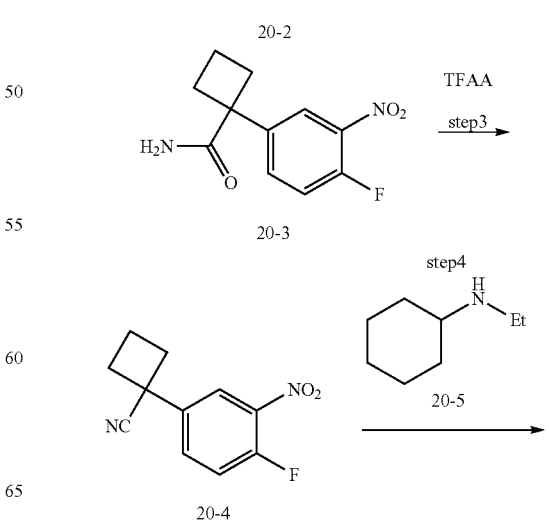

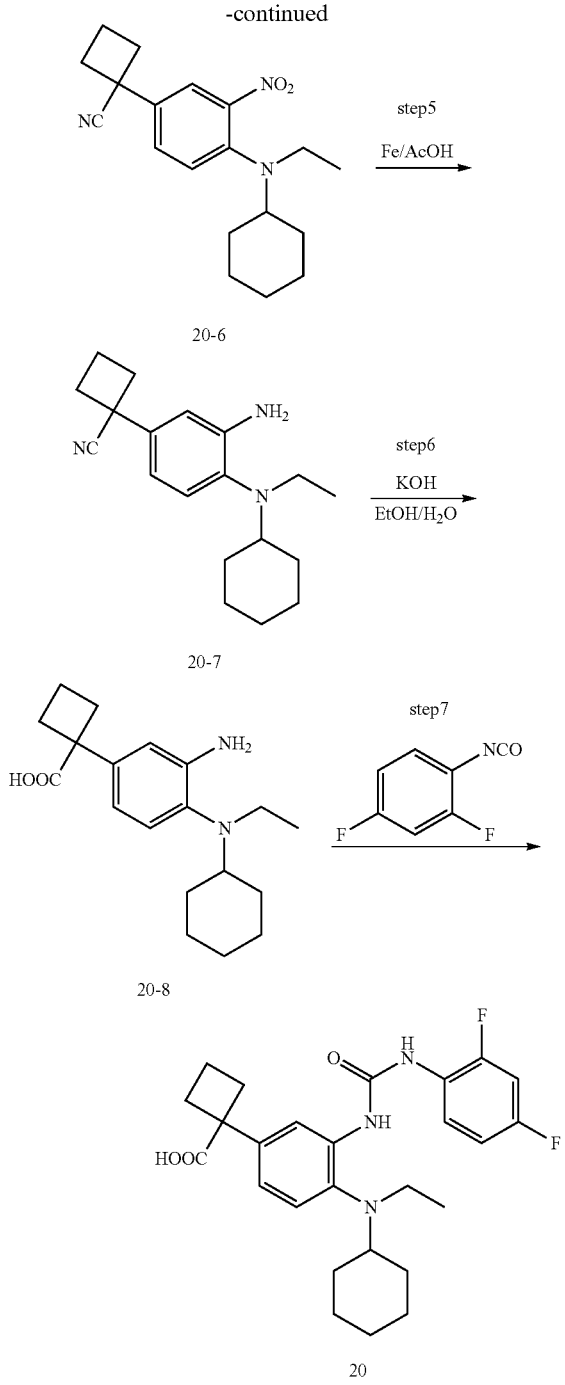

Step 1. Synthesis of 20-2

To a solution of 2-(4-fluorophenyl)acetonitrile (20 g, 148.00 mmol) in tetrahydrofuran (200 mL) at 0° C., was added sodium hydride (10.66 g, 444.17 mmol) portionwise. The mixture was stirred at 0° C. for 30 min, followed by the addition of 1,3-dibromopropane (32.58 g, 161.38 mmol). The resulting mixture was stirred at room temperature for overnight. The reaction was quenched with saturated ammonium chloride (50 mL), and extracted with ethyl acetate (300 mL×3). The organic phase was washed with brine (300 mL×2), dried over anhydrous sodium sulfate, and concentrated under vacuum. The residue was purified by silica gel column with ethyl acetate/petroleum ether (1/20) as the eluent to afford the desired product (13.6 g, 52% yield).

Step 2. Synthesis of 20-3

To a solution of 1-(4-fluorophenyl)cyclobutane-1-carbonitrile (13.6 g, 77.6 mmol) in sulfuric acid (136 mL) at 0° C., was added potassium nitrate (11.6 g, 114.7 mmol) in portions. The reaction was then stirred at room temperature for overnight. The reaction was quenched with water (500 mL), and extracted with ethyl acetate (300 mL×3). The organic phase was washed with brine (200 mL×2), dried over anhydrous sodium sulfate, and concentrated under vacuum. The residue was purified by silica gel column with ethyl acetate/petroleum ether (2/3) as the eluent to afford the desired product (12.6 g, 39% yield).

Step 3. Synthesis of 20-4

To a solution of 1-(4-fluoro-3-nitrophenyl)cyclobutane-1-carboxamide (12.6 g, 52.89 mmol) in 1,4-dioxne (126 mL), was added trifluoroacetic anhydride (16 mL) and triethylamine (6.7 mL). The resulting mixture was then heated to 100° C. for overnight. The reaction was cooled to room temperature, diluted with water (100 mL), and extracted with ethyl acetate (160 mL×3). The organic phase was washed with brine (100 mL×5), dried over anhydrous sodium sulfate, and concentrated under vacuum. The residue was purified by silica gel column with ethyl acetate/petroleum ether (1/9) as the eluent to afford the desired product (10.5 g, 90% yield).

Step 4. Synthesis of 20-6

To a solution of 1-(4-fluoro-3-nitrophenyl)cyclobutane-1-carbonitrile (600 mg, 2.72 mmol) and N-ethylcyclohexanamine (416 mg, 3.27 mmol) in dimethyl sufoxide (6 mL), was added N,N-diisopropylethylamine (1057.1 mg, 8.18 mmol). The resulting mixture was stirred at 100° C. for overnight. The reaction was cooled to room temperature, diluted with ethyl acetate (100 mL), and washed with water (100 mL×2) and brine (100 mL). The organic phase was dried over anhydrous sodium sulfate and concentrated under vacuum. The residue was purified by Flash-Prep-HPLC with the following conditions (IntelFlash-1): [Column: silica gel column; Mobile Phase: methanol/dichloromethane from 0% increasing to 8% within 20 min; Detector, UV 254 nm] to afford the desired product (700 mg, 78% yield).

Step 5. Synthesis of 20-7

To a solution of 1-[4-[cyclohexyl(ethyl)amino]-3-nitrophenyl]cyclobutane-1-carbonitrile (700 mg, 2.14 mmol) in acetic acid (7 mL), was added iron (2.39 g, 42.79 mmol). The mixture was stirred at room temperature for 30 min before water (100 mL) was added. The pH value of the mixture was adjusted to 9 with aqueous sodium carbonate. The solid was filtered off and the filtrate was extracted with ethyl acetate (100 mL×3), and washed with brine (200 mL). The organic phase was dried over anhydrous sodium sulfate and concentrated under vacuum to afford the desired product (600 mg, 94% yield).

Step 6. Synthesis of 20-8

To a solution of 1-[3-amino-4-[cyclohexyl(ethyl)amino]phenyl]cyclobutane-1-carbonitrile (550 mg, 1.85 mmol) in ethanol (9 mL) and water (3 mL), was added potassium hydroxide (1.56 g, 27.76 mmol). The resulting mixture was stirred at 100° C. for 23 h. The reaction was cooled to room temperature and diluted with water (100 mL). The pH value of the mixture was adjusted to 4 with hydrogen chloride (1 N), and then extracted with ethyl acetate (100 mL×3). The organic phase was washed with brine (100 mL), dried over anhydrous sodium sulfate, and concentrated under vacuum to afford the desired product (450 mg, 77% yield).

Step 7. Synthesis of 20

To a solution of 1-[3-amino-4-[cyclohexyl(ethyl)amino]phenyl]cyclobutane-1-carboxylic acid (210 mg, 0.66 mmol)

and 2,4-difluoro-1-isocyanatobenzene (154.7 mg, 1.00 mmol) in tetrahydrofuran (5 mL), was added triethylamine (200.9 mg, 1.99 mmol). The reaction was stirred at room temperature for 2.5 h before ethyl acetate (50 mL) was added. The mixture was washed with water (50 mL×2) and brine (50 mL), and the organic phase was dried over anhydrous sodium sulfate and concentrated under vacuum. The residue was purified by Prep-HPLC with the following conditions: [Column, X Bridge Prep C18 OBD Column, 19*150 mm 5 um; mobile phase, water (10 mmol/L NH$_4$HCO$_3$)/CH$_3$CN; MeCN from 25.0% to 55.0% in 8 min; Detector, UV 245 nm] to afford the desired product (80.4 mg, 26% yield) as a white solid. LCMS (ES, m/z): 472.5 [M+H]$^+$; $^1$HNMR: (300 MHz, DMSO-d$_6$, ppm): δ9.39 (s, 1H), 8.74 (s, 1H), 8.19-7.94 (m, 2H), 7.33-7.26 (m, 1H), 7.22-6.97 (m, 2H), 6.91-6.81 (m, 1H), 3.00 (q, J=7.0 Hz, 2H), 2.75-2.60 (m, 3H), 2.42-2.25 (m, 2H), 1.97-1.53 (m, 7H), 1.20-1.00 (m, 5H), 0.82 (t, J=7.0 Hz, 3H).

Example 21

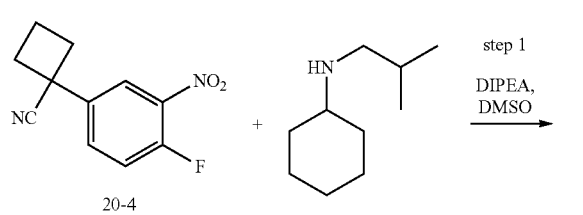

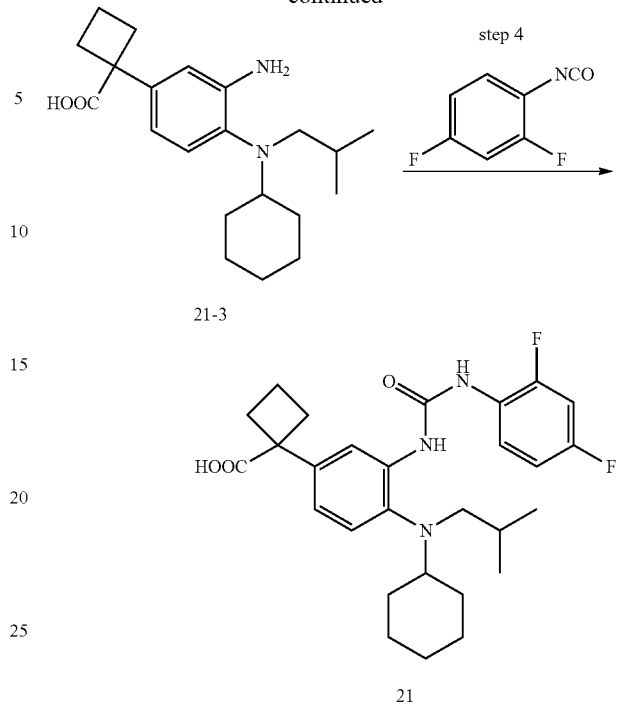

Step 1. Synthesis of 21-1

To a solution of 1-(4-fluoro-3-nitrophenyl)cyclobutane-1-carbonitrile (1 g, 4.54 mmol) in dimethyl sulfoxide (10 mL), were added N,N-diisopropylethylamine (1.76 g, 13.62 mmol) and then N-(2-methylpropyl)cyclohexanamine (777 mg, 5.00 mmol). The mixture was stirred at 100° C. for 16 h. After cooling to room temperature, the mixture was concentrated under vacuum. The residue was purified by Flash-Prep-HPLC with the following conditions: [Column: C18 silica gel; mobile phase A: water (0.05% TFA)), Mobile phase B: CAN; Gradient: 45% to 100% ACN; Detector: UV 254 nm] to afford the desired product (0.8 g, 50% yield).

Step 2. Synthesis of 21-2

To a solution of 1-[4-[cyclohexyl(2-methylpropyl)amino]-3-nitrophenyl]cyclobutane-1-carbonitrile (800 mg, 2.25 mmol) in ethyl acetate (5 mL) and acetic acid (5 mL) was added iron (1.26 g, 22.56 mmol). The reaction was then stirred at room temperature for 0.5 h. The mixture was diluted with ethyl acetate (1500 mL), and the solid was filtered off. The pH value of the filtrate was adjusted to 9 with sodium carbonate. The organic phase was washed with brine (50 mL×2), dried over anhydrous sodium sulfate, and concentrated under vacuum. The residue was purified by silica gel column with ethyl acetate/petroleum ether (1/6) as the eluent to afford the desired product (0.5 g, 68% yield).

Step 3. Synthesis of 21-3

To a solution of 1-[3-amino-4-[cyclohexyl(2-methylpropyl)amino]phenyl]cyclobutane-1-carbonitrile (300 mg, 0.92 mmol) in ethanol (6 mL) and water(1.5 mL) was added potassium hydroxide (900 mg, 16.04 mmol). The reaction was then stirred at 95° C. for 16 h. After cooling to room temperature, the mixture was concentrated under vacuum and the residue was dissolved in water (50 mL). The pH value of the mixture was adjusted to 4 with hydrogen chloride (1 N). The mixture was extracted with ethyl acetate (50 mL×2), and washed with saturation brine (50 mL×2). The organic phase was dried over anhydrous sodium sulfate and concentrated under vacuum to afford the desired product (0.3 g, 94% yield).

Step 4. Synthesis of 21

To a solution of 1-[3-amino-4-[cyclohexyl(2-methylpropyl)amino]phenyl]cyclobutane-1-carboxylic acid (300 mg, 0.87 mmol) in tetrahydrofuran (6 mL) were added triethylamine (264 mg, 2.61 mmol) and 2,4-difluoro-1-isocyanatobenzene (149 mg, 0.96 mmol). The reaction was then stirred at room temperature for 1.5 h. The mixture was concentrated under vacuum and the residue was purified by Prep-HPLC with the following conditions: [Column: Waters X-bridge C18, 5 um, 19×150 mm; Mobile phase A: water (0.05% NH$_4$HCO$_3$), Mobile phase B: CAN; Gradient: 25% CAN to 50% ACN in 8 min; Detector: UV 254 nm] to afford the desired product (62.5 mg, 14% yield) as a white solid. LCMS: (ES, m/z): 500.30 [M+H]$^+$. $^1$H NMR (300 MHz, DMSO-d$_6$, ppm): δ 9.31 (s, 1H), 8.09 (s, 1H), 7.87-7.79 (m, 2H), 7.27-7.21 (m, 1H), 7.05-6.95 (m, 2H), 6.81-6.78 (m, 1H), 2.83-2.52 (m, 4H), 2.28-2.12 (m, 2H), 1.93-1.53 (m, 6H), 1.52-1.38 (m, 1H), 1.37-0.86 (m, 6H), 0.75 (d, J=6.5 Hz, 6H).

Example 22

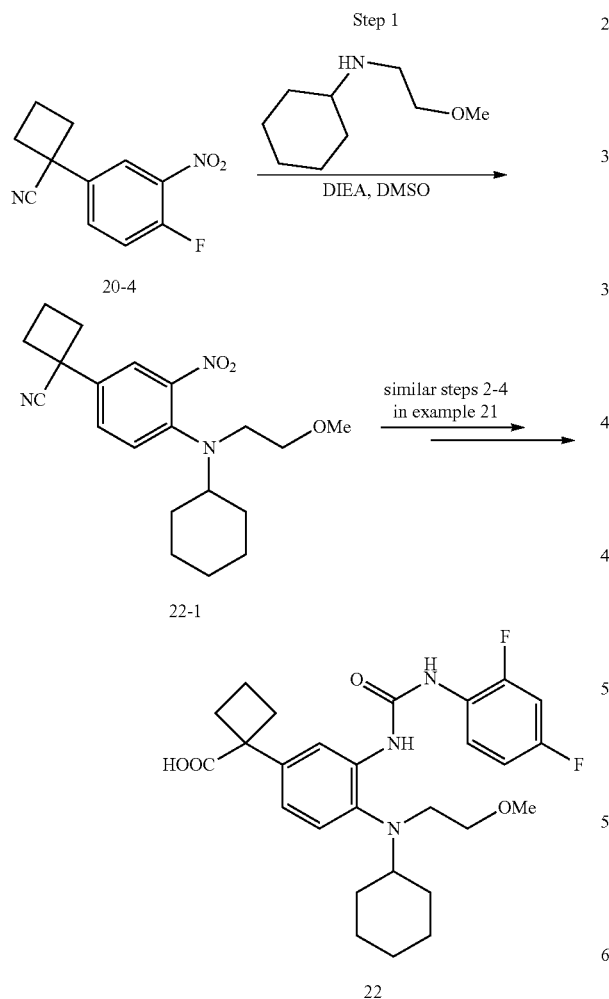

Step 1. Synthesis of 22-1

To a solution of 1-(4-fluoro-3-nitrophenyl)cyclobutane-1-carbonitrile (1 g, 4.54 mmol) in dimethyl sufoxide (10 mL), was added N-(2-methoxyethyl)cyclohexanamine (1.16 g, 7.38 mmol) and N,N-diisopropylethylamine (1.74 g). The mixture was then stirred at 100° C. for overnight. The reaction was cooled to room temperature, quenched by addition of water (50 mL), and extracted with ethyl acetate (300 mL×3). The organic phase was dried over anhydrous sodium sulfate and concentrated under vacuum to afford the desired product (0.7 g, 43% yield).

Followed similar steps 2-4 in example 21 to synthesize 22

Example 22: LCMS (ES, m/z): 502.4 [M+H]$^+$; $^1$HNMR (300 MHz, DMSO-d$_6$): δ 9.34 (s, 1H), 8.61 (s, 1H), 8.06 (d, J=1.8 Hz, 1H), 8.01-7.93 (m, 1H), 7.33-7.26 (m, 1H), 7.16 (d, J=8.1 Hz, 1H), 7.06-7.00 (m, 1H), 6.87-6.84 (m, 1H), 3.24-3.07 (m, 7H), 2.78-2.62 (m, 3H), 2.31-2.26 (m , 2H), 1.89-1.66 (m, 6H), 1.53-1.49 (m, 1H), 1.23-1.00 (m, 4H).

Example 23

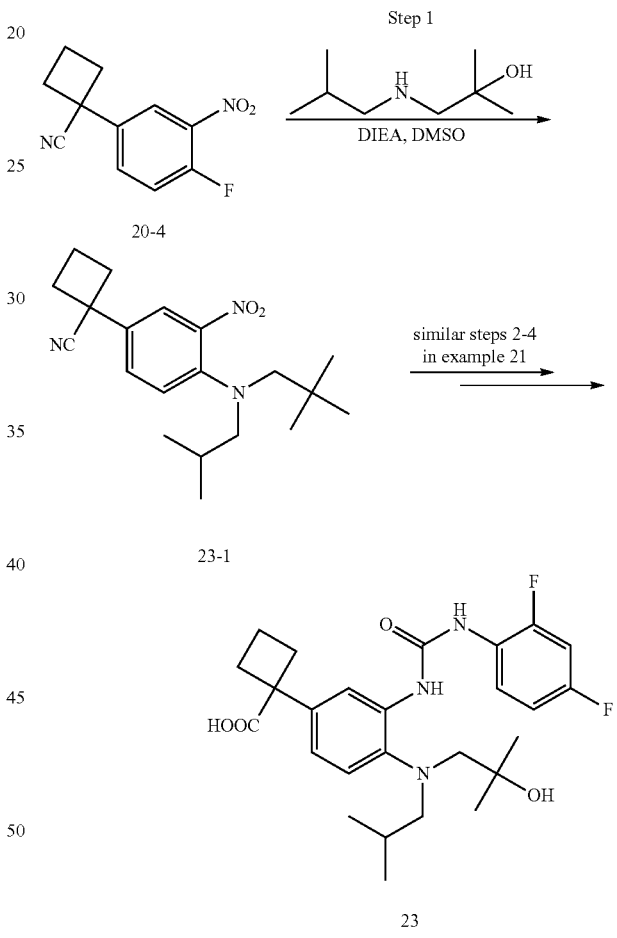

Step 1. Synthesis of 23-1

To a solution of 1-(4-fluoro-3-nitrophenyl)cyclobutane-1-carbonitrile (500 mg, 2.27 mmol) in dimethyl sulfoxide (10 mL), was added 2-methyl-1-[(2-methylpropyl)amino]propan-2-ol (330 mg, 2.27 mmol) and N,N-diisopropylethylamine (354 mg, 2.72 mmol). The resulting mixture was stirred at 100° C. for 12 h. After cooling to room temperature, the mixture was diluted with water (50 mL), and extracted with ethyl acetate (50 mL×3). The organic was washed with brine (50 mL), dried over anhydrous sodium sulfate, and concentrated under vacuum to afford the desired product (350 mg, 45%).

Followed similar steps 2-4 in example 21 to synthesize 23

Example 23: LCMS (ES, m/z): 490.3 [M+H]⁺; ¹HNMR (300 MHz, CD₃OD, ppm): δ7.98 (s, 1H), 7.93-7.85 (m, 1H), 7.25 (d, J=8.4 Hz, 1H), 7.05-6.90 (m, 3H), 3.02 (s, 2H), 2.87 (d, J=6.9 Hz, 2H), 2.82-2.74 (m, 2H), 2.52-2.42 (m, 2H), 2.01-1.92 (m, 1H), 1.92-1.83 (m, 1H), 1.60-1.55 (m, 1H), 1.14 (s, 6H), 0.87 (d, J=6.6 Hz, 6H).

Example 24

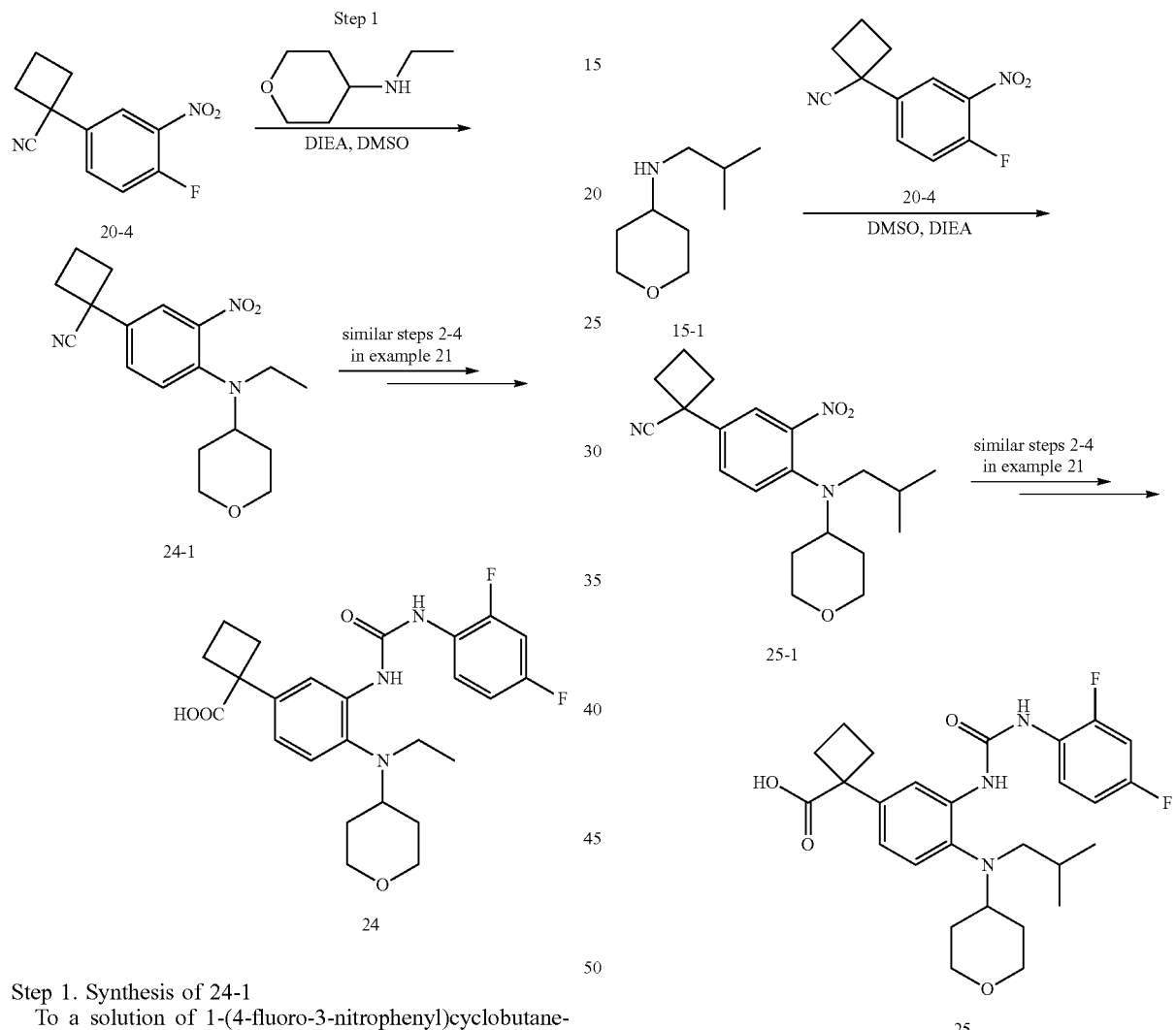

Step 1. Synthesis of 24-1

To a solution of 1-(4-fluoro-3-nitrophenyl)cyclobutane-1-carbonitrile (500 mg, 2.27 mmol) in dimethyl sufoxide (6 mL), was added N-ethyloxan-4-amine (350 mg, 2.71 mmol) and N,N-diisopropylethylamine (870 mg). The resulting mixture was then stirred at 100° C. for overnight. The reaction was cooled to room temperature, diluted with water (10 mL), and extracted with ethyl acetate (30 mL×3). The organic phase was washed with brine (30 mL×5), dried over anhydrous sodium sulfate, and concentrated under vacuum. The residue was purified by silica gel column with ethyl acetate/petroleum ether (3/2) as the eluent to afford the desired product (480 mg, 64% yield).

Followed similar steps 2-4 in example 21 to synthesize 24.

Example 24: LCMS (ES, m/z): 474.3 [M+H]⁺; ¹H NMR (300 MHz, DMSO-d₆, ppm): δ 9.42 (s, 1H), 8.80 (s, 1H), 8.14-8.13 (d, J=2.1 Hz, 1H), 8.07-7.99 (m, 1H), 7.34-7.26 (m ,1H), 7.17 (d, J=8.2 Hz, 1H), 7.06-7.00 (m, 1H), 6.87 (dd, J=8.1, 2.1 Hz, 1H), 3.84-3.81 (m, 2H), 3.27-3.23 (m, 2H), 3.19-2.95 (m, 3H), 2.72-2.63 (d, J=4.5 Hz, 2H), 2.39-2.29 (m, 2H), 1.97-1.69 (m, 4H), 1.42-1.37 (m, 2H), 0.84-0.79 (m, 3H).

Example 25

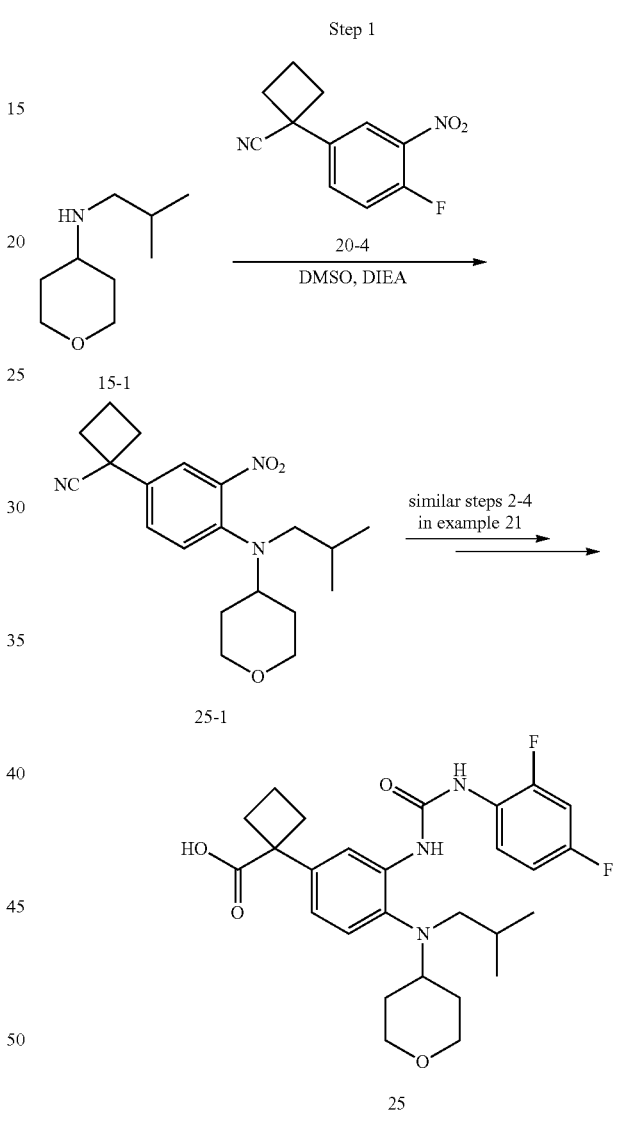

Step 1. Synthesis of 25-1

A solution of 1-(4-fluoro-3-nitrophenyl)cyclobutane-1-carbonitrile (1 g, 4.54 mmol), N-(2-methylpropyl)oxan-4-amine (1.43 g, 9.09 mmol), and N,N-diisopropylethylamine (2.34 g, 18.11 mmol) in DMSO (20 mL) was stirred at 100° C. for 16 h. The mixture was then cooled to room temperature, diluted with water (200 mL), and extracted with ethyl acetate (100 mL×2). The organic phase was washed with water (100 mL×5) and brine (30 mL×2), dried over anhydrous sodium sulfate, and concentrated under vacuum. The residue was purified by silica gel column with ethyl acetate/petroleum ether (1/10) as eluent to afford the desired product (0.4 g, 19% yield).

Followed similar steps 2-4 in example 21 to synthesize 25.

Example 25: LCMS (ES, m/z): 502.4 [M+H]⁺; ¹HNMR: (300 MHz, DMSO-d₆, ppm): δ 11.8 (brs, 1H), 9.42 (s, 1H), 8.38 (s, 1H), 8.02 (d, J=1.8, 1 H), 8.00-7.82 (m, 1H), 7.34-7.30 (m, 1H), 7.29-7.16 (m, 1H), 7.10-6.90 (m, 1H), 6.93-6.80 (m, 1H), 3.85-3.81 (m, 2H), 3.25-3.15 (m, 2H), 2.95-2.59 (m, 5H), 2.42-2.12 (m, 2H), 2.00-1.62 (m, 4H), 1.61-1.37 (m, 2H), 1.36-1.17 (m, 1H), 0.82 (d, J=6.6 Hz, 6H).

Example 26

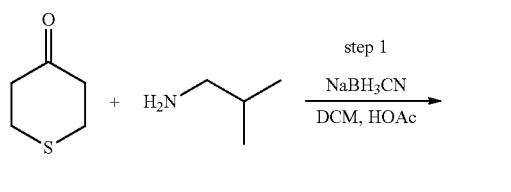

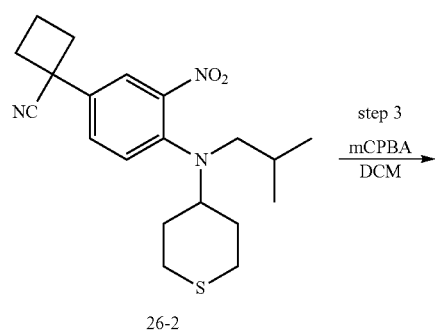

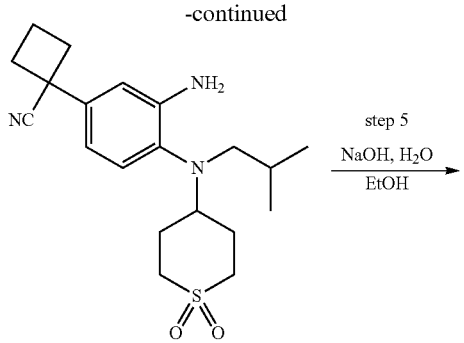

Step 1. Synthesis of 26-1

To a solution of thian-4-one (4.77 g, 41.06 mmol) and 2-methylpropan-1-amine (2 g, 27.35 mmol) in dichloromethane (60 mL) was added acetic acid (0.1 mL). The reaction was then stirred at room temperature for 0.5 h. Sodium cyanoborohydride (6.87 g, 109.33 mmol) was added and then the reaction was stirred at room temperature for 16 h. The mixture was diluted with ethyl acetate (200 mL), washed with brine (30 mL×2), dried over anhydrous sodium sulfate, and concentrated under vacuum. The residue was purified by silica gel column with ethyl acetate/petroleum ether (1/7) as the eluent to afford the desired product (1.4 g, 30% yield).

Step 2. Synthesis of 26-2

To a solution of 1-(4-fluoro-3-nitrophenyl)cyclobutane-1-carbonitrile (1.04 g, 4.72 mmol) and N-(2-methylpropyl) thian-4-amine (750 mg, 4.33 mmol) in dimethyl sulfoxide (10 mL) was added N,N-diisopropylethylamine (835 mg, 6.46 mmol). The reaction was then stirred at 100° C. for 2 days. The mixture was cooled to room temperature and diluted with water (100 mL). The mixture was extracted with ethyl acetate (100 mL×2), and washed with water (100 mL×3) and brine (100 mL). The organic phase was dried over anhydrous sodium sulfate and concentrated under vacuum. The residue was purified by Flash-Prep-HPLC with the following conditions: [Column: C18 silica gel; Mobile phase A: water (0.05% TFA), Mobile phase B: CAN; Gradient: 55% Can to 95% ACN; Detector: UV 254 nm] to afford the desired product (370 mg, 21% yield).

Step 3. Synthesis of 26-3

To a solution of 1-[4-[(2-methylpropyl)(thian-4-yl) amino]-3-nitrophenyl]cyclobutane-1-carbonitrile (340 mg, 0.91 mmol) in dichloromethane (10 mL) at 0° C., was added 3-chlorobenzene-1-carboperoxoic acid (240 mg, 1.39 mmol). The mixture was then stirred at 0° C. for 0.5 h and at room temperature for another 1.5 h. The solid was filtered off and the filtrate was concentrated under vacuum. The residue was purified by silica gel column with ethyl acetate/petroleum ether (1/2) as the eluent to afford the desired product (380 mg, crude).

Step 4. Synthesis of 26-4

To a mixture of 26-3 (330 mg, 0.81 mmol) in ethyl acetate (8 mL) and methanol (8 mL) was added nickel (200 mg, 3.41 mmol). The suspension was degassed under vacuum and purged with $H_2$ three times. The mixture was stirred under $H_2$ balloon at room temperature for 30 min. The solid was filtered off and the filtrate was concentrated under vacuum to afford the desired product (265 mg, 87% yield).

Step 5. Synthesis of 26-5

To a solution of 26-4 (265 mg, 0.71 mmol) in ethanol (6 mL) and water (1.5 mL) was added sodium hydroxide (1.2 g, 30.00 mmol). The mixture was then stirred at 90° C. for 16 h. The reaction was cooled to room temperature and diluted with ethyl acetate (100 mL) and water (100 mL). The pH value of the mixture was adjusted to 4 with hydrogen chloride (1 N). The mixture was extracted with ethyl acetate (100 mL×2), and washed with brine (100 mL×2). The organic phase was dried over anhydrous sodium sulfate and concentrated under vacuum to afford the desired product (180 mg, 65% yield).

Step 6. Synthesis of 26

To a solution of 26-4 (180 mg, 0.46 mmol) in tetrahydrofuran (5 mL), were added 2,4-difluoro-1-isocyanatobenzene (78 mg, 0.50 mmol) and triethylamine (69 mg, 0.68 mmol) sequentially. The mixture was then stirred at room temperature for 2 h. The mixture was concentrated under vacuum and the residue was purified by Prep-HPLC with the following conditions: [Column: X bridge, C18, 5 um, 19×150 mm; Mobile phase A: water (0.05% $NH_4HCO_3$), Mobile phase B: ACN; Gradient: 35% ACN to 60% ACN in 8 min; Detector: UV 254 nm] to afford the desired product (92.2 mg, 37% yield) as a white solid. LCMS: (ES, m/z): 550.1 [M+H]$^+$. $^1$H-NMR: (300 MHz, DMSO-d$_6$, ppm): δ 9.44 (s, 1H), 8.21 (s, 1H), 8.05 (s, 1H), 7.99-7.91 (m, 1H), 7.35-7.27 (m, 1H), 7.16 (d, J=8.1 Hz, 1H), 7.11-6.98 (m, 1H), 6.89-6.85 (m, 1H), 3.25-3.10 (m, 2H), 3.09-2.92 (m, 4H), 2.84-2.60 (m, 4H), 2.39-2.19 (m, 4H), 2.02-1.82 (m, 2H),1.81-1.68 (m, 1H), 1.41-1.21 (m, 1H), 0.83 (d, J=6.6 Hz, 6H).

Example 27

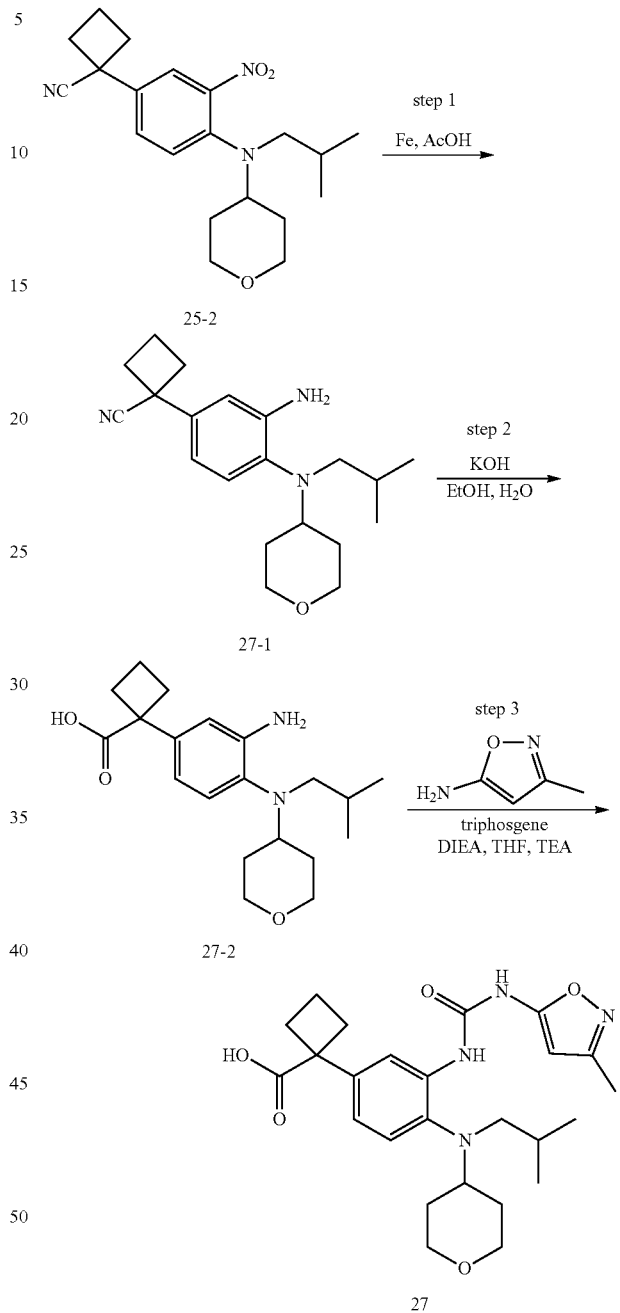

Step 1. Synthesis of 27-1

To a solution of 1-[4-[(2-methylpropyl)(oxan-4-yl) amino]-3-nitrophenyl]cyclobutane-1-carbonitrile (250 mg, 0.70 mmol) in acetic acid (2.5 mL), was added iron (392 mg). The resulting solution was stirred at room temperature for 0.5 h. The reaction was diluted with ethyl acetate (50 mL) and water (50 mL), and the pH value of the mixture was adjusted to 9 with aqueous sodium carbonate. The solid was filtered off and the filtrate was extracted with ethyl acetate (50 mL×2). The organic phase was washed with brine (50 mL×2) and water (60 mL×2), dried over anhydrous sodium sulfate, and concentrated under vacuum. The residue was purified by silica gel column with ethyl acetate/petroleum ether (1/2) as the eluent to afford the desired product (80 mg, 35% yield).

Step 2. Synthesis of 27-2

To a solution of 1-[3-amino-4-[(2-methylpropyl)(oxan-4-yl)amino]phenyl]cyclobutane-1-carbonitrile (80 mg, 0.24 mmol) in ethanol (3 mL) and water (1 mL), was added potassium hydroxide (449 mg, 8.00 mmol). The resulting solution was stirred at 95° C. for 16 h. After cooling to room temperature, the mixture was concentrated under vacuum. The residue was dissolved in water (50 mL), and the pH value of the solution was adjusted to 4 with hydrogen chloride (1 N). The resulting mixture was extracted with ethyl acetate (50 mL×2). The organic phase was washed with brine (50 mL×2), dried over anhydrous sodium sulfate, and concentrated under vacuum to afford the desired product (70 mg, 83% yield).

Step 3. Synthesis of 27

To a solution of 3-methyl-1,2-oxazol-5-amine (57 mg, 0.58 mmol) in tetrahydrofuran (1.5 mL), were added N,N-diisopropylethylamine (101 mg, 0.78 mmol) and then a solution of ditrichloromethyl carbonate (58 mg, 0.20 mmol) in tetrahydrofuran (1.5 mL). The resulting solution was stirred at room temperature for 10 min. A solution of 1-[3-amino-4-[(2-methylpropyl)(oxan-4-yl)amino]phenyl]cyclobutane-1-carboxylic acid (70 mg, 0.20 mmol) in tetrahydrofuran (1.5 mL) and triethylamine (87 mg, 0.86 mmol) were added, the reaction was stirred at room temperature for another 1 h. The resulting solution was then concentrated under vacuum and the residue was purified by Flash-Prep-HPLC with the following conditions [Column: C18 silica gel; Mobile phase A: ACN, Mobile phase B: water (0.05% FA)/; Gradient: 28% ACN to 55% ACN in 8 min; Detector, UV 254 nm] to afford the desired product (10.5 mg) as a white solid. LCMS (ES, m/z): 471.3 [M+H]$^+$. $^1$HNMR: (300 MHz, DMSO-d$_6$, ppm): δ 11.28 (s, 1H), 8.51 (s, 1H), 8.10 (s, 1H), 8.23 (d, J=8.1 Hz, 1H), 6.92 (dd, J=2.1, 8.1 Hz, 1H), 6.00 (s, 1H), 3.90-3.78 (m, 2H), 3.24-3.16 (m, 2H), 2.86-2.62 (m, 5H), 2.43-2.30 (m, 2H), 2.21-2.13 (m, 3H), 2.00-2.66 (m, 4H), 1.60-1.47 (m, 2H), 1.37-1.21 (m, 1H), 0.82 (d, J=6.0 Hz, 6H).

Example 28

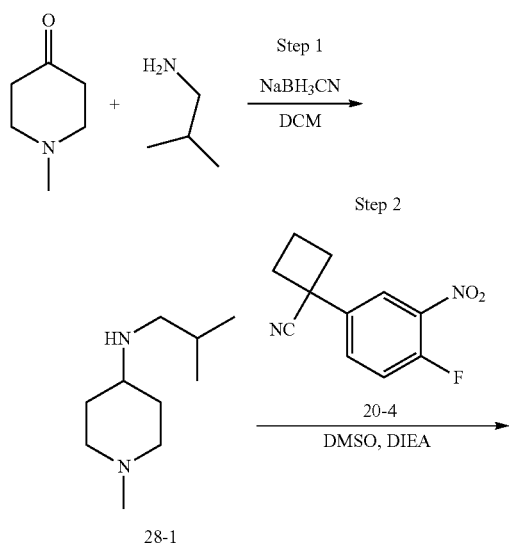

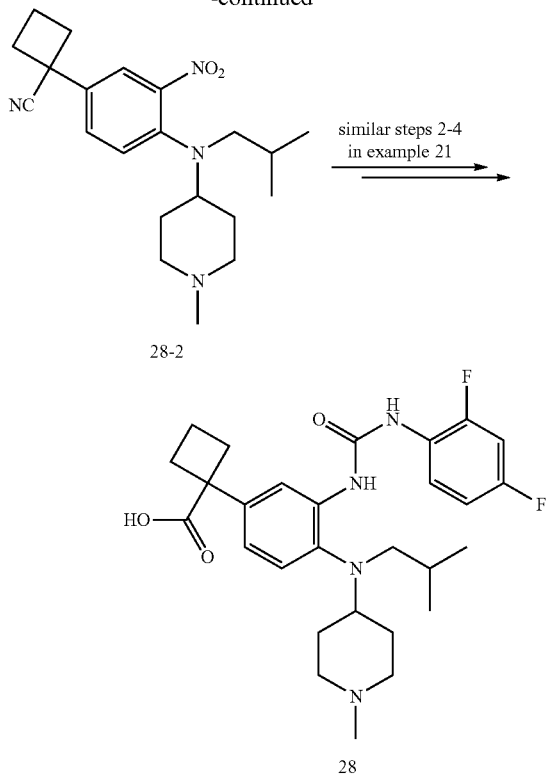

Step 1. Synthesis of 28-1

To a solution of 1-methylpiperidin-4-one (3.06 g, 27.07 mmol) and 2-methylpropan-1-amine (1.8 g, 24.61 mmol) in dichloromethane (40 mL) at 0° C., was added acetic acid (0.1 mL, cat.). Sodium cyanoborohydride (6.2 g, 98.51 mmol, 4.00 equiv) was added, and the reaction was then stirred at room temperature for 2.5 h. The reaction mixture was diluted with ethyl acetate (400 mL), and washed with water (400 mL×2) and brine (400 mL). The organic phase was dried over anhydrous sodium sulfate and concentrated under vacuum. The residue was dissolved in methanol (3 mL), and a solution of oxalic acid dihydrate (2.2 g) in methanol (10 mL) was added. The solids were collected by filtration and re-dissolved in water (50 mL). The pH value of the solution was adjusted to 9 with aqueous sodium hydroxide (15%). The resulting mixture was extracted with dichloromethane (400 mL×4). The organic phase was dried over anhydrous sodium sulfate and concentrated under vacuum to afford the desired product (650 mg, 16% yield)

Step 2. Synthesis of 28-2

To a solution of 1-methyl-N-(2-methylpropyl)piperidin-4-amine (441.4 mg, 2.59 mmol) and 1-(4-fluoro-3-nitrophenyl)cyclobutane-1-carbonitrile (474 mg, 2.15 mmol) in dimethyl sulfoxide (6 mL) was added N,N-diisopropylethylamine (883.1 mg, 6.83 mmol). The reaction was then stirred at 100° C. for 16 h. The reaction mixture was cooled to room temperature and diluted with ethyl acetate (100 mL). The mixture was washed with water (100 mL×2) and brine (100 mL). The organic phase was dried over anhydrous sodium sulfate and concentrated under vacuum. The residue was purified by Flash-Prep-HPLC with the following conditions: [Column: silica gel; Mobile phase A: dichloromethane, Mobile phase B: methanol; Gradient: 0% methanol to 8% methanol in 20 min; Detector: UV 254 nm] to afford the desired product (600 mg, 75% yield).

Followed similar steps 2-4 in example 21 to synthesize 28.

Example 28: LRMS: (ES, m/z): 515.3 [M+H]+. ¹HNMR (300 MHz, DMSO-d₆, ppm): δ 9.41 (s, 1H), 8.31 (s, 1H), 7.97-7.88 (m, 2H), 7.34-7.26 (m, 1H), 7.15 (d, J=8.1 Hz, 1H), 7.07-7.04 (m, 1H), 6.87 (dd, J=8.1, 2.4 Hz, 1H), 2.77-2.63 (m, 5H), 2.39-2.27 (m, 2H), 2.08 (s, 3H), 1.87-1.73 (m, 6H), 1.52-1.21 (m, 5H), 0.82 (d, J=6.6 Hz, 6H).

Example 29

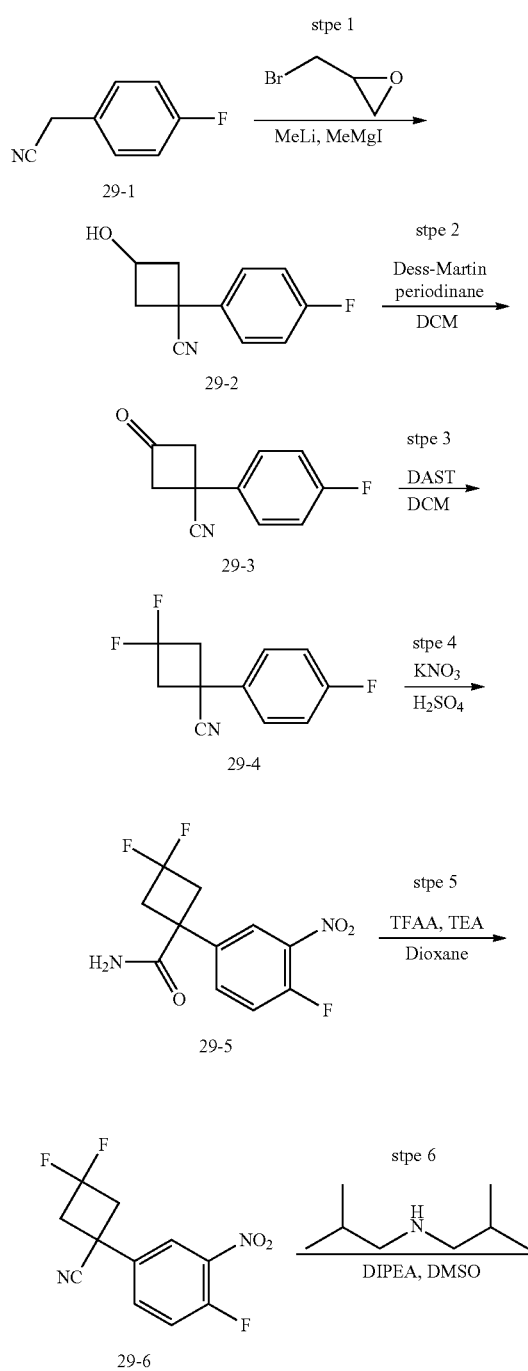

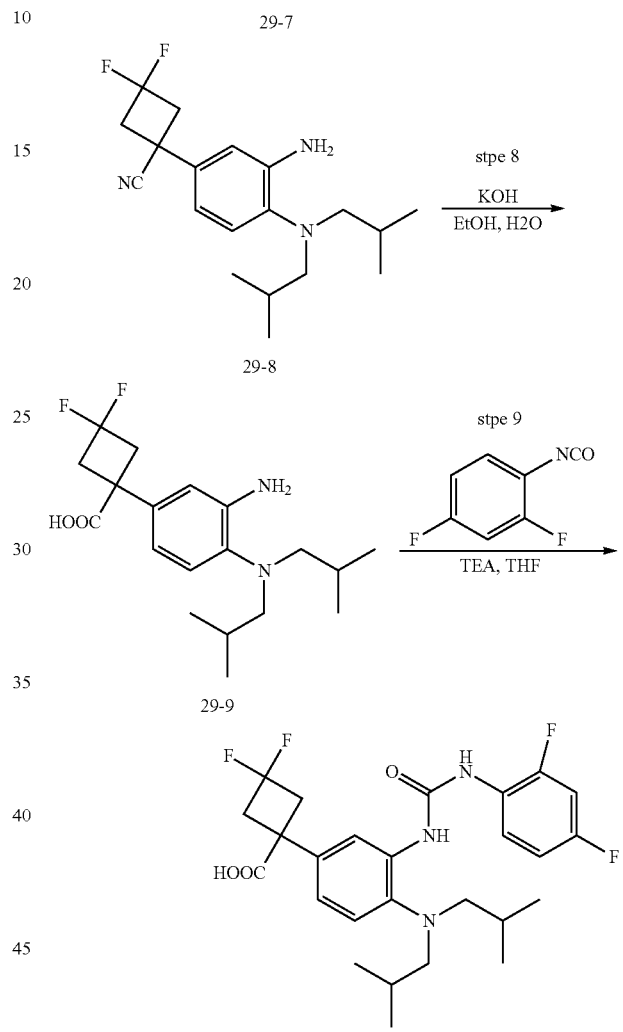

Step 1. Synthesis of 29-2

To a solution of 2-(4-fluorophenyl)acetonitrile (1.35 g, 9.99 mmol) in tetrahydrofuran (10 mL) at −78° C., was added MeLi (10 mL, 1 M) dropwise. The resulting mixture was stirred at the same temperature for 30 min, and followed by addition of 2-(bromomethyl)oxirane (1.37 g, 10.00 mmol) and methylmagnesiumiodide (4 mL) sequentially. The resulting mixture was allowed to warm to room temperature and stirred for another 12 h. The reaction was quenched by addition of water/ice (200 mL), and extracted with ethyl acetate (50 mL×3). The organic phase was dried over anhydrous sodium sulfate, and concentrated under vacuum. The residue was purified by silica gel column with ethyl acetate/petroleum ether (1/20) as the eluent to afford the desired product (1.3 g, 68% yield).

Step 2. Synthesis of 29-3

To a solution of 1-(4-fluorophenyl)-3-hydroxycyclobutane-1-carbonitrile (750 mg, 3.92 mmol) in dichloromethane (10 mL) at 0° C., was added Dess-Martin periodinane (2.5 g, 0.01 mmol) in portions. The resulting mixture was then stirred at room temperature for 12 h before quenched by addition of water/ice (100 mL). The solid was filtered off, and washed with dichloromethane (50 mL×2). The filtrate was then extracted with dichloromethane (50 mL×2). The organic phase was dried over anhydrous sodium sulfate, and concentrated under vacuum. The residue was purified by silica gel column with ethyl acetate/petroleum ether (1/20) as the eluent to afford the desired product (550 mg, 74% yield).

Step 3. Synthesis of 29-4

To a solution of 1-(4-fluorophenyl)-3-oxocyclobutane-1-carbonitrile (210 mg, 1.11 mmol) in dichloromethane (2 mL) at 0° C., was added diethylaminosulfur trifluoride (563 mg, 3.49 mmol) dropwise. The mixture was then stirred at room temperature for 12 h. The reaction was quenched by addition of water/ice (20 mL), extracted with ethyl acetate (10 mL×3), and washed with brine (60 mL). The organic phase was dried over anhydrous sodium sulfate and concentrated under vacuum. The residue was purified by silica gel column with ethyl acetate/petroleum ether (1/10) as the eluent to afford the desired product (160 mg, 68% yield).

Step 4. Synthesis of 29-5

To a solution of 3,3-difluoro-1-(4-fluorophenyl)cyclobutane-1-carbonitrile (160 mg, 0.76 mmol) in concentrated sulfuric acid (2 mL) at 0° C., was added potassium nitrate (92 mg) in portions. The mixture was then stirred at room temperature for 12 h. The reaction was quenched by the addition of water/ice (20 mL), extracted with ethyl acetate (20 mL×3), and washed with brine (60 mL). The organic phase was dried over anhydrous sodium sulfate and concentrated under vacuum. The residue was purified by silica gel column with ethyl acetate/petroleum ether (1/30) as the eluent to afford the desired product (150 mg, 72% yield).

Step 5. Synthesis of 29-6

To a solution of 3,3-difluoro-1-(4-fluoro-3-nitrophenyl)cyclobutane-1-carboxamide (150 mg, 0.55 mmol) in 1,4-dioxane (5 mL), was added trifluoroacetic anhydride (0.5 mL) and triethylamine (1.1 mL). The resulting mixture was the stirred at 120° C. for 12 h. The reaction was cooled to room temperature, quenched by the addition of water/ice (20 mL), extracted with ethyl acetate (20 mL×3), and washed with brine (60 mL). The organic phase was dried over anhydrous sodium sulfate and concentrated under vacuum. The residue was purified by silica gel column with ethyl acetate/petroleum ether (1/20) as the eluent to afford the desired product (100 mg, 71% yield).

Step 6. Synthesis of 29-7

To a solution of 3,3-difluoro-1-(4-fluoro-3-nitrophenyl)cyclobutane-1-carbonitrile (100 mg, 0.39 mmol, 1.00 equiv) and N,N-diisopropylethylamine (76 mg, 0.59 mmol) in dimethyl sufoxide (2 mL), was added bis(2-methylpropyl)amine (60 mg, 0.46 mmol). The mixture was then stirred at 90° C. for 12 h. The reaction was cooled to room temperature, quenched by addition of water/ice (50 mL), extracted with ethyl acetate (50 mL×3), and washed with brine (20 mL). The organic phase was dried over anhydrous sodium sulfate and concentrated under vacuum. The residue was purified by silica gel column with ethyl acetate/petroleum ether (1/20) as the eluent to afford the desired product (60 mg, 42% yield).

Step 7. Synthesis of 29-8

To a solution of 3,3-difluoro-1-(4-fluoro-3-nitrophenyl)cyclobutane-1-carbonitrile (100 mg, 0.39 mmol) and N,N-diisopropylethylamine (76 mg, 0.59 mmol) in dimethyl sufoxide (2 mL), was added bis(2-methylpropyl)amine (60 mg, 0.46 mmol). The resulting mixture was then stirred at 90° C. for 12 h. The reaction was cooled to room temperature, quenched by the addition of water/ice (50 mL), extracted with ethyl acetate (50 mL×3), and washed with brine (20 mL). The organic phase was dried over anhydrous sodium sulfate and concentrated under vacuum. The residue was purified by silica gel column with ethyl acetate/petroleum ether (1/20) as the eluent to afford the desired product (60 mg, 42% yield).

Step 8. Synthesis of 29-9

To a solution of 1-[3-amino-4-[bis(2-methylpropyl)amino]phenyl]-3,3-difluorocyclobutane-1-carbonitrile (40 mg, 0.12 mmol) in ethanol (2 mL) and water (1 mL), was added potassium hydroxide (10 mg, 0.18 mmol). The resulting mixture was then stirred at room temperature for 36 h. Water (10 mL) was added, the mixture was extracted with ethyl acetate (10 mL×2). The combined organic phase was washed with brine (10 mL×3), dried over anhydrous sodium sulfate and concentrated under vacuum. The residue was purified by Pre-TLC with ethyl acetate/petroleum ether (1/10) to afford the desired product (40 mg, 88% yield).

Step 9. Synthesis of 29

To a solution of 1-[3-amino-4-[bis(2-methylpropyl)amino]phenyl]-3,3-difluorocyclobutane-1-carboxylic acid (40 mg, 0.11 mmol) and triethylamine (17 mg, 0.17 mmol) in tetrahydrofuran (4 mL), was added 2,4-difluoro-1-isocyanatobenzene (21 mg, 0.14 mmol). The resulting mixture was then stirred at room temperature for 12 h. The reaction was quenched by addition of water/ice (20 mL), and extracted with ethyl acetate (10 mL×3). The organic phase was washed with brine (30 mL×2), dried over anhydrous sodium sulfate and concentrated under vacuum. The residue was purified by Pre-TLC to afford the desired product (15.7 mg, 27% yield). LCMS (ES, m/z): 510.5 [M+H]+; 1HNMR: (300 MHz, DMSO-$d_6$, ppm): δ 13.01 (brs, 1H), 9.31 (s, 1H), 8.1 (s, 1H), 7.97-7.85 (m, 2H), 7.31 (t, J=6 Hz, 1H), 7.17 (d, J=6 Hz, 1H), 7.06 (t, J=6 Hz, 1H), 6.93 (t, J=6 Hz, 1H), 3.25 (s, 1H), 3.00-2.86 (m, 3H), 2.67 (d, J=6 Hz, 4H), 1.70-1.61 (m, 2H), 0.91 (s, 12H).

Example 30

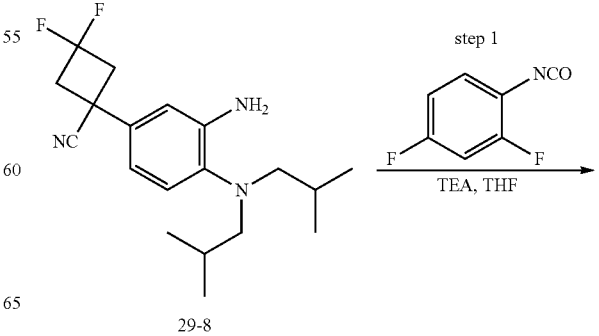

189
-continued

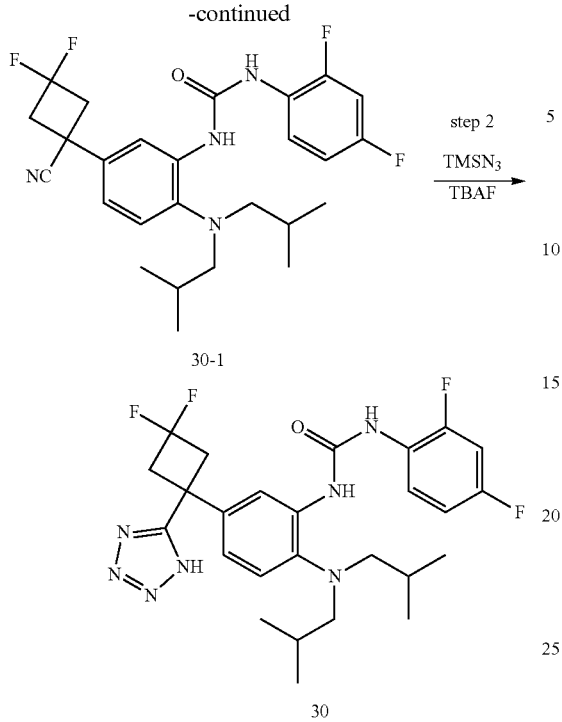

30-1

30

Step 1. Synthesis of 30-1

To a solution of 1-[3-amino-4-[bis(2-methylpropyl)amino]phenyl]-3,3-difluorocyclobutane-1-carbonitrile (500 mg, 1.49 mmol) and triethylamine (196 mg, 1.94 mmol) in dichloromethane (5 mL), was added 2,4-difluoro-1-isocyanatobenzene (254 mg, 1.64 mmol). The resulting mixture was then stirred at room temperature for 12 h. The reaction was quenched by addition of water/ice (50 mL), extracted with ethyl acetate (30 mL×3), and washed with brine (50 mL×2). The organic layer was dried over anhydrous sodium sulfate and concentrated under vacuum. The residue was purified by silica gel column with ethyl acetate/petroleum ether (1/20) as the eluent to afford the desired product (700 mg, 96% yield).

Step 2 Synthesis of 30

A solution of 1-[2-[bis(2-methylpropyl)amino]-5-(1-cyano-3,3-difluorocyclobutyl)phenyl]-3-(2,4-difluorophenyl)urea (500 g, 1.02 mol), trimethylsilyl azide (1.2 g, 10.42 mmol) and tetrabutylammonium fluoride (2.7 g, 10.33 mmol) was stirred at 85° C. for 12 h. The reaction was then cooled to room temperature, and quenched by addition of water/ice (100 mL). The mixture was extracted with ethyl acetate (100 mL×3), and washed with brine (50 mL×2). The organic layer was dried over anhydrous sodium sulfate and concentrated under vacuum. The residue was purified by Prep-HPLC with the following conditions: [Column: X Bbridge Prep C18 OBD,19×150 nm 5 um; mobile phase water (0.05% TFA) and ACN/MEOH (15% up to 60.0% in 8 min); Detector, UV 254 nm] to afford the desired product (132.9 mg, 24% yield) as a white solid. LCMS (ES, m/z): 534.2 [M+H]+. 1HNMR: (300 MHz, DMSO-$d_6$, ppm): δ 9.33 (s, 1H), 8.06 (s, 1H), 7.96-7.87 (m, 2H), 7.31 (t, J=6 Hz, 1H), 7.19 (d, J=8.4 Hz, 1H), 7.08-6.95 (m, 2H), 3.44-3.35 (m, 4H), 2.66 (d, J=6.9 Hz, 4H), 1.68-1.59 (m, 2H), 0.83 (d, J=6 Hz,12H).

190

Example 31

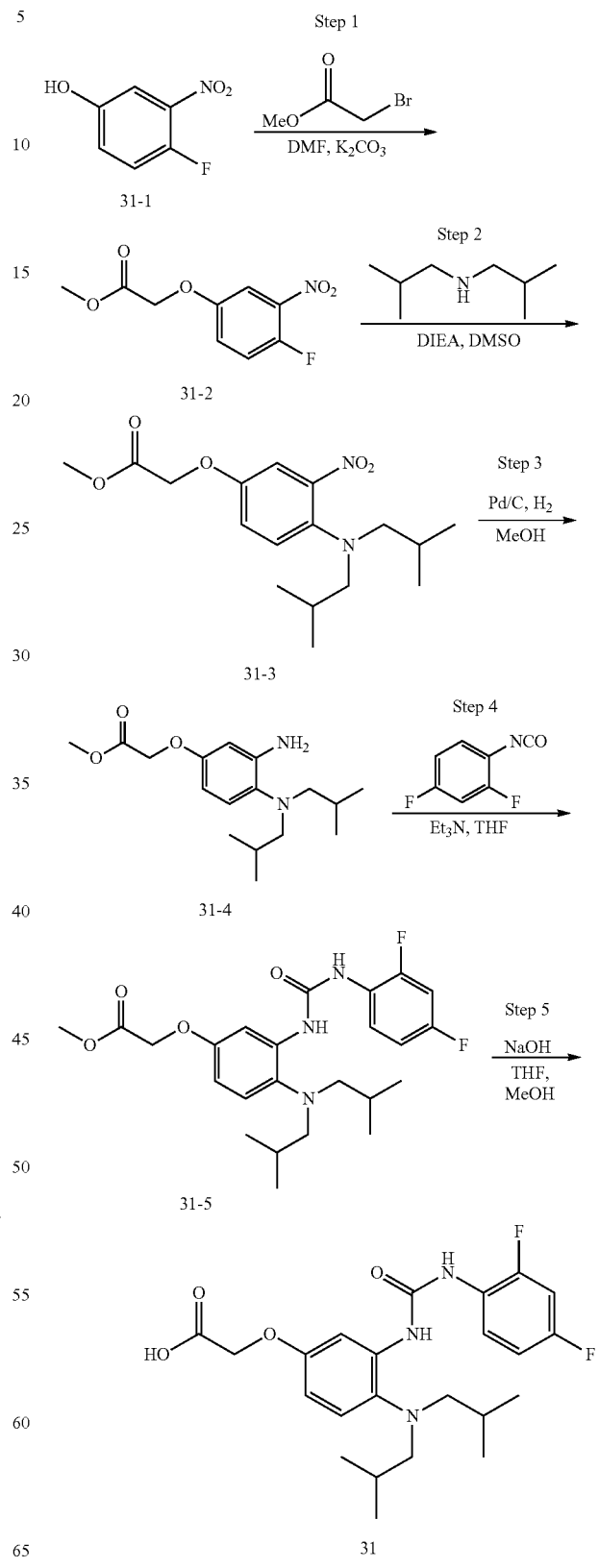

Step 1. Synthesis of 31-2

A solution of 4-fluoro-3-nitrophenol (1 g, 6.37 mmol) and potassium carbonate (1.76 g, 12.73 mmol) in N,N-dimethylformamide (15 mL) was cooled to 0° C. Methyl 2-bromoacetate (1.17 g, 7.65 mmol) was added dropwise. The mixture was stirred at room temperature for overnight. The reaction was then quenched by the addition of water (15 mL), and extracted with ethyl acetate (50 mL×3). The organic layer was washed with brine (50 mL×3), dried over anhydrous sodium sulfate, and concentrated under vacuum. The residue was purified by silica gel column with ethyl acetate/petroleum ether (1:10-1:5) as the eluent to afford the desired product (800 mg, 55% yield).

Step 2. Synthesis of 31-3

A solution of methyl 2-(4-fluoro-3-nitrophenoxy)acetate (800 mg, 3.49 mmol), bis(2-methylpropyl)amine (676 mg, 5.23 mmol), and N-ethyl-N-isopropylpropan-2-amine (1.35 g, 10.45 mmol) in dimethyl sulphoxide (10 mL) was stirred at 60° C. for 4 h. The reaction was then cooled to room temperature and diluted with water (10 mL). The mixture was extracted with ethyl acetate (50 mL×3). The organic layer was washed with brine (50 mL×3), dried over anhydrous sodium sulfate, and concentrated under vacuum. The residue was purified by silica gel column with ethyl acetate/petroleum ether (1:20-1:5) as the eluent to afford the desired product (800 mg, 68% yield).

Step 3. Synthesis of 31-4

To a solution of methyl 2-[4-[bis(2-methylpropyl)amino]-3-nitrophenoxy]acetate (800 mg, 2.36 mmol) in ethyl acetate (10 mL) and methanol (1 mL), palladium on carbon (500 mg) was added. The mixture was stirred at room temperature for 2 h under hydrogen balloon. The solid was filtered off and washed with methanol (10 mL×3). The filtrate was concentrated under vacuum and the residue was purified by silica gel column with ethyl acetate/petroleum ether (1:10~1:3) as the eluent to afford the desired product (400 mg, 55% yield).

Step 4. Synthesis of 31-5

To a solution of methyl 2-[3-amino-4-[bis(2-methylpropyl)amino]phenoxy]acetate (300 mg, 0.97 mmol) in tetrahydrofuran (5 mL), was added triethylamine (147 mg, 1.45 mmol) and then 2,4-difluoro-1-isocyanatobenzene (181 mg, 1.17 mmol). The mixture was stirred at room temperature for 2 h and then concentrated under vacuum. The residue was purified by silica gel column with ethyl acetate/petroleum ether (1:10-1:3) as the eluent to afford the desired product (180 mg, 40% yield).

Step 5. Synthesis of 31

To a solution of methyl 2-[4-[bis(2-methylpropyl)amino]-3-[[(2,4-difluorophenyl)carbamoyl]amino]phenoxy]acetate (150 mg, 0.32 mmol) in tetrahydrofuran (5 mL) and methanol (1 mL), sodium hydroxide (0.3 mL, 15% aq.) was added. The reaction was stirred at room temperature for 2 h. The mixture was concentrated under vacuum and the residue was purified by Prep-HPLC with the following conditions: [Column, Waters X-bridge RP18, 19*150 mm, 5 um; mobile phase, ACN/water (0.05% TFA) from 17% to 43% within 7 min, flow rate: 20 mL/min; Detector, 254 nm] to afford the desired product (30.7 mg, 21% yield) as an off-white solid. LCMS (ES, m/z): 450.2 [M+H]$^+$; 1HNMR: (300 MHz, DMSO-d$_6$, ppm): δ 12.90 (s, 1H), 9.33 (s, 1H), 8.23 (s, 1H), 7.91-7.82 (m, 1H), 7.59 (d, J=2.7 Hz, 1H), 7.33-7.25 (m, 1H), 7.12 (d, J=8.7 Hz, 1H), 7.08-7.02 (m, 1H), 6.51 (dd, J=8.7, 2.7 Hz, 1H), 4.54 (s, 2H), 2.61 (d, J=6.9 Hz, 4H), 1.64-1.55 (m, 2H), 0.83 (d, J=6.6 Hz, 12H).

Example 32

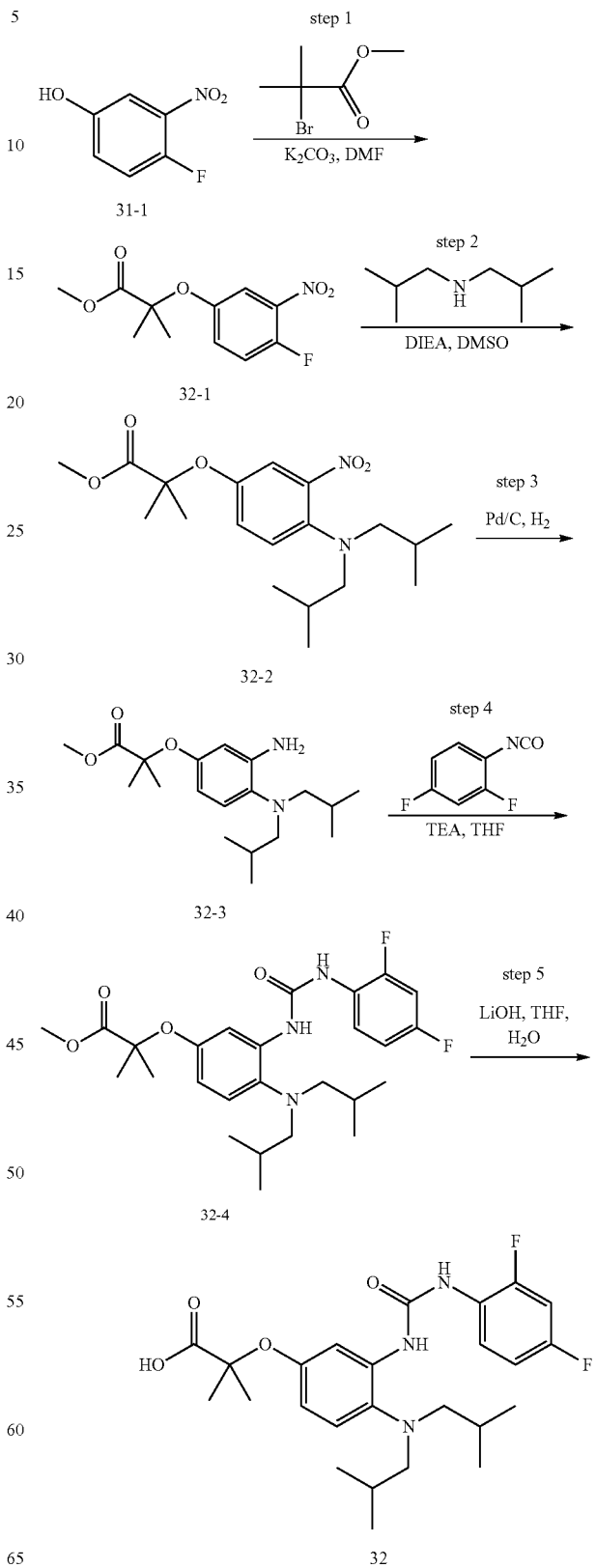

Step 1. Synthesis of 32-1

To a solution of 4-fluoro-3-nitrophenol (10 g, 63.65 mmol) and potassium carbonate (17 g, 123.00 mmol) in N,N-dimethylformamide (40 mL), was added methyl 2-bromo-2-methylpropanoate (23 g, 127.05 mmol). After stirring at 60° C. for 2.5 h, the reaction was quenched by addition of water (150 mL), and the mixture was extracted with ethyl acetate. The organic phase was washed with brine, dried over anhydrous sodium sulfate, and concentrated under vacuum. The residue was purified by silica gel column with ethyl acetate/petroleum ether (1/50) as eluent to afford the desired product (11 g, 67% yield).

Step 2. Synthesis of 32-2

A solution of methyl 2-(4-fluoro-3-nitrophenoxy)-2-methylpropanoate (10 g, 38.88 mmol), diisopropylethylamine (10 g, 77.38 mmol) and bis(2-methylpropyl)amine (7 g, 54.16 mmol) in dimethylsulfoxide (40 mL) was stirred at 100° C. overnight. After cooled to room temperature, the reaction was quenched with water (100 mL), and extracted with ethyl acetate. The organic phase was washed with water, brine, dried over anhydrous sodium sulfate, and concentrated under vacuum to afford the desired product (11 g, 77% yield).

Step 3. Synthesis of 32-3

A mixture of methyl 2-[4-[bis(2-methylpropyl)amino]-3-nitrophenoxy]-2-methylpropanoate (6 g, 16.37 mmol) and palladium on carbon (0.9 g) in methanol (20 mL) was stirred under hydrogen balloon at room temperature for overnight. The mixture was filtered through Celite and the filtrate was concentrated under vacuum. The residue was purified by silica gel column with ethyl acetate/petroleum ether (1/20) as eluent to afford the desired product (3.1 g, 56% yield).

Step 4. Synthesis of 32-4

To a solution of methyl 2-[3-amino-4-[bis(2-methylpropyl)amino]phenoxy]-2-methylpropanoate (500 mg, 1.49 mmol) in tetrahydrofuran (10 mL), were added triethylamine (451 mg, 4.46 mmol) and then 2,4-difluoro-1-isocyanatobenzene (346 mg, 2.23 mmol). The resulting mixture was then stirred at room temperature for 3 h. The reaction was quenched by addition of water, and extracted with ethyl acetate. The organic layer was washed with water and brine, dried over anhydrous sodium sulfate, and concentrated under vacuum. The residue was purified by silica gel column with ethyl acetate/petroleum ether (1/25) as eluent to afford the desired product (570 mg, 78% yield).

Step 5. Synthesis of 32

A mixture of 32-4 (650 mg, 1.32 mmol), lithium hydroxide (64 mg, 2.67 mmol) in tetrahydrofuran (8 ml) and water (4 ml) was stirred at room temperature for 20 h. The pH value of the solution was adjusted to 7 with aqueous hydrogen chloride (2 N). The mixture was then extracted with ethyl acetate. The organic phase was washed with brine, dried over anhydrous sodium sulfate, and concentrated under vacuum. The residue was purified by Prep-HPLC (column: XBridge Shield RP18 OBD Column, 5 um, 19×150 mm; mobile phase A: water with 0.05% ammonium bicarbonate, mobile Phase B: acetonitrile; flow rate: 25 mL/min; gradient: 25% B to 85% B in 8 min; detector: UV 254 nm). The collected fraction was concentrated to afford the desired product (95.3 mg, 14% yield) as a white solid. LRMS (ES, m/z): 478.3 [M+H]+. 1HNMR (300 MHz, DMSO-D$_6$, ppm) δ 9.29 (s, 1H), 8.11 (s, 1H), 7.92-7.84 (m, 1H), 7.44 (d, J=3 Hz, 1H), 7.34-7.26 (m, 1H), 7.08-7.02 (m, 2H), 6.48 (dd, J=8.4 Hz, J=2.4 Hz, 1H), 2.58 (d, J=6.9 Hz, 4H), 1.63-1.58 (m, 2H), 1.42 (s, 6H), 0.83 (d, J=6.6 Hz, 12H).

Example 33

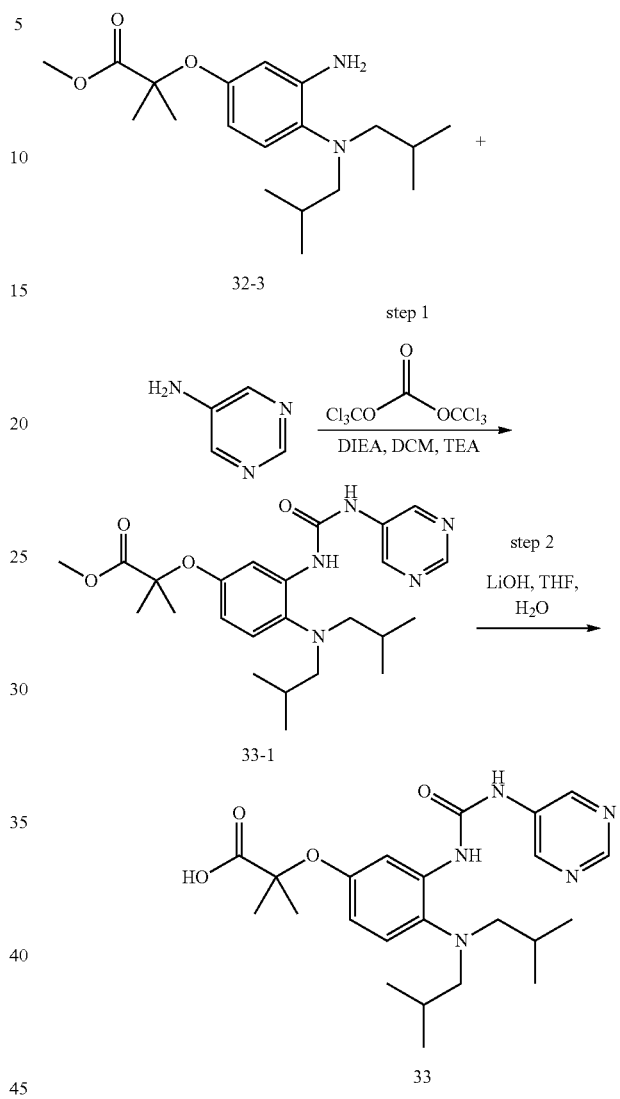

Step 1. Synthesis of 33-1

To a solution of pyrimidin-5-amine (565 mg, 5.94 mmol) and diisopropylethylamine (1.046 g, 8.09 mmol) in dichloromethane (12 mL), was added a solution of ditrichloromethyl carbonate (601 mg, 2.03 mmol) in dichloromethane (6 mL). The resulting mixture was stirred at room temperature for 15 min, and 32-3 (500 mg, 1.49 mmol) and triethylamine (902 mg, 8.91 mmol, 6.00 equiv) were added sequentially. The reaction mixture was stirred at room temperature for 5 h and then the reaction was quenched by addition of methanol and then water. The reaction was extracted with dichloromethane, washed with water and brine, and dried over anhydrous sodium sulfate. After concentration, the residue was purified by silica gel column with ethyl acetate/petroleum ether (1/5) as the eluent to afford the desired product (570 mg, 84% yield).

Step 2. Synthesis of 33

A mixture of 33-1 (500 mg, 1.09 mmol), lithium hydroxide (53 mg, 2.21 mmol) in tetrahydrofuran (6 mL) and water (4 mL) was stirred at room temperature for overnight. The pH value of the solution was adjusted to 7 with aqueous hydrogen chloride (2 N). The product was extracted with ethyl acetate, washed with brine, dried over anhydrous sodium sulfate, and concentrated under vacuum. The residue was purified by Prep-HPLC (Column: XBridge Shield RP18 OBD Column, 5 um, 19×150 mm; Mobile Phase A: Water with 0.05% NH$_4$HCO$_3$, Mobile Phase B: ACN; Flow rate: 25 mL/min; Gradient: 25% B to 85% B in 8 min; detector: UV 254 nm). The collected fraction was concentrated to afford the desired product (122.9 mg, 25% yield) as a white solid. LRMS (ES, m/z): 444.4 [M+H]$^+$. $^1$HNMR (300 MHz, DMSO-D$_6$, ppm) δ 9.92 (s, 1H), 8.91 (s, 2H), 8.82 (s, 1H), 8.20 (s, 1H), 7.58 (d, J=2.4 Hz, 1H), 7.12 (d, J=8.4 Hz, 1H), 6.49 (d, J=8.4 Hz, 1H), 2.62 (d, J=6.6 Hz, 4H), 1.62 (m, 2H), 1.47 (s, 6H), 0.85 (d, J=6.6 Hz, 12H).

Example 34

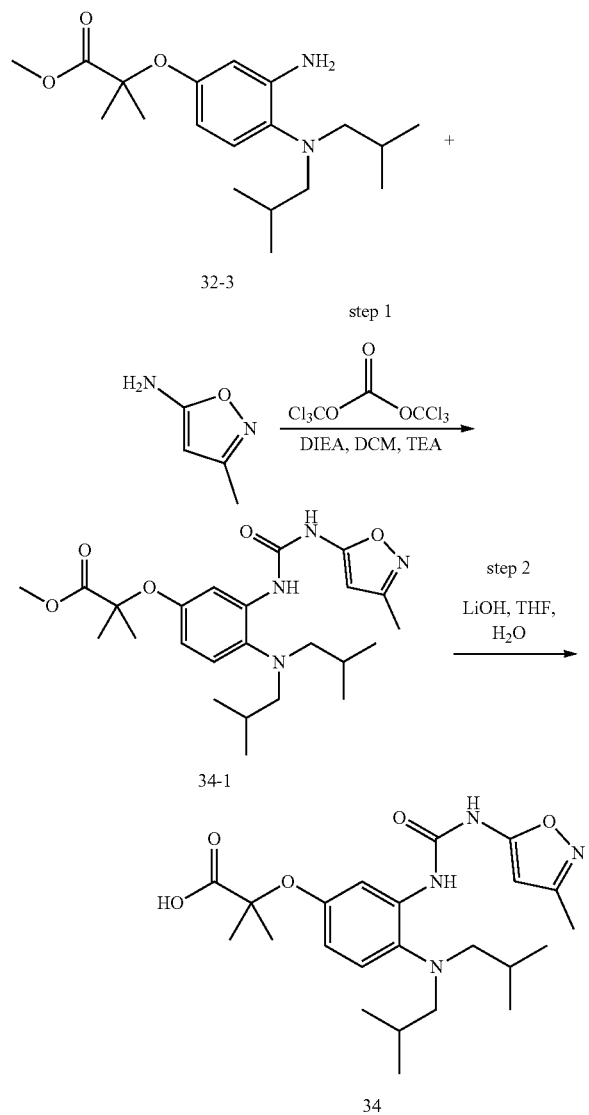

Step 1. Synthesis of 34-1

To a solution of 3-methyl-1,2-oxazol-5-amine (583 mg, 5.94 mmol) and diisopropylethylamine (1.04 g, 8.08 mmol) in dichloromethane (12 mL), was added dropwise a solution of ditrichloromethyl carbonate (601 mg, 2.03 mmol) in dichloromethane (6 mL). The resulting mixture was stirred at room temperature for 20 min. A solution of 32-3 (500 mg, 1.49 mmol) in dichloromethane (2 mL) and triethylamine (902 mg, 8.91 mmol) was added and the reaction mixture was stirred at room temperature for another 5 h. Water and dichloromethane were added. The organic phase was separated, washed with brine, dried over anhydrous sodium sulfate, and concentrated under vacuum. The residue was purified by silica gel column with ethyl acetate/petroleum ether (1/20) as the eluent to afford the desired product (580 mg, 85% yield).

Step 2. Synthesis of 34

A mixture of 34-1 (500 mg, 1.09 mmol), lithium hydroxide (52 mg, 2.17 mmol) in tetrahydrofuran (6 mL) and water (4 mL) was stirred at room temperature for overnight. The pH value of the solution was adjusted to 7 with aqueous hydrogen chloride (2 N). The product was extracted with ethyl acetate, washed with brine, dried over anhydrous sodium sulfate, and concentrated under vacuum. The residue was purified by Prep-HPLC (column: XBridge Shield RP18 OBD Column, 5 um, 19×150 mm; mobile phase A: water with 0.05% ammonium bicarbonate, mobile Phase B: acetonitrile; flow rate: 25 mL/min; gradient: 25% B to 85% B in 8 min; detector: UV 254 nm). The collected fraction was concentrated to afford the desired product (58.8 mg, 12% yield) as white solid. LRMS (ES, m/z): 447.3 [M+H]$^+$. $^1$HNMR: (300 MHz, DMSO-D$_6$, ppm) δ 11.23 (s, br, 1H), 8.25 (s, 1H), 7.53 (d, J=2.4 Hz, 1H), 7.10 (d, J=8.7 Hz, 1H), 6.50 (dd, J=8.7 Hz, J=2.4 Hz, 1H), 5.95 (s, 1H), 2.58 (d, J=6.6 Hz, 4H), 2.17 (s, 3H), 1.62-1.51 (m, 2H), 1.46 (s, 6H), 0.84 (d, J=6.3 Hz, 12H).

Example 35

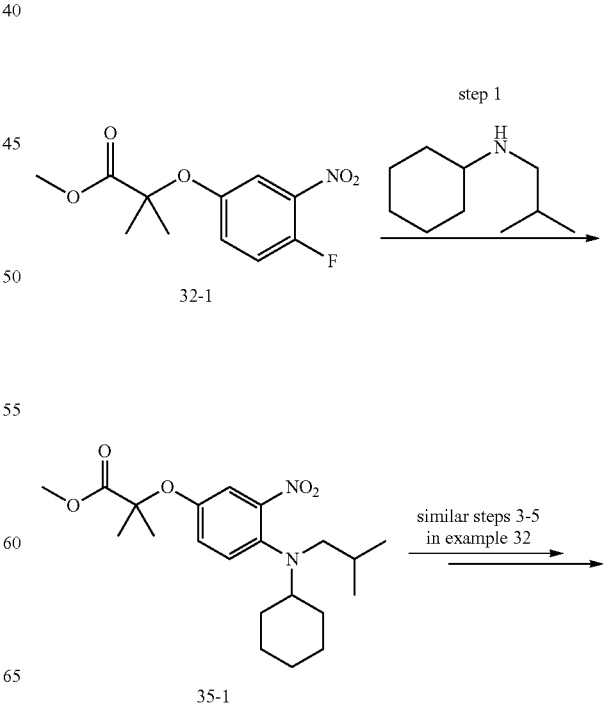

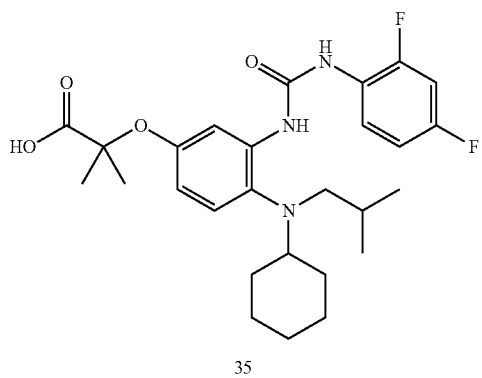

35

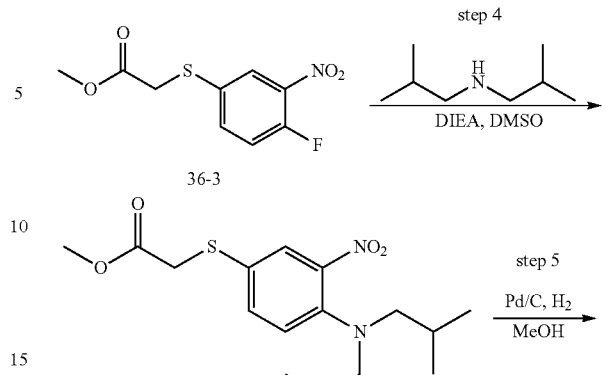

Step 1. Synthesis of 35-1

A solution of methyl 2-(4-fluoro-3-nitrophenoxy)-2-methylpropanoate (500 mg, 1.95 mmol), N-isobutylcyclohexanamine (450 mg, 2.93 mmol) and N,N-diisopropylethylamine (750 mg, 5.85 mmol) in dimethyl sufoxide (10 mL) was stirred at 110° C. for overnight. The reaction was cooled to room temperature and diluted with ethyl acetate (100 mL). The mixture was washed with water (60 mL) and brine (60 mL). The organic phase was dried over anhydrous sodium sulfate and concentrated under vacuum. The residue was purified by silica gel column with ethyl acetate/petroleum ether (1/8) as the eluent to afford the desired product (250 mg, 33% yield).

Followed similar steps 3-5 in example 32 to synthesize 35

Example 35: LCMS (ES, m/z): 504.4 [M+H]$^+$; $^1$HNMR (300 MHz, DMSO-d$_6$, ppm): δ 9.38 (s, 1H), 8.27 (s, 1H), 7.91-7.83 (m, 1H), 7.55 (s, 1H), 7.34-7.25 (m, 1H), 7.08-6.98 (m, 2H), 6.44 (d, J=9.0 Hz, 1H), 2.83-2.62 (m, 3H), 1.96-1.81 (m, 2H), 1.78-1.61 (m, 2H), 1.58-1.26 (m, 8H), 1.23-1.11 (m, 5H), 0.82 (d, J=6.6 Hz, 6H).

Example 36

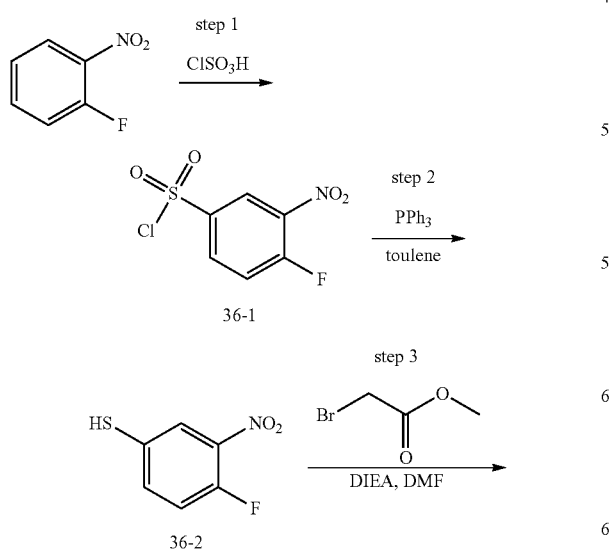

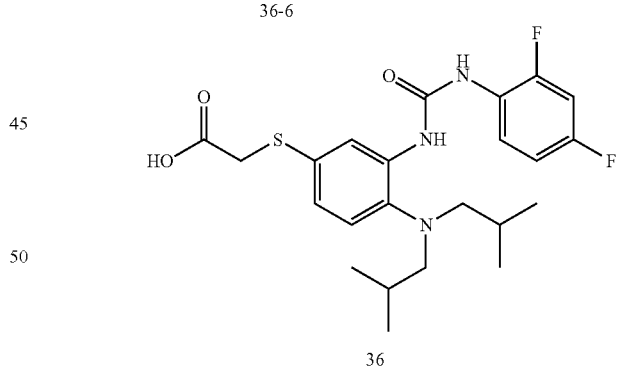

36

Step 1. Synthesis of 36-1

Into a 50-mL 3-bottom flask purged and maintained under an inert atmosphere of nitrogen, was placed sulfurochloridic acid (19.6 g, 168.21 mmol). This was followed by addition of 1-fluoro-2-nitrobenzene (10 g, 70.87 mmol) dropwise with stirring at 65° C. in 5 min. The resulting solution was stirred at 90° C. for overnight. The reaction was cooled to room temperature, and then poured into 50 mL of water/ice. The mixture was extracted with 3×50 mL of dichloromethane. The organic layer was washed with 100 mL of saturated sodium bicarbonate and then 2×100 mL of brine, dried over anhydrous sodium sulfate, and concentrated under vacuum to afford the desired product (9 g, 53% yield).

Step 2. Synthesis of 36-2

Into a 250-mL 3-necked round-bottom flask purged and maintained with an inert atmosphere of nitrogen, was placed a solution of 4-fluoro-3-nitrobenzene-1-sulfonyl chloride (9 g, 37.56 mmol) in toluene (90 mL). This was followed by addition of $PPh_3$ (29.5 g, 112.47 mmol) in several batches in 60 min (exothermic). The resulting solution was stirred for 1 h. To this, water (50 mL) was carefully added maintaining the reaction temperature less than 45° C. The resulting solution was stirred for 1 h at room temperature. The reaction mixture was extracted with 3×100 mL of dichloromethane. The combined organic layers were washed with 3×200 mL of brine, dried over anhydrous sodium sulfate, and concentrated under vacuum. The residue was applied onto a silica gel column with ethyl acetate/petroleum ether (1:10-1:3) to afford the desired product (4 g, 61% yield).

Step 3. Synthesis of 36-3

Into a 100-mL 3-necked round-bottom flask purged and maintained under an inert atmosphere of nitrogen, was placed a solution of 4-fluoro-3-nitrobenzene-1-thiol (4 g, 23.10 mmol) and methyl 2-bromoacetate (4.24 g, 27.72 mmol) in N,N-dimethylformamide (50 mL). This was followed by the addition of DIEA (5.97 g, 46.19 mmol) dropwise with stirring at 0° C. in 10 min. The resulting solution was stirred at 50° C. for overnight. The reaction mixture was cooled to room temperature. The resulting solution was diluted with 50 mL of $H_2O$. The reaction was extracted with 3×50 mL of ethyl acetate. The combined organic layers were washed with 3×50 mL of brine, dried over anhydrous sodium sulfate, and concentrated under vacuum. The residue was applied onto a silica gel column with ethyl acetate/petroleum ether (1:10-1:3) to afford the desired product (4 g, 71% yield).

Step 4. Synthesis of 36-4

Into a 100-mL 3-necked round-bottom flask purged and maintained under an inert atmosphere of nitrogen, was placed a solution of methyl 2-[(4-fluoro-3-nitrophenyl)sulfanyl]acetate (4 g, 16.31 mmol), bis(2-methylpropyl)amine (3.16 g, 24.45 mmol, 1.5 equiv), and DIEA (4.2 g, 32.50 mmol, 2.0 equiv) in DMSO (40 mL). The reaction was stirred at 80° C. for overnight. The mixture was cooled to room temperature. The resulting solution was diluted with 40 mL of $H_2O$, and extracted with 3×50 mL of ethyl acetate. The combined organic layer was washed with 3×50 mL of brine, dried over anhydrous sodium sulfate, and concentrated under vacuum. The residue was applied onto a silica gel column with ethyl acetate/petroleum ether (1:10-1:3) to afford the desired product (3.1 g, 54% yield).

Step 5. Synthesis of 36-5

Into a 100-mL round-bottom flask, was placed a solution of methyl 2-([4-[bis(2-methylpropyl)amino]-3-nitrophenyl]sulfanyl)acetate (3 g, 8.46 mmol) and palladium on carbon (100 mg) in ethyl acetate (30 mL) and MeOH (5 mL). The flask was evacuated and flushed three times with nitrogen, followed by flushing with hydrogen. The mixture was stirred 3 h at room temperature under an atmosphere of hydrogen (balloon). The solid was filtered off. The filtrate was concentrated under vacuum to afford the desired product (2 g, 73% yield).

Step 6. Synthesis of 36-6

Into a 100-mL 3-necked round-bottom flask, was placed a solution of methyl 2-([3-amino-4-[bis(2-methylpropyl)amino]phenyl]sulfanyl)acetate (2 g, 6.16 mmol), 2,4-difluoro-1-isocyanatobenzene (1.15 g, 7.41 mmol), and triethylamine (1.25 g, 12.35 mmol) in tetrahydrofuran (50 mL). The reaction was stirred at room temperature for overnight. The resulting mixture was concentrated under vacuum. The residue was applied onto a silica gel column with ethyl acetate/petroleum ether (1:10-1:1) to afford the desired product (1.5 g, 51% yield).

Step 7. Synthesis of 36

To a solution of methyl 2-([4-[bis(2-methylpropyl)amino]-3-[[(2,4-difluorophenyl)carbamoyl]amino]phenyl]sulfanyl)acetate (250 mg, 0.52 mmol) in ethanol (3 mL) and $H_2O$ (0.5 mL), was added sodium hydroxide (15% aq) (0.5 mL). The resulting solution was stirred at room temperature for 3 h. The pH value of the solution was adjusted to 6 with hydrogen chloride (1 N). The resulting mixture was concentrated under vacuum. The crude product was purified by Prep-HPLC with the following conditions: Column, Waters X-bridge RP18, 19*150 mm, 5 um; mobile phase, ACN/water (0.05% $NH_3H_2O$) from 15% to 40% within 6.5 min, flow rate: 20 mL/min; Detector, 254 nm. This resulted in the desired product (60 mg, 25% yield) as a white solid. LCMS (ES, m/z): 466 $[M+H]^+$. HNMR (300 MHz, DMSO-$d_6$, ppm): δ 9.33 (s, 1H), 8.10 (s, 1H), 7.97-7.88 (m, 2H), 7.30 (t, J=6.6 Hz, 1H), 7.28 (d, J=6.0 Hz, 1H), 7.17-7.02 (m, 1H), 6.94 (dd, J=8.4, 2.4 Hz, 1H), 3.38 (s, 2H), 2.67 (d, J=6.9 Hz, 4H), 1.69-1.60 (m, 2H), 0.83 (d, J=6.6 Hz, 12H).

Example 37

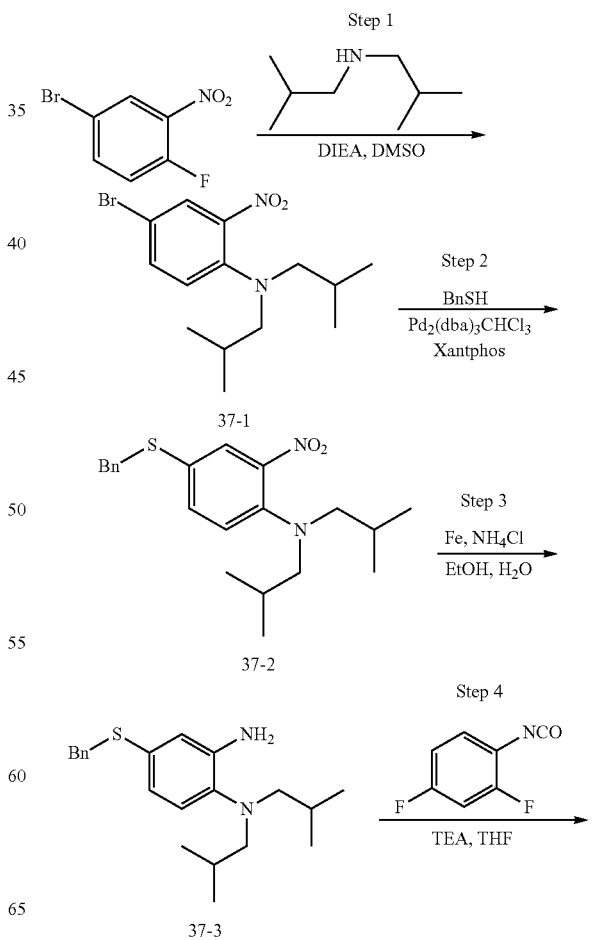

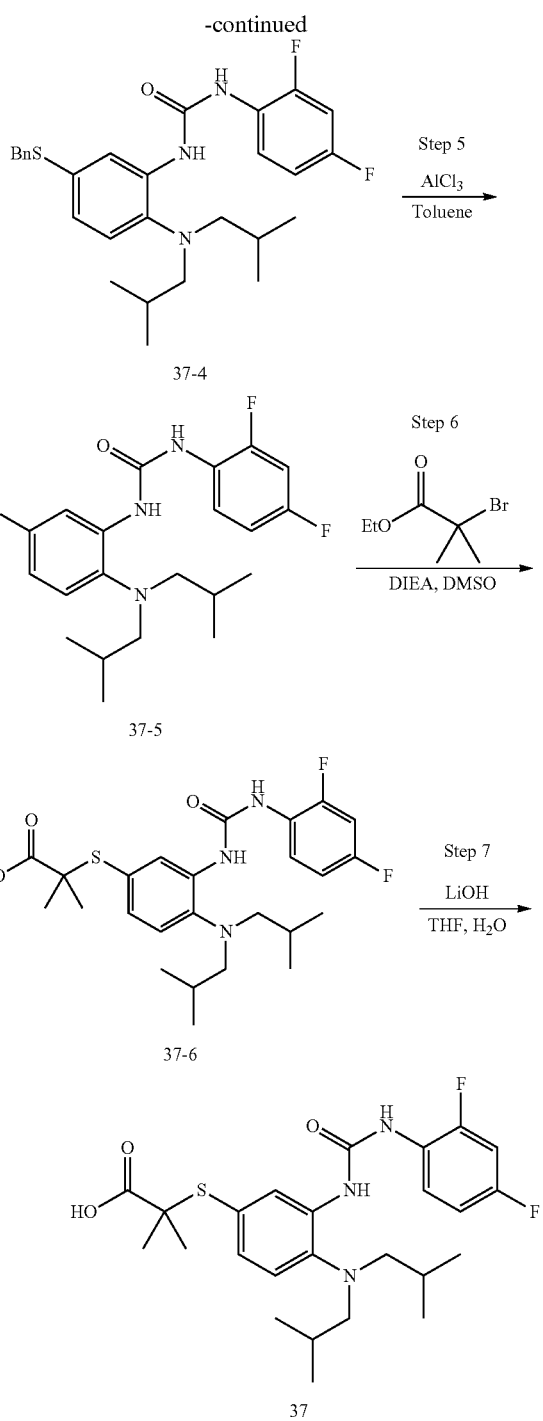

Step 1. Synthesis of 37-1

To a solution of 4-bromo-1-fluoro-2-nitrobenzene (5 g, 22.73 mmol) in dimethyl sulfoxide (50 mL) were added bis(2-methylpropyl)amine (3.53 g, 27.31 mmol) and then N,N-diisopropylethylamine (3.53 g, 27.36 mmol). The reaction was then stirred at 100° C. for 12 h. After cooling to room temperature, the mixture was diluted with water (200 mL), and extracted with ethyl acetate (200 mL×3). The organic phase was washed with brine (200 mL) and concentrated under vacuum to afford the desired product (7 g, 94% yield).

Step 2. Synthesis of 37-2

A solution of 4-bromo-N,N-bis(2-methylpropyl)-2-nitroaniline (7 g, 21.26 mmol), phenylmethanethiol (3.125 g, 25.16 mmol), Pd$_2$(dba)$_3$CHCl$_3$ (2.2 g, 2.13 mmol), Xant-Phos (1.23 g, 2.12 mmol), and triethylamine (4.31 g, 42.67 mmol) in dioxane (100 mL) was stirred at 100° C. for 2 h. After cooling to room temperature, the mixture was concentrated under vacuum. The residue was purified by silica gel column with ethyl acetate/petroleum ether (1/15-1/10) as the eluent to afford the desired product (4 g, 51% yield).

Step 3. Synthesis of 37-3

To a solution of 4-(benzylsulfanyl)-N,N-bis(2-methylpropyl)-2-nitroaniline (1 g, 2.68 mmol) in ethanol (20 mL) and water (2 mL), was added iron (750 mg, 13.43 mmol) and then ammonium chloride (710 mg, 13.40 mmol). The reaction was then stirred at 80° C. for 1 h. After cooling to room temperature, the mixture was diluted with water (50 mL), and extracted with ethyl acetate (50 mL×3). The organic phase was concentrated under vacuum and the residue was purified by silica gel column with ethyl acetate/petroleum ether (1/10-1/3) as the eluent to afford the desired product (340 mg, 37% yield).

Step 4. Synthesis of 37-4

To a solution of 4-(benzylsulfanyl)-1-N,1-N-bis(2-methylpropyl)benzene-1,2-diamine (200 mg, 0.58 mmol) and triethylamine (71 mg, 0.70 mmol) in tetrahydrofuran (10 mL) was added 2,4-difluoro-1-isocyanatobenzene (109 mg, 0.70 mmol). The reaction was then stirred at room temperature for 30 min. The reaction was quenched by addition of water (10 mL), and the mixture was extracted with ethyl acetate (15 mL×3). The combined organic layer was washed with 3×50 mL of brine, dried over anhydrous sodium sulfate, and concentrated under vacuum to afford the desired product (150 mg, 52% yield).

Step 5. Synthesis of 37-5

To a solution of 3-[5-(benzylsulfanyl)-2-[bis(2-methylpropyl)amino]phenyl]-1-(2,4-difluorophenyl)urea (150 mg, 0.30 mmol) in Toluene (5 mL) was added aluminium chloride (398 mg, 2.98 mmol) portionwise. The resulting mixture was then stirred at room temperature for 2 h. The reaction was diluted with water (10 mL), and extracted with ethyl acetate (15 mL×3). The combined organic layer was washed with 3×50 mL of brine, dried over anhydrous sodium sulfate, and concentrated under vacuum to afford the desired product (70 mg, 57% yield).

Step 6. Synthesis of 37-6

To a solution of 3-[2-[bis(2-methylpropyl)amino]-5-sulfanylphenyl]-1-(2,4-difluorophenyl)urea (70 mg, 0.17 mmol) and N,N-diisopropylethylamine (33.5 mg, 0.26 mmol) in dimethyl sulfoxide (1 mL), was added ethyl 2-bromo-2-methylpropanoate (36.7 mg, 0.19 mmol). The reaction was stirred at room temperature for 1 h. The mixture was diluted with water (5 mL), and extracted with ethyl acetate (5 mL×3). The organic phase was washed with brine (5 mL), dried over anhydrous sodium sulfate, and concentrated under vacuum. The residue was purified by silica gel column with ethyl acetate/petroleum ether (1/5-1/3) as the eluent to afford the desired product (60 mg, 67% yield).

Step 7. Synthesis of 37

To a solution of ethyl 2-([4-[bis(2-methylpropyl)amino]-3-[[(2,4-difluorophenyl)carbamoyl]amino]phenyl]sulfanyl)-2-methylpropanoate (60 mg, 0.12 mmol) in tetrahydrofuran (1 mL) and water (0.2 mL), was added lithium hydroxide monohydrate (6.9 mg, 0.29 mmol). The reaction was stirred at 60° C. for 12 h. After cooling to room temperature, the mixture was concentrated under vacuum and the residue was purified by Flash-Prep-HPLC [Column:

Waters X-bridge C18, 5 um, 19×150 mm; Mobile phase A: water (0.05% NH$_4$HCO$_3$), Mobile phase B: CAN; Gradient: 50% ACN to 90% CAN in 10 min; Detector: UV 254 nm] to afford the desired product (12 mg, 21% yield) as a white solid. LCMS: (ES, m/z): 494.2 [M+H]$^+$. $^1$HNMR: (300 MHz, CD$_3$OD): δ 8.03 (s, 1H), 7.84-7.76 (m, 1H), 7.20-7.12 (m, 2H), 7.06-6.91 (m, 2H), 2.74 (d, J=14.1 Hz, 4H), 1.78-1.69 (m, 2H), 1.46 (s, 6H), 0.87 (d, J=6.6 Hz, 12H).

Example 38

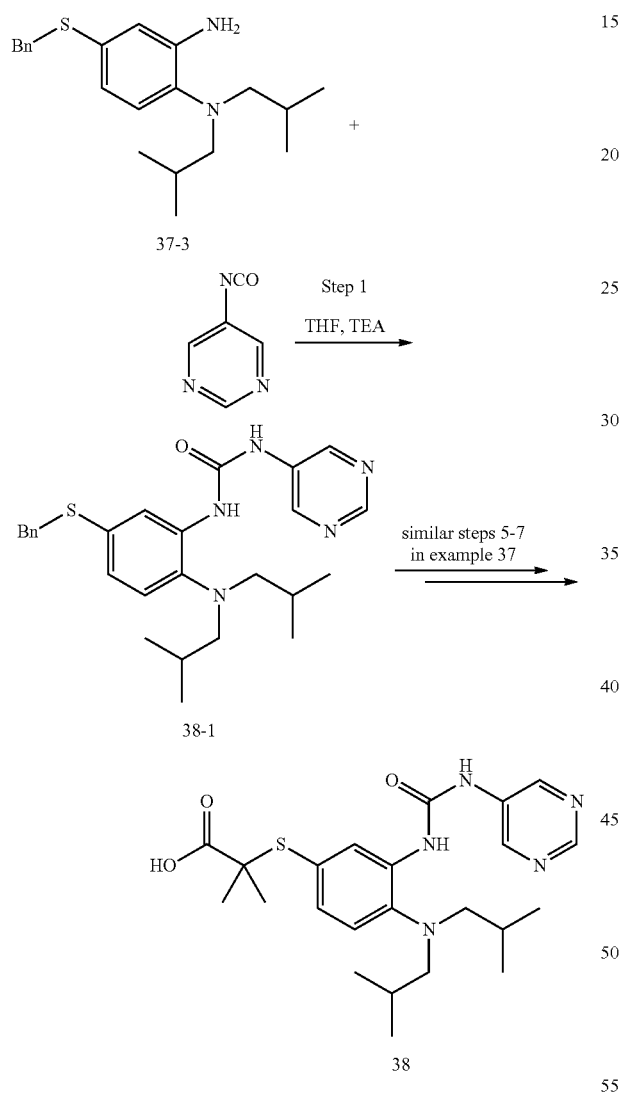

silica gel column with ethyl acetate/petroleum ether (2/3) as the eluent to afford the desired product (600 mg, 74% yield).

Followed similar steps 5-7 in example 37 to synthesize 38

Example 38: LCMS (ES, m/z): 460.2 [M+H]$^+$. $^1$H NMR (300 MHz, CD$_3$OD): δ 8.97 (s, 2H), 8.79 (s, 1H), 8.15 (s, 1H), 7.20 (s, 2H), 2.75(d, J=6.9 Hz, 4H), 1.79-1.70 (m, 2H), 1.45 (s, 6H), 0.91 (d, J=6.6 Hz, 12H).

Example 39

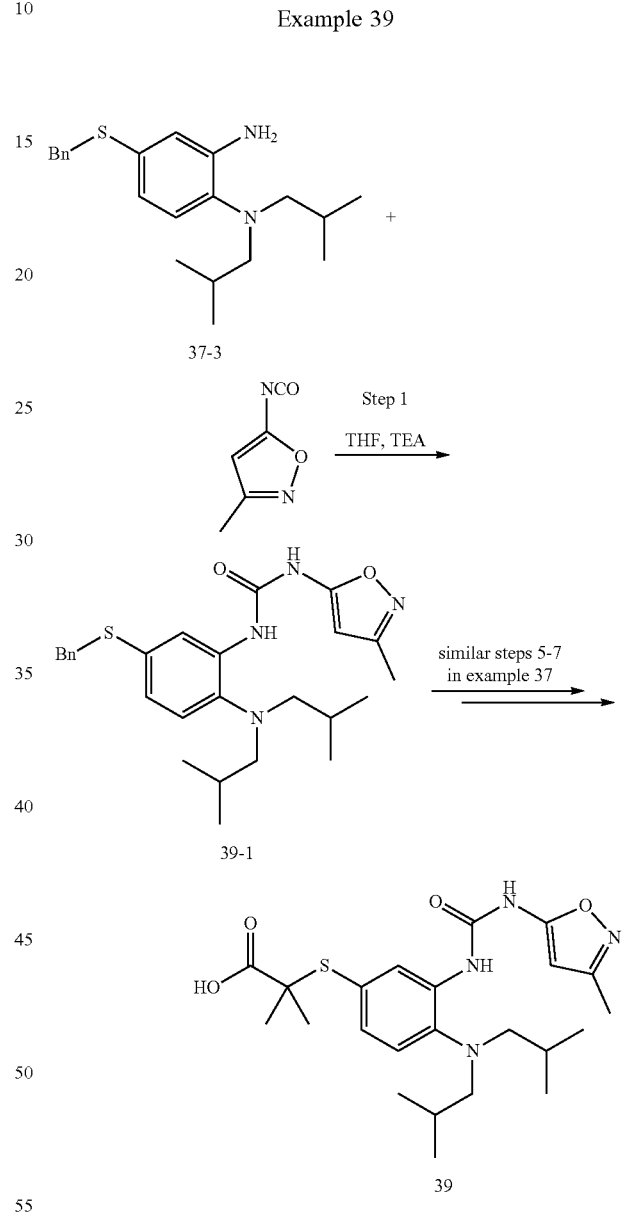

Step 1. Synthesis of 38-1

To a solution of 4-(benzylthio)-N1,N1-diisobutylbenzene-1,2-diamine (600 mg, 1.75 mmol) in tetrahydrofuran (10 mL), was added 5-isocyanatopyrimidine (862 mg, 7.12 mmol) and then triethylamine (930 mg, 9.19 mmol). The reaction was stirred at room temperature for 2 h. The mixture was diluted with water (50 mL), and extracted with ethyl acetate (50 mL×3). The organic phase was washed with brine (50 mL×2), dried over anhydrous sodium sulfate, and concentrated under vacuum. The residue was purified by Step 1. Synthesis of 39-1

To a solution of 4-(benzylthio)-N1,N1-diisobutylbenzene-1,2-diamine (175 mg, 0.51 mmol) in tetrahydrofuran (10 mL), was added 5-isocyanato-3-methylisoxazole (253 mg, 2.04 mmol) and then triethylamine (310 mg, 3.07 mmol). The reaction was then stirred at room temperature for overnight, at 45° C. for 12 h, and then at 75° C. for 36 h. The mixture was cooled to room temperature, and then quenched by addition of water/ice (50 mL). The mixture was extracted with ethyl acetate (20 mL×3), and washed with brine (20 mL×2). The organic phase was dried over anhydrous sodium sulfate and concentrated under vacuum to afford the desired product (100 mg, 42% yield).

Followed similar steps 5-7 in example 37 to synthesize 39

Example 39: LCMS (ES, m/z): 463.6 [M+H]$^+$. $^1$HNMR: (300 MHz, CH$_3$OD, ppm): δ 8.15 (s, 1H), 7.20 (s, 2H), 6.06 (s, 1H), 2.73 (d, J=6.9 Hz, 4H), 2.24 (s, 3H), 1.77-1.66 (m, 2H), 1.45 (s, 6H), 0.89 (d, J=6.6 Hz, 12H).

Example 40

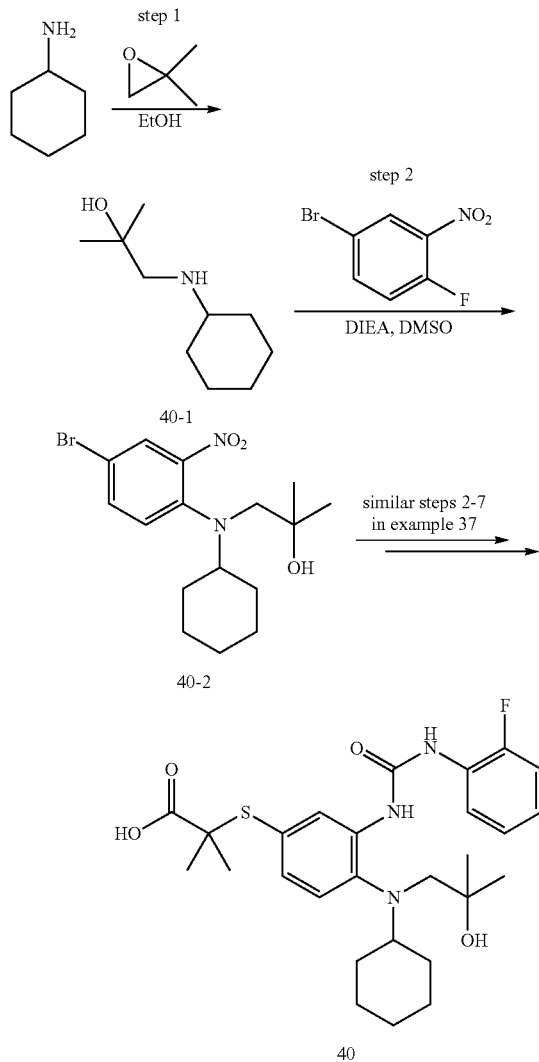

Step 1. Synthesis of 40-1

Into a 50 mL sealed tube, were added cyclohexanamine (2 g, 20.17 mmol), 2,2-dimethyloxirane (1.45 g, 20.11 mmol), and ethanol (10 mL). The resulting solution was stirred at 100° C. for 2 days. After cooling to room temperature, petroleum ether (20 mL) was added and the solid was filtered off. The filtrate was concentrated under vacuum and the crude product was purified by silica gel column with methanol and dichloromethane (1:10) as eluent to afford the desired product (2.4 g, 69% yield).

Step 2. Synthesis of 40-2

To a solution of 4-bromo-1-fluoro-2-nitrobenzene (1.45 g, 6.57 mmol) and diisopropylethylamine (1.70 g, 13.15 mmol) in dimethylsulfoxide (10 mL), was added 41-1 (1.35 g, 7.88 mmol). The reaction mixture was stirred at 120° C. for 1 day. The reaction was quenched by addition of water (100 mL) and the mixture was extracted with ethyl acetate (50 mL×3). The combined organic layer was dried over anhydrous sodium sulfate and concentrated under vacuum. The residue was purified by silica gel column with ethyl acetate/petroleum ether (1/10) as eluent to afford the desired product (1.42 g, 58% yield).

Followed similar steps 2-7 in example 37 to synthesize 40.

Example 40: LRMS (ES, m/z) 536.4[M+H]$^+$. $^1$HNMR (300 MHz, MeOD, ppm) 8.14 (s, 1H), 8.14-7.93 (m, 1H), 7.27 (d, J=8.4 Hz, 1H), 7.25-7.14 (m, 1H), 7.07-6.92 (m, 2H), 4.62 (br, 1H), 3.14 (br, 2H), 2.61-2.60 (m, 1H), 1.93 (d, J=10.8 Hz, 2H), 1.74 (d, J=10.4 Hz, 2H), 1.57 (d, J=11.1 Hz, 1H), 1.44 (s, 6H), 1.36-1.03 (m, 5H), 1.00 (s, 6H).

Example 41

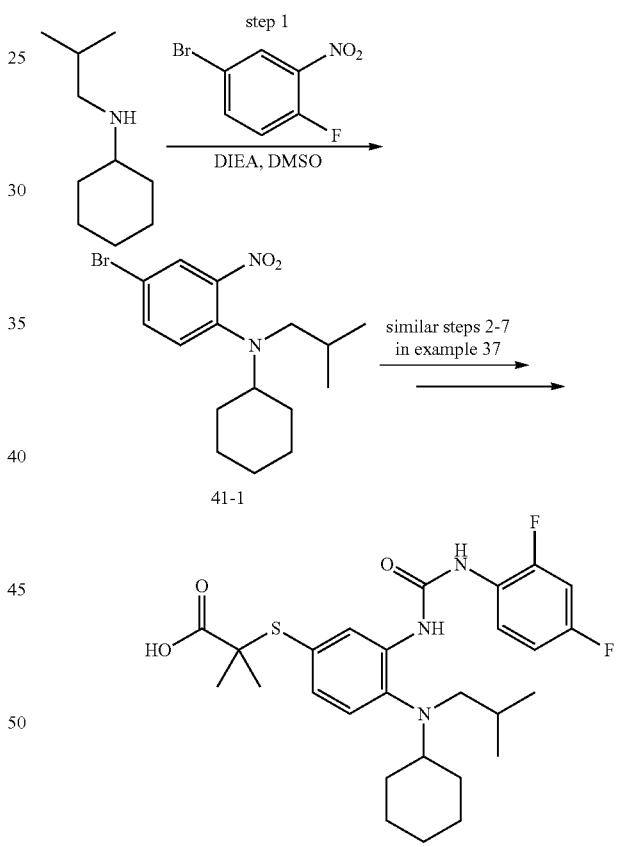

Step 1. Synthesis of 41-1

A solution of N-isobutylcyclohexanamine (1.0 g, 6.45 mmol), 4-bromo-1-fluoro-2-nitrobenzene (1.42 g, 6.45 mmol), and N,N-diisopropylethylamine (1.66 g, 12.9 mmol) in dimethyl sufoxide (20 mL) was stirred at 110° C. for overnight. The reaction was cooled to room temperature, and diluted with ethyl acetate (100 mL). The organic phase was washed with water (60 mL) and brine (60 mL), dried over anhydrous sodium sulfate, and concentrated under vacuum. The residue was purified by silica gel column with ethyl acetate/petroleum ether (1/10) as the eluent to afford the desired product (1.34 g, 59% yield).

Followed similar steps 2-7 in example 37 to synthesize 41

Example 41: LCMS (ES, m/z): 520.4 [M+H]+; 1HNMR (300 MHz, DMSO-d6, ppm): δ 12.72 (brs, 1H), 9.40 (s, 1H), 8.09 (s, 1H), 8.02 (s, 1H), 8.01-7.88 (m, 1H), 7.36-7.28 (m, 1H), 7.17-7.14 (m, 1H), 7.06-7.04 (m, 2H), 2.79 (d, J=6.0 Hz, 2H), 2.62-2.55 (m, 1H), 1.86-1.83 (m, 2H), 1.78-1.66 (m, 2H), 1.58-1.48 (m, 1H), 1.42-1.23 (m, 8 H), 1.21-0.98 (m, 4H), 0.82 (d, J=6.6 Hz, 6H).

Example 42

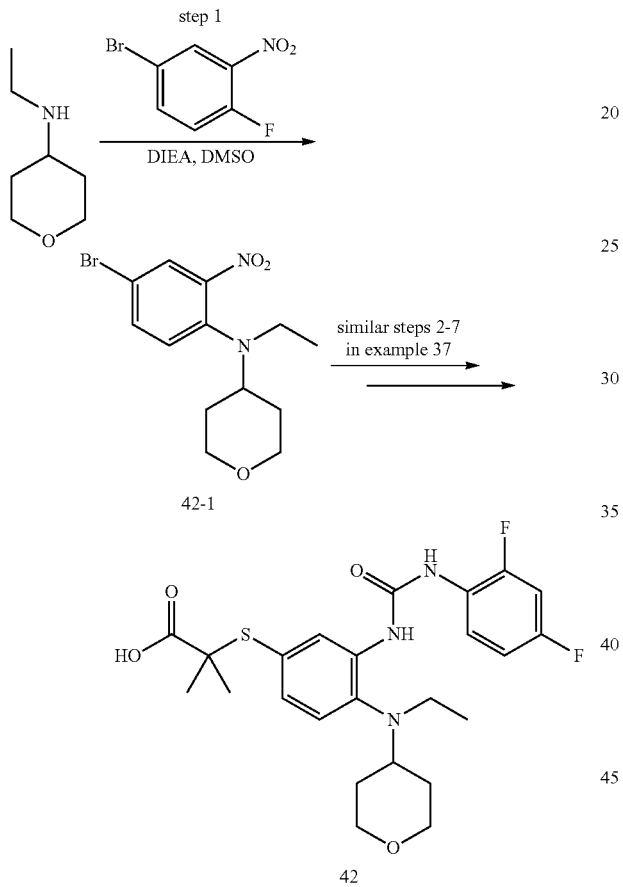

Step 1. Synthesis of 42-1

To a solution of 4-bromo-1-fluoro-2-nitrobenzene (6.1 g, 27.73 mmol) in DMSO (2 mL), was added diisopropylethylamine (7.2 g, 55.81 mmol) and then N-ethyloxan-4-amine (2.4 g, 18.58 mmol). After stirring at 140° C. for overnight, the reaction mixture was cooled to room temperature and water (60 mL) was added. The reaction mixture was extracted with ethyl acetate (60 mL×3). The combined organic layer was washed with brine (60 mL×2), dried over anhydrous sodium sulfate, and concentrated under vacuum. The residue was purified by column chromatography on silica gel with ethyl acetate/petroleum ether (1/40) to afford N-(4-bromo-2-nitrophenyl)-N-ethyloxan-4-amine (5.5 g, 60% yield).

Followed similar steps 2-7 in example 37 to synthesize 42.

Example 42: LC-MS (ES, m/z): [M+H]+ 494.4. 1HNMR (300 MHz, DMSO-d6, ppm): δ 9.43 (s, 1H), 8.78 (s, 1H), 8.27 (d, J=2.1 Hz, 1H), 8.06-7.98 (m, 1H), 7.34-7.26 (m, 1H), 7.20 (d, J=8.1 Hz, 1H), 7.07-7.00 (m, 2H), 3.82 (d, J=1.2 Hz, 2H), 3.27-3.18 (m, 2H), 3.03-2.95 (m, 3H), 1.69 (d, J=6.6 Hz, 2H), 1.45-1.22 (m, 8H), 0.79 (t, J=6.9 Hz, 3H).

Example 43

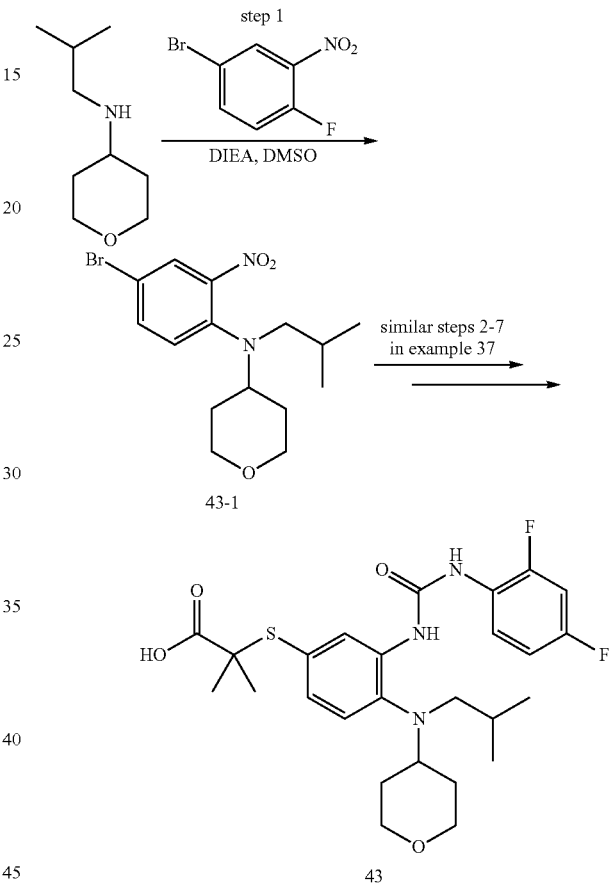

Step 1. Synthesis of 43-1

To a solution of oxan-4-one (7.5 g, 75 mmol) in tetrahydrofuran (60 mL) at room temperature, was added 2-methylpropan-1-amine (4.96 g, 68 mmol) and then acetic acid (1.5 mL). The resulting solution was stirred for 1 h at room temperature. To this was added NaBH(OAc)3 (28.83 g). After stirring at room temperature for overnight, the reaction was quenched by addition of water (50 mL) and the mixture was extracted with ethyl acetate (60 mL×3). The combined organic layer was washed with brine (60×3), dried over anhydrous sodium sulfate, and concentrated under vacuum to afford N-(2-methylpropyl)oxan-4-amine (6.2 g, crude).

Followed similar steps 2-7 in example 37 to synthesize 43.

Example 43: LC-MS (ES, m/z): 522.4 [M+H]+. 1HNMR (300 MHz, CDCl3-d6, ppm) δ 8.53 (s, 1H), 8.03 (s, 1H), 7.64-7.47 (m, 1H), 7.13-7.05 (m, 1H), 6.91 (t, 2H), 3.91 (d, J=11.1 Hz, 2H), 3.25-3.17 (m, 2H), 2.72-2.63 (m, 2H), 1.70-1.20 (m, 12H), 0.70 (d, J=6.3 Hz, 6H).

Example 44

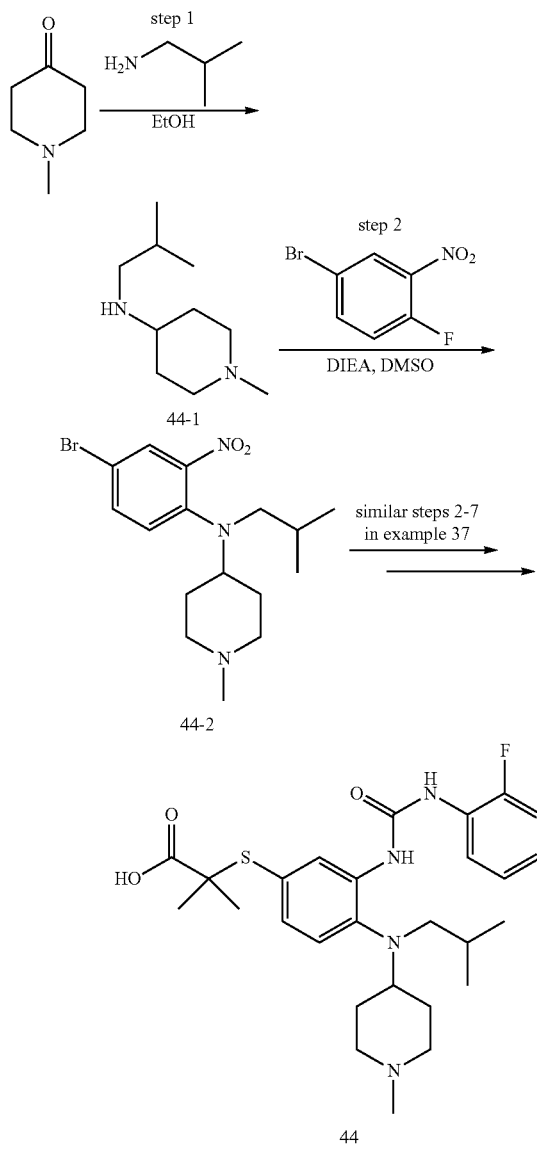

44

Step 1. Synthesis of 44-1

To a solution of 2-methylpropan-1-amine (5.76 g, 78.76 mmol) and 1-methylpiperidin-4-one (9.80 g, 86.60 mmol) in dichloromethane (130 mL), was added sodium cyanoborohydride (50.1 g, 236.39 mmol) portionwise. The reaction was then stirred at room temperature for 16 h. The solid was filtered off and the mixture was diluted with water (500 mL). The pH value of the mixture was adjusted to 9 with sodium bicarbonate. The mixture was extracted with dichloromethane (500 mL×4). The organic phase was washed with brine (1000 mL), dried over anhydrous sodium sulfate, and concentrated under vacuum to afford the desired product (6 g, 45% yield).

Step 2. Synthesis of 44-2

A solution of 1-methyl-N-(2-methylpropyl)piperidin-4-amine (1.98 g, 11.64 mmol), 4-bromo-1-fluoro-2-nitrobenzene (1.7 g, 7.73 mmol), and N,N-diisopropylethylamine (3.01 g, 23.30 mmol) in dimethyl sulfoxide (20 mL) was stirred at 100° C. for 17 h. After cooling to room temperature, the mixture was diluted with water (200 mL), and extracted with ethyl acetate (200 mL×3). The organic phase was washed with brine (500 mL×2), dried over anhydrous sodium sulfate, and concentrated under vacuum. The residue was purified by Flash-Prep-HPLC with the following conditions: [Column: silica gel; Mobile phase A: petroleum ether, Mobile phase B: ethyl acetate; Gradient: 0% ethyl acetate to 100% ethyl acetate within 25 min; Detector: UV 254 nm] to afford the desired product (1.2 g, 42% yield).

Followed similar steps 2-7 in example 37 to synthesize 44.

Example 44: LCMS (ES, m/z): 535.4 [M+H]$^+$; $^1$H NMR (300 MHz, DMSO-d$_6$, ppm): δ 9.45 (s, 1H), 8.29 (s, 1H), 8.12 (d, J=2.1 Hz, 1H), 7.98-7.90 (m, 1H), 7.35-7.28 (m, 1H), 7.20 (d, J=8.1 Hz, 1H), 7.09-7.02 (m, 2H), 2.80-2.72 (m, 4H), 2.66-2.58 (m, 1H), 2.11 (s, 3H), 1.85-1.73 (m, 4H), 1.57-1.46 (m, 2H), 1.36-1.29 (m, 7H), 0.82 (d, J=6.6 Hz, 6H).

Example 45

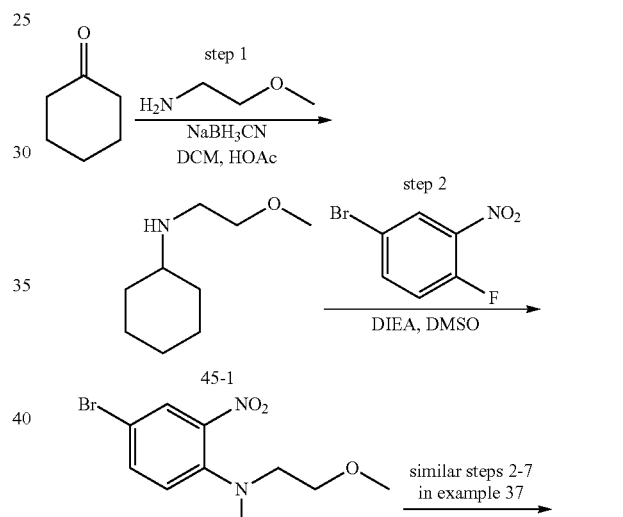

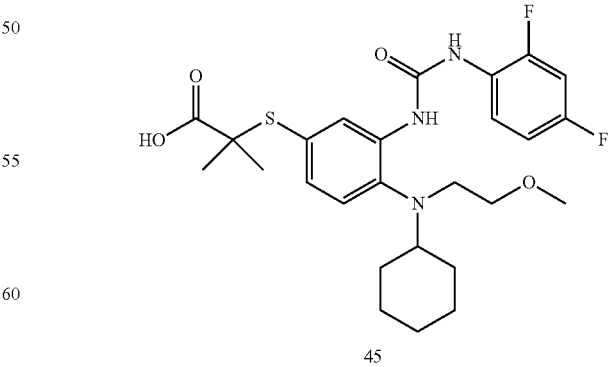

45

Step 1. Synthesis of 45-1

To a solution of cyclohexanone (7.8 g, 79.48 mmol) and 2-methoxyethan-1-amine (5 g, 66.57 mmol) in dichloromethane (75 mL), was added acetic acid (0.1 mL). The reaction was stirred at 25° C. for 0.5 h. Sodium cyanoborohydride (16.7 g, 265.75 mmol) was added and the mixture was stirred at 25° C. for another 5 h. The reaction was quenched by addition of saturated ammonium chloride solution (50 mL). The resulting mixture was extracted with dichloromethane (50 mL×2), and washed with brine (50 mL×2). The organic phase was dried over anhydrous sodium sulfate and concentrated under vacuum. The residue was purified by silica gel column with ethyl acetate/petroleum ether (1/4-100/1) as the eluent to afford the desired product (6 g, 57% yield).

Step 2. Synthesis of 45-2

To a solution of N-(2-methoxyethyl)cyclohexanamine (5 g, 31.80 mmol) and 4-bromo-1-fluoro-2-nitrobenzene (8.4 g, 38.18 mmol) in dimethyl sulfoxide (30 mL), was added N,N-diisopropylethylamine (6.2 g, 47.97 mmol). The reaction was then stirred at 100° C. for 16 h. The reaction was cooled to room temperature, diluted with water (200 mL), and extracted with ethyl acetate (200 mL×2). The organic phase was washed with water (100 mL×2) and brine (100 mL×2), dried over anhydrous sodium sulfate, and concentrated under vacuum. The residue was purified by Flash-Prep-HPLC with the following conditions: [Column: C18 silica gel; Mobile phase A: water (0.05% TFA), Mobile phase B: ACN, Gradient: 55% CAN to 100% ACN; Detector: UV 254 nm] to afford the desired product (8 g, 70% yield).

Followed similar steps 2-7 in example 37 to synthesize 45

Example 45: LCMS (ES, m/z): 522.2 [M+H]$^+$. $^1$HNMR: (300 MHz, DMSO-$d_6$, ppm): δ 9.40 (s, 1H), 8.62 (s, 1H), 8.19 (d, J=1.8 Hz, 1H), 8.01-7.93 (m, 1H), 7.35-7.19 (m, 2H), 7.08-7.01 (m, 2H), 3.25-3.14 (m, 4H), 3.12 (s, 3H), 2.62-2.80 (m, 1H), 1.80-1.98 (m, 2H), 1.79-1.60 (m, 2H), 1.59-1.43 (m, 1H), 1.32 (s, 6H), 1.20-0.90 (m, 5H).

Example 46

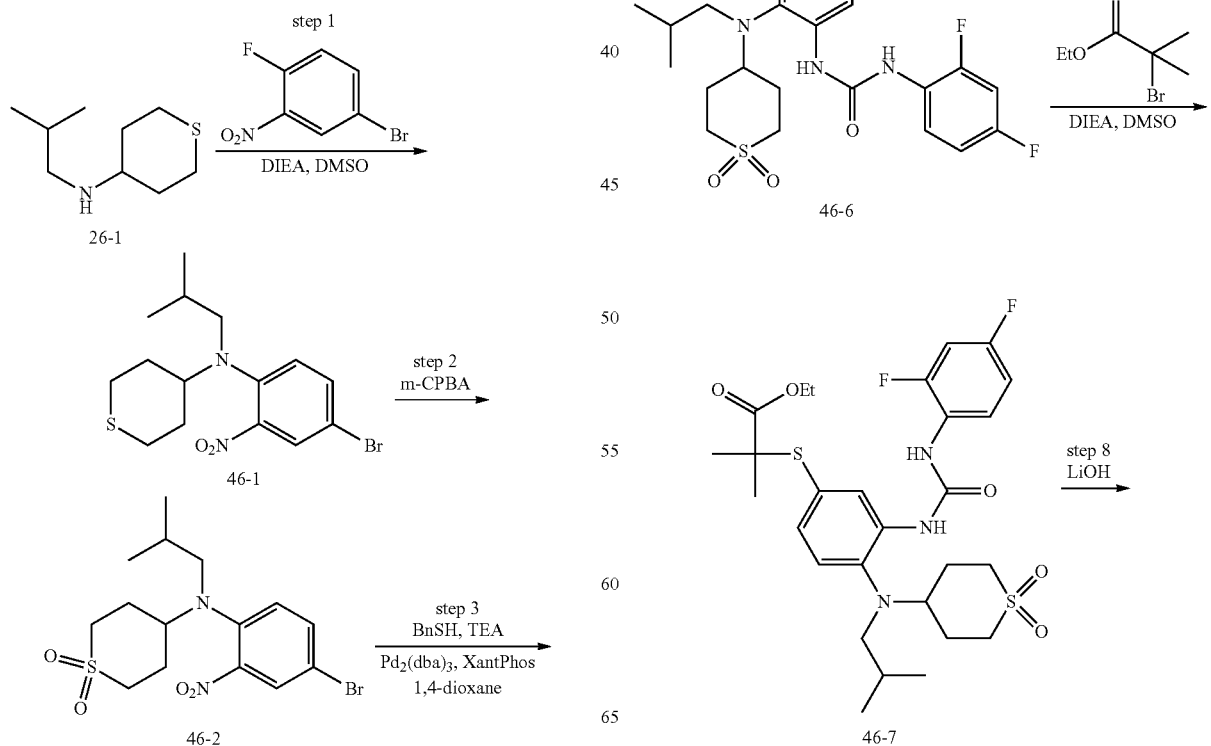

-continued

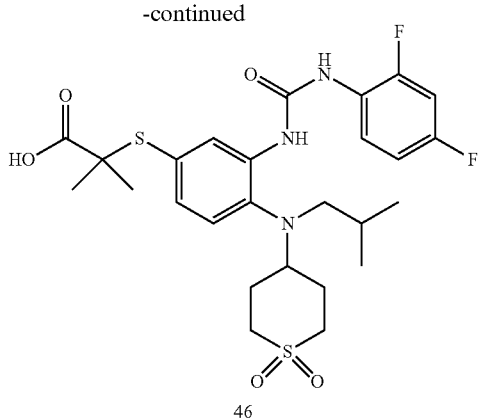

46

Step 1. Synthesis of 46-1

A solution of N-(2-methylpropyl)thian-4-amine (3.1 g, 17.89 mmol), 4-bromo-1-fluoro-2-nitrobenzene (3.94 g, 17.91 mmol), and N,N-diisopropylethylamine (4.62 g, 35.75 mmol) in dimethyl sulfoxide (30 mL) with stirring at 110° C. for overnight. After cooled down to the room temperature, the reaction was diluted with ethyl acetate (200 mL). The organic phase was washed with water (80 mL) and brine (80 mL), dried over anhydrous sodium sulfate, and concentrated under vacuum. The residue was purified by silica gel column with ethyl acetate/petroleum ether (1/10) as the eluent to afford the desired product (1.5 g, 22% yield).

Step 2. Synthesis of 46-2

To a solution of N-(4-bromo-2-nitrophenyl)-N-(2-methylpropyl)thian-4-amine (1.5 g, 4.02 mmol) in dichloromethane (20 mL) was added 3-Chloroperbenzoic acid (2.1 g, 12.17 mmol). The reaction was stirred at room temperature for 2 h, and the mixture was then diluted with dichloromethane (50 mL). The reaction was washed with saturated sodium bisulfite solution (30 mL), water (30 mL), and brine (30 mL). The organic phase was dried over anhydrous sodium sulfate and concentrated under vacuum. The residue was purified by silica gel column with ethyl acetate/petroleum ether (1/5) as the eluent to afford the desired product (0.6 g, 37% yield).

Step 3. Synthesis of 46-3

A solution of 46-2 (200 mg, 0.49 mmol), phenylmethanethiol (68 mg, 0.55 mmol), Pd$_2$(dba)$_3$·CHCl$_3$ (26 mg, 0.03 mmol), XantPhos (30 mg, 0.05 mmol), and triethylamine (76 mg) in 1,4-dioxane (3 mL) was stirred at 100° C. for 1 h. The mixture was then diluted with ethyl acetate (30 mL), and the solid was filtered off. The filtrate was dried over anhydrous sodium sulfate and concentrated under vacuum. The residue was purified by silica gel column with ethyl acetate/petroleum ether (1/5) as the eluent to afford the desired product (150 mg, 68% yield).

Step 4. Synthesis of 46-4

To a solution of 46-3 (150 mg, 0.33 mmol) in acetic acid (5 mL) was added iron (187 mg, 3.35 mmol), and the reaction was then stirred at room temperature for 0.5 h. The mixture was diluted with ethyl acetate (50 mL). The solid was filtered off, and the filtrate was washed with saturated sodium carbonate solution (30 mL) and brine (30 mL). The organic phase was dried over anhydrous sodium sulfate and concentrated under vacuum. The residue was purified by silica gel column with ethyl acetate/petroleum ether (1/5) as the eluent to afford the desired product (130 mg, 93% yield).

Step 5. Synthesis of 46-5

A solution of 46-4 (130 mg, 0.31 mmol), 2,4-difluoro-1-isocyanatobenzene (73 mg, 0.47 mmol) and triethylamine (95 mg, 0.94 mmol) in tetrahydrofuran (3 mL) was stirred at room temperature for 30 min. The mixture was diluted with ethyl acetate (30 mL), and washed with water (20 mL) and brine (20 mL). The organic phase was dried over anhydrous sodium sulfate and concentrated under vacuum. The residue was purified by silica gel column with ethyl acetate/petroleum ether (1/2) as the eluent to afford the desired product (120 mg, 67% yield).

Step 6. Synthesis of 46-6

To a solution of 46-5 (120 mg, 0.21 mmo) in toluene (5 mL) was added AlCl$_3$ (240 mg, 1.80 mmol), and the reaction was stirred at room temperature for 30 min. The mixture was diluted with water (10 mL) and extracted with ethyl acetate (10 mL×2). The organic phase was dried over anhydrous sodium sulfate and concentrated under vacuum to afford the desired product (80 mg, 79% yield).

Step 7. Synthesis of 46-7

A solution of ethyl 2-bromo-2-methylpropanoate (51 mg, 0.26 mmol), 46-6 (80 mg, 0.17 mmol), and N,N-diisopropylethylamine (44 mg, 0.34 mmol) in dimethyl sulfoxide (3 mL) was stirred at room temperature overnight. The reaction was diluted with ethyl acetate (20 mL), and washed with water (10 mL) and brine (10 mL). The organic phase was dried over anhydrous sodium sulfate and concentrated under vacuum. The residue was purified by silica gel column with ethyl acetate/petroleum ether (1/5) as the eluent to afford the desired product (70 mg, 71% yield).

Step 8. Synthesis of 46

To a solution of 46-7 (70 mg, 0.12 mmol) in ethanol (1.5 mL) and water (0.5 mL), was added LiOH (160 mg, 6.68 mmol). The resulting mixture was stirred at 75° C. for 1 h. The reaction was then cooled to room temperature and diluted with water (20 mL). The mixture was extracted with ethyl acetate (30 mL). The organic phase was dried over anhydrous sodium sulfate and concentrated under vacuum. The residue was purified by Prep-HPLC with the following conditions: [Column: X Bridge Shield RP18 OBD, 5 um, 19×150 mm; Mobile phase A: Waters (10 mmol/L NH$_4$HCO$_3$), Mobile Phase B: CAN; Gradient: 15% ACN to 40% in 8 min; Detector: UV 254 nm] to afford the desired product (27.6 mg, 41% yield). LCMS: (ES, m/z): 570.2 [M+H]$^+$; $^1$H NMR (300 MHz, DMSO-d$_6$): ppm δ 9.48 (s, 1H), 8.18 (s, 2H), 8.00-7.92 (m, 1H), 7.36-7.28 (m, 1H), 7.21-7.18 (m, 1H), 7.09-7.03 (m, 2H), 3.24-3.15 (m, 2H), 3.10-2.93 (m, 3H), 2.90-2.73 (m, 2H), 2.26-2.21 (m, 2H), 2.01-1.89 (m, 2H), 1.39-1.33 (m, 7H), 0.82 (d, J=6.6 Hz, 6H).

Example 47

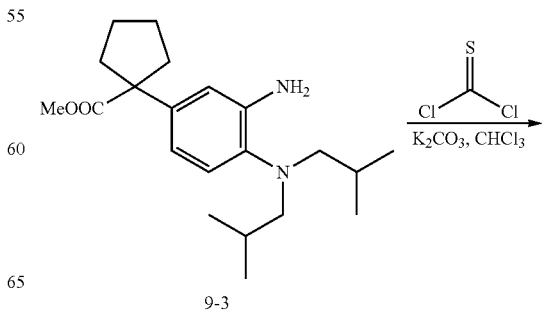

9-3

215

-continued

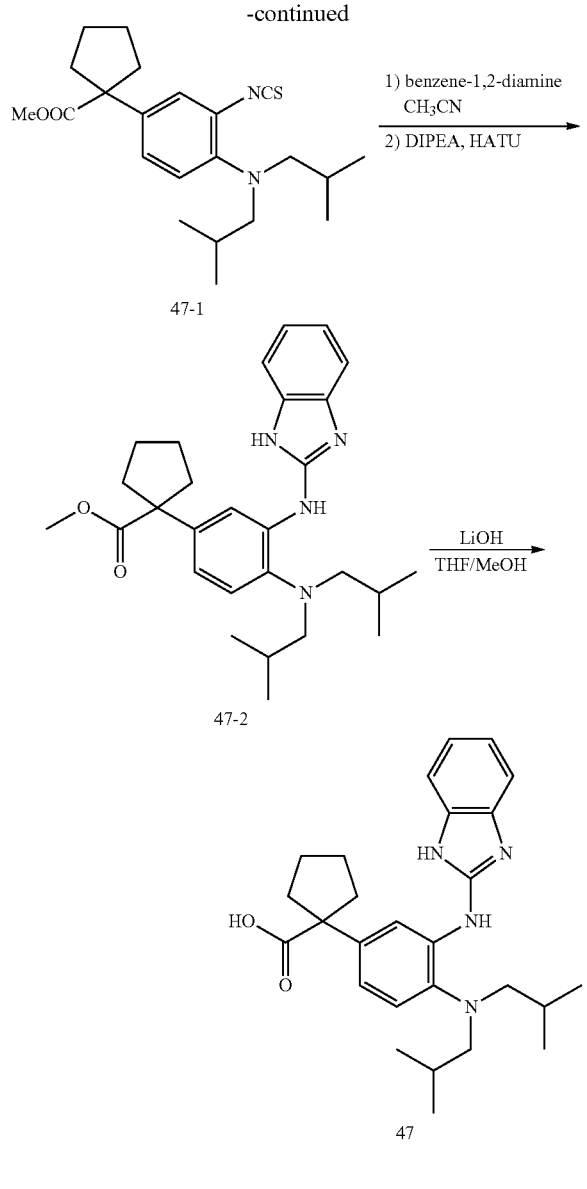

216

Step 3. Synthesis of 47

A solution of 47-2 (110 mg, 0.24 mmol) and lithium hydroxide (0.7 mL, 0.7 mmol, 1 M aq.) in tetrahydrofuran/methanol (1.4 mL, v/v=1/1) was stirred at 60° C. for 24 hour. The reaction was cooled down and the pH of the solution was adjusted to 6 with 1 N HCl. The reaction was diluted with ethyl acetate (50 mL). The organic layer was washed with water (50 mL) and brine (50 mL), dried over sodium sulfate, filtered, and concentrated. The residue was purified by reversed-HPLC (acetonitrile/0.02% ammonium hydroxide aq=10%-95%) to afford the desired product (11.73 mg, 11% yield). LCMS (ES, m/z): 449.2 [M+H]$^+$. HNMR (400 MHz, DMSO-$d_6$, ppm): δ 12.15-12.08 (m, 1H), 11.73 (s, 1H), 8.64 (s, 1H), 8.23 (s, 1H), 7.30-7.16 (m, 3H), 6.97-6.87 (m 3H), 2.59-2.48 (m, 6H), 1.78-1.56 (m, 8H), 0.86 (d, J=6.4 Hz, 12H).

Example 48

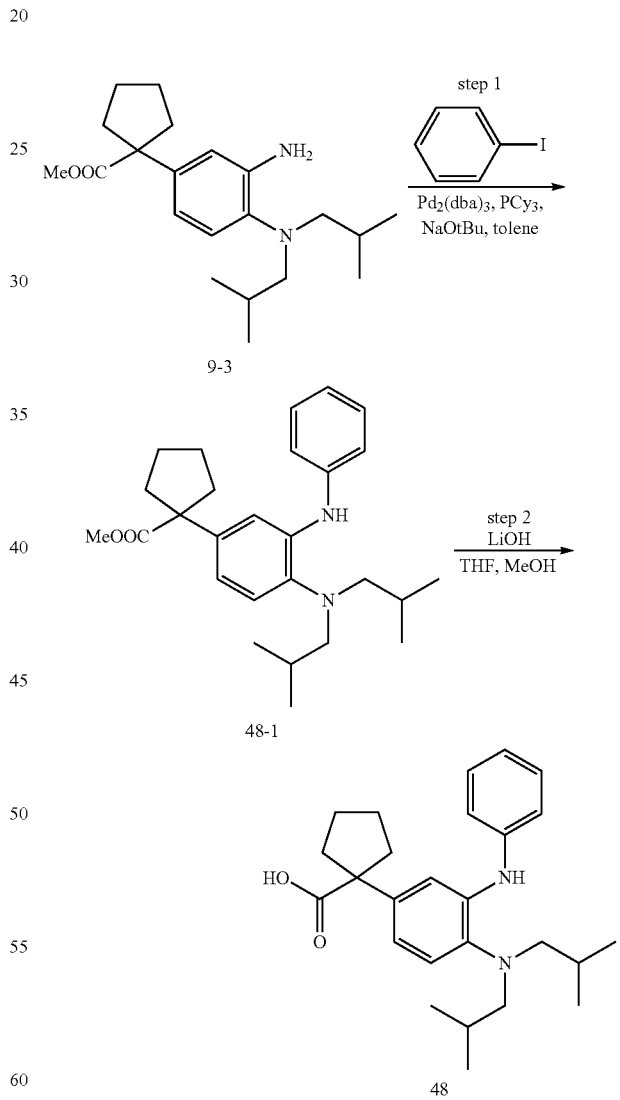

Step 1. Synthesis of 48-1

A solution of 9-3 (121 mg, 0.35 mmol), iodobenzene (143 mg, 0.7 mmol), Pd$_2$(dba)$_3$ (16 mg, 0.018 mmol), PCy$_3$ (10 mg, 0.035 mmol), and sodium tert-butoxide (50 mg, 0.5 mmol) in toluene (5 mL) was stirred at 120° C. for 3 hour Step 1. Synthesis of 47-1

To a solution of 9-3 (346 mg, 1 mmol) in chloroform (12 mL) at rt, was added potassium carbonate (552 mg, 4 mmol). After the reaction was cooled down to 0° C., a solution of thiophosgen (230 mg, 2 mmol) in chloroform (8 mL) was added dropwise. The reaction mixture was stirred at 0° C. for 3 hour. The solid was filtered and the filtrate was concentrated. The crude product was purified by prep. TLC plates (petroleum ether/ethyl acetate=10/1) to afford the desired product (180 mg, 46% yield).

Step 2. Synthesis of 47-2

A solution of 47-1 (194 mg, 0.5 mmol) in acetonitrile (10 mL) and 1,2-diaminobenzene (54 mg, 0.5 mmol) was stirred at room temperature for 16 h. N,N-diisopropylethylamine (129 mg, 1 mmol) and HATU (285 mg, 0.75 mmol) were added, and the reaction was stirred at room temperature for another hour. The reaction was diluted with ethyl acetate (50 mL). The organic layer was washed with water (50 mL) and brine (50 mL), dried over sodium sulfate, filtered, and concentrated. The crude product was purified by reversed-HPLC (acetonitrile/0.05% TFA.=10%-95%) to afford the desired product (110 mg, 47% yield).

under microwave condition. Ethyl acetate (50 mL) was added, and the reaction was washed with water (50 mL) and brine (50 mL). The organic layer was dried over sodium sulfate, filtered, and concentrated. The residue was purified by pre-TLC (petroleum ether/ethyl acetate=10/1) to give the desired product (53 mg, 36% yield).

Step 2. Synthesis of 48

To a solution of 48-1 (53 mg, 0.125 mmol) in tetrahydrofuran/methanol (1 mL, v/v=1/1) was added lithium hydroxide (0.5 mL, 0.5 mmol, 1N) at room temperature. The reaction mixture was stirred at 60° C. for 24 hour. The reaction was cooled down and the pH of the solution was adjusted to 6 with 1 N HCl. The reaction was diluted with ethyl acetate (50 mL). The organic layer was washed with water and brine, dried over sodium sulfate, filtered, and concentrated. The residue was purified by pre-TLC (petroleum ether/ethyl acetate=7/1) to afford the desired product (40 mg, 78% yield). LCMS (ES, m/z): 409.2 [M+H]$^+$. HNMR (400 MHz, CD$_3$OD, ppm): δ 7.35 (d, J=2.0 Hz, 1H), 7.24-7.20 (m, 2H), 7.10-7.05 (m, 3H), 6.87-6.84 (m 2H), 2.58-2.53 (m, 6H), 1.83-1.80 (m, 2H), 1.71-1.67 (m, 6H), 0.87 (d, J=6.4 Hz, 12H).

Example 49

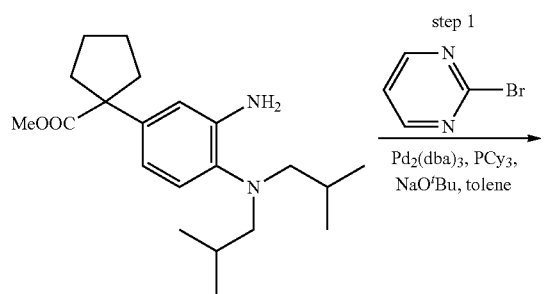

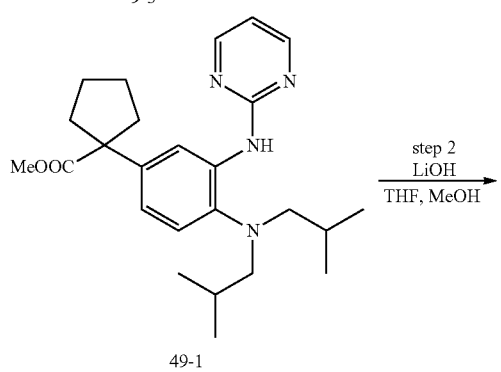

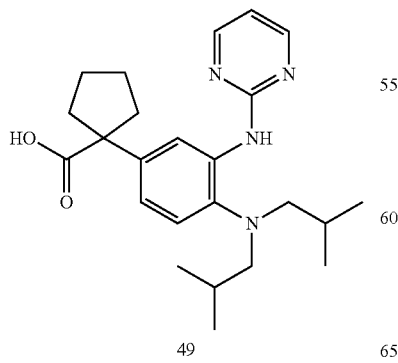

Step 1. Synthesis of 49-1

A solution of 9-3 (277 mg, 0.8 mmol), 2-bromopyrimidine (254 mg, 1.6 mmol), Pd$_2$(dba)$_3$ (37 mg, 0.04 mmol), PCy$_3$ (22 mg, 0.08 mmol), and sodium tert-butoxide (115 mg, 1.2 mmol) in toluene (5 mL) was stirred at 150° C. for 3 hour under microwave condition. Ethyl acetate (50 mL) was added, and the reaction was washed with water (50 mL) and brine (50 mL). The organic layer was dried over sodium sulfate, filtered, and concentrated. The residue was purified by prep. TLC plates (petroleum ether/ethyl acetate=10/1) to give the desired product.

Step 2. Synthesis of 49

To a solution of 49-1 (40 mg, 0.8 mmol) in tetrahydrofuran/methanol (4.8 mL, v/v=1/1) was added lithium hydroxide (2.4 mL, 2.4 mmol, 1N) at room temperature. The reaction mixture was stirred at 60° C. for 24 hour. The reaction was cooled down and the pH of the solution was adjusted to 6 with 1 N HCl. The reaction was diluted with ethyl acetate (50 mL). The organic layer was washed with water and brine, dried over sodium sulfate, filtered, and concentrated. The residue was purified by HPLC to afford the desired product (8.92 mg, 19% yield). LCMS (ES, m/z): 411.2 [M+H]$^+$. HNMR (400 MHz, CD$_3$OD, ppm): δ 8.59 (s, 1H), 8.44 (d, J=4.8 Hz, 2H), 7.19 (d, J=8.4 Hz, 1H), 7.01 (d, J=8.0 Hz, 1H), 6.79 (t, J=4.8 Hz, 1H), 2.65-2.58 (m, 6H), 1.93-1.91 (m, 2H), 1.74-1.65 (m, 6H), 0.91 (d, J=6.4 Hz, 12H).

Example 50

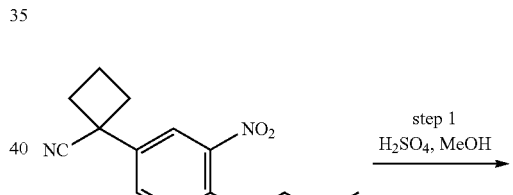

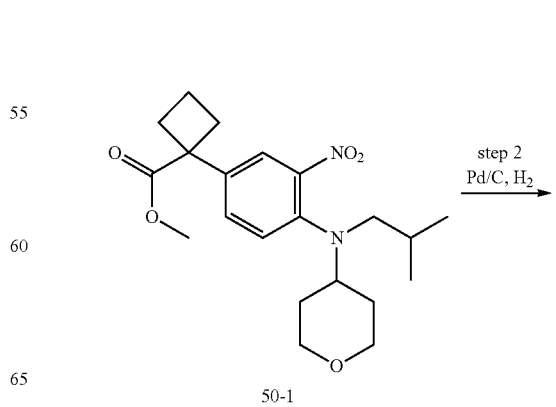

-continued

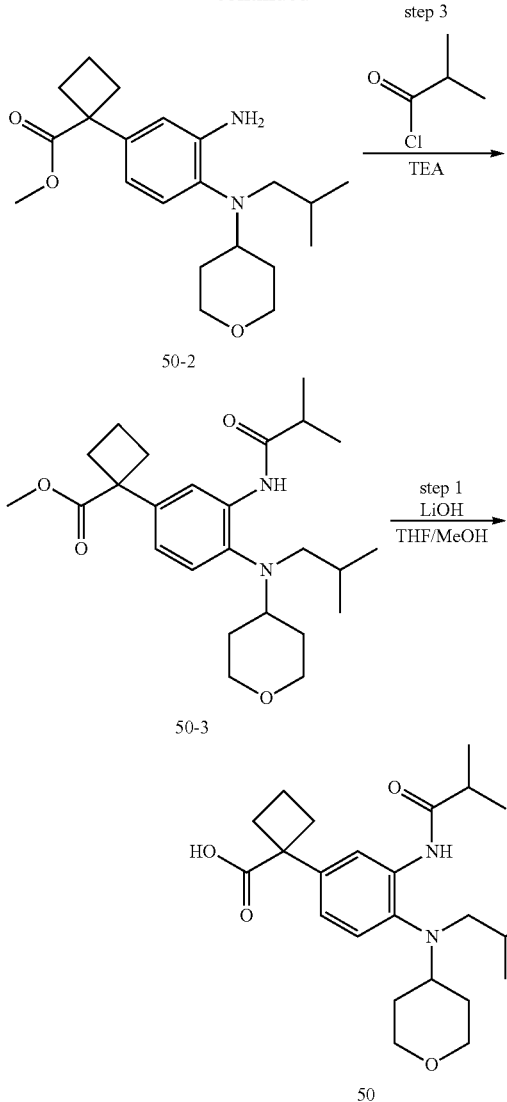

Step 1. Synthesis of 50-1

To a solution of 25-2 (500 mg, 1.4 mmol) in methanol (4 mL), was added sulphuric acid (2 mL) at 0° C. The reaction was stirred at 80° C. for 16 hours. The mixture was extracted with ethyl acetate (50 mL) and washed with sodium bicarbonate solution (100 mL). The organic layer was dried over sodium sulfate, filtered, and concentrated. The residual was purified by chromatography on a silica gel column (petroleum ether/ethyl acetate=4/1) to afford the desired product (130 mg, 23% yield).

Step 2. Synthesis of 50-2

To a solution of 50-1 (80 mg, 0.2 mmol) in methanol (5 mL) was added palladium on carbon (40 mg). The reaction was stirred for 2 hours at room temperature under hydrogen. The mixture was filtered and the filtrate was concentrated to afford the desired product (50 mg, 69% yield).

Step 3. Synthesis of 50-3

To a solution of 50-2 (50 mg, 0.14 mmol) in dichloromethane (5 mL), was added triethylamine (43 mg, 0.42 mmol) and then isobutyryl chloride (30 mg, 0.28 mmol). The reaction was stirred at room temperature for 16 hours. The mixture was extracted with ethyl acetate (50 mL) and washed with water (50 mL). The organic layer was dried over sodium sulfate, filtered, and concentrated. The residual was purified by pre-TLC (petroleum ether/ethyl acetate=4/1) to afford the desired product (30 mg, 50% yield).

Step 4. Synthesis of 50

To a solution of 50-3 (30 mg, 0.07 mmol) in methanol (1 mL) and tetrahydrofuran (1 mL), was added lithium hydroxide solution (1 mL, 1N). The reaction was stirred at 60° C. for 16 hours. The mixture was acidified with hydrochloric acid (1 N) and then extracted with ethyl acetate (50 mL). The organic layer was dried over sodium sulfate, filtered, and concentrated. The residual was purified by pre-HPLC to afford the desired product as a white solid (10 mg, 34% yield). LCMS (ES, m/z): 417.2 [M+H]$^+$. HNMR (400 MHz, DMSO-$d_6$, ppm): δ 8.83 (s, 1H), 8.24 (d, J=2.0 Hz, 1H), 7.24 (d, J=8.4 Hz, 1H), 6.92 (dd, J1=8.4 Hz, J2=2.0 Hz, 1H), 3.82-3.79 (m, 2H), 3.17 (t, J=11.2 Hz, 2H), 2.80-2.73 (m, 3H), 2.68-2.61 (m, 2H), 2.59-2.54 (m, 1H), 2.37-2.29 (m, 2H),1.88-1.86 (m, 1H), 1.77-1.73 (m, 1H), 1.62-1.59 (m, 2H), 1.50-1.42 (m, 2H), 1.28-1.23 (m, 1H),1.11 (d, J=6.8 Hz, 6H), 0.79 (d, J=6.4 Hz, 6H).

Example 51

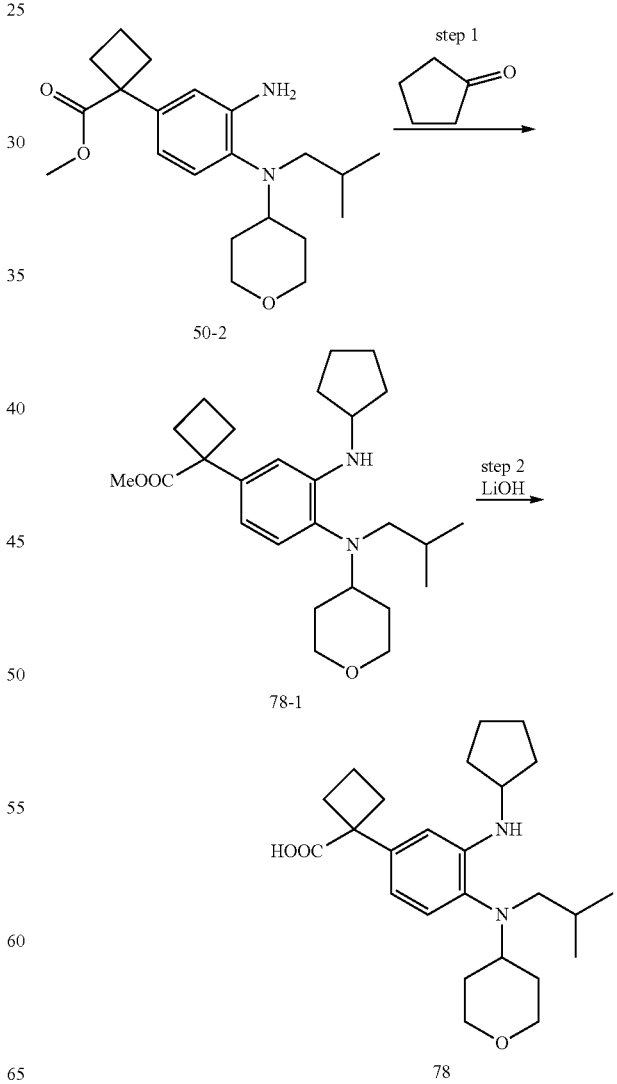

Step 1. Synthesis of 78-1

To a stirred solution of 50-2 (105 mg, 0.29 mmol) in 1,2-Dichloroethane (5 mL), were added cyclopentanone (90 mg, 1.07 mmol) and trifluoroacetic acid (90 mg, 0.79 mmol). The mixture was stirred at room temperature for 1 h, then tetramethylammonium triacetoxyborohydride (150 mg, 0.57 mmol) was added. The mixture was stirred at 60° C. for 16 h. After cooled down, the reaction mixture was extracted with ethyl acetate (50 mL). The organic phase was washed with aqueous NaHCO$_3$ (20 mL) and brine (10 mL), dried over anhydrous sodium sulfate, and concentrated under vacuum. The residue was purified by pre-TLC (eluent: petroleum ether:ethyl acetate=4:1) to afford the desired product (50 mg, 40% yield).

Step 2. Synthesis of 78

To a solution of 78-1 (50 mg, 0.12 mmol) in tetrahydrofuran (1.5 mL) and methyl alcohol (1.5 mL), was added lithium hydroxide (1 M, 1.5, mL, 1.5 mmol). The mixture was stirred at 60° C. for 3 h. After cooled down, the reaction was acidified to pH=4 with hydrochloric acid (1N), and extracted with EtOAc. The organic phase was washed with brine (10 mL), dried over anhydrous sodium sulfate, and concentrated under vacuum to afford the desired product (22 mg, 44% yield). LCMS (ES, m/z): 415.3 [M+H]$^+$. $^1$HNMR: (400 MHz, CD$_3$OD, ppm): δ 7.00 (d, J=8.0 Hz, 1H), 6.59-6.54 (m, 2H), 3.91(d, J=11.2 Hz, 2H), 3.79-3.77 (m, 1H), 3.32-3.26(m, 1H), 3.26-3.21(m, 1H), 2.98 (d, J=9.6 Hz, 1H), 2.78-2.71 (m, 3H), 2.56-2.41 (m, 3H), 2.00-1.92 (m, 3H), 1.86-1.37 (m, 12H), 0.82(dd, J1=24.8 Hz, J2=6.4 Hz, 6H).

Example 52

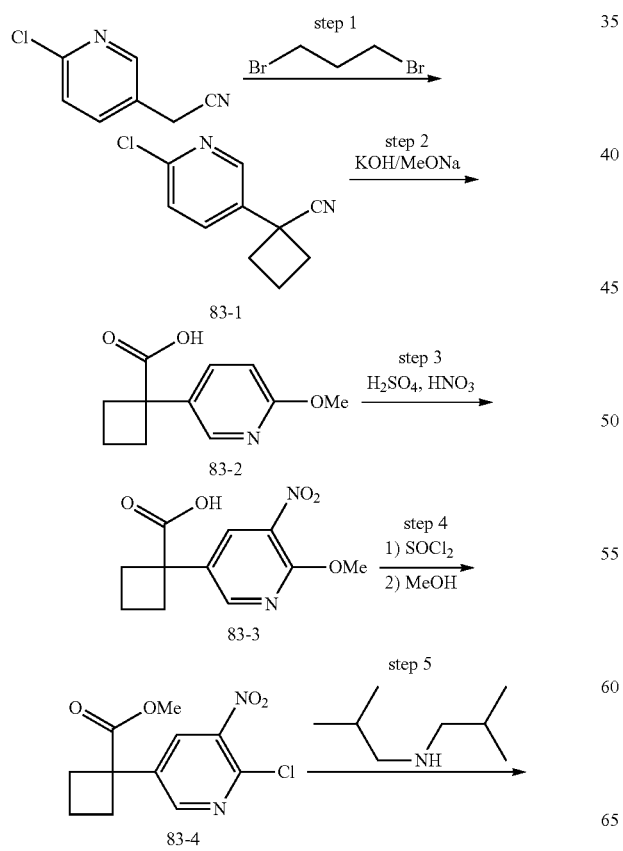

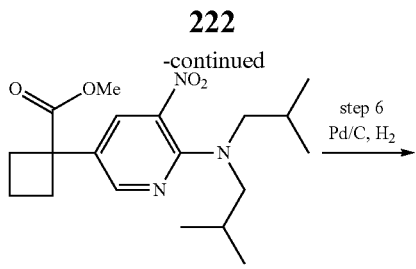

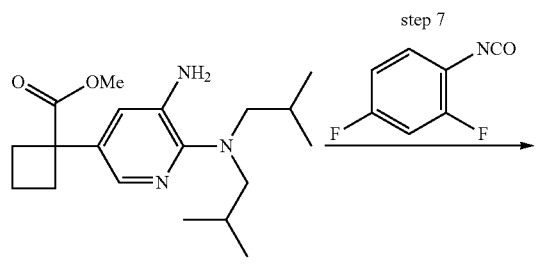

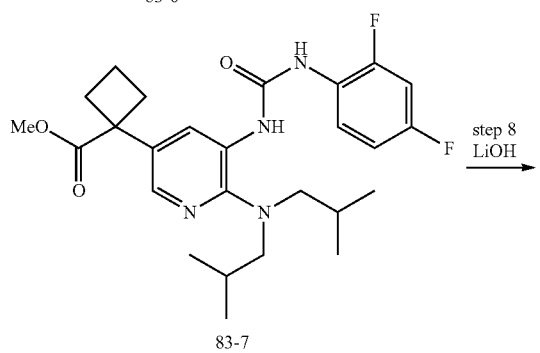

Step 1. Synthesis of 83-1

To a solution of 2-chloro-5-pyridineacetonitrile (14.3 g, 94 mmol) in dimethylformamide (120 mL) at 0° C., was added sodium hydride (8.6 g, 216 mmol, 60% in oil) portion-wise over 20 minutes. The mixture was stirred for a further 20 minutes and 1,3-dibromopropane (20 g, 98.7 mmol) was added. The reaction mixture was warmed to room temperature and stirred for 2 h. The reaction was quenched by water (50 mL). Ethyl acetate (200 mL) was added and the organic phase was washed with water (100 mL) and brine (100 mL). The organic layer was dried over sodium sulfate, filtered, and concentrated. The crude product was purified by chromatography on a silica gel column (petroleum ether to petroleum ether/ethyl acetate=3/1) to afford the desired product (9.4 g, 52% yield).

Step 2. Synthesis of 83-2

To a solution of potassium hydroxide (840 mg, 15 mmol) in water/methanol (6 mL, v/v=1/2) at room temperature, were added sodium methoxide (3.6 g, 20 mmol, 30% in methanol) and 83-1 (960 mg, 5 mmol). The reaction was then heated to 100° C. for 48 h. After cooled to 0° C., the mixture was adjusted to pH-5 with 1N HCl. The mixture was diluted with water (50 mL), and extracted with dichloromethane (50 mL×4). The organic layer was dried over sodium sulfate, filtered, and concentrated to afford the desired product (950 mg, 92% yield).

Step 3. Synthesis of 83-3

To a solution of 83-2 (350 mg, 1.7 mmol) in concentrated sulfuric acid (2 mL) at 0° C., was added concentrated nitric acid (1 mL) dropwise. The reaction was heated to 50° C. for 16 h. After cooled to room temperature, the mixture was poured into ice water, and the pH value of the mixture was adjusted to 4 with 50% sodium hydroxide at 0° C. The mixture was extracted with dichloromethane (50 mL×3). The organic layer was dried over sodium sulfate, filtered, and concentrated. The residue was purified by reversed HPLC (MeCN/0.05% TFA aq=5%-95%) to afford the desired product (180 mg, 42% yield).

Step 4. Synthesis of 83-4

To a solution of 83-3 (504 mg, 2 mmol) in thionyl chloride (3 mL) at 0° C., was added dimethylformamide (292 mg, 4 mmol) dropwise. The reaction was heated to 80° C. for 16 h, and then concentrated. The residue was dissolved in dichloromethane (5 mL), and then methanol (1 mL) was added at 0° C. The mixture was stirred for 0.5 h at room temperature. The mixture was concentrated and purified by reversed HPLC (MeCN/0.05% TFA aq=5%~95%) to afford the desired product (400 mg, 74% yield).

Step 5. Synthesis of 83-5

To a solution of 83-4 (135 mg, 0.5 mmol) in N-methyl-2-pyrrolidone (2 mL), were added N,N-diisopropylethylamine (97 mg, 0.75 mmol) and diisobutylamine (97 mg, 0.75 mmol). The reaction was stirred at 90° C. for 16 h. The mixture was purified by reversed HPLC directly (MeCN/0.05% TFA aq=5%~95%) to afford the desired product (168 mg, 93% yield).

Step 6. Synthesis of 83-6

To a solution of 83-5 (554 mg, 1.5 mmol) in methanol (10 mL) was added palladium 10% on carbon (110 mg). The reaction was stirred for 2 hour at room temperature under hydrogen. The mixture was filtered and the filtrate was concentrated. The crude product was purified by chromatography on a silica gel column (petroleum ether to petroleum ether/ethyl acetate=5/1) to afford the desired product (400 mg, 80% yield).

Step 7. Synthesis of 83-7

To a solution of 83-6 (80 mg, 0.24 mmol) in tetrahydrofuran (10 mL) at 0° C., were added triethylamine (50 mg, 0.48 mmol) and 2,4-difluoro-1-isocyanatobenzene (75 mg, 0.48 mmol). The reaction was stirred at room temperature for 2 h. The mixture was extracted with ethyl acetate (50 mL) and washed with water (50 mL). The organic phase was concentrated and purified by pre-TLC (petroleum ether/ethyl acetate=6/1) to afford the desired product (80 mg, 68% yield).

Step 8. Synthesis of 83

To a solution of 83-7 (80 mg, 0.16 mmol) in methanol (2 mL) and tetrahydrofuran (2 mL), was added lithium hydroxide solution(2 mL, 1M, 2 mmol). The reaction was stirred for 5 hour at 60° C. The mixture was acidized with hydrochloric acid (1 N) and extracted with ethyl acetate (50 mL). The organic layer was dried over sodium sulfate, filtered, and concentrated. The residual was purified by Pre-TLC (eluent: petroleum ether:ethyl acetate=1:1) to afford the desired product (65.2 mg, white solid, 86% yield). LCMS (ES, m/z): 475.3 [M+H]$^+$. HNMR (400 MHz, DMSO-d$_6$, ppm): δ 12.41 (brs, 1H), 9.28 (s, 1H), 8.05-7.94 (m, 3H), 7.86 (d, J=2.0 Hz, 1H), 7.32-7.26 (m, 1H), 7.03-6.99 (m, 1H), 2.96 (d, J=6.8 Hz, 4H), 2.67-2.60 (m, 2H), 2.38-2.31(m, 2H), 1.95-1.86 (m, 1H),1.80-1.75 (m, 1H), 1.73-1.66(m, 2H), 0.76 (d, J=6.4 Hz, 12H).

Example 53

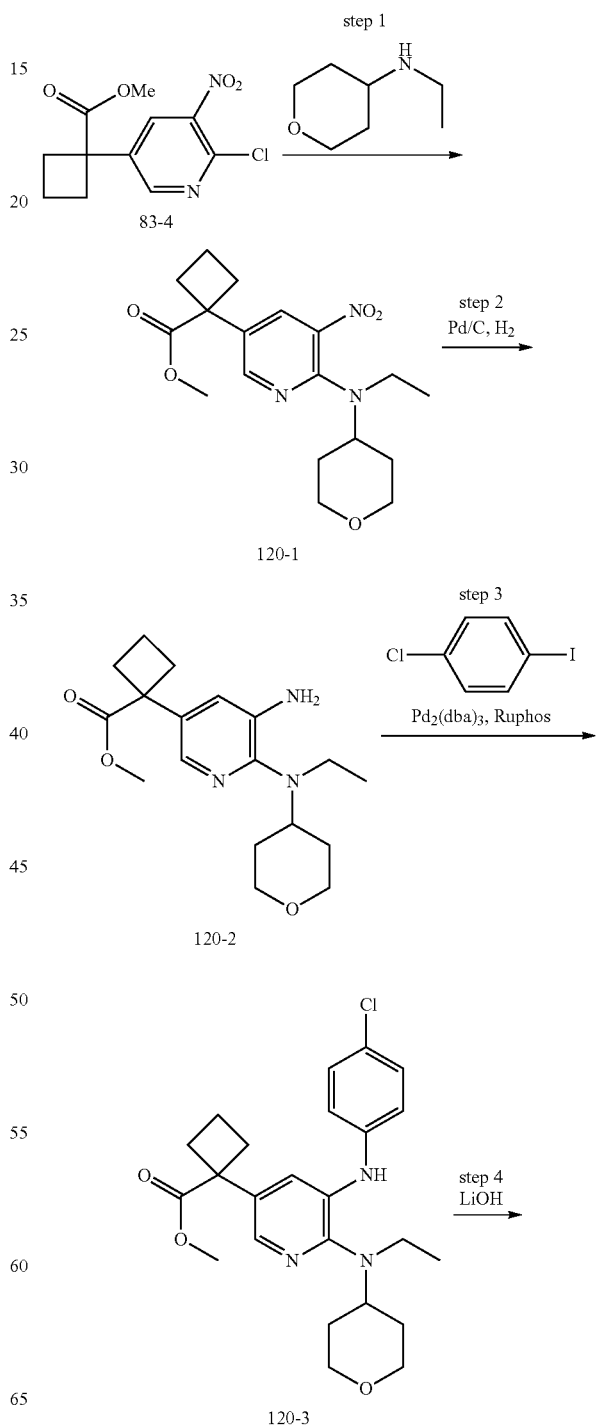

-continued

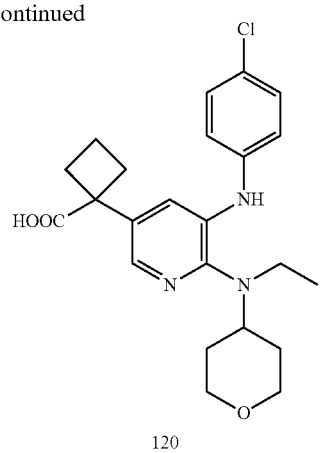

120

Step 1. Synthesis of 120-1

To a solution of 83-4 (1.7 g, 6.3 mmol) in dimethyl sulfoxide (30 mL) was added N-ethyloxan-4-amine (1.6 g, 12.6 mmol) and N,N-diisopropylethylamine (1.6 g, 12.6 mmol). The reaction was stirred for 16 h at 90° C. After cooled down, the reaction was diluted with ethyl acetate (100 mL), and washed with water (100 mL) and brine (100 mL). The organic layer was dried over sodium sulfate, filtered, and concentrated. The residue was purified by chromatography on a silica gel column (petroleum ether to petroleum ether/ethyl acetate=4/1) to give the desired product (1.6 g, 69% yield) as a yellow oil.

Step 2. Synthesis of 120-2

To a solution of 120-1 (1.6 g, 4.4 mmol) in methanol (50 mL) was added 10% palladium on carbon (320 mg). The reaction was stirred for 2 h at room temperature under hydrogen. The mixture was filtered, and concentrated. The crude product was purified by chromatography on a silica gel column (petroleum ether to petroleum ether/ethyl acetate=1/1) to give the desired product (950 mg, 65% yield) as a light grey oil.

Step 3. Synthesis of 120-3

To a mixture of 120-2 (80 mg, 0.24 mmol), 1-chloro-4-iodobenzene (114 mg, 0.48 mmol) and sodium tert-butoxide (46 mg, 0.48 mmol) in methylbenzene (4 mL), was added tris(dibenzylideneacetone)dipalladium(0) (11 mg, 0.012 mmol) and 2-dicyclohexylphosphino-2',6'-diisopropoxybiphenyl (11 mg, 0.024 mmol). The mixture was stirred under $N_2$ at 120° C. in microwave for 30 min. After the completion of the reaction, water (10 mL) was added, and the reaction mixture was extracted with ethyl acetate (20 mL). The organic phase was washed with brine (10 mL), dried over sodium sulfate, and concentrated. The crude product was purified by preparative TLC (eluent: petroleum ether/ethyl acetate=1/1) to give the desired product (45 mg, 42% yield) as a yellow gel.

Step 4. Synthesis of 120

To a mixture of 120-3 (45 mg, 0.1 mmol) in tetrahydrofuran (1.5 mL) and methyl alcohol (1.5 mL) was added lithium hydroxide (1M, 1.5 mL), the mixture was stirred at 60° C. for 3 h After the completion of the reaction, the mixture was acidified to pH=3 with hydrochloric acid (1M), and extracted with ethyl acetate (20 mL) The organic phase was washed with brine (10 mL), dried over sodium sulfate, and concentrated. The crude product was purified by preparative TLC (eluent: dichloromethane/methyl alcohol=10/1) to give the desired product (32 mg, 73% yield) as a white solid.

Example 54: Inhibition of Kynurenine Production in HeLa Cells

The effect of compounds described herein on the inhibition of kynurenine production in HeLa cells (derived from human cervical cancer) was determined. Exemplary results are shown in Table 2. HeLa cells were seeded into a 96-well culture plate at a density of $5 \times 10^3$ per well in RPMI1640/phenol red free media (from GIBCO) with 2 mM L-glutamine and 10% fetal bovine serum (FBS, from GIBCO) and grown overnight in a 37° C. incubator with 5% $CO_2$. Twenty-four hours later, human IFN-γ (from GIBCO) (final concentration 50 ng/mL) and test compound solutions (serially diluted to different wells) were added to each well with a final volume of 200 uL per well. Forty-eight hours after incubation with compounds, 140 uL supernatant was taken from each well and was transferred to a new 96-well plate. Ten microliters of 6.1 N trichloroacetic acid were added into each well, mixed and incubated at 50° C. for 30 minutes. The reaction mixture was then centrifuged for 10 minutes at 2500 rpm and 100 uL of the supernatant per well was transferred to another 96 well plate and mixed with 100 uL of 2% (w/v) p-dimethylaminobenzaldehyde in acetic acid. The yellow color derived from kynurenine was measured at 480 nm using a SPECTRAmax i3 reader. Each compound concentration was done in triplicates and compound IC50 value was calculated using nonlinear regression using Graphpad Prism 5.0.

The inhibitory activity of representative compounds described herein, compared with another IDO inhibitor, such as INCB-24360, Controls 1 and 2 are shown in Table 2.

TABLE 2

Inhibitory Activity of Representative Compounds

| Compound | $IC_{50}$ (nM) | Compound | $IC_{50}$ (nM) |
|---|---|---|---|
| INCB-24360 | 6.9 | — | — |
| Control 1* | 0.8 | Control 2** | 3 |
| 1 | 129.6 | 2 | 9.1 |
| 3A | 9.1 | 3B | 0.6 |
| 4 | 14.9 | 5A | 19.7 |
| 5b | 0.7 | 6 | 8.5 |
| 7 | 6.3 | 8 | 47.0 |
| 9 | 2.2 | 10 | 0.9 |
| 11 | 0.9 | 12 | 0.5 |
| 13 | 0.6 | 14 | 0.5 |
| 15 | 1.4 | 16 | 1.5 |
| 17 | 0.8 | 18 | 6.6 |
| 19 | 1.0 | 20 | 0.5 |
| 21 | 0.6 | 22 | 2.1 |
| 23 | 61.5 | 24 | 2.2 |
| 25 | 0.6 | 27 | 5.7 |
| 28 | >316 | 29 | 4.0 |
| 30 | 1.0 | 31 | 11.8 |
| 32 | 0.8 | 33 | 48 |
| 34 | 7.7 | 35 | 1.9 |
| 36 | 2.8 | 37 | 19.9 |
| 41 | 6.4 | 43 | 134 |
| 45 | 78 | 47 | 5.6 |
| 48 | 8.4 | 49 | >316 |
| 50 | >316 | 51 | 2.3 |
| 52 | 0.3 | 53 | 1.0 |
| 54 | 0.6 | 55 | 0.3 |
| 56 | 0.2 | 57 | 0.2 |
| 59A | 12.7 | 59B | 0.1 |
| 60A | 33 | 60B | 2.8 |
| 61A | 0.3 | 61B | 0.3 |
| 62A | 1.4 | 62B | 0.2 |
| 63A | 2.5 | 63B | −0.6 |
| 64A | 4.2 | 64B | 0.2 |
| 65A | 0.8 | 65B | 12 |
| 68A | 0.4 | 68B | 0.7 |

TABLE 2-continued

Inhibitory Activity of Representative Compounds

| Compound | IC$_{50}$ (nM) | Compound | IC$_{50}$ (nM) |
|---|---|---|---|
| 69 | 3.9 | 70A | 0.4 |
| 70B | 0.4 | 71A | 0.3 |
| 71B | 0.9 | 72 | 0.2 |
| 73 | 0.4 | 74 | 1.9 |
| 75 | 0.3 | 76 | 1.1 |
| 77 | 3 | 78 | 13.9 |
| 80 | 29 | 83 | 5.4 |
| 84 | 0.4 | 85 | 19 |
| 86 | 0.3 | 87 | 6.5 |
| 88 | 1.7 | 89 | 6.3 |
| 90 | 33 | 91 | 0.3 |
| 92 | 0.2 | 93 | 0.3 |
| 94 | 0.2 | 95 | 0.4 |
| 96 | 0.4 | 97 | 2.4 |
| 98 | 2.8 | 99 | 3.9 |
| 100 | 3.5 | 101 | 0.2 |
| 102 | 0.2 | 103 | 20 |
| 104 | 1.8 | 105 | 0.3 |
| 106 | 0.4 | 107 | 0.4 |
| 108 | 0.3 | 109 | >316 |
| 110 | 1.0 | 111 | 0.8 |
| 112 | 0.2 | 113 | 0.4 |
| 114 | 25 | 115 | 0.1 |
| 116 | 0.5 | 117 | 0.9 |
| 118 | 0.2 | 119 | 1.7 |
| 120 | 0.1 | 121 | 4.1 |
| 122 | 2.3 | 123 | 0.3 |
| 124 | 11.3 | 125 | 0.5 |
| 126 | 7.5 | 127 | 22 |
| 128 | 9.3 | | |

*Control 1: 3-(3-(3-(2,4-difluorophenyl)ureido)-4-(diisobutylamino)phenyl)-4,4,4-trifluorobutanoic acid. See Example 30 of WO2014/150646
**Control 2: (1R,2S)-2-(4-(diisobutylamino)-3-(3-(3-methylisoxazol-5-yl)ureido)phenyl)cyclopropanecarboxylic acid. See Example 30 of WO2014/150677

Example 55: Inhibition of Kynurenine Production in SKOV-3 Cells

The effect of compounds described herein on the inhibition of kynurenine production in SKOV-3 cells (derived from human ovarian cancer) was determined using a similar experimental procedure as described in Example A. Exemplary results are shown in FIG. 1.

The assay was performed similarly as described in Example A, except the SKOV-3 cells were grown in DMEM media with 10% FBS. FIG. 1 shows the IC$_{50}$ for INCB-24360 and compound 9 were determined at 10.2 nM and 7.4 nM, respectively. The structure of compound 9 is shown below:

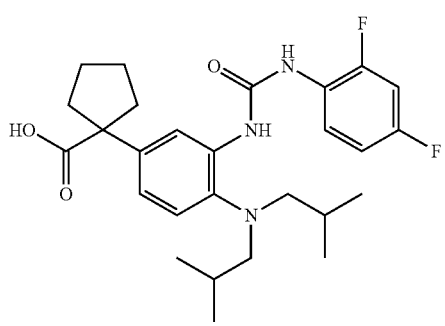

9

Example 56: Inhibition of LPS Induced Plasma Kynurenine in Mice

Figure 2:
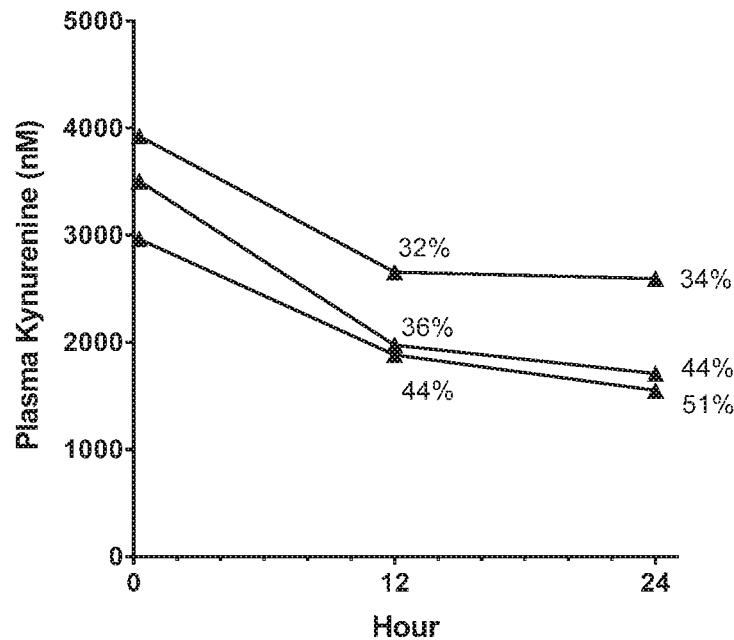
FIG. 2 is a chart showing LPS-induced mouse plasma kynurenine levels in the presence or absence of Compound 9.
Figure 2:
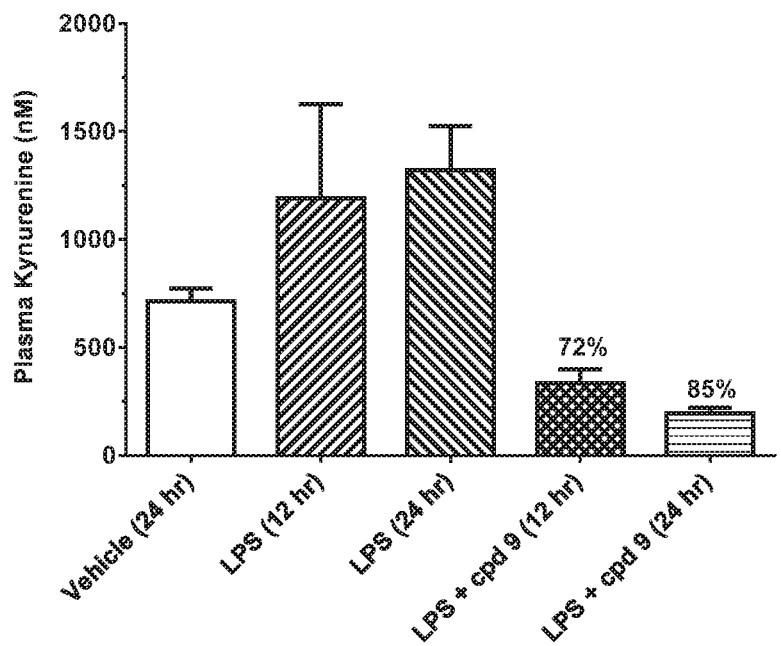

The effect of compounds described herein on the inhibition of lipopolysaccharide (LPS)-induced plasma kynurenine in mouse was determined. Exemplary results are shown in FIG. 2. Female Balb/c mouse (~20 g, obtained from Vital River Laboratory Animal Co. LTD) was treated with either vehicle control (saline) or 5 mg/kg LPS via intraperitoneal injection, followed by an oral dose of 30 mpk compound 9 within 5 minutes of LPS injection. Blood samples (500 uL) were collected into K$_2$EDTA tube via retro-orbital puncture at 12 and 24 hrs (terminal bleeding) after treatment with LPS or LPS plus compound 9. For vehicle control group, plasma samples were collected at 24 hour post dose. Blood samples were put on ice after collection and centrifuged at 4° C. (2000 g, 5 minutes) immediately after collection to obtain the plasma. Plasma kynurenine level was determined by LC-MS/MS analysis. Each group contains 3 mice and mean plasma kynurenine level was plotted in FIG. 2. FIG. 2 shows LPS induced mouse plasma kynurenine level compared to the baseline (vehicle control group) and simultaneous treatment of LPS with IDO inhibitor compound 9 reduced the plasma kynurenine to the level below the baseline, with 72% drop and 85% drop at 12 and 24 hour time points, respectively, compare to the LPS treatment alone.

Example 57: Human Hepatocyte Clearance Study

The in vitro human hepatocyte clearance of compounds described here was studied using pooled human hepatocytes purchased from BioreclamationIVT (Westbury, N.Y., Cat #X008001, Lot #TQJ). The assay was conducted according to manufacture's instruction. Briefly, 10 mM stock solutions of test compounds and positive control (Verapamil) were prepared in 100% DMSO. Thawing media (50 mL) used in the study consists of: 31 mL Williams E medium (GIBCO Cat #12551-032); 15 mL isotonic percoll (GE Healthcare Cat #17-0891-09); 500 uL 100× GlutaMax (GIBCO Cat #35050); 750 uL HEPES (GIBCO Cat #15630-080); 2.5 mL FBS (Corning Cat #35-076-CVR); 50 uL human insulin (GIBCO Cat #12585-014) and 5 uL dexamethasone (NICPBP). Incubation media is made of Williams E medium supplemented with 1× GlutaMax. Both thawing medium and incubation medium (serum-free) were placed in a 37° C. water bath for at least 15 minutes prior to use. Compound stock solutions were diluted to 100 μM by combining 198 μL of 50% acetonitrile/50% water and 2 μL of 10 mM stock solution. Verapamil was use as positive control in the assay. Vials of cryopreserved hepatocytes were removed from storage and thawed in a 37° C. water bath with gentle shaking. Contents of the vial were poured into the 50 mL thawing medium conical tube. Vials were centrifuged at 100 g for 10 minutes at room temperature. Thawing medium was aspirated and hepatocytes were re-suspended with serum-free incubation medium to yield ~1.5×10$^6$ cells/mL. Hepatocyte viability and density were counted using a Trypan Blue exclusion, and then cells were diluted with serum-free incubation medium to a working cell density of 0.5×10$^6$ viable cells/mL. Then, a portion of the hepatocytes at 0.5×10$^6$ viable cells/mL was boiled for 5 minutes prior to adding to the plate as negative control to eliminate the enzymatic activity so that little or no substrate turnover should be observed. The boiled hepatocytes were used to prepare negative samples. Aliquots of 198 μL hepatocytes were dispensed into each well of a 96-well non-coated plate. The plate was placed in the incubator on an orbital shaker at 500 rpm for approximately 10 minutes. Aliquots of 2 µL of the 100 µM test compound or positive control were added into respective wells of the non-coated 96-well plate to start the reaction. This assay was performed in duplicate. The plate was incubated in the incubator on an orbital shaker at 500 rpm for the designated time points. Twenty-five microliter of contents were transferred and mixed with 6 volumes (150 µL) of cold acetonitrile with IS (200 nM imipramine, 200 nM labetalol and 200 nM diclofenac) to terminate the reaction at time points of 0, 15, 30, 60, 90 and 120 minutes. Samples were centrifuged at 3,220 g for 25 minutes and aliquots of 150 µL of the supernatants were used for LC-MS/MS analysis. For data analysis, all calculations were carried out using Microsoft Excel. Peak areas were determined from extracted ion chromatograms. The in vitro half-life ($t_{1/2}$) of parent compound was determined by regression analysis of the percent parent disappearance vs. time curve. The in vitro half-life (in vitro $t_{1/2}$) was determined from the slope value: in vitro $t_{1/2}$=0.693/k. Conversion of the in vitro $t_{1/2}$ (in minutes) into the scale-up unbound intrinsic clearance (Scaled-up unbound $CL_{int}$, in mL/min/kg) was done using the following equation (mean of duplicate determinations): Scaled-up unbound $CL_{int}$=kV/N×scaling factor, where V=incubation volume (0.5 mL); N=number of hepatocytes per well (0.25×10$^6$ cells). Scaling factors for in vivo intrinsic clearance prediction using human hepatocytes are listed as: liver weight (g liver/kg body weight): 25.7; hepatocyte concentration (10$^6$ cells/g liver): 99; scaling factor: 2544.3.

TABLE 3

Human Hepatocyte Clearance of Exemplary Compounds

| Compound | Human Hepatocyte Remaining Percentage @ 120 min (%) | Human In vitro $T_{1/2}$ (min) | Human In vitro $CL_{int}$ (µL/min/10$^6$ cells) | Human Scale-up $CL_{int}$ (mL/min/kg) |
|---|---|---|---|---|
| INCB-24360 | 35 | 73 | 19 | 48 |
| Control 1* | 76 | 336 | 4.1 | 11 |
| 3B | 98 | 2111 | 0.7 | 1.8 |
| 9 | 79 | 423 | 3 | 10 |
| 16 | 101 | 1882 | 0.7 | 1.8 |
| 25 | 89 | 902 | 1.5 | 3.9 |
| 48 | 105 | 1733 | 0.8 | 2 |
| 75 | 88 | 534 | 2.6 | 6.6 |
| 84 | 80 | 623 | 2.2 | 5.7 |
| 86 | 75 | 268 | 5.2 | 13 |
| 91 | 92 | 1060 | 1.3 | 3.3 |
| 105 | 81 | 275 | 5.1 | 13 |
| 106 | 69 | 198 | 7 | 18 |
| 107 | 76 | 252 | 5.5 | 14 |
| 110 | 71 | 216 | 6.4 | 16 |
| 111 | 63 | 179 | 7.7 | 20 |
| 115 | 83 | 381 | 3.6 | 9.3 |
| 117 | 93 | 2125 | 0.7 | 1.7 |
| 118 | 85 | 416 | 3.3 | 8.5 |
| 120 | 94 | 1023 | 1.4 | 3.5 |
| 123 | 100 | 964 | 1.4 | 3.7 |
| 125 | 97 | 1593 | 0.9 | 2.2 |

*Control 1: 3-(3-(3-(2,4-difluorophenyl)ureido)-4-(diisobutylamino)phenyl)-4,4,4-trifluorobutanoic acid. See Example 30 of WO2014/150646.

Example 58: Inhibition of IDO in Human Whole Blood Assay

About 50-80 mL of human blood was collected in a tube with sodium heparin from each healthy donor. The tube containing human blood was kept on a rotator till ready for use. The following solutions were prepared for the assay: 10× LPS (Sigma #L2630) solution at 1000 ng/ml in RPMI media (with 10 mM HEPES), 10× INF-gamma (R&D Systems #CA31639) solution in RPMI media (with 10 mM HEPES), 75× compound/inhibitor solution in 100% DMSO. The entire content of human blood was poured from the tube into a reservoir dish and ~120 uL blood was transferred from the dish into each well of a 96-well plate (polypropylene U bottom clear plate). Then 15 uL each of 10× LPS and 10× INF-gamma, 2 uL of 75× compound solution were added into each well. The 96-well plate was gently rotated to mix the solutions and was then covered with a breathable membrane. The plate is transferred to cell culture incubator (37° C. with 5% $CO_2$). After 18 hr of incubation, the plate was spun at 1800 rpm for 10 min with no brake to separate plasma from blood cells. Sixty microliter of plasma was gently removed without disturbing the cells from each well. The kynurenine and tryptophan in the plasma are analyzed by LC-MS method.

Figure 3:
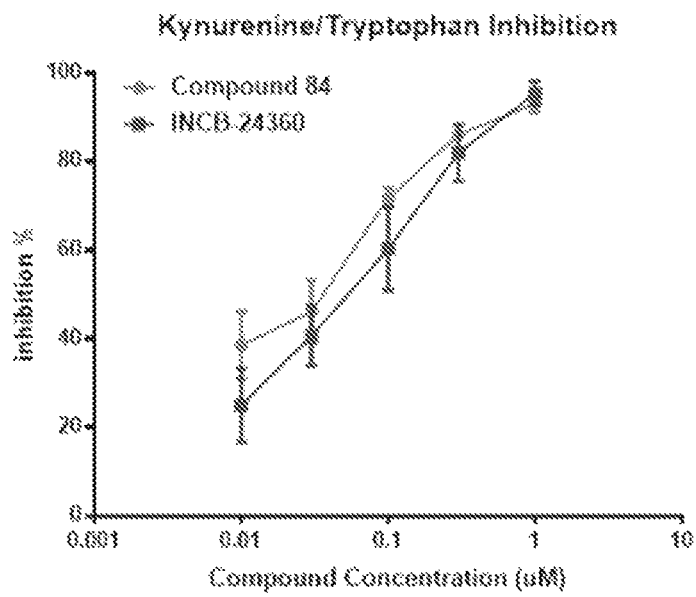
FIG. 3 includes charts showing the reduction of kynurenine in human whole blood sample after compound treatment. Panel A: Percentage inhibition of kynurenine to tryptophan ratio by compound 84 and compound INCB-24360, respectively, as a function of the concentration of each compound. Panel B: Percentage inhibition of kynurenine by compound 84 and compound INCB-24360, respectively, as a function of the concentration of each compound.
Figure 3:
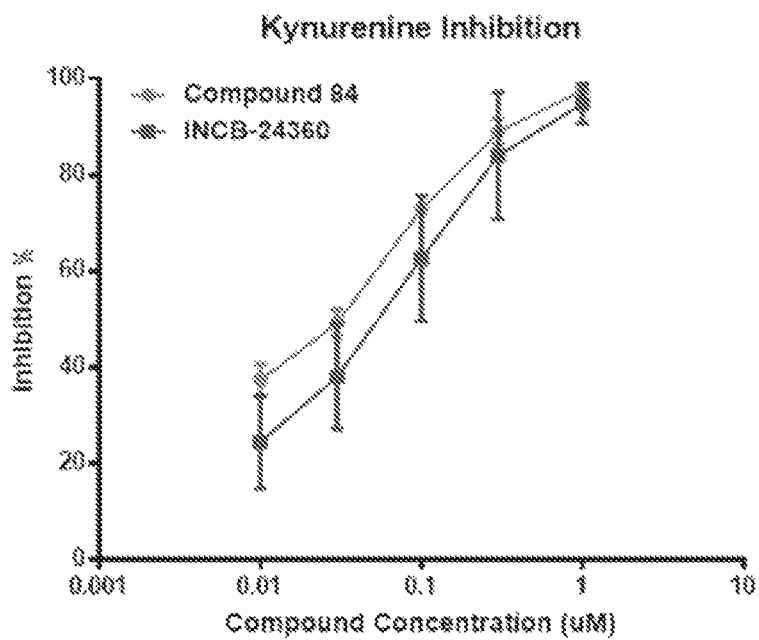

FIG. 3, panel A shows the percentage inhibition of kynurenine/tryptophan ratio by compound 84 and compound INCB-24360, respectively, as a function of the concentration of each compound. FIG. 3, panel B shows the percentage inhibition of kynurenine by compound 84 and compound INCB-24360, respectively, as a function of the concentration of each compound.

Example 59: T Cells and HeLa Cells Co-Culture Assay

Figure 4:
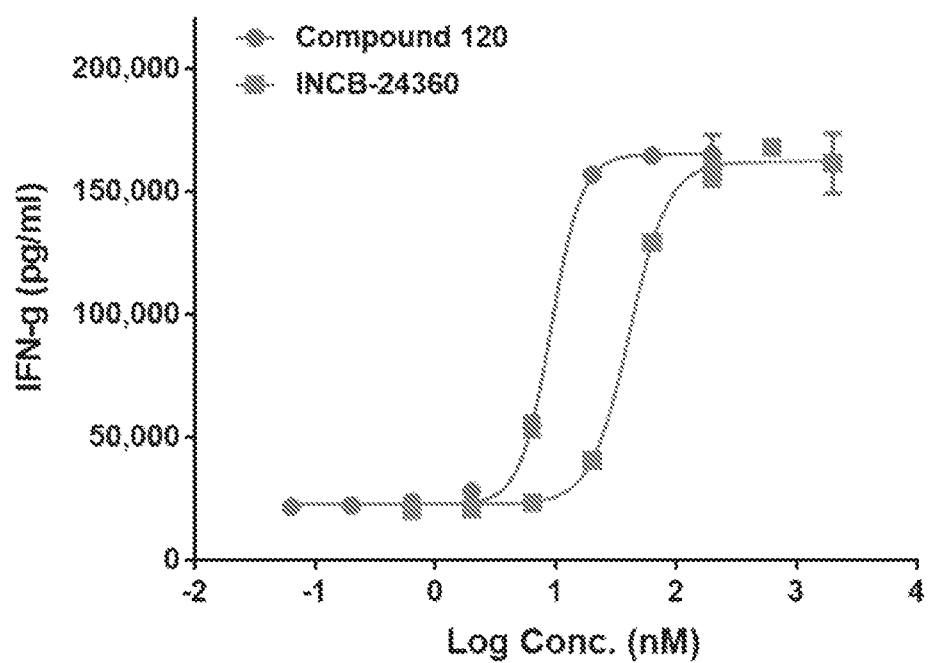
FIG. 4 is a chart showing IDO inhibitors increased the production of IFN-gamma in the T cells and HeLa cells co-culture media, suggesting activation of T cells by IDO inhibitor. $EC_{50}$ of INCB-24360 and compound 120 in this assay were 41 nM and 9.1 nM, respectively.

HeLa cells were seeded into 96-well plate (5000 cells per well in 100 µL of cell growth media DMEM with 10% FBS and 1% pen/strep) and incubated at 37° C. with 5% $CO_2$. After overnight incubation, 200 µL of INF-gamma (50 ng/ml in frowth media) was added to the plate and returned to incubator for another 48 hr. SepMate™-50 centrifuge tube was used to isolate PBMC from human donor according to manufacture's instruction (Stemcell). The CD3 T cell was then isolated from the PBMC using EasySep Human T cell isolation kit (Stemcell). Wash the 96-well plat twice with 200 µL of co-culture media (RPMI-1640+10% FBS+1% Pen/strep). Adjust the CD3 T cells density to 5×10$^5$ cells/ml with high dose anti-CD3/CD28 beads and co-culture medium (RPMI-1640+10% FBS+1% Pen/strep) and seed 200 µL/well into 96-well plate. Compound at different concentration was added to each well and the plate was incubated for a further 72 hr. Level of INF-gamma in the co-culture media (100 µL) was analyzed using the Human IFN-gamma ELISA Ready-SET-GO kit from eBioscience. The results obtained from this example are shown in FIG. 4.

Equivalents and Scope

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

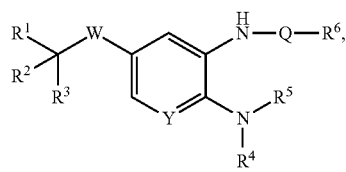
(I)

or a pharmaceutically acceptable salt thereof, wherein:

W is a bond;

Q is a bond;

Y is —N═;

$R^1$ is —C(═O)OH, —C(═O)$OR^{10}$, or

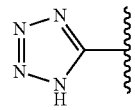

$R^2$ and $R^3$ are each independently hydrogen, halogen, $C_1$-$C_6$ alkyl, or $R^2$ and $R^3$ are joined to form a cyclopropyl, cyclobutyl, cyclopentyl, cyclohexyl, or tetrahydropyranyl ring, each of which is unsubstituted or substituted with fluorine;

$R^4$ and $R^5$ are each independently hydrogen, $C_1$-$C_6$ alkyl, $C_2$-$C_6$ alkenyl, $C_5$-$C_8$ cycloalkenyl, $C_2$-$C_{10}$ alkynyl, $C_3$-$C_8$ cycloalkyl, or 3- to 12-membered heterocyclyl, wherein the alkyl, alkenyl, cycloalkenyl, alkynyl, cycloalkyl, or heterocyclyl is unsubstituted or substituted with a substituent selected from hydroxyl, methyl, $CF_3$, cyclopropyl, fluorine, $C_{1-6}$ alkoxy substituted phenyl, $CF_3O$-phenyl, $C_{1-6}$ alkoxy, and $CF_3O$—; or $R^4$ and $R^5$ are joined together with the N they are attached to form one of the following:

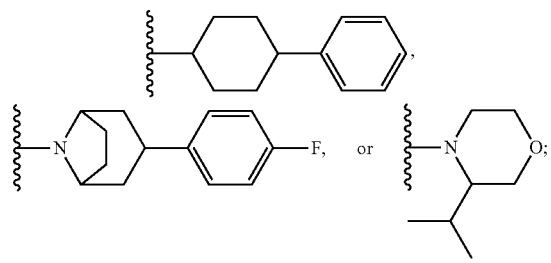

$R^6$ is $C_1$-$C_6$ alkyl, $C_3$-$C_8$ cycloalkyl; $C_2$-$C_6$ alkenyl, $C_2$-$C_6$ alkynyl, $C_5$-$C_8$ cycloalkenyl, aryl, 4 to 7-membered monocyclic heterocyclyl, 7 to 10-membered bicyclic heterocyclyl, 5 to 6-membered monocyclic heteroaryl, or 8- to 10-membered bicyclic heteroaryl, wherein the alkyl, cycloalkyl, alkenyl, alkynyl, cycloalkenyl, aryl, heterocyclyl, or heteroaryl is unsubstituted or substituted with a substituent selected from $C_1$-$C_6$ alkyl, halogen, —CN, OH, $C_1$-$C_6$ alkoxy, and $CH_3SO_2$; and $R^{10}$ is substituted or unsubstituted $C_1$-$C_6$ alkyl, or substituted or unsubstituted $C_2$-$C_6$ alkenyl.

2. The compound of claim 1, wherein $R^1$ is: —C(═O)OH or

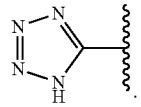
.

3. The compound of claim 1, wherein $R^2$ and $R^3$ are joined to form an unsubstituted cyclopropyl, unsubstituted cyclobutyl,

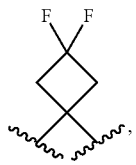 [SMILES: *C1(*)CC(F)(F)C1]

unsubstituted cyclopentyl, or unsubstituted cyclohexyl ring.

4. The compound of claim 1, wherein $R^4$ and $R^5$ are each independently $C_1$-$C_6$ alkyl, $C_3$-$C_8$ cycloalkyl, or 3- to 12-membered heterocyclyl, wherein the alkyl, cycloalkyl, or heterocyclyl is unsubstituted or substituted with a substituent selected from hydroxyl, methyl, $CF_3$, cyclopropyl, fluorine, $C_{1-6}$ alkoxy substituted phenyl, $CF_3O$-phenyl, $C_{1-6}$ alkoxy, and $CF_3O$—.

5. The compound of claim 4, wherein $R^4$ and $R^5$ are each independently of the formula:

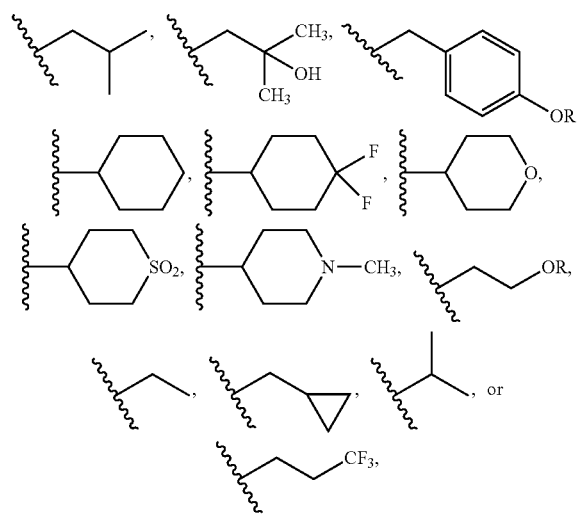

wherein R is $C_1$-$C_6$ alkyl or $CF_3$.

6. The compound of claim 1, wherein $R^6$ is of the formula:

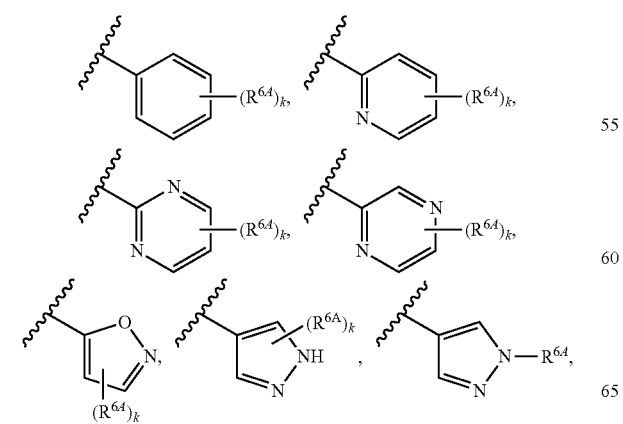

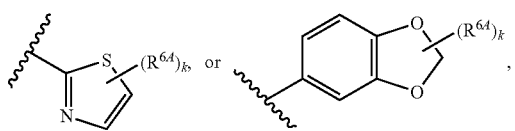

wherein $R^{6A}$ is hydrogen, $C_1$-$C_6$ alkyl, halogen, —CN, $OR^{6a}$, or $CH_3SO_2$;

wherein $R^{6a}$ is hydrogen, or $C_1$-$C_6$ alkyl; and k is 0, 1, or 2.

7. The compound of claim 1, wherein $R^6$ is of the formula:

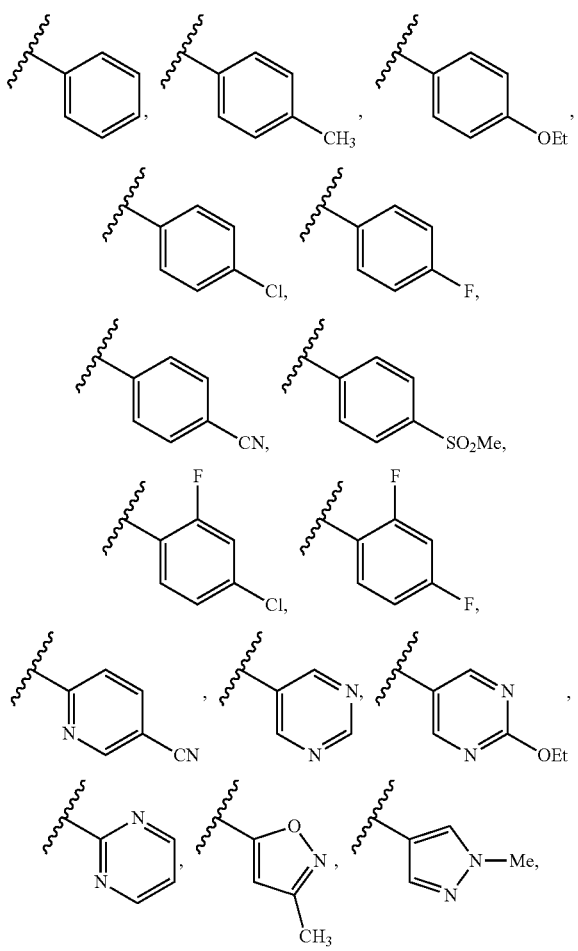

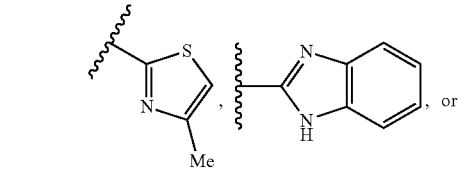

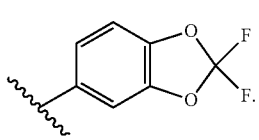

8. The compound of claim 1, wherein the compound is:
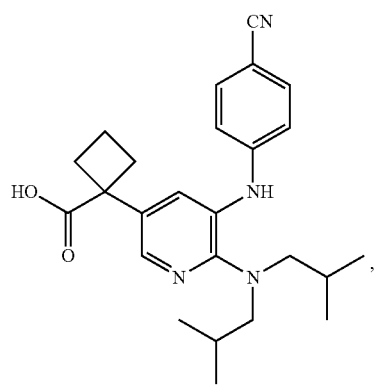
84
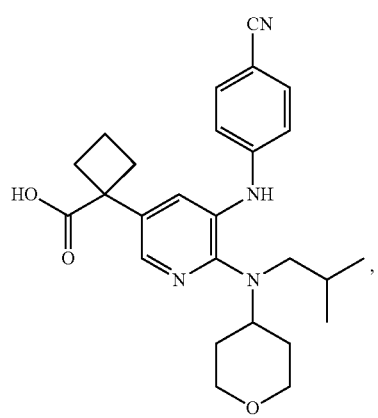
91
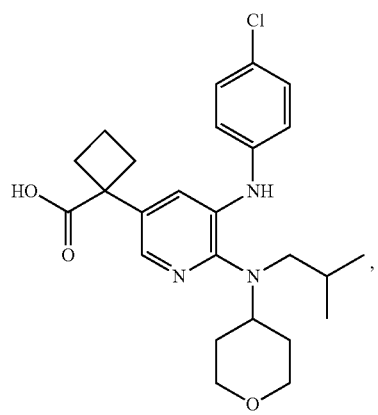
92
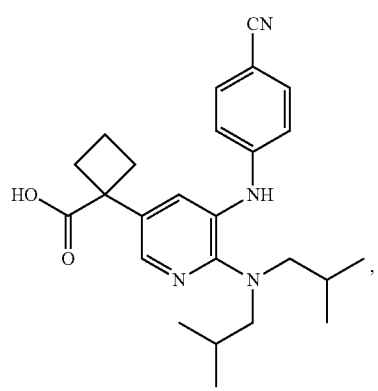
93
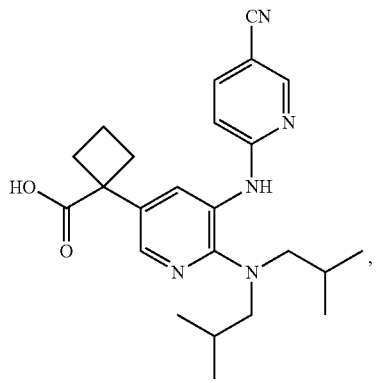
106
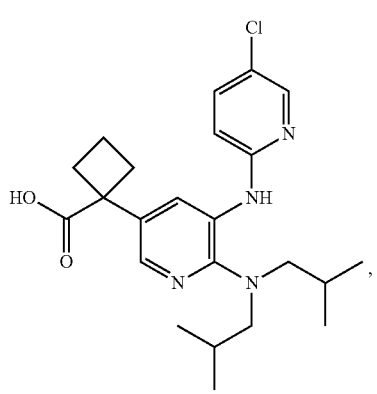
107
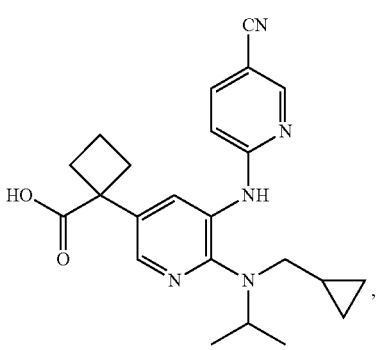
110
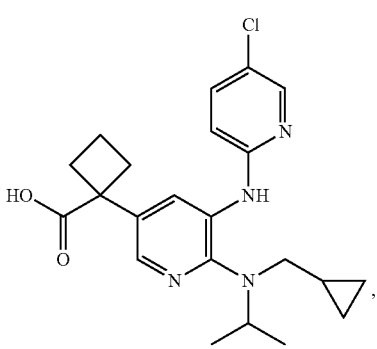
111

116 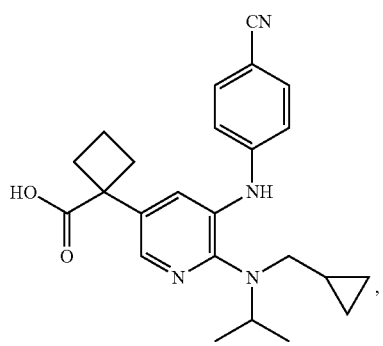
119 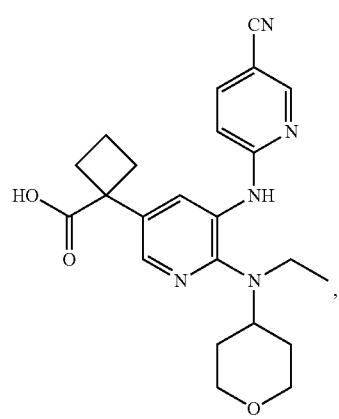
120 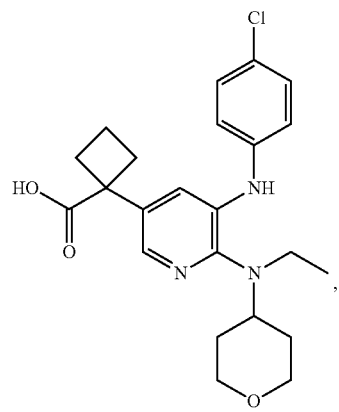
122 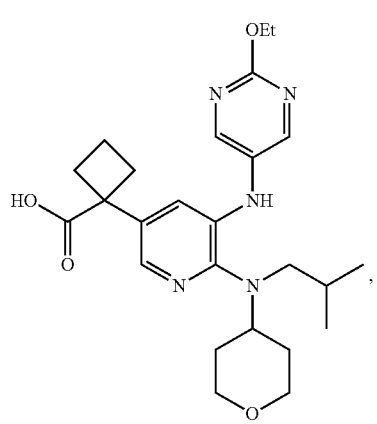
123 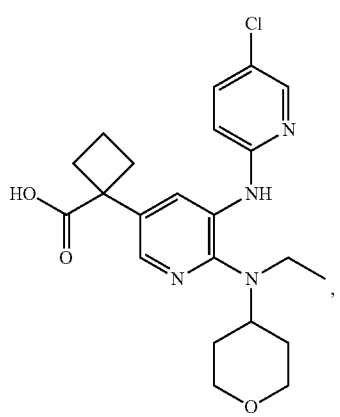
124 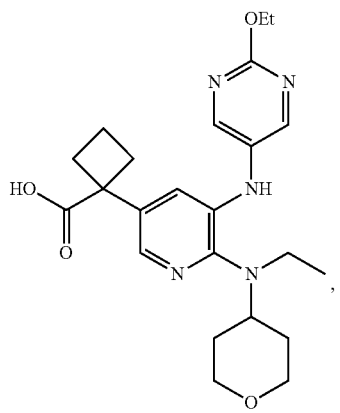
125 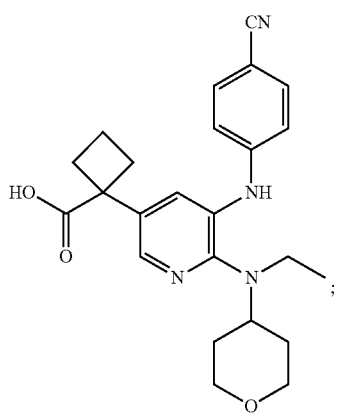
126 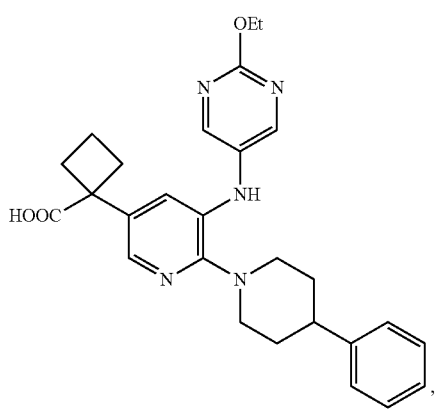

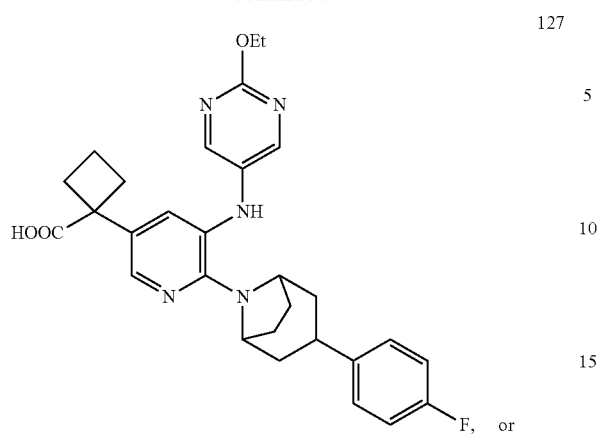
127
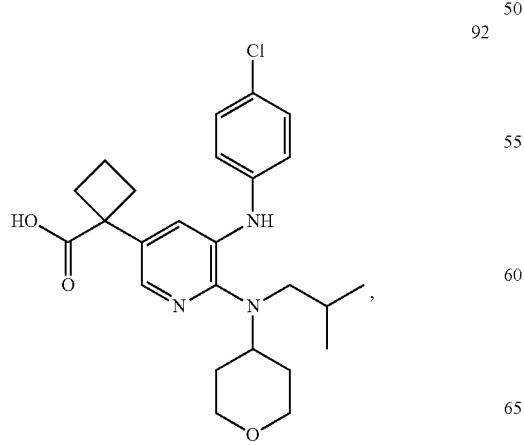
128
or a pharmaceutically acceptable salt thereof.
9. A pharmaceutical composition comprising a compound of claim 1, or a pharmaceutically acceptable salt thereof, and a pharmaceutically acceptable excipient.
10. The compound of claim 1, wherein the compound is:
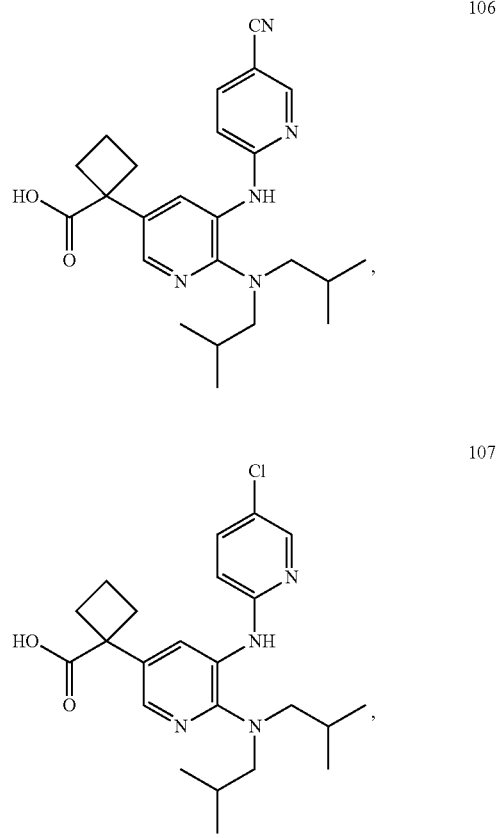
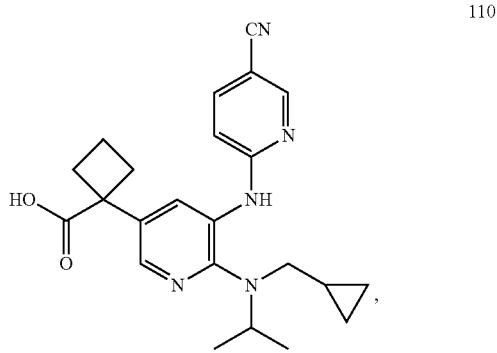 [SMILES: CC(C)N(CC1CC1)c1ncc(C2(C(=O)O)CCC2)cc1Nc1ccc(C#N)cc1]

or a pharmaceutically acceptable salt thereof.

11. The compound of claim 1, wherein the compound is
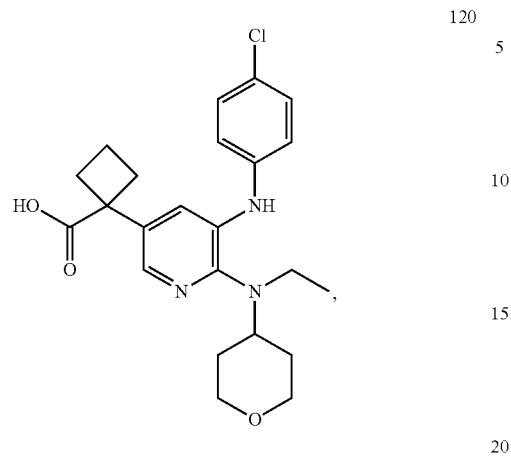
or a pharmaceutically acceptable salt thereof.
* * * * *